(12) United States Patent
Zavada et al.

(10) Patent No.: US 7,115,715 B2
(45) Date of Patent: Oct. 3, 2006

(54) ANTI-IDIOTYPE ANTIBODIES TO MN PROTEINS AND MN POLYPEPTIDES

(75) Inventors: Jan Zavada, Prague (CZ); Silvia Pastorekova, Bratislava (SK); Jaromir Pastorek, Bratislava (SK)

(73) Assignee: Institute of Virology Slovak Academy of Sciences, Bratislava (SK)

( * ) Notice: Subject to any disclaimer, the term of this patent is extended or adjusted under 35 U.S.C. 154(b) by 90 days.

(21) Appl. No.: 09/967,237

(22) Filed: Sep. 27, 2001

(65) Prior Publication Data

US 2003/0049828 A1 Mar. 13, 2003

Related U.S. Application Data

(60) Division of application No. 09/178,115, filed on Oct. 23, 1998, now Pat. No. 6,297,041, which is a continuation-in-part of application No. 08/787,739, filed on Jan. 24, 1997, now Pat. No. 6,027,887, which is a continuation-in-part of application No. 08/485,049, filed on Jun. 7, 1995, now Pat. No. 6,204,370, and a continuation-in-part of application No. 08/486,756, filed on Jun. 7, 1995, now Pat. No. 5,981,711, and a continuation-in-part of application No. 08/477,504, filed on Jun. 7, 1995, now Pat. No. 5,972,353, and a continuation-in-part of application No. 08/481,658, filed on Jun. 7, 1995, now Pat. No. 5,955,075, and a continuation-in-part of application No. 08/485,862, filed on Jun. 7, 1995, now Pat. No. 5,989,838, and a continuation-in-part of application No. 08/485,863, filed on Jun. 7, 1995, now Pat. No. 6,093,548, and a continuation-in-part of application No. 08/487,077, filed on Jun. 7, 1995, now Pat. No. 6,069,242, which is a continuation-in-part of application No. 08/260,190, filed on Jun. 15, 1994, now Pat. No. 6,774,117, which is a continuation-in-part of application No. 08/177,093, filed on Dec. 30, 1993, now Pat. No. 6,051,226, which is a continuation-in-part of application No. 07/964,589, filed on Oct. 21, 1992, now Pat. No. 5,387,676.

(30) Foreign Application Priority Data

Mar. 11, 1992 (CZ) ................................ PV-709-92

(51) Int. Cl.
C07K 16/00 (2006.01)
C12P 21/08 (2006.01)
C12P 21/04 (2006.01)
A61K 39/395 (2006.01)

(52) U.S. Cl. .................... 530/387.2; 530/388.26; 530/388.8; 424/131.1; 424/146.1; 424/155.1; 435/70.21

(58) Field of Classification Search ............ 424/130.1, 424/131.1, 133.1, 155.1, 184.1, 146.1; 530/387.1, 530/387.2, 388.25, 300, 350, 388.26, 388.8
See application file for complete search history.

(56) References Cited

U.S. PATENT DOCUMENTS

| 5,270,202 | A | * | 12/1993 | Raychaudhuri |
| 5,387,676 | A | | 2/1995 | Zavada et al. |
| 5,585,479 | A | | 12/1996 | Hoke et al. |
| 6,235,280 | B1 | * | 5/2001 | Chatterjee et al. |
| 6,632,431 | B1 | * | 10/2003 | Wu |

FOREIGN PATENT DOCUMENTS

| WO | 8808854 | 11/1988 |
| WO | 9318152 | 9/1993 |
| WO | 9534650 | 12/1995 |

OTHER PUBLICATIONS

William E. Paul, ed., Fundamental Immunology, 3rd ed. p. 242, 1993.*
Raychaudhuri et al. The Journal of Immunology, 13(5):1743-1749, 1986.*
Uemura et al. British journal of Cancer, 81(4):741-746, 1999.*
Anton et al., "Localized renal-cell carcinoma: detection of abnormal cells in peritumoral tissue. A cytophotometry and immunocytochemistry study," *World J. Urol.*, 13(3): 149-152 (1995).
Bander et al., "Renal cancer imaging with monoclonal antibody G250," *J. Urol.*, 155 (5 Suppl.): 583A (Abstract 1088) (1996).
Brewer et al., "A Study of Biomarkers in Cervical Carcinoma and Clinical Correlation of the Novel Biomarker MN," *Gynecologic Oncology*, 63: 337-344 (1996).
Costa et al., "MN Protein Immunolocalization in Uterine Cervix Carcinoma With Glandular Differentiation—A Clinicopathologic Study of a New Cancer-specific Biomarker," *International Journal of Surgical Pathology*, 3(2): 73-82 (1995).

(Continued)

*Primary Examiner*—Larry R. Helms
*Assistant Examiner*—David J. Blanchard
(74) *Attorney, Agent, or Firm*—Leona L. Lauder; Joan C. Harland

(57) ABSTRACT

Herein disclosed is a novel oncogene named MN or alternatively MN/CA IX. Abnormal expression of the MN gene is shown to signify oncogenesis, and diagnostic/prognostic methods for pre-neoplastic/neoplastic disease to detect or detect and quantitate such abnormal MN gene expression. Also disclosed are methods to treat pre-neoplastic/neoplastic disease involving the MN gene and protein, e.g., methods comprising the use of MN-specific antibodies, anti-idiotype antibodies thereto, and anti-anti-idiotype antibodies, and the use of MN antisense nucleic acids. Further disclosed are methods to identify and block MN binding site(s) and identify MN protein partners(s).

3 Claims, 14 Drawing Sheets

OTHER PUBLICATIONS

Costa, M., "MN and Ki67 (MIB-1) in Uterine Cervix Carcinoma: Novel Biomarkers With Divergent Utility," *Human Pathology*, 27(3): 217-219 (Mar. 1996).
Cote, "Protein Antigen Helps Identify Early Cervical Abnormalities," *Women's Health Weekly*: News Section, p. 7 (Mar. 30, 1998).
Divgi et al., "Scintigraphy of Renal Cell Carcinoma with I-131 Labelled Monoclonal Antibody (MAB) G250," *European Journal of Nuclear Medicine*, 19(8): 578 (Abstract 121-3) (Aug. 23, 1992).
Divgi et al., "Radioimmunotherapy (RIT) with I-131 Monoclonal Antibody (Mab) G250 in Metastatic Renal Cancer," *Proceedings of the 41st Annual Meeting*, 35(5): 101P (Abstract #401) (May 1994).
Divgi et al., "Radioimmunotherapy with I-131-G250 in Metastatic Renal Cell Cancer (RCC)," *J. Nucl. Med.*, 36 (5 Suppl.): 913P (Abstract 956; May 1995).
Frohman et al., "Rapid production of full-length cDNAs from rare transcripts: Amplification using a single gene-specific oligonucleotide primer," *PNAS* (USA), 85: 8998-9002 (Dec. 1988).
Frosch et al., "Cloning and characterisation of an immunodominant major surface antigen of *Echinococcus multilocularis,*" *Molecular and Biochemical Parasitology*, 48: 121-130 (1991).
Ivanov et al., "Down-regulation of transmembrane carbonic anhydrases in renal cell carcinoma cell lines by wild-type von Hippel-Lindau transgenes," *PNAS* (USA) 95: 12596-12601 (Oct. 1998).
Karttunen et al., "Colorectal Tumors Show Abnormal Expression of MN/CA IX," *Pathology Research and Practice 193/5-6*: 392 Abstract No. P198 (Abstract from European Congress on Pathology at Maastricht; Aug. 31-Sep. 4, 1997).
Kranenborg et al., "Development and Characterization of Anti-Renal Cell Carcinoma X Antichelate Bispecific Monoclonal Antibodies for Two-Phase Targeting of Renal Cell Carcinoma," *Cancer Res.*, 55 (23 Suppl.) 5864s-5867s (1995).
Kurth et al., "Characterization of Human Renal Cell Carcinoma Tumor Lines by Means of Monoclonal Antibodies," *Prostate*, 6(4): 451 (Abstract) (1985).
Liao et al., "Identification of the MN Antigen as a Diagnostic Biomarker of Cervical Intraepithelial Squamous and Glandular Neoplasia and Cervical Carcinomas," *American Journal of Pathology*, 145(3): 598-609 (Sep. 1994).
Liao and Stanbridge, "Expression of the MN Antigen in Cervical Papanicolaou Smears Is an Early Diagnostic Biomarker of Cervical Dysplasia," *Cancer Epidemiology, Biomarkers & Prevention*, 5: 549-557 (Jul. 1996).
Liao et al., "Identification of the MN/CA9 Protein As a Reliable Diagnostic Biomarker of Clear Cell Carcinoma of the Kidney," *Cancer Research*, 57: 2827-2831 (Jul. 15, 1997).
Luiten et al., "Target-Specific Activation of Mast Cells by Immunoglobulin E Reactive with a Renal Cell Carcinoma-Associated Antigen," *Laboratory Investigation*, 74(2): 467-475 (1996).
Luiten et al., "Generation of chimeric bispecific G250/anti-CD3 monoclonal antibody, a tool to combat renal cell carcinoma," *British Journal of Cancer*, 74(5): 735-744 (1996).
Luner et al., "Monoclonal Antibodies to Kidney and Tumor-associated Surface Antigens of Human Renal Cell Carcinoma," *Cancer Res.*, 46(11): 5816-5820 (1986).
McKiernan et al., "Expression of the Tumor-associated Gene *MN*: A Potential Biomarker for Human Renal Cell Carcinoma," *Cancer Research*, 57: 2362-2365 (Jun. 15, 1997).
Moon et al., "A Highly Restricted Antigen for Renal Cell Carcinoma Defined by a Monoclonal Antibody," *Hybridoma*, 4(2): 163-172 (1985).
Nakagawa et al., "MN as a Potential Target in Renal Cell Carcinoma," *J. Urology*, 159 (5 Suppl.): 187, Abstract 720 (May 1998).
Oosterwijk and Debruyne, "Radiolabeled monoclonal antibody G250 in renal-cell carcinoma," *World Journal of Urology*, 13: 186-190 (1995).
Oosterwijk et al., "The Expression of Renal Antigens in Renal Cell Carcinoma," *World Journal of Urology*, 2(2): 156-158 (1984).
Oosterwijk et al., "Monoclonal Antibodies that Discriminate Between Renal Cell Carcinomas (RCC) and Other Malignancies," *Prostate*, 6(4): 451-452 (Abstract) (1985).
Oosterwijk et al., "Immunohistochemical Analysis of Monoclonal Antibodies to Renal Antigens—Application in the Diagnosis of Renal Cell Carcinoma," *American Journal of Pathology*, 123(2): 301-309 (May 1986).
Oosterwijk et al., "Monoclonal Antibody G250 Recognizes a Determinant Present in Renal-Cell Carcinoma and Absent from Normal Kidney," *Int. J. Cancer*, 38: 489-494 (1986).
Oosterwijk et al., "Relationship between DNA Ploidy, Antigen Expression and Survival in Renal Cell Carcinoma," *Int. J. Cancer*, 42: 703-708 (1988).
Oosterwijk et al., "Expression of Intermediate-sized Filaments in Developing and Adult Human Kidney and Renal Cell Carcinoma," *The Journal of Histochemistry and Cytochemistry*, 38(3): 385-392 (1990).
Oosterwijk et al., "Antibody Localization in Human Renal Cell Carcinoma: A Phase I Study of Monoclonal Antibody G250," *Journal of Clinical Oncology*, 11(4): 738-750 (Apr. 1993).
Oosterwijk et al., "The Use of Monoclonal Antibody G250 in the Therapy of Renal-Cell Carcinoma," *Seminars in Oncology*, 22(1): 34-41 (Feb. 1995).
Oosterwijk et al., "Molecular characterization of the Renal Cell Carcinoma-associated antigen G250," *Proceedings of the American Association for Cancer Research*, 37: 461 (Abstract #3147) (Mar. 1996).
Oosterwijk et al., "Molecular Characterization of the Renal Cell Carcinoma-Associated Antigen G250," *J. Urol.*, 155: 925 (May 1996).
Opavsky et al., "Regulation of MN Expression," *Cell Biology International*, 18(5): Abstract No. Mo-58 (1994).
Opavsky et al., "Human MN/CA9 Gene a Novel Member of the Carbonic Anhydrase Family: Structure and Exon to Protein Domain Relationships," *Genomics*, 33: 480-487 (1996).
Pastorek et al., "The Structure and Expression of MN Gene, Coding for a Tumor-Associated Protein p54/58N," *J. Cancer Res., Clin. Oncol*, 119 (Suppl. 1) 10/113 (1993).
Pastorek et al., "Cloning and characterization of MN, a human tumor-associated protein with a domain homologous to carbonic anhydrase and a putative helix-loop-helix DNA binding segment," *Oncogene*, 9: 2877-2888 (1994).
Pastorek et al., "MN—A Novel Type of Oncoprotein," *Cell Biology International*, 18(5) : Abstract No. Mo-57 (1994).
Pastorekova et al., "A Novel Quasi-viral Agent, MaTU, Is a Two-Component System," *Virology*, 187: 620-626 (1992).
Pastorekova et al., "Transformation of Mammalian Cells by MN Oncogene," *Cell Biology International*, 18(5): Abstract No. Mo-56 (1994).
Pastorekova et al., "MN/CA IX, a Carbonic Anhydrase Isoenzyme Implicated in Carcinogenesis," Abstract submitted to International Conference on Experimental and Clinical Oncology, Greece (Oct. 3-5, 1996).
Pastorekova et al., "Carbonic Anhydrase IX, MN/CA IX: Analysis of Stomach Complementary DNA Sequence and Expression in Human and Rat Alimentary Tracts," *Gastroenterology*, 112: 398-408 (1997).
Resnick et al., "Viral and Histopathologic Correlates of MN and MIB-1 Expression in Cervical Intraepithelial Neoplasia," *Human Pathology*, 27(3): 234-239 (Mar. 1996).
Reuters News Report, "Biomarker Resolves Ambiguous Pap Smears" (Mar. 26, 1998).
Saarnio et al., "Distribution of carbonic anhydrase isoenzymes I, II, IV, V, VI and MN/CA IX in the human intestine. An immunohistochemical study," Abstract submitted to the meeting for United European Gastroenterological Week, Paris (Nov. 2-6, 1996).
Saarnio et al., "Expression of a Novel Carbonic Anhydrase Isoenzyme, MN/CA IX, In Gallbladder and Hepatitic Tumours," *Gut*, 41(3) : PA186-A186 (1997).
Saarnio et al., "Immunohistochemistry of Carbonic Anhydrase Isozyme IX (MN/CA IX) in Human Gut Reveals Polarized Expression in the Epithelial Cells with the Highest Proliferative Capacity," *Journal of Histochemistry & Cytochemistry 46*(4): 497-504 (1998).
Saarnio et al., "Immunohistochemical Study of Colorectal Tumors for Expression of a Novel Transmembrane Carbonic Anhydrase, MN/CA IX, with Potential Value as a Marker of Cell Proliferation," *American Journal of Pathology*, 153(1): 279-285 (Jul. 1998).

Stanbridge, E., "Cervical marker can help resolve ambiguous Pap smears," *Diagnostics Intelligence*, 10(5): 11 (1998).

Steffens et al., "Radioimmunotargeting with I$^{131}$ labeled chimeric G250 monoclonal antibody in patients with renal cell carcinoma," *J. Nucl. Med.*, 37 (5 Suppl.): 169P (1996).

Steffens et al., "Targeting of Renal Cell Carcinoma with Iodine-131-Labeled Chimeric Monoclonal Antibody G250," *Journal of Clinical Oncology*, 15(4): 1529-1537 (Apr. 1997).

Steffens et al., "Radioimmunotherapy with $^{131}$I-cG250 Monoclonal antibody in Patients with Metastasized RCC, Phase I/II Study," *J. Urology*, 159 (5 Suppl.): Abstract 562 (May 1998).

Surfus et al., "Anti-Renal-Cell Carcinoma Chimeric Antibody G250 Facilitates Antibody-Dependent Cellular Cytotoxicity with In Vitro and In Vivo Interleukin-2-Activated Effectors," *Journal of Immunotherapy* 19(3): 184-191 (1996).

Surfus et al., "Renal Cell Human-Mouse Chimeric Antibody G250 Mediates Antibody Dependent Cellular Cytotoxicity (ADCC)," *Biological Abstracts*, 47(9): 161224 (Abstract 3922) (1995).

Turner et al., "MN Antigen Expression in Normal, Preneoplastic, and Neoplastic Esophagus: a Clinicopathological Study of a New Cancer-Associated Biomarker," *Hum. Pathol.*, 28(6): 740-744 (Jun. 1997).

Tweedie and Edwards, "Mouse Carbonic Anhydrase III: Nucleotide Sequence and Expression Studies," *Biochemical Genetics*, 27(1/2): 17-30 (1989).

Uemura et al., "Internal Image Anti-Idiotype Antibodies Related to Renal-Cell Carcinoma-Associated Antigen G250," *Int. J. Cancer*, 56: 609-614 (1994).

Uemura et al., "Vaccination with Anti-Idiotype Antibodies Mimicking a Renal Cell Carcinoma-Associated Antigen Induces Tumor Immunity," *Int. J. Cancer*, 58: 555-561 (1994).

Uemura et al., "Immunization with Anti-Idiotype Monoclonal Antibodies Bearing the Internal Image of the Renal-Cell Carcinoma-Associated Antigen G250 Induces Specific Cellular Immune Responses," *Int. J. Cancer*, 59: 802-807 (1994).

Uemura et al., "Anti-tumor effects of vaccination with internal image anti-idiotype monoclonal antibodies," *Biotherapy* (Japan), 9(3): 294-295 (1995) (English Language Summary).

Uemura et al., "Possible tools for active specific immunotherapy with anit-idiotype antibodies in human renal cell carcinoma," *Biotherapy* (Japan), 10(3): 241-244 (1996) (English Lanuage Summary).

Uemura et al., "Expression of Tumor-Associated Antigen MN/G250 in Urologic Carcinoma: Potential Therapeutic Target," *Journal Urology*, 157 (4-Supp.): 377 (Apr. 16, 1997).

Uemura et al., "MN Target Immunotherapy for Renal Cell Carcinoma," *J. Urology*, 159 (5 Suppl.): 187, Abstract No. 724 (1998).

Van Dijk et al., "Induction of Tumor-Cell Lysis by Bi-Specific Monoclonal Antibodies Recognizing Renal-Cell Carcinoma and CD3 Antigen," *Int. J. Cancer*, 43: 344-349 (1989).

Van Dijk et al., "Therapeutic Effects of Monoclonal Antibody G250, Interferons and Tumor Necrosis Factor, In Mice with Renal-Cell Carcinoma Xenografts," *Int. J. Cancer*, 56: 262-268 (1994).

Vermylen et al., "Expression of the MN antigen as a biomarker of lung carcinoma and associated precancerous conditions," *Proceedings of the American Association for Cancer Research*, (Abstract #2280) (Mar. 1998).

Vessella et al., "Monoclonal antibodies to human renal cell carcinoma: recognition of shared and restricted tissue antigens," *Cancer Res.*, 45(12, Pt. 1): 6131-6139 (1985).

Young and Davis, "Efficient Isolation of Genes by Using Antibody Probes," *PNAS* (USA) 80: 1194-1198 (Mar. 1983).

Zavada, "The Pseudotypic Paradox," *J. gen. Virol.*, 63: 15-24 (1982).

Zavada and Zavadova, "A Transmissible Antigen Detected in Two Cell Lines Derived from Human Tumours," *J. gen. Virol.*, 24: 327-337 (1974).

Zavada and Zavadova, "An unusual transmissible agent—MaTu," *Arch. Virol.*, 118: 189-197 (1991).

Zavada et al., "VSV Pseudotype Produced in Cell Line derived from Human Mammary Carcinoma," *Nature New Biology*, 240: 124-125 (Nov. 22, 1972).

Zavada et al., "Tumorigenicity-Related Expression of MaTu Proteins in HeLa x Fibroblast Hybrids," Abstract presented at the XIX Meeting of the European Tumor Virus Group (May 1-4, 1991).

Zavada et al., "A Presumed New Oncoprotein—MN—Used as Experimental Antitumor Vaccine," *J. Cancer Res. Clin. Oncol.*, 119, (Suppl. 1) 2/24 (1993).

Zavada et al., "Expression of MaTu-MN Protein in Human Tumor Cultures and in Clinical Specimens," *Int. J. Cancer*, 54: 268-274 (1993).

Zavada et al., "MN—A Novel Type of Human Oncogene," Abstract submitted to EMBL Conference: Oncogenes & Growth Control, Heidelberg (Apr. 21-24, 1996).

Zavada et al., "A novel oncoprotein, MN, implicated in cervical carcinoma," Abstract submitted to ETVG Meeting, Innsbruck (Mar. 1997).

Zavada et al., "Transient transformation of mammalian cells by MN protein, a tumor-associated cell adhesion molecule with carbonic anhydrase activity," *International Journal of Oncology*, 10: 857-863 (1997).

Zavadova et al., "Novel tumor-associated MN protein is a cell adhesion molecule," for conference on Molecular Genetics of Cancer, Oxford, Sep. 1997.

Blouin et al., "Definition of the human renal cell carcinoma phenotype using monoclonal and polyclonal antibodies: a tumor marker study," *Exp. Pathol.*, 36(3): 147-163 (1989) (Abstract only).

Ebert and Bander, "Immunodiagnosis of renal cell carcinoma," *Immunol. Ser.*, 53: 469-483 (1990) (Abstract only).

Finstad et al., "Specificity analysis of mouse monoclonal antibodies defining cell surface antigens of human renal cancer," *PNAS* (USA) 82: 2955-2959 (May 1985).

Klingel et al., "Expression of differentiation antigens and growth-related genes in normal kidney, autosomal dominant polycystic kidney disease, and renal cell carcinoma,"*Am. J. Kidney Dis.*, 19(1): 22-30 (Jan. 1992) (Abstract only).

Scharfe et al., "Tumour-Specific Monoclonal Antibodies for Renal Cell Carcinoma," *Eur. Urol.*, 11: 117-120 (1985).

Terashima et al., "Production of monoclonal antibody to renal cell carcinoma," *Nippon Hinyokika Gakkai Zasshi.*, 80(6): 838-846 (Jun. 1989) (Abstract only).

Tokuyama and Tokuyama, "Mouse monoclonal antibodies with restricted specificity for human renal cell carcinoma and ability to modulate the tumor cell growth in vitro," *Hybridoma*, 7(2): 155-165 (Apr. 1988) (Abstract only).

Ueda et al., "Cell surface antigens of human renal cancer defined by mouse monoclonal antibodies: Identification of tissue-specific kidney glycoproteins," *PNAS* (USA), 78(8): 5122-5126 (Aug. 1981).

\* cited by examiner

| | | | | | | | | | | | |
|---|---|---|---|---|---|---|---|---|---|---|---|
| 349 | V | M | L | S | A | K | Q | L | H | T | L | W | 364 |
| 1057 | GTG | ATG | CTG | AGT | GCT | AAG | CAG | CTC | CAC | ACC | CTC | TGG | 1104 |
| 365 | G | P | G | D | S | R | L | Q | L | N | F | P | 380 |
| 1105 | GGA | CCT | GGT | GAC | TCT | CGG | CTA | CAG | CTG | AAC | TTC | CCT | 1152 |
| 381 | L | N | G | R | A | V | I | E | A | S | F | R | 396 |
| 1153 | TTG | AAT | GGG | CGA | GTG | ATT | GAG | GCC | TCC | TTC | TTC | CGA | 1200 |
| 397 | S | P | R | A | A | E | P | V | Q | L | N | A | 412 |
| 1201 | AGT | CCT | CGG | GCT | GCT | GAG | CCA | GTC | CAG | CTG | AAT | GCG | 1248 |
| 413 | G | D | I | L | A | V | F | L | G | C | L | A | 428 |
| 1249 | GGT | GAC | ATC | CTA | GCC | GTG | TTT | CTT | GGC | TGC | CTG | GCT | 1296 |
| 429 | V | A | F | L | V | Q | M | R | R | H | R | V | 444 |
| 1297 | GTC | GCG | TTC | CTT | GTG | CAG | ATG | AGA | AGG | CAC | AGA | GGA | 1344 |
| 445 | G | G | V | S | Y | R | P | A | E | V | T | K | 460 |
| 1345 | GGG | GGT | GTG | AGC | TAC | CGC | CCA | GCA | GAG | GTA | ACT | AAA | 1392 |
| | G | G | D | L | E | N | C | P | V | L | G | A | * | |
| 1393 | AGG | CTG | GAT | CTT | GAA | AAC | TGT | CCT | GTC | CTG | GGA | GCC | TAG | 1440 |
| 1441 | GGA | GCC | GGT | AAC | TGT | CCT | GTC | CTG | CTC | ATT | ATG | CCA | CTT | CCT | TTT | AAC | 1488 |
| 1489 | TGC | CAA | GAA | ATT | TTT | TAA | AAT | AAA | TAT | TTA | TAA | T | | | | | 1522 |

```
  1                                                       M   A   P   L   C   P   S   P   W   L   P   L
  1                                       ACA GTC AGC CGC ATG GCT CCC CTG TGC CCC AGC CCC TGG CTC CCT CTG    12
                                                                                                             48
 13   L   I   P   A   P   A   P   A   L   L   L   L   L   L   L   Q   P   W   L   S   Q   V   T   L   S
 49  TTG ATC CCG GCC CCT GCT CCG GCT CCA CTT CTG CTG CTG CTG CTG CAA CCT TGG CTG AGT TCA CTG GTG ACT CTG    28
                                                                                                             96
 29   L   L   M   L   M   P   V   H   P   Q   R   L   P   R   M   Q   L   L   L   M   P   V   H   P
 97  CTG CTT CTG ATG CCT GTC CAT CCC CAG CGG TTG CCC AGG ATG CAG CTG CTG CTG CTG ATG CCT GTC CAT CCC   44
                                                                                                            144
 45   E   D   S   P   L   G   G   S   S   G   E   D   P   L   G   G   S   S   G   E   D   P   L
145  GAG GAT TCC CCC TTG GGA GGA GGC TCT TCT GGG GAA GAT CCA CTG GGA GGA GGC TCT TCT GGG GAA GAT CCA   60
                                                                                                            192
 61   G   E   E   D   L   P   S   E   E   D   R   E   E   D   R   E   E   D   R   E   E   D
193  GGC GAG GAG GAT CTG CCC AGT GAA GAG GAT CGG GAA GAG GAT CGG GAA GAG GAT CGG GAA GAG GAT          76
                                                                                                            240
 77   P   P   G   E   D   L   P   K   V   P   L   E   E   E   S   E   E   K   P   G   E   K
241  CCA CCC GGA GAG GAT CTA CCT AAA GTT CCC CTA GAG GAG GAG TCA GAA GAG AAA CCT GGA GAG AAG           92
                                                                                                            288
 93   E   D   L   E   V   K   P   T   V   E   A   K   E   D   P   G   D   D   Q   P   G   E
289  GAG GAT CTA CCT GAA GTT AAG CCT ACT GTT GAG GCT AAA GAA GAT CCT GGA GAT GAC CAG CCT GGA GAG       108
                                                                                                            336
109   K   L   N   A   H   R   D   K   P   W   R   V   S   L   S   P   Q   S   L   C   L
337  AAG TTA AAT GCC CAC AGG GAC AAA CCT TGG CGG GTG TCC CGG AGT CCC CAG AGT CAA TCC TGC CTG          124
                                                                                                            384
125   P   Q   N   Y   G   D   G   E   K   D   P   P   R   V   P   A   S   H   H   C   H
385  CCC CAG AAT TAT GGA GAC GGC GAA AAA GAC CCG CCC CGG GTG CCC CCA AGT CAG CAG AGT CAT CAT          140
                                                                                                            432
141   W   R   Y   G   D   G   W   R   Y   G   D   G   W   R   Y   G   D   G   C   A
433  TGG CGC TAT GGA GAC GGC TGG CGG TAT GGA GAC GGC TGG CGG TAT GGA GAC GGC TGC GCC                 156
                                                                                                            480
157   A   G   R   F   Q   S   P   V   D   I   R   P   Q   L   A   A
481  GCG GGC CGC TTC CAG TCC CCG GTG GAT ATC CGC CCC CAG CTC GCC GCC                                 172
                                                                                                            528
```

| | | | | | | | | | | | | |
|---|---|---|---|---|---|---|---|---|---|---|---|---|
| 173 | F | C | P | A | L | R | P | L | E | L | L | G | F | Q | L | P | 188 |
| 529 | TTC | TGC | CCG | GCC | CTG | CGC | CCC | CTG | GAA | CTC | CTG | GGC | TTC | CAG | CTC | CCG | 576 |
| 189 | P | L | P | E | L | R | L | R | N | N | G | H | S | V | Q | L | 204 |
| 577 | CCG | CTC | CCA | GAA | CTG | CGC | CTG | CGC | AAC | AAT | GGC | CAC | AGT | CAA | CTG | CTG | 624 |
| 205 | T | L | P | P | G | L | E | M | A | L | G | P | R | E | Y | 220 |
| 625 | ACC | CTG | CCT | GGG | CTA | GAG | ATG | GCT | CTG | GGT | CCC | CGG | GAG | TAC | 672 |
| 221 | R | A | L | Q | L | H | W | G | A | G | R | P | G | 236 |
| 673 | CGG | GCT | CTG | CAG | CTG | CAT | TGG | GGG | GCT | GCA | GGT | CCG | GGC | 720 |
| 237 | S | E | H | T | V | E | H | R | F | P | A | E | I | H | V | 252 |
| 721 | TCG | GAG | CAC | ACT | GTG | GAA | CAC | CGT | TTC | CCT | GCC | GAG | ATC | CAC | GTG | 768 |
| 253 | V | H | L | S | T | A | F | A | R | V | D | E | A | L | G | R | 268 |
| 769 | GTT | CAC | CTC | AGC | ACC | GCC | TTT | GCC | AGA | GTT | GAC | GAG | GCC | TTG | GGG | CGC | 816 |
| 269 | P | G | G | L | A | V | L | A | F | L | E | G | P | E | 284 |
| 817 | CCG | GGA | GGC | CTG | GCC | GTG | TTG | GCC | TTT | CTG | GAG | GGC | CCG | GAA | 864 |
| 285 | E | N | S | A | Y | E | Q | L | S | R | L | E | I | S | A | 300 |
| 865 | GAA | AAC | AGT | GCC | TAT | GAG | CAG | CTG | TCT | CGC | CTG | GAA | ATC | TCT | GCT | 912 |
| 301 | E | G | S | D | F | T | S | R | L | D | G | Y | Q | L | A | L | 316 |
| 913 | GAG | GGC | TCA | GAC | TTC | ACT | AGC | CGC | TTG | GAC | GGA | TAT | CAA | CTG | GCA | CTC | 960 |
| 317 | L | P | S | Y | V | R | Y | F | Q | G | S | L | T | 332 |
| 961 | CTG | CCC | TCT | TAC | GTC | CGC | TAC | TTC | CAA | GGG | TCT | CTG | ACT | 1008 |
| 333 | T | P | A | C | Q | V | G | N | F | T | Q | T | 348 |
| 1009 | ACA | CCG | GCC | TGT | CAG | GTC | GGT | AAC | TTT | ACT | CAG | ACA | 1056 |

```
 9901 gctaattgat tagaatgaag cttgagaaat ctcccagcat ccctctcgca aaagaatccc
 9961 cccccctttt tttaaagata gggtctcact ctgtttgccc caggctgggg tgttgtggca
10021 cgatcatagc tcactgcagc ctcgaactcc taggctcagg caatcctttc accttagctt
10081 ctcaaagcac tgggactgta ggcatgagcc actgtgcctg gcccaaacg gccctttac
10141 ttggcttta ggaagcaaaa acggtgctta tcttacccct tctcgtgtat ccaccctcat
10201 cccttggctg gcctcttctg gagactgagg cactatgggg ctgcctgaga actcggggca
10261 ggggtggtgg agtgcactga ggcaggtgtt gaggaactct gcagacccct cttccttccc
10321 aaagcagccc tctctgctct ccatcgcagG TGACATCCTA GCCCTGGTTT TTGGCCTCCT
10381 TTTTGCTGTC ACCAGCGTCG CGTTCCTTGT GCAGATGAGA AGGCAGCACA Ggtattacac
10441 tgacccttc ttcaggcaca agcttccccc acccctgtgg agtcacttca tgcaaagcgc
10501 atgcaaatga gctgctcctg ggccagtttt ctgattagcc tttcctgttg tgtacacaca
10561 gAAGGGGAAC CAAAGGGGGT GTGAGCTACC GCCCAGCAGA GGTAGCCGAG ACTGGAGCCT
10621 AGAGGCTGGA TCTTGGAGAA TGTGAGAAGC CAGCCAGAGG CATCTGAGGG GGAGCCGGTA
10681 ACTGTCCTGT CCTGCTCATT ATGCCACTTC CTTTTAACTG CCAAGAAATT TTTTAAAATA
10741 AATATTTATA ATaaaatatg ctttagtcac ctttgttccc caaatcagaa ggaggtattt
10801 gaattccta ttactgttat tagcaccaat ttagtggtaa tgcattattt ctattacagt
10861 tcggcctcct tccacacatc actccaatgt gttgctcc
```

```
   1  ggatcctgtt gactcgtgac cttaccccca acctgtgct ctctgaaaca tgagctgtgt
  61  ccactcaggg ttaaatggat taaggcggt gcaagatgtg ctttgttaaa cagatgcttg
 121  aagcagcat gctcgttaag agtcatcacc aatcctaat ctcaagtaat cagggacaca
 181  aacactgcgg aaggccgcag ggtcctctgc ctaggaaaac cagagacctt tgttcacttg
 241  tttatctgac cttccctcca ctattgtcca tgaccctgcc aaatccccct ctgtgagaaa
 301  cacccaagaa ttatcaataa aaaaataaat ttaaaaaaaa aatacaaaaa aaaaaaaaaa
 361  aaaaaaaaaa gacttacgaa tagttattga taaatgaata gctattggta aagccaagta
 421  aatgatcata ttcaaaacca gacggccatc atcacagctc aagtctacct gatttgatct
 481  ctttatcatt gtcattcttt ggattcacta gattagtcat catcctcaaa attctcccc
 541  aagttctaat tacgttccaa acattaggg gttacatgaa gcttgaacct actacctct
 601  ttgcttttga gccatgagtt gtaggaatga cottacatgc cottacatgc tgggattaa
 661  tttaaacttt acctctaagt cagttgggta gcctttggct tattttgta gctaattttg
 721  tagttaatgg atgcactgtg aatcttgcta tgatagtttt cctccacact ttgccactag
 781  gggtaggtag gtactcagtt ttcagtaatt gcttacctaa gaccctaagc cctattctc
 841  ttgtactggc ctttatctgt aatatgggca tatttaatac aatataattt ttggagtttt
 901  tttgtttgtt tgtttgtttg ttttttgag acggagtctt gcatctgtca tgcccaggct
 961  ggagtagcag tggtgccatc tcggctcact gcaagctcca cctcccgagt tcacgccatt
1021  ttcctgcctc agcctcccga gtagctggga ctacaggcgc ccgccaccat gcccggctaa
1081  tttttttgtat tttggtaga gacgggtttt caccgtgtta gccagaatgg tctcgatctc
1141  ctgactcgt gatccacccg cctcggcctc ccaaagttct gggattacag gtgtgagcca
1201  ccgcacctgg ccaatttttt gagtctttta aagtaaaaat atgtccttgta agctggtaac
1261  tatggtacat ttcctttat taatgtggtg ctgacggtca tataggttct tttgagtttg
1321  gcatgcatat gctactttt gcagtccttt cattacattt tctctctttc atttgaagag
1381  catgttatat ctttagctt cacttgcttt aaaaggttct ctcattagcc taacacagtg
1441  tcattgttgg taccacttgg atcataagtg gaaaaacagt caagaaattg cacctgagg
1501  cttgtttgta agaggatga ttcaggtgaa tctgacacta agaaactccc ctacctgagg
1561  tctgagattc ctctgacatt gctgtatata ggctttttcct ttgacagcct gtgactgcgg
1621  actatttc ttaagcaaga tatgcaaga tctgcatgt cttttccag agagaggtct
1681  catatatga ctctttta tatagacagg gaaacttgtt tccatatttc aggaatgttt
1741  gcttgtgtt tatgcttttt tatagacagg ccacgctttc cctcagtgac ccaaaagagg
1801  tgggaattgt tattggatat catcattggc tacaagaaat tgacctttga aacaattaag
1861  ggttcataat ctcaattctg tcagaattgg tacaagaaat agctgctatg tttcttgaca
1921  ttccacttgg taggaaataa gaatgtgaaa ctcttcagtt ggtgtgtgtc cct?gttttt
```

FIG._2A

```
1981  ttgcaatttc  cttcctactg  tgttaaaaaa  aagtatgatc  ttgctctgag  aggtgaggca
2041  ttcttaatca  tgatctttaa  agatcaataa  tataatcctt  tcaaggatta  tgtcttatt
2101  ataataaaga  taatttgtct  ttaacagaat  caataatata  atcccttaaa  ggattatatc
2161  tttgctgggc  gcagtggctc  acacctgtaa  tcccagcact  ttgggtggcc  aagtggaag
2221  gatcaaattt  gcctacttct  atattatctt  ctaaagcaga  attcatctct  cttccctcaa
2281  tatgatgata  ttgacagggt  ttgccctcac  tcactagatt  gtgagctcct  gctcagggca
2341  ggtagcgttt  tttgttttg   ttttgttttt  tctttttga   gacagggtct  tgctctgtca
2401  cccaggccag  agtgcaatgg  tacagtctca  gctcactgca  gcctcaaccg  cctcggctca
2461  aaccatcatc  ccatttcagc  ctcctgagta  gctgggacta  caggcacatg  ccattacacc
2521  tggctaattt  ttttgtattt  ctagtagaga  cagggtttgc  ccatgttgcc  cgggctggtc
2581  tcgaactcct  ggactcaagc  aatccaccca  cctcagcctc  ccaaaatgag  ggaccgtgtc
2641  ttattcattt  ccatgtccct  agtccatagc  ccagtgctgg  acctatggta  gtactaaata
2701  aatatttgtt  gaatgcaata  gtaaatagca  tttcagggag  caagaactag  attaacaaag
2761  gtggtaaaag  gttggagaa   aaaaataata  gtttaatttg  gctagagtat  gagggagagt
2821  agtagagac   aagatggaaa  ggtctcttgg  gcaaggtttt  gaaggaagtt  ggaagtcaga
2881  agtacacaat  gtgcatatcg  tggcaggcag  tggggagcca  atgaaggctt  ttgagcagga
2941  gagtaatgtg  ttgaaaaata  aatataggtt  aaacctatca  agccccctct  gacacataca
3001  cttgcttttc  attcaagctc  aagtttgtct  cccacatacc  cattacttaa  ctcaccctcg
3061  ggctcccta   gcagcctgcc  ctacccttct  acctgctcc   tgtggagtc   agggatgtat
3121  acatgagctg  ctttccctct  cagccagagg  acatggggg   ccccagctcc  cctgccttc
3181  cccttctgtg  cctgagctg   ggaagcaggc  cagggttagc  cagggtctgc  tggcaagcag
3241  ctgggtggtg  ccaggagag   cctgcatagt  gccaggtggt  gccttgggtt  ccaagctagt
3301  ccatgccccc  gataaccttc  tgcctgtgca  cacacctgcc  cctcactcca  cccccatcct
3361  agctttggta  tggggagag   ggcacagggc  cagacaaaac  tgtgagactt  tggctccatc
3421  tctgcaaaag  ggcgctctgt  gagtcagcct  gctcccctcc  agcttgctc   ctccccacc
3481  cagctctcgt  ttccaatgca  cgtacagccc  gtacacaccg  tgtgctggga  cacccACAG
3541  TCAGCCGCAT  GGCTCCCCTG  TGCCCCAGCC  CCTGGCTCCC  TCTGTTGATC  CCGGCCCTG
3601  CTCCAGGCCT  CACTGTGCAA  CTGCTGCTGT  CACTGCTGCT  TCTGGTGCCT  GTCCATCCCC
3661  AGAGGTTGCC  CCGGATGCAG  CCTTGGAGG   AGGCTCTTCT  GGGAAGATG
3721  ACCCACTGGG  CGAGGAGGAT  CTGCCCAGTG  AAGAGATTC   ACCCAGAGAG  GAGGATCCAC
3781  CCGAGAGGA   GGATCTACCT  GGAGAGGAGA  ATCTACCTGG  AGAGGAGGAT  CTACCTGAAG
3841  TTAAGCCTAA  ATCAGAAGAA  GAGGGCTCCC  TGAAGTTAGA  ATGCCCACAG  ACTGTTGAGG
3901  CTCCTGGAGA  TCCTTCAAGAA  CCCCAGAATA  ATGCCCACAG  GGACAAAGAA  Ggtaagtggt
```

FIG._2B

```
3961  catcaatctc caaatccagg ttccaggagg ttcatgactc ccctcccata cccagccta
4021  ggctctgttc actcagggaa ggaggggaga ctgtactccc cacagaagcc cttccagagg
4081  tcccatacca atatcccat ccccactctc ggaggtagaa agggacagat gtggagagaa
4141  aataaaaagg gtgcaaaagg agagaggtga gctgatgag atgggagaga aggggaggc
4201  tggagaagag aaaggatga aactgcaga tgagaggaaa aatgtgcaga cagagaaaaa
4261  aaataggtgg agaaggagag tcagagagtt tgagggaaag agaaaaggaa agcttgggag
4321  gtgaagtggg taccagagac aagcaagaag agctggtaga agtcatctca tcttaggcta
4381  caatgaggaa ttgagaccta ggaagaaggg acacagcagg tagagaaacg tggctttcttg
4441  actcccaagc caggaatttg gggaaagggg ttggagacca tacaaggcag aggatgagt
4501  ggggagaaga aagaagggag aaaggaaaga tggtgtactc actcatttgg gactcaggac
4561  tgaagtgccc actcactttt ttttttttt tttttgagac aaactttcac tttgttgcc
4621  caggctggag tgcaatgcg cgatctcggc tcactgcaac ctccacctcc cgggttcaag
4681  tgattctcct gcctcagcct ctagccaagt agctgcgatt acaggcatgc gccaccacgc
4741  ccggctaatt tttgtatttt tagtagagac gggtttcgc catgttggtc agcctggtct
4801  cgaactcctg atctcaggtg atccaaccac cctgccctcc caaagtgctg ggattatagg
4861  cgtgagccac agcgcctggc ctgaagcagc cactcactt tacagaccct aagacaatga
4921  ttgcaagctg gtaggattgc tgtttggccc accagctgc ggtgttgagt ttgggtgcgg
4981  tctcctgtgc tttgcacctg gcccgcttaa ggcatttgtt acccgtaatg ctcctgtaag
5041  gcatctgcgt ttgtgacatc gttttggtcg caggaaaggg attggggctc taagcttgag
5101  cggttcatcc ttttcattta tacagGGGAT GACCAGAGTC ATTGGCGCTA TGGAGgtgag
5161  acacccaccc gctgcacaga cccaatctgg gaacctgctc ctgtggatct ccctacagc
5221  cgtccctgaa cactggtccc gggcgtccca accgccac accgtcccac ccctccacct
5281  tttctacccg ggttccctaa gttcctgacc taggcgtcag acttcctcac tatactctcc
5341  caccccagGC GACCCGCCCT GGCCCCAGCC GTCCCCAGCC TGCGCGGGCC GCTTCCAGTC
5401  CCCGGTGGAT ATCCGCCCCC AGCTCGCCCG CTTCTGCCCG GCCCTGCCTG CCCTGGAACT
5461  CCTGGGCTTC CAGCTCCCCA CGCTCCCAGA ACTGCGCCTG CGCAACAATG GCCACAGTGg
5521  tgagggggtc tccccgcga gacttgggga tgggggggg cgcagggaag ggaaccgtcg
5581  cgcagtgcct gcccggggt tggctgcc ctaccgggcg gggccggctc acttgcctct
5641  ccctacgcag TGCAACTGAC CCTGCCTCCT GGGCTAGAGA TGGCTCTGGG TCCCGGCGG
5701  GAGTACCGGG CTCTGCAGCT GCATCTGCAC CAGGTCGTCC CAGGTCGTCG GGGCTCGGAG
5761  CACACTGTGG AAGGCCACCG TTTCCCTGCC GAGgtgagcg cggactgcc gagaagggc
5821  aaaggagcgg ggcgacggg ggccagagac gtggccctct cctaccctcg tgtcctttc
5881  agATCCACGT GGTTCACCTC AGCACCGGCC TGACGAGAGT TTGCCAGAGT TTGGGGCGCC
```

FIG. 2C

```
5941 CGGGAGGCCT GGCCGTGTTG GCCGCCTTTC TGGAGgtacc agatcctgga cacccctac
6001 tccccgcttt cccatcccat gctcctcccg gactctatcg tggagccaga gaccccatcc
6061 cagcaagctc actcaggccc ctggctgaca aactcattca cgcactgttt gttcatttaa
6121 cacccactgt gaaccaggca ccagccccca acaaggattc tgaagctgta ggtcctgcc
6181 tctaaggagc ccacagccag tgggggaggc tgacatgaca gacacatagg aaggacatag
6241 taaagatggt ggtcacagag gaggtgacac ttaaagcctt cactgatgaa aaagaaaag
6301 aggtgttcat tgcagaggaa acagaatgtg caaagactca gaatatggcc tatttaggga
6361 atggctacat acaccatgat tagaggaggc ccagtaaagg gaagggatgg tgagatgcct
6421 gctagttca ctcactcact tttatttatt tattatttt tttgacagtc tctctgtcgc
6481 ccaggctgga gtgcagtggt gtgatcttgg gtcactgcaa cttccgcctc ccggttcaa
6541 gggattctcc tgcctcagct tcctgagtag ctggggttac agtgtgtgc caccatgccc
6601 agctaatttt ttttgtatt tttagtagac aggggttcac catgttggtc aggctggtct
6661 caaactcctg gcctcaagtg atccgcctga ctcagcctac caaagtgctg attacaagtg
6721 tgagccaccg tgccagcca cactcactga ttcttttaatg ccagccacac agcacaaagt
6781 tcagagaaat gcctccatca tagcatgtca atatgttcat actcttaggt tcatgatgtt
6841 cttaacatta ggttcataag caaataaga aaaaagaata ataaataaaa gaagtggcat
6901 gtcaagacct cacctgaaaa gccaaacaca gaatcatgaa ggtgaatgca gaggtgacac
6961 caacacaag gtgtatatat ggtttcctgt gggggtatg tacggaggca gcagtgagtg
7021 agactgcaaa cgtcagaagg gcacgggtca ctgagagcct agtatcctag gcagtgggc
7081 tctctccctc tctctccagc ttgtcattga aaaccaacca accaagcttg ttggttcgca
7141 cagcaagagt acatagagtt tgaaataata catagatttt taagagggag acactgtctc
7201 taaaaaaaa aacaacagca acaacaaaaa gcaacaacca ttacaatttt atgttccctc
7261 agcattctca gagctgagga atgggagagg actatgggaa ctgtcttaca cccccttcat gttccgcct
7321 tcagccatgg ccctggatac atgcactcat ctgtcttaca atgtcattcc cccagGAGGG
7381 CCCGGAAGAA AACAGTGCCT ATGAGCAGTT GCTGTCTCGC TTGGAAGAAA TCGCTGAGGA
7441 AGtcagttt gttggtctgg ccactaatct ctggtggccta gttcataaag aatcaccctt
7501 tggagcttca ggtctgaggc tggagatggg ctcctccag tgcaggaggg attgaagcat
7561 gagccagcgc tcatcttgat aataaccatg aagctgacag acacagttac ccgcaaacgg
7621 ctgcctacag attgaaaacc aagcaaaaac cgccgggcac ggtggctcac gcctgtaatc
7681 ccagcacttt ggaggccaa ggcaggtgga tcacgaggtc aagagatcaa gaccatcctg
7741 gccaacatgg tgaaacccca tctctactaa aaatacgaaa aaatagccag gcgtggtggc
7801 gggtgcctgt aatcccagct actcgggagg ctgaggcagg agaatggcat gaacccggga
7861 ggcagaagtt gcagtgagcc gagatcgtgc cactgcactc cagcctgggc aacagagcga
```

FIG. _2D

```
7921  gactcttgtc  tcaaaaaaaa  aaaaaaaaaa  gaaaaccaag  caaaaaccaa  aatgagacaa
7981  aaaaaacaag  accaaaaaat  ggtgtttgga  aattgtcaag  gtcaagtctg  gagagctaaa
8041  cttttctga   gaactgttta  tcttaataa   gcatcaaata  ttttaacttt  gtaaatactt
8101  ttgttggaaa  tcgttctctt  cttagtcact  ctgggtcat   tttaaatctc  acttactcta
8161  ctagacctt   taggtttctg  ctagactagg  tagaactctg  cctttgcatt  tcttgtgtct
8221  gttttgtata  gttatcaata  ttcatattta  tttacaagtt  attcagatca  tttttcttt
8281  tcttttttt   tttttttt    tttttacat   ctttagtaga  gacagggttt  caccatattg
8341  gccaggctgc  tctcaaactc  ctgacccttgt gatccaccag  cctcggcctc  ccaaagtgct
8401  gggattcatt  tttttctttt  aatttgctct  gggcttaaac  ttgtggccca  gcactttatg
8461  atggtacaca  gagttaagag  tgtagactca  gacgtcttt   ctccttttct  tctcttcctt
8521  cctcccttcc  ctcccacctt  cccttctctc  cttccttttt  ttcttctcct  cttgcttcct
8581  caggcctctt  ccagttgctc  caaagccctg  tactttttt   tgagttaacg  tcttatggga
8641  agggcctgca  cttagtgaag  aagtggtctc  agagttgagt  tacccttggct  tctgggaggt
8701  gaaactgtat  ccctataccc  tgaagcttta  aggggtgca   atgtagatga  gaccccaaca
8761  tagatcctct  tcacagGCTC  AGAGACTCAG  GTCCCAGGAC  TGGACATATC  TGCACTCCTG
8821  CCCTCTGACT  TCAGCCGCTA  CTTCCAATAT  GAGGGGTCTC  TGACTACACC  GCCCTGTGCC
8881  CAGGGTGTCA  TCTGGACTGT  GTTTAACCAG  ACAGTGATGC  TGAGTGCTAA  GCAGgtgggc
8941  ctggggtgtg  tgtggacaca  gtgggtgcgg  gggaaagagg  atgtaagatg  agatgagaaa
9001  caggagaaga  aagaaaatcaa ggctgggctc  tgtggcttac  gcctataatc  ccaccacgtt
9061  gggaggctga  ggtgggagaa  tggtttgagc  ccaggagttc  aagacaaggc  gggcaacat
9121  agtgtgaccc  catctctacc  aaaaaaaccc  caacaaaaacc ggaagatcgc  gggcatggtg
9181  gtatgcggcc  tagtcccagc  tactcaagga  ggctgaggtg  gctgaggtg   ttgattccag
9241  gagtttgaga  ctgcagtgag  ctatgatccc  accactgcct  accatcttta  ggatacattt
9301  atttattat   aaaagaaatc  agagaggctgg  atggggaata  caggagctgg  agggtggagc
9361  cctgaggtgc  tggttgtgag  ctgcctggg   accctgttt   cctgtcatgc  catgaaccca
9421  cccacactgt  ccactgacct  ccctagCTCC  ACACCCTCTC  TGACACCCTG  TGGGGACCTG
9481  GTGACTCTCG  GCTACAGCTG  AACTTCCGAG  CGACGCAGCC  TTTGAATGGG  CGAGTGATTG
9541  AGGCCTCCTT  CCCTGCTGGA  GTGGACAGCA  GTCCTCGGGC  TGCTGAGCCA  Ggtacagctt
9601  tgtctggttt  cccccagcc   agtagtcct   tatcctccca  tgtgtgtgcc  agtgtctgtc
9661  attggtggtc  acagcccgcc  tctcacatct  cctttttctc  tccagTCCAG  CTGAATTCCT
9721  GCCTGGCTGC  TGgtgagtct  gccccctctc  ttggtcctga  tgccaggaga  ctcctcagca
9781  ccattcagcc  ccaggctgc   tcaggaccgc  ctctgctccc  tctcctttc   tgcagaacag
9841  acccaaccc   caatattaga  gaggcagatc  atggtgggga  ttccccagag  gtcccagag
```

FIG._2E

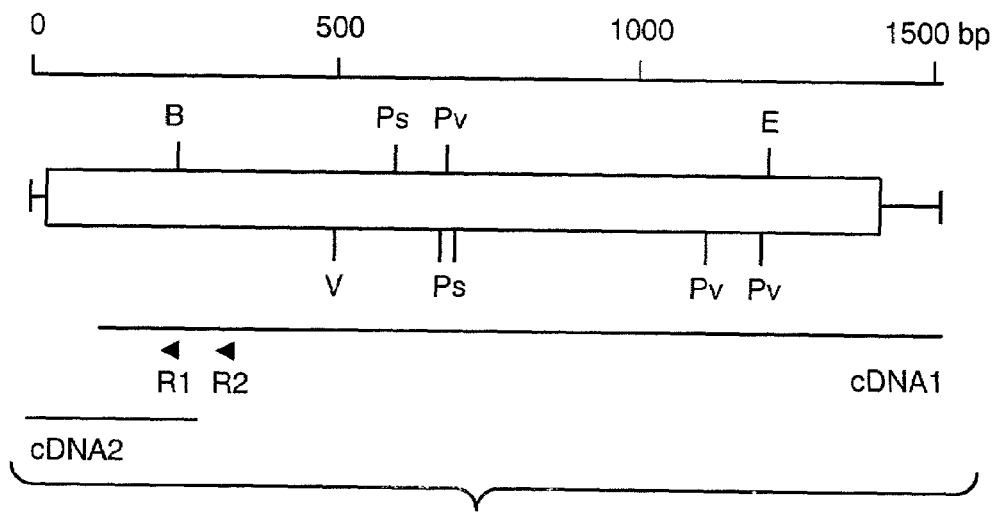
FIG._3
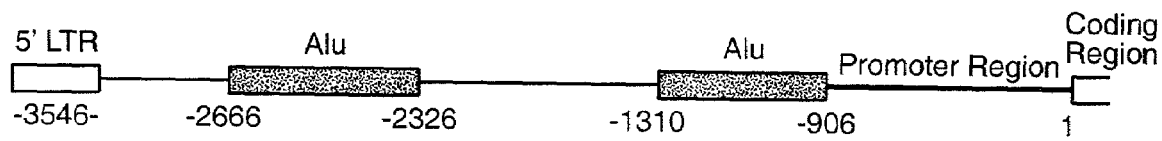
FIG._4
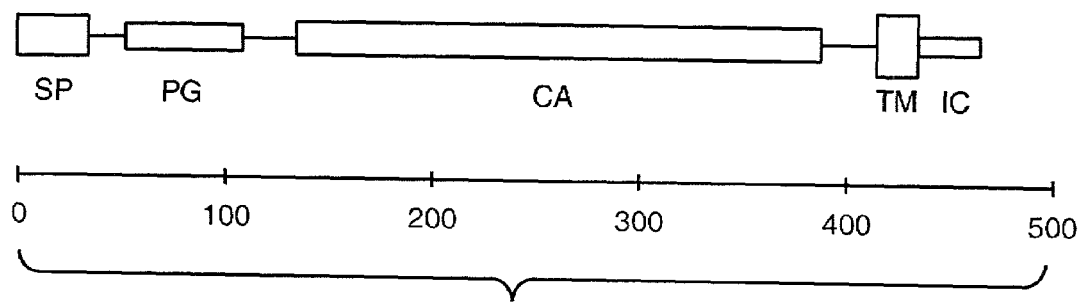
FIG._8

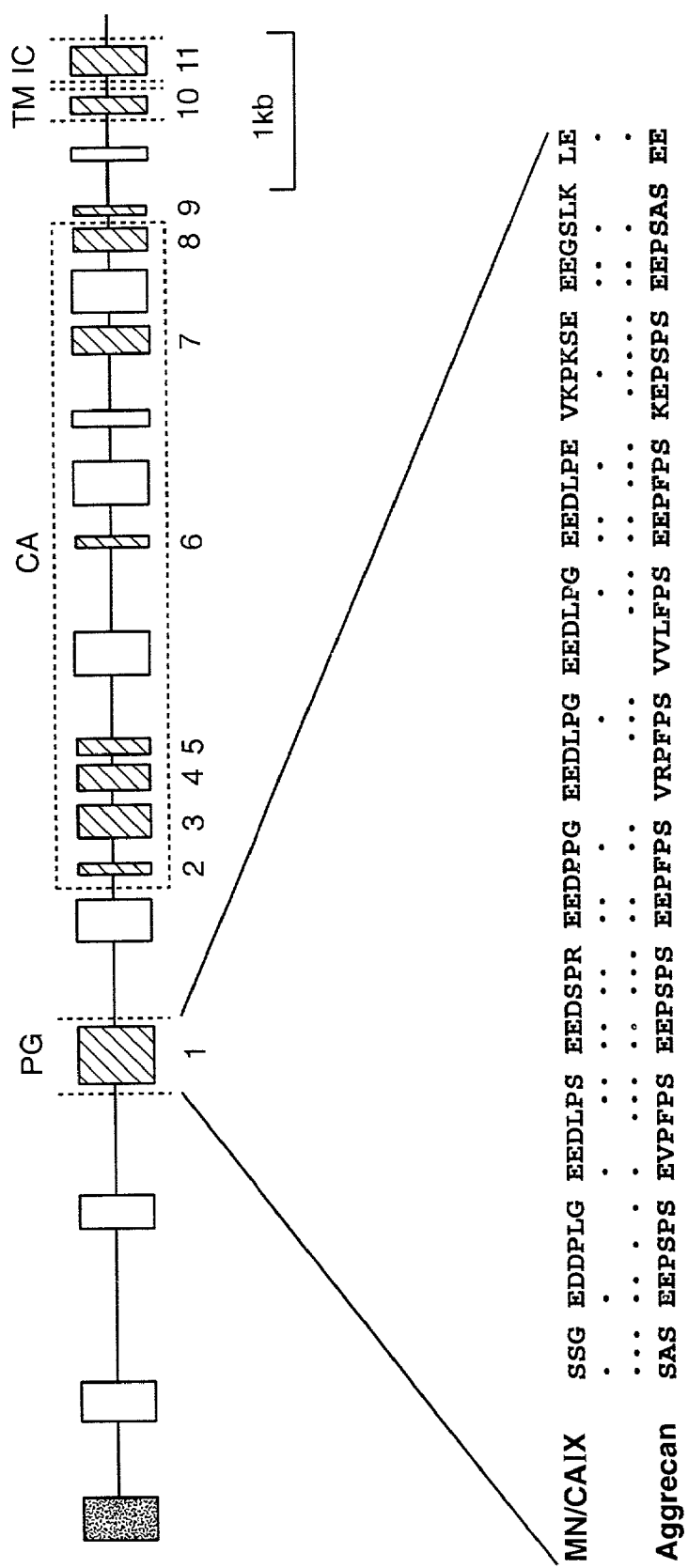
FIG._5

```
-506  CTTGCTTTTC ATTCAAGCTC AAGTTTGTCT CCCACATACC CATTACTTAA CTCACCCTCG

-446  GGCTCCCCTA GCAGCCTGCC CTACCTCTTT ACCTGCTTCC TGGTTGGAGTC AGGGATGTAT
      ‾‾‾‾‾‾‾‾‾‾ ‾‾‾‾‾‾‾‾‾‾
         AP2

-386  ACATGAGCTG CTTTCCCTCT CAGCCAGAGG ACATGGGGGG CCCCAGCTCC CCTGCCTTTC

-326  CCCTTCTGTG CCTGGAGCTG GGAAGCAGGC CAGGGTTAGC TGAGGCTGGC TGGCAAGCAG

-266  CTGGGGTGGTG CCAGGGAGAG CCTGCATAGT GCCAGGTGGT GCCTTGGGTT CCAAGCTAGT
                                         ‾‾‾‾‾‾‾‾‾‾ ‾‾‾‾‾‾‾‾‾‾
                                              VII                  p53

-206  CCATGGCCCC GATAACCTTC TGCCTGTGCA CACACCCTGCC CCTCACTCCA CCCCCATCCT
      ‾‾‾‾‾
       VI                                                       Inr V

-146  AGCTTTGGTA TGGGGGAGAG GGCACAGGGC CAGACAAACC GCTCCCCCTCC TGTGAGACTT
      ‾‾‾‾‾‾‾‾‾‾ ‾‾‾‾‾‾‾‾‾‾                                         ‾‾‾‾‾
             IV                                                       AP1

-86   TCTGCAAAAG GGCGCTCTGT GAGTCAGCCT GCTCCCCTCC AGGCTTGCTC TGGCTCCATC
      ‾‾‾‾‾‾‾‾‾‾ ‾‾‾‾‾‾‾‾‾‾ ‾‾‾‾‾‾‾‾‾‾                ‾‾‾‾‾‾‾‾‾‾ ‾‾‾‾‾‾‾‾‾‾
               II                AP1                     p53         III Inr
                                 ***

-26   CAGCTCTCGT TTCCAATGCA CGTACAGCCC GTACACACCG TGTGCTGGGA CACCCCACAG
      ‾‾‾‾‾‾‾‾‾‾                                                  ‾‾‾‾‾‾‾‾‾‾
          I                                                           AP2
```

FIG._6

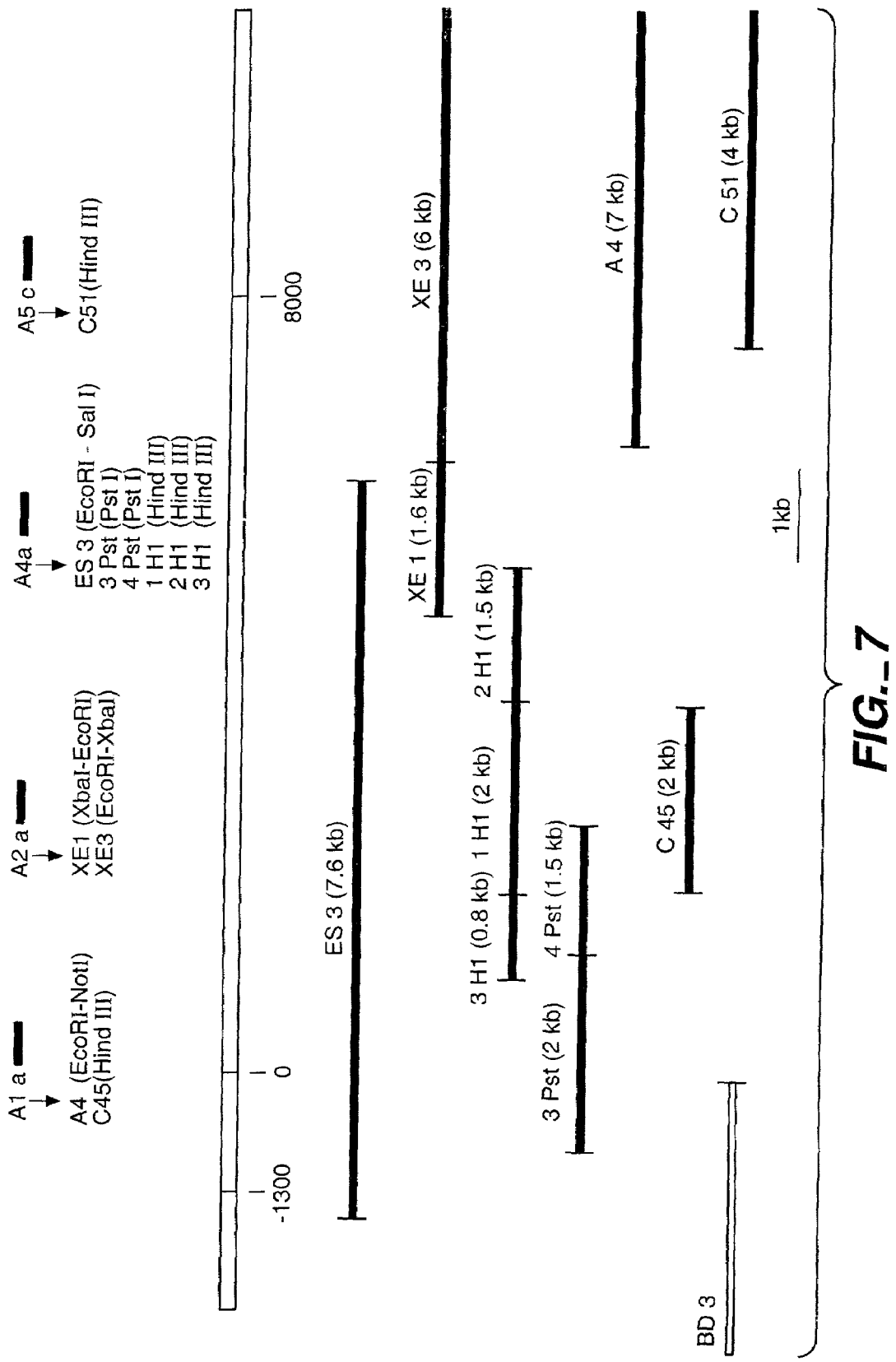
FIG._7

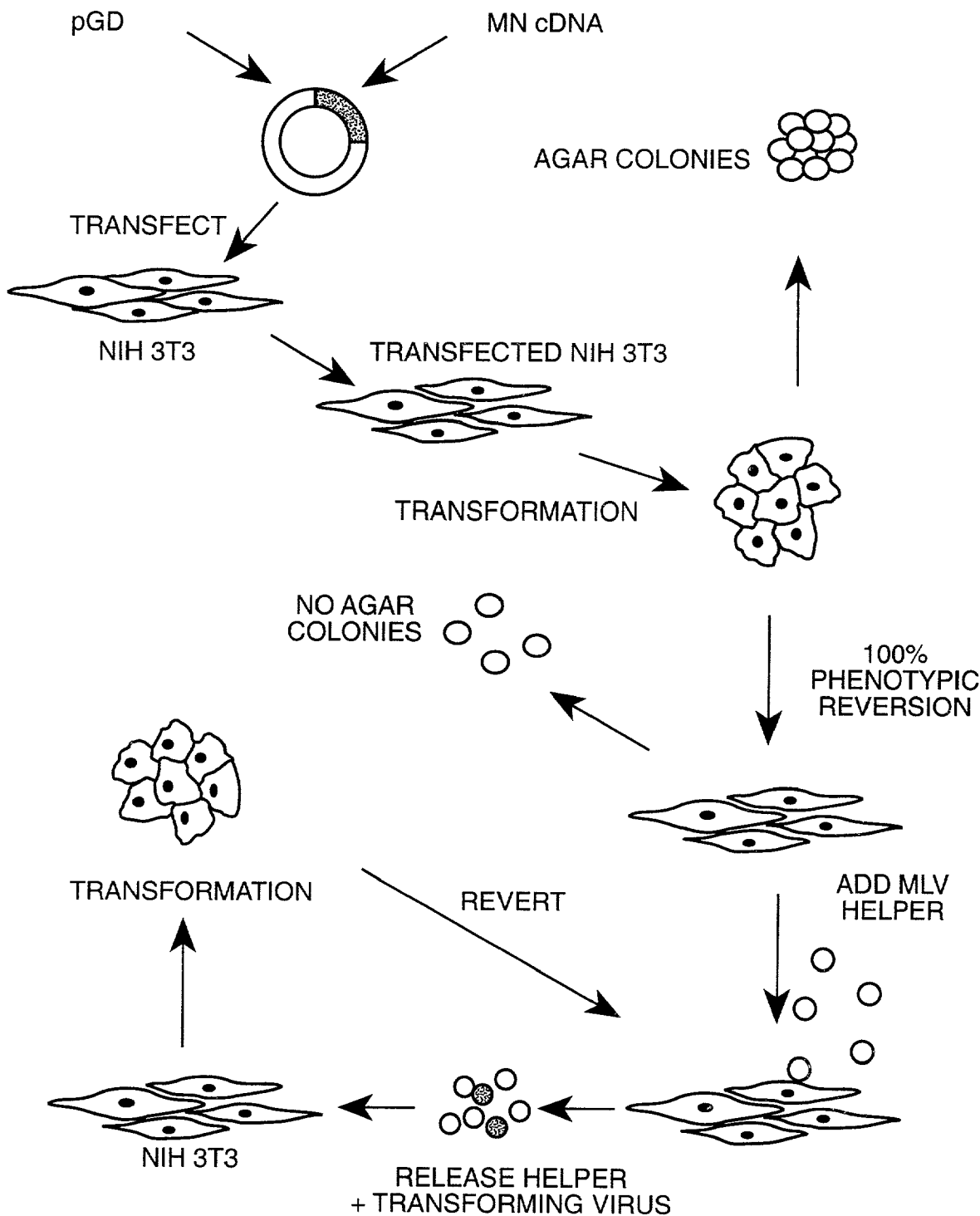
FIG._9

ANTI-IDIOTYPE ANTIBODIES TO MN PROTEINS AND MN POLYPEPTIDES

This application is a divisional of U.S. Ser. No. 09/178,115, filed Oct. 23, 1998, now U.S. Pat. No. 6,297,041, which is a continuation-in-part of U.S. Ser. No. 08/787,739 filed Jan. 24, 1997, now U.S. Pat. No. 6,027,887 which is a continuation-in-part of the following seven U.S. Serial Nos., all of which were filed on Jun. 7, 1995: 08/485,049, (now U.S. Pat. No. 6,204,370), 08/486,756, (now U.S. Pat. 5,981,711), 08,477,504, (now U.S. Pat. No. 5,972,353), 08/481,658, (now U.S. Pat. 5,955,075), 08/485,862, (now U.S. Pat. 6,093,548) and 08/487,077 (now U.S. Pat. 6,069,242). Those seven applications are continuations-in-parts of U.S. Ser. No. 08/260,190, filed Jun. 15, 1994, now U.S. Pat. 6,774,117, which is a continuatios-in-part of U.S. Ser. No. 08/177,093, filed Dec. 30, 1993, now U.S. Pat. 6,051,226, which is a continuation-in-part of U.S. Ser. No. 07/964,589, filed Oct. 21, 1992, now U.S. Pat. 5,387,676. The application declares priority under 35 U.S.C. 120 from those U.S. applications and patents.

FIELD OF THE INVENTION

The present invention is in the general area of medical genetics and in the fields of biochemical engineering, immunochemistry and oncology. More specifically, it relates to the MN gene—a cellular gene considered to be an oncogene, which encodes the oncoprotein now known alternatively as the MN protein, the MN/CA IX isoenzyme or the MN/G250 protein.

BACKGROUND OF THE INVENTION

Zavada et al., International Publication Number WO 93/18152 (published 16 Sep. 1993) and U.S. Pat. No. 5,387,676 (issued Feb. 7, 1996), describe the elucidation of the biological and molecular nature of MaTu which resulted in the discovery of the MN gene and protein. The MN gene was found to be present in the chromosomal DNA of all vertebrates tested, and its expression to be strongly correlated with tumorigenicity.

The MN protein is now considered to be the first tumor-associated carbonic anhydrase (CA) isoenzyme that has been described. Carbonic anhydrases (CAs) form a large family of genes encoding zinc metalloenzymes of great physiological importance. As catalysts of reversible hydration of carbon dioxide, these enzymes participate in a variety of biological processes, including respiration, calcification, acid-base balance, bone resorption, formation of aqueous humor, cerebrospinal fluid, saliva and gastric acid [reviewed in Dodgson et al., *The Carbonic Anhydrases*, Plenum Press, New York-London, pp. 398 (1991)]. CAs are widely distributed in different living organisms.

In mammals, at least seven isoenzymes (CA I–VII) and a few CA-related proteins (CARP/CA VIII, RPTP-β, RPTP-т) had been identified [Hewett-Emmett and Tashian, *Mol. Phyl. Evol.*, 5: 50–77 (1996)], when analysis of the MN deduced amino acid sequence revealed a striking homology between the central part of the MN protein and carbonic anhydrases, with the conserved zinc-binding site as well as the enzyme's active center. Then MN protein was found to bind zinc and to have CA activity. Based on that data, the MN protein is now considered to be the ninth carbonic anhydrase isoenzyme—MN/CA IX. [Opavsky et al., *Genomics*, 33: 480–487 (May 1996)]. [See also, Hewett-Emmett, supra, wherein CA IX is suggested as a nomenclatural designation.]

CAs and CA-related proteins show extensive diversity in both their tissue distribution and in their putative or established biological functions [Tashian, R. E., *Adv. in Genetics*, 30: 321–356 (1992)]. Some of the CAs are expressed in almost all tissues (CA II), while the expression of others appears to be more restricted (CA VI and CA VII in salivary glands). In cells, they may reside in the cytoplasm (CA I, CA II, CA III, and CA VII), in mitochondria (CA V), in secretory granules (CA VI), or they may associate with membrane (CA IV). Occasionally, nuclear localization of some isoenzymes has been noted [Parkkila et al., *Gut*, 35: 646–650 (1994); Parkkilla et al., *Histochem. I.*, 27: 133–138 (1995); Mori et al., *Gastroenterol.*, 105: 820–826 (1993)].

The CAs and CA-related proteins also differ in kinetic properties and susceptibility to inhibitors [Sly and Hu, *Annu. Rev. Biochem.*, 64: 375–401 (1995)]. In the alimentary tract, carbonic anhydrase activity is involved in many important functions, such as saliva secretion, production of gastric acid, pancreatic juice and bile, intestinal water and ion transport, fatty acid uptake and biogenesis in the liver. At least seven CA isoenzymes have been demonstrated in different regions of the alimentary tract. However, biochemical, histochemical and immunocytochemical studies have revealed a considerable heterogeneity in their levels and distribution [Swensen, E. R., "Distribution and functions of carbonic anhydrase in the gastrointestinal tract," In: *The Carbonic Anhydrases, Cellular Physiology and Molecular Genetics*, (Dodgson et al. eds.) Plenum Press, New York, pages 265–287 (1991); and Parkkila and Parkkila, *Scan J. Gastroenterol.*, 31: 305–317 (1996)]. While CA II is found along the entire alimentary canal, CA IV is linked to the lower gastrointestinal tract, CA I, III and V are present in only a few tissues, and the expression of CA VI and VII is restricted to salivary glands [Parkkila et al., *Gut*, 35: 646–650 (1994); Fleming et al., *J. Clin. Invest.*, 96: 2907–2913 (1995); Parkkila et al., *Hematology*, 24: 104 (1996)].

MN/CA IX has a number of properties that distinguish it from other known CA isoenzymes and evince its relevance to oncogenesis. Those properties include its density dependent expression in cell culture, (e.g., HeLa cells), its correlation with the tumorigenic phenotype of somatic cell hybrids between HeLa and normal human fibroblasts, its close association with several human carcinomas and its absence from corresponding normal tissues [e.g., Zavada et al., *Int. J. Cancer*, 54: 268–274 (1993); Pastorekova et al., *Virology*, 187: 620–626 (1992); Liao et al., *Am. J. Pathol.*, 145: 598–609 (1994); Pastorek et al., *Oncogene*, 9: 2788–2888 (1994); Cote, *Women's Health Weekly: News Section*, p. 7 (Mar. 30, 1998); Liao et al., *Cancer Res.*, 57: 2827 (1997); Vermylen et al., "Expression of the MN antigen as a biomarker of lung carcinoma and associated precancerous conditions," *Proceedings AACR*, 39: 334 (1998); McKiernan et al., *Cancer Res.*, 57: 2362 (1997); and Turner et al., *Hum. Pathol.*, 28(6): 740 (1997)]. In addition, the in vitro transformation potential of MN/CA IX cDNA has been demonstrated in NIH 3T3 fibroblasts [Pastorek et al., id.].

The MN protein has also been identified with the G250 antigen. Uemura et al., "Expression of Tumor-Associated Antigen MN/G250 in Urologic Carcinoma: Potential Therapeutic Target," *J. Urol.*, 157 (4 Suppl.): 377 (Abstract 1475; 1997) states: "Sequence analysis and database searching revealed that G250 antigen is identical to MN, a human tumor-associated antigen identified in cervical carcinoma (Pastorek et al., 1994)."

The MN protein was first identified in HeLa cells, derived from a human carcinoma of cervix uteri. As indicated above, MN gene expression is strongly associated with tumorigenicity. It is found in many types of human carcinomas (notably uterine cervical, ovarian, endometrial, renal, bladder, breast, colorectal, lung, esophageal, and prostate, among others). Very few normal tissues have been found to express MN protein to any significant degree. As detailed herein, those MN-expressing normal tissues include the human gastric mucosa and gallbladder epithelium, and some other normal tissues of the alimentary tract. Paradoxically, as shown herein, MN gene expression has been found to be lost or reduced in carcinomas and other preneoplastic/neoplastic diseases in some tissues that normally express MN, e.g., gastric mucosa.

In general, as elucidated by the examples herein, oncogenesis may be signified by the abnormal expression of MN protein. For example, oncogenesis may be signified: (1) when MN protein is present in a tissue which normally does not express MN protein to any significant degree; (2) when MN protein is absent from a tissue that normally expresses it; (3) when MN gene expression is at a significantly increased level, or at a significantly reduced level from that normally expressed in a tissue; or (4) when MN protein is expressed in an abnormal location within a cell.

SUMMARY OF THE INVENTION

The discovery of the MN gene and protein and thus, of substantially complementary MN genes and proteins encoded thereby, led to the finding that the expression of MN proteins was associated with tumorigenicity. That finding resulted in the creation of methods that are diagnostic/prognostic for cancer and precancerous conditions. Methods and compositions are provided for identifying the onset and presence of neoplastic disease by detecting or detecting and quantitating abnormal MN gene expression in vertebrates.

Such abnormal MN gene expression can be detected or detected and quantitated by a variety of conventional assays in vertebrate samples, for example, by immunoassays using MN-specific antibodies to detect or detect and quantitate MN antigen, by hybridization assays or by PCR assays, such as RT-PCR, using MN nucleic acids, such as, MN cDNA, to detect or detect and quantitate MN nucleic acids, such as, MN mRNA.

Vertebrate samples, preferably mammalian, more preferably human, can include tissue sections, tissue extracts, tissue smears, cells (whole or lysed), and cell extracts. MN antigen, preferably in a soluble form, more preferably as the MN extracellular domain, can also be found in body fluids as an indicator of preneoplastic/neoplastic disease.

Preferred body fluids to assay according to this invention include blood, serum, plasma, semen, breast exudate, saliva, tears, sputum, mucous, urine, gastric secretions, fecal suspensions, bile, lymph, cytosols, ascites, pleural effusions, amniotic fluid, bladder washes, bronchioalveolar lavages and cerebrospinal fluid.

Preferred samples and body fluids would in general depend upon the type of preneoplastic/neoplastic disease for which the diagnosis/prognosis is sought. For example, serum could be a more preferred body fluid to test for renal cell carcinoma, breast, bladder or prostate cancer; however, urine could be a more preferred body fluid to test for urinary tract tumors, as renal cell carcinoma or bladder cancer. Still further preferred for testing for abnormal MN gene expression associated with urinary tract cancer, especially bladder cancer, could be exfoliated cells from urine. Mucous from the intestines and fecal suspensions could be preferred samples to test for duodenal, ileal, jejunal, and/or colorectal cancers, whereas gastric secretions and bile could be preferred body fluids to test respectively for stomach, and gallbladder/liver duct cancers.

The present invention is useful for detecting a wide variety of neoplastic and/or preneoplastic diseases. Exemplary diseases include carcinomas, such as mammary, lung, esophageal, prostate, bladder, renal, ovarian, gastrointestinal, uterine, uterine cervical, endometrial, squamous cell and adenosquamous carcinomas; and head and neck cancers; mesodermal tumors, such as neuroblastomas and retinoblastomas; sarcomas, such as osteosarcomas and Ewing's sarcoma; and melanomas. Of particular interest are head and neck cancers, gynecologic cancers including ovarian, cervical, vaginal, endometrial and vulval cancers; gastrointestinal cancer, such as, esophageal, stomach, intestinal, colon and rectal cancers; urinary tract cancer, such as, bladder and kidney cancers; skin cancer; liver cancer; prostate cancer; lung cancer; and breast cancer. Of still further particular interest are gynecologic cancers; breast cancer; urinary tract cancers, especially renal and bladder cancers; lung cancer; esphageal cancer; and colorectal cancer. Even further of particular interest are esophageal, lung, renal, colorectal, gynecologic and breast cancers. Gynecologic cancers of particular interest are carcinomas of the uterine cervix, endometrium and ovaries; more particularly such gynecologic cancers include cervical squamous cell carcinomas, adenosquamous carcinomas, adenocarcinomas as well as gynecologic precancerous conditions, such as metaplastic cervical tissues and condylomas.

As indicated above, most normal tissues do not express MN protein. Thus, for most preneoplastic/neoplastic diseases, abnormal MN gene expression is indicated by evidence of significant MN gene expression. The reverse may be true for preneoplastic/neoplastic disease of tissues that normally express MN protein, e.g., the gastric mucosa. MN protein is normally expressed abundantly in the gastric mucosa and gallbladder epithelium. However, in the case of preneoplastic/neoplastic disease, MN protein is absent from or at a significantly reduced level of expression in the gastric mucosa. The absence or reduced MN expression in the gastric mucosa is thus indicative of oncogenesis, and signaled, for example, by the absence or reduced amount of MN protein and/or MN gene transcription in vertebrate samples. Some evidence suggests in the case of biliary epithelial tumors that MN expression becomes weaker with increase of severity of dysplasia in premalignant lesions and decrease of differentiation in carcinomas. [Saarnio et al., Gut, 41(3): 186 (1997).] Also, the abnormal expression of MN may be signaled by its expression at an enhanced level at a different location than it is normally expressed, e.g. other than in the basolateral surfaces of the epithelial cells of the ascending colon.

The immunoassays of this invention can be embodied in test kits which comprise MN proteins/polypeptides and/or MN-specific antibodies. Such test kits can be in solid phase formats, but are not limited thereto, and can also be in liquid phase format, and can be based on immunohistochemical assays, ELISAS, particle assays, radiometric or fluorometric assays either unamplified or amplified, using, for example, avidin/biotin technology.

Test kits of this invention can comprise the nucleic acid probes of the invention which are useful diagnostically/prognostically for neoplastic and/or preneoplastic disease. Preferred test kits comprise means for detecting or measuring the hybridization of said probes to the MN gene or to the mRNA product of the MN gene, such as a visualizing means.

Further, this invention is directed to the MN gene, fragments thereof and the related cDNA which are useful, for example, as follows: 1) to produce MN proteins/polypeptides by biochemical engineering; 2) to prepare nucleic acid probes to test for the presence of the MN gene in cells of a subject; 3) to prepare appropriate polymerase chain reaction (PCR) primers for use, for example, in PCR-based assays or to produce nucleic acid probes; 4) to identify MN proteins and polypeptides as well as homologs or near homologs thereto; 5) to identify various mRNAs transcribed from MN genes in various tissues and cell lines, preferably human; and 6) to identify mutations in MN genes. The invention further concerns purified and isolated DNA molecules comprising the MN gene or fragments thereof, or the related cDNA or fragments thereof.

This invention in one aspect concerns isolated nucleic acid sequences that encode MN proteins or polypeptides wherein the nucleotide sequences for said nucleic acids are selected from the group consisting of:

(a) SEQ ID NO: 1;

(b) nucleotide (nt) sequences that hybridize specifically under stringent conditions, for example, of 50% formamide at 42° C., to SEQ ID NO: 1 or to its complement;

(c) nucleotide sequences that differ from SEQ ID NO: 1 or from the nucleotide sequences of (b) in codon sequence because of the degeneracy of the genetic code. Further, such nucleic acid sequences are selected from nucleotide sequences that but for the degeneracy of the genetic code would hybridize to SEQ ID NO: 1 or to its complement under stringent hybridization conditions.

This invention also concerns MN genomic sequences shown in FIG. 2A-F, that is, SEQ ID NO: 5, as well as nt sequences that hybridize specifically to it or its complement under stringent conditions, wherein such nt sequences hybridize specifically to regions of the MN genomic sequence that are unique to MN, and do not hybridize specifically under such stringent conditions to nt sequences not unique to MN, such as, Alu sequences or long terminal repeat (LTR) sequences, or would so hybridize to SEQ ID NO: 5 or to its complement under such conditions, but for the degeneracy of the genetic code. Degenerate variants of SEQ ID NOS: 1 and 5 are within the scope of the invention.

Further, this invention concerns nucleic acid probes which are fragments of the isolated nucleic acids that encode MN proteins or polypeptides and/or are from the MN genomic sequence which meet the above hybridization criteria. Preferably said nucleic acid probes are comprised of at least 25 nts, more preferably at least 27 nts, still more preferably at least 29 nts, further preferably at least 50 nts, further more preferably at least 100 nts, and even more preferably at least 150 nts.

Still further, this invention is directed to isolated nucleic acids containing at least twenty-five nucleotides selected from the group consisting of:

(a) SEQ ID NOS: 1, 3, 5, 7, 8, 17, 18, 27–49, 55–66, 88–96, 110 and 115 and sequences that are complementary to SEQ ID NOS: 1, 3, 5, 7, 8, 17, 18, 27–49, 55–66, 88–96, 110 and 115;

(b) nucleotide sequences that hybridize under standard stringent hybridization conditions, for example, of 50% formamide at 42° C., to one or more of the following nucleotide sequences: SEQ ID NOS: 1, 3, 5, 7, 8, 17, 18, 27–49, 55–66, 88–96, 110 and 115 and the respective complements of SEQ ID NOS: 1, 3, 5, 7, 8, 17, 18, 27–49, 55–66, 88–96, 110 and 115, but do not hybridize specifically under such stringent conditions to nt sequences not unique to MN, such as, Alu sequences or LTR sequences; and (c) nucleotide sequences that differ from the nucleotide sequences of (a) and (b) in codon sequence because of the degeneracy of the genetic code. The invention also concerns nucleic acids that but for the degeneracy of the genetic code would hybridize specifically to the nucleic acids of (a) and (b) under standard stringent hybridization conditions. Further this invention concerns nucleic acids of (b) and (c) that hybridize partially or wholly to the non-coding regions of SEQ ID NO: 5 or its complement as, for example, sequences that function as nucleic acid probes to identify MN nucleic acid sequences, but do not hybridize specifically to regions of the MN genomic region that are not unique to MN. Conventional technology can be used to determine whether the nucleic acids of (b) and (c) or of fragments of SEQ ID NO: 5 are useful to identify MN nucleic acid sequences, for example, as outlined in Benton and Davis, *Science,* 196: 180(1977) and Fuscoe et al. *Genomics,* 5: 100(1989). In general, such nucleic acids are preferably at least 25 nts, more preferably at least 27 nts, still more preferably at least 29 nts, further preferably at least 50 nts, and still more preferably at least 100 nts. An exemplary and preferred nucleic acid probe is SEQ ID NO: 55 (a 470 bp probe useful in RNase portection assays).

Fragments of the isolated nucleic acids of the invention, can also be used as PCR primers, e.g. in RT-PCR, to detect MN expression, to amplify segments of MN genes, and to identify mutations in MN genes. Typically, said PCR primers are olignucleotides, preferably having a length of about 14 nts to about 25 nts, more preferably from about 16 to 20 nts, but they may be considerably longer. Exemplary primers may be from about 16 nucleotides to about 50 nucleotides, preferably from about 17 nucleotides to about 45 nucleotides.

Further, the invention concerns the use of such PCR primers in methods to detect mutations in an isolated MN gene and/or fragment(s) thereof. For example, such methods can comprise amplifying one or more fragment(s) of an MN gene by PCR, and determining whether any of said one or more fragments contain mutations, by, for example, comparing the size of the amplified fragments to those of similarly amplified corresponding fragments of MN genes known to be normal, by using a PCR-single-strand conformation polymorphism assay or a denaturing gradient gel electrophoretic assay.

This invention also concerns nucleic acids which encode MN proteins or polypeptides that are specifically bound by monoclonal antibodies designated M75 that are produced by the hybridoma VU-M75 deposited at the American Type Culture Collection (ATCC), now at 10801 University Avenue, Manassas, Va. 20110-22209 (USA) under ATCC No. HB 11128, and/or by monoclonal antibodies designated MN12 produced by the hybridoma MN 12.2.2 deposited at the ATCC under ATCC No. HB 11647.

This invention further concerns isolated nucleic acids containing at least sixteen nts, preferably at least twenty-seven nts, more preferably at least twenty-nine nts, still more preferably at least fifty nts, wherein said nucleic acid is selected from the group consisting of:

(a) the MN nucleic acids contained in plasmids A4a, XE1 and XE3 which were deposited at the ATCC under the respective ATCC Nos. 97199, 97200, and 97198;

(b) nucleic acids that hybridize specifically under stringent conditions to regions of those MN nucleic acids of (a) that are unique to the MN gene, that do not hybridize specifically under such stringent conditions to nt sequences that are not unique to MN, such as, Alu sequences or LTR sequences; and (c) nucleic acids that differ from the nucleic acids of (a) or (b) in codon sequence due to the degeneracy of the genetic code. Such isolated nucleic acids, for example, can be polymerase chain reaction (PCR) primers.

The invention further concerns isolated nucleic acids that code for an MN protein, MN fusion protein or MN polypeptide that is operatively linked to an expression control sequence within a vector; unicellular hosts, prokaryotic or eukaryotic, that are transformed or transfected therewith; and methods of recombinantly producing MN proteins, MN fusion proteins and MN polypeptides comprising transforming or transfecting unicellular hosts with said nucleic acid operatively linked to an expression control sequence, culturing said transformed or transfected unicellular hosts so that said MN proteins, fusion proteins or polypeptides are expressed, and extracting and isolating said MN protein fusion protein or polypeptide.

Recombinant nucleic acids that encode MN fusion proteins are claimed as comprising an MN protein or MN polypeptide and a non-MN protein or polypeptide wherein the nucleotide sequence for the portion of the nucleic acid encoding the MN protein or polypeptide is selected from the group consisting of:

(a) SEQ ID NO: 1;

(b) nucleotide sequences that hybridize under stringent conditions to SEQ ID NO: 1 or to its complement; and (c) degenerate variants of SEQ ID NO: 1, and of the nucleotide sequences of (b); wherein the nucleic acid encoding said MN protein or polypeptide preferably contains at least twenty-five nts.

Said non-MN protein or polypeptide may preferably be nonimmunogenic to humans and not typically reactive to antibodies in human body fluids. Examples of such a DNA sequence is the alpha-peptide coding region of beta-galactosidase and a sequence coding for glutathione S-transferase (GST) or a fragment thereof. However, in some instances, a non-MN protein or polypeptide that is serologically active, immunogenic and/or antigenic may be preferred as a fusion partner to a MN antigen. Further, claimed herein are such recombinant fusion proteins/polypeptides which are substantially pure and non-naturally occurring. Exemplary fusion proteins of this invention are GST-MN, MN-Fc and MN-PA, described infra.

In HeLa and in tumorigenic HeLa x fibroblast hybrid (H/F-T) cells, MN protein is manifested as a "twin" protein p54/58N; it is glycosylated and forms disulfide-linked oligomers. As determined by electrophoresis upon reducing gels, MN proteins have molecular weights in the range of from about 40 kd to about 70 kd, preferably from about 45 kd to about 65 kd, more preferably from about 48 kd to about 58 kd. Upon non-reducing gels, MN proteins in the form of oligomers have molecular weights in the range of from about 145 kd to about 220 kd, preferably from about 150 to about 200 kd, still more preferably from about 150 to about 155 kd, and further preferably from about 152 to about 154 kd. A predicted amino acid sequence for a preferred MN protein of this invention is shown in FIG. 1 [SEQ. ID. NO. 2].

Other particular MN proteins or polypeptides are exemplified by the putative MN signal peptide shown as the first thirty-seven amino acids in FIG. 1 [SEQ ID NO: 6], preferred MN antigen epitopes [represented by, e.g., SEQ ID NOS: 10–16 and 98–103], and domains of the MN protein represented in FIG. 1 amino acids (aa) 38–414 (SEQ ID NO: 87; the extracellular domain), aa 415–434 (SEQ ID NO: 52; the transmembrane domain), aa 435–459 (SEQ ID NO: 53; the intracellular domain), aa 53–111 (SEQ ID NO: 50; the proteoglycan-like domain); and aa 135–391 (SEQ ID NO: 51; the CA domain). Also, of particular importance is the region within the proteoglycan-like domain, aa 61–96 (SEQ ID NO: 97) which contains a 6-fold tandem repeat of 6 amino acids, and within which the epitope for the M75 MAb resides in at least two copies, and within which the MN binding site is considered to be located. An alternative MN binding site may be located in the CA domain.

Identified herein is the location of the MN protein binding site. Also identified are MN oligopeptides that compete for attachment to cells with immobilized MN protein. Such oligopeptides prevent cell-cell adhesion and the formation of intercellular contacts.

Disclosed herein are cell adhesion assay methods that are used to identify binding site(s) on the MN protein to which vertebrate cells, preferably mammalian cells bind. Such a MN binding site is then identified as a therapeutic target which can be blocked with proteins/polypeptides, MN-specific antibodies or organic molecules that specifically bind to said site.

Further disclosed are therapeutic methods to treat patients with preneoplastic/neoplastic disease associated with or characterized by abnormal MN expression, which methods are based on blocking said MN binding site with proteins/polypeptides, MN-specific antibodies or organic molecules, that bind specifically to said binding site. The growth of a vertebrate preneoplastic/neoplastic cell that abnormally expresses MN protein can be inhibited by administering such proteins/polypeptides, MN-specific antibodies or organic molecules in a therapeutically effective amount in a physiologically acceptable formulation. Such a preferred therapeutic protein/polypeptide is herein considered to comprise an amino acid sequence selected from the group consisting of SEQ ID NOS: 107–109. Such heptapeptides are considered to be comprised by MN protein partner(s). Blocking the interaction between MN protein and its binding partner(s), is expected to lead to a decrease of tumor growth.

A preferred MN-specific antibody for such a therapeutic use would be a MN-specific antibody that has an epitope selected from the group consisting of SEQ ID NOS: 10 and 98–103. The M75 MAb is an especially preferred MN-specific antibody for use in cancer therapy. Such therapeutic methods are preferably directed to mammals and more preferably to humans.

Also provided are therapeutic methods wherein the growth of a vertebrate, preferably mammalian, more preferably human, preneoplastic or neoplastic cell that abnormally expresses MN protein is inhibited. Said methods comprise transfecting said cell with a vector comprising an expression control sequence operatively linked to a nucleic acid encoding the variable domains of an MN-specific antibody, wherein said domains are separated by a flexible linker peptide, preferably SEQ ID NO: 116. Preferably said expression control sequence comprises the MN gene promoter.

Alternatively, such therapeutic methods comprise transfecting said cell with a vector comprising a nucleic acid that encodes a cytotoxic protein/polypeptide, such as HSVtk, operatively linked to the MN gene promoter. Such a therapeutic vector may also comprise a nucleic acid encoding a cytokine, such as, IL-2 or IFN.

Still further, such therapeutic/prophylactic methods comprise inducing MN-specific antibody production within a patient by injecting said patient with an anti-idiotype antibody to a MN-specific antibody. Still further, such therapeutic methods can include treating a patient with a preneoplastic and/or neoplastic disease characterized by abnormal MN expression by administering to said patient a therapeutically effective amount of an anti-anti-idiotype MN-specific antibody serum, alone or in combination with one or more cytokines, preferably with IFN and/or IL-2.

The invention further relates to the biochemical engineering of the MN gene, fragments thereof or related cDNA. For example, said gene or a fragment thereof or related cDNA can be inserted into a suitable expression vector, wherein it is operatively linked to an expression control sequence; host cells, preferably unicellular, can be transformed or transfected with such an expression vector; and an MN protein/polypeptide, preferably an MN protein, is expressed therein. Such a recombinant protein or polypeptide can be glycosylated or nonglycosylated, preferably glycosylated, and can be purified to substantial purity. The invention further concerns MN proteins/polypeptides which are synthetically or otherwise biologically prepared.

Disclosed herein are biologically active MN proteins and MN polypeptides that are useful as vaccines to protect vertebrates, preferably mammals, more preferably humans, against neoplastic diseases associated with abnormal MN expression. Such vaccines are also useful to boost a patient's immunity to such a disease. Such vaccines can alternatively comprise an anti-idiotype MN-specific antibody. Such vaccines are administered in a therapeutically effective amount in a physiologically acceptable formulation.

A preferred biologically active MN protein or MN polypeptide is considered to comprise an amino acid sequence from SEQ ID NOS: 50, 51, or 97. Such a preferred MN protein or MN polypeptide may comprise or have an amino acid sequence selected from the group consisting of SEQ ID NOS: 10 and 97–106. MN-specific antibodies that bind to such biologically active MN proteins and polypeptides are also preferred. Particularly preferred are such MN proteins and MN polypeptides that are specifically bound by the M75 MAb, or the MN12 MAb, preferably by the M75 MAb, such as, the synthetic peptides represented by SEQ ID NOS: 104–106.

Also disclosed are anti-idiotype antibodies to MN-specific antibodies, and anti-anti-idiotype antibodies thereto, polyclonal or monoclonal. Such anti-idiotype antibodies are useful as vaccines, and the anti-anti-idiotype antibody sera are therapeutically useful against neoplastic diseases associated with abnormal MN expression.

MN proteins/polypeptides can be used in assays to detect MN antigen in patient samples and in serological assays to test for MN-specific antibodies. MN proteins/polypeptides of this invention are serologically active, immunogenic and/or antigenic. They can further be used as immunogens to produce MN-specific antibodies, polyclonal and/or monoclonal, as well as an immune T-cell response.

The invention is directed to MN-specific antibodies, which can be used diagnostically/prognostically and may be used therapeutically. Preferred according to this invention are MN-specific antibodies reactive with the epitopes represented respectively by the amino acid sequences of the MN protein shown in FIG. 1 as follows: aa 62–67 (SEQ ID NO: 10); aa 61–66, aa 79–84, aa 85–90 and aa 91–96 (SEQ ID NO: 98); aa 62–65, aa 80–83, aa 86–89 and aa 92–95 (SEQ ID NO: 99); aa 62–66, aa 80–84, aa 86–90 and aa 92–96 (SEQ ID NO: 100); aa 63–68 (SEQ ID NO: 101); aa 62–68 (SEQ ID NO: 102); aa 82–87 and aa 88–93 (SEQ ID NO: 103); aa 55–60 (SEQ ID NO: 11); aa 127–147 (SEQ ID NO: 12); aa 36–51 (SEQ ID NO: 13); aa 68–91 (SEQ ID NO: 14); aa 279–291 (SEQ ID NO: 15); and aa 435–450 (SEQ ID NO: 16). More preferred are antibodies reactive with epitopes represented by SEQ ID NOS: 10, 98–103, 11 and 12. Still more preferred are antibodies reactive with the epitopes represented by SEQ. ID NOS: 10, 98–103 and 11. Most preferred are monoclonal antibodies reactive with the epitope represented by SEQ ID NOS: 10 and 98–103.

Also preferred according to this invention are antibodies prepared against recombinantly produced MN proteins as, for example, GST-MN, MN 20-19, MN-Fc and MN-PA. Also preferred are MN-specific antibodies prepared against glycosylated MN proteins, such as, MN 20-19 expressed in baculovirus infected Sf9 cells.

A hybridoma that produces a representative MN-specific antibody, the monoclonal antibody M75 (Mab M75), was deposited at the ATCC under Number HB 11128 as indicated above. The M75 antibody was used to discover and identify the MN protein and can be used to identify readily MN antigen in Western blots, in radioimmunoaSsays and immunohistochemically, for example, in tissue samples that are fresh, frozen, or formalin-, alcohol-, acetone- or otherwise fixed and/or paraffin-embedded and deparaffinized. Another representative MN-specific antibody, Mab MN12, is secreted by the hybridoma MN 12.2.2, which was deposited at the ATCC under the designation HB 11647.

MN-specific antibodies can be used, for example, in laboratory diagnostics, using immunofluorescence microscopy or immunohistochemical staining; as a component in immunoassays for detecting and/or quantitating MN antigen in, for example, clinical samples; as probes for immunoblotting to detect MN antigen; in immunoelectron microscopy with colloid gold beads for localization of MN proteins and/or polypeptides in cells; and in genetic engineering for cloning the MN gene or fragments thereof, or related cDNA. Such MN-specific antibodies can be used as components of diagnostic/prognostic kits, for example, for in vitro use on histological sections; such antibodies can also and used for in vivo diagnostics/prognostics, for example, such antibodies can be labeled appropriately, as with a suitable radioactive isotope, and used in vivo to locate metastases by scintigraphy. Further such antibodies may be used in vivo therapeutically to treat cancer patients with or without toxic and/or cytostatic agents attached thereto. Such MN-specific antibodies for therapeutic use may be directed to the extracellular (EC), transmembrane (TM) and/or intracellular (IC) domains of MN. Further, such antibodies can be used in vivo to detect the presence of neoplastic and/or preneoplastic disease. Still further, such antibodies can be used to affinity purify MN proteins and polypeptides.

This invention also concerns methods of treating neoplastic disease and/or preneoplastic disease comprising inhibiting the expression of MN genes by administering antisense nucleic acid sequences that are complementary to mRNA transcribed from MN genes. Said antisense nucleic acid sequences are those that hybridize specifically to such mRNA under stringent hybridization conditions. Preferred are antisense nucleic acid sequences that are complementary to sequences at the 5' end of the MN cDNA sequence shown in FIG. 1, more preferably to the 5' leader sequence of said mRNA. Preferably said antisense nucleic acid sequences are oligonucleotides.

This invention also concerns vaccines comprising an immunogenic amount of one or more substantially pure MN proteins and/or polypeptides or anti-idiotype antibodies (including variations thereof), dispersed in a physiologically acceptable, nontoxic vehicle, which amount is effective to immunize a vertebrate, preferably a mammal, more preferably a human, against a preneoplastic/neoplastic disease associated with the expression of MN proteins. Said proteins can be recombinantly, synthetically or otherwise biologically produced. A particular use of said vaccine would be to prevent recidivism and/or metastasis. For example, it could be administered to a patient who has had an MN-carrying tumor surgically removed, to prevent recurrence of the tumor.

The MN gene promoter is characterized herein. The identification of the binding site for a repressor of MN transcription is disclosed. Identification of the protein that binds to the repressor and modification of its binding properties is another route to modulate MN expression leading to cancer therapies. Suppression of MN expression in tumor cells by over expression of a negative regulator is expected to lead to a decrease of tumor growth.

| Abbreviations | |
|---|---|
| The following abbreviations are used herein: | |
| aa | amino acid |
| ATCC | American Type Culture Collection |
| bp | base pairs |
| BLV | bovine leukemia virus |
| BSA | bovine serum albumin |
| BRL | Bethesda Research Laboratories |
| CA | carbonic anhydrase |
| CAM | cell adhesion molecule |
| CARP | carbonic anhydrase related protein |
| CAT | chloramphenicol acetyltransferase |
| Ci | curie |
| cm | centimeter |
| CMV | cytomegalovirus |
| cpm | counts per minute |
| C-terminus | carboxyl-terminus |
| CTL | cytotoxic T lymphocytes |
| ° C. | degrees centigrade |
| DEAE | diethylaminoethyl |
| DMEM | Dulbecco modified Eagle medium |
| ds | double-stranded |
| EDTA | ethylenediaminetetraacetate |
| EGF | epidermal growth factor |
| EIA | enzyme immunoassay |
| ELISA | enzyme-linked immunosorbent assay |
| EMSA | electrophoretic mobility shift assay |
| F | fibroblasts |
| FACS | cytofluorometric study |
| FCS | fetal calf serum |
| FITC | fluorescein isothiocyanate |
| FTP | DNase 1 footprinting analysis |
| GST-MN | fusion protein MN glutathione S-transferase |
| GVC | ganciclovir |
| H | HeLa cells |
| H-E | haematoxylin-eosin |
| HEF | human embryo fibroblasts |
| HeLa K | standard type of HeLa cells |
| HeLa S | Stanbridge's mutant HeLa D98/AH.2 |
| H/F-T | hybrid HeLa fibroblast cells that are tumorigenic; derived from HeLa D98/AH.2 |
| H/F-N | hybrid HeLa fibroblast cells that are nontumorigenic; derived from HeLa D98/AH.2 |
| HPV | Human papilloma virus |
| HRP | horseradish peroxidase |
| HSV | Herpes simplex virus |
| IC | intracellular |
| IFN | interferon |
| IL-2 | interleukin-2 |
| Inr | initiator |
| IPTG | isopropyl-beta-D-thiogalacto-pyranoside |
| kb | kilobase |
| kbp | kilobase pairs |
| kd or kDa | kilodaltons |
| KS | keratan sulphate |
| LCMV | lymphocytic choriomeningitis virus |
| LTR | long terminal repeat |
| M | molar |
| mA | milliampere |
| MAb | monoclonal antibody |
| MCSF | macrophage colony stimulating factor |
| ME | mercaptoethanol |
| MEM | minimal essential medium |
| min. | minute(s) |
| mg | milligram |
| ml | milliliter |

-continued

| | |
|---|---|
| mM | millimolar |
| MMC | mitomycin C |
| mmol | millimole |
| MLV | murine leukemia virus |
| N | normal concentration |
| NEG | negative |
| ng | nanogram |
| nm | nanometer |
| nt | nucleotide |
| N-terminus | amino-terminus |
| ODN | oligodeoxynucleotide |
| ORF | open reading frame |
| PA | Protein A |
| PBS | phosphate buffered saline |
| PCR | polymerase chain reaction |
| PEST | combination of one-letter abbreviations for proline, glutamic acid, serine, threonine |
| PG | proteoglycan |
| pI | isoelectric point |
| PMA | phorbol 12-myristate 13-acetate |
| POS | positive |
| Py | pyrimidine |
| RACE | rapid amplification of cDNA ends |
| RCC | renal cell carcinoma |
| RIA | radioimmunoassay |
| RIP | radioimmunoprecipitation |
| RIPA | radioimmunoprecipitation assay |
| RNP | RNase protection assay |
| RT-PCT | reverse transcription polymerase chain reaction |
| SAC | *Staphylococcus aureus* cells |
| *S. aureus* | *Staphylococcus aureus* |
| sc | subcutaneous |
| SDRE | serum dose response element |
| SDS | sodium dodecyl sulfate |
| SDS-PAGE | sodium dodecyl sulfate-polyacrylamide gel electrophoresis |
| SINE | short interspersed repeated sequence |
| SP | signal peptide |
| SP-RIA | solid-phase radioimmunoassay |
| SSDS | synthetic splice donor site |
| SSH | subtractive suppressive PCR |
| SSPE | NaCl (0.18 M), sodium phosphate (0.01 M), EDTA (0.001 M) |
| TBE | Tris-borate/EDTA electrophoresis buffer |
| TC | tissue culture |
| TCA | trichloroacetic acid |
| TC media | tissue culture media |
| TC | tissue culture |
| tk | thymidine kinase |
| TM | transmembrane |
| TMB | tetramethylbenzidine |
| Tris | tris (hydroxymethyl) aminomethane |
| µCi | microcurie |
| µg | microgram |
| µl | microliter |
| µM | micromolar |
| VSV | vesicular stomatitis virus |
| VV | vaccinia virus |
| X-MLV | xenotropic murine leukemia virus |

Cell Lines

| | |
|---|---|
| AGS | cell line derived from a primary adenogastric carcinoma [Barranco and Townsend, Cancer Res., 43: 1703 (1983) and Invest. New Drugs, 1: 117 (1983)]; available from the ATCC under CRL-1739; |
| BL-3 | bovine B lymphocytes [ATCC CRL-8037; leukemia cell suspension; J. Natl. Cancer Inst. (Bethesda) 40: 737 (1968)]; |
| C33 | a cell line derived from a human cervical carcinoma biopsy [Auersperg, N., J. Nat'l. Cancer Inst. (Bethesda), 32: 135–148 (1964)]; available from the ATCC under HTB-31; |
| C33A | human cervical carcinoma cells [ATCC HTB-31; J. Natl. Cancer Inst. (Bethesda) 32: 135 (1964)]; |
| COS | simian cell line [Gluzman, Y., Cell, 23: 175 (1981)]; |
| HeLa K | standard type of HeLa cells; aneuploid, epithelial-like cell line isolated from a human cervical adenocarcinoma [Gey et al., Cancer Res., 12: 264 (1952); Jones et al., Obstet. Gynecol., 38: 945–949 (1971)] obtained from Professor B. Korych, [Institute of Medical Microbiology and Immunology, Charles University; Prague, Czech Republic]; |

| | |
|---|---|
| HeLa D98/AH.2 (also HeLa s) | Mutant HeLa clone that is hypoxanthine guanine phosphoribosyl transferase-deficient (HGPRT) kindly provided by Eric J. Stanbridge [Department of Microbiology, College of Medicine, University of California, Irvine, CA (USA)] and reported in Stanbridge et al., Science, 215: 252–259 (15 January 1982); parent of hybrid cells H/F-N and H/F-T, also obtained from E. J. Stanbridge; |
| KATO III | cell line prepared from a metastatic form of a gastric carcinoma [Sekiguichi et al., Japan J. Exp. Med., 48: 61 (1978)]; available from the ATCC under HTB-103; |
| NIH-3T3 | murine fibroblast cell line reported in Aaronson, Science, 237: 178 (1987); |
| QT35 | quail fibrosarcoma cells [ECACC: 93120832; Cell, 11: 95 (1977)]; |
| Raj | human Burkitt's lymphoma cell line [ATCC CCL-86; Lancet, 1: 238 (1964)]; |
| Rat2TK | cell line (rat embryo, thymidine kinase mutant) was derived from a subclone of a 5'-bromo-deoxyuridine resistant strain of the Fischer rat fibroblast 3T3-like cell line Rat1; the cells lack appreciable levels of nuclear thymidine kinase [Ahrens, B., Virology, 113: 408 (1981)]; |
| SiHa | human cervical squamous carcinoma cell line [ATCC HTB-35; Friedl et al., Proc. Soc. Exp. Biol. Med., 135: 543 (1990)]; |
| XC | cells derived from a rat rhabdomyosarcoma induced with Rous sarcoma virus-induced rat sarcoma [Svoboda, J., Natl. Cancer Center Institute Monograph No. 17, IN: "International Conference on Avian Tumor Viruses" (J. W. Beard ed.), pp. 277–298 (1964)], kindly provided by Jan Svoboda [Institute of Molecular Genetics, Czechoslovak Academy of Sciences; Prague, Czech Republic]; and |
| CGL1 | H/F-N hybrid cells (HeLa D98/AH.2 derivative); |
| CGL2 | H/F-N hybrid cells (HeLa D98/AH.2 derivative); |
| CGL3 | H/F-T hybrid cells (HeLa D98/AH.2 derivative); |
| CGL4 | H/F-T hybrid cells (HeLa D98/Ah.2 derivative). |

Nucleotide and Amino Acid Sequence Symbols

The following symbols are used to represent nucleotides herein:

| Base Symbol | Meaning |
|---|---|
| A | adenine |
| C | cytosine |
| G | guanine |
| T | thymine |
| U | uracil |
| I | inosine |
| M | A or C |
| R | A or G |
| W | A or T/U |
| S | C or G |
| Y | C or T/U |
| K | G or T/U |
| V | A or C or G |
| H | A or C or T/U |
| D | A or G or T/U |
| B | C or G or T/U |
| N/X | A or C or G or T/U |

| Amino acid name | 3 Ltr. Abbrev. | 1 Ltr. Abbrev. |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unknown or other | | X |

There are twenty main amino acids, each of which is specified by a different arrangement of three adjacent nucleotides (triplet code or codon), and which are linked together in a specific order to form a characteristic protein. A three-letter or one-letter convention is used herein to identify said amino acids, as, for example, in FIG. 1 as follows:

BRIEF DESCRIPTION OF THE FIGURES

FIG. 1A-C provides the nucleotide sequence for a MN cDNA [SEQ ID NO: 1] clone isolated as described herein. FIG. 1A-C also sets forth the predicted amino acid sequence [SEQ ID NO: 2] encoded by the cDNA.

FIG. 2A-F provides a 10,898 bp complete genomic sequence of MN [SEQ ID NO: 5]. The base count is as follows: 2654 A; 2739 C; 2645 G; and 2859 T. The 11 exons are in general shown in capital letters, but exon 1 is considered to begin at position 3507 as determined by RNase protection assay.

FIG. 3 is a restriction map of the full-length MN cDNA. The open reading frame is shown as an open box. The thick lines below the restriction map illustrate the sizes and positions of two overlapping cDNA clones. The horizontal arrows indicate the positions of primers R1 [SEQ ID NO: 7] and R2 [SEQ ID NO: 8] used for the 5' end RACE. Relevant restriction sites are BamHI (B), EcoRV (V), EcoRI (E), PstI (Ps), PvuII (Pv).

FIG. 4 schematically represents the 5' MN genomic region of a MN genomic clone wherein the numbering corresponds to transcription initiation sites estimated by RACE.

FIG. 5 provides an exon-intron map of the human MN/CA IX gene. The positions and sizes of the exons (numbered, filled boxes), Alu repeat elements (open boxes) and an LTR-related sequence (first unnumbered grey or stippled box) are adjusted to the indicated scale. The exons corresponding to individual MN/CA IX protein domains are enclosed in dashed frames designated PG (proteoglycan-like domain), CA (carbonic anhydrase domain), TM (transmembrane anchor) and IC (intracytoplasmic tail). Below the map, the alignment of amino acid sequences illustrates the extent of homology between the MN/CA IX protein PG region (aa 53–111) [SEQ ID NO: 50] and the human aggrecan (aa 781–839) [SEQ ID NO: 54].

FIG. 6 is a nucleotide sequence for the proposed promoter of the human MN gene [SEQ ID NO: 27]. The nucleotides are numbered from the transcription initiation site according to RNase protection assay. Potential regulatory elements are overlined. Transcription start sites are indicated by asterisks (RNase protection) and dots (RACE) above the corresponding nucleotides. The sequence of the 1st exon begins under the asterisks. FTP analysis of the MN4 promoter fragment revealed 5 regions (I–V) protected at both the coding and noncoding strands, and two regions (VI and VII) protected at the coding strand but not at the noncoding strand.

FIG. 7 provides a schematic of the alignment of MN genomic clones according to their position related to the transcription initiation site. All the genomic fragments except Bd3 were isolated from a lambda FIX II genomic library derived from HeLa cells. Clone Bd3 was derived from a human fetal brain library.

FIG. 8 schematically represents the MN protein structure. The abbreviations are the same as used in FIG. 5. The scale indicates the number of amino acids.

FIG. 9 outlines an experiment designed to explain the mechanism of reversion of NIH3T3 cells transformed with the MN coding sequence (pGD.MN).

DETAILED DESCRIPTION

The terms "MN/CA IX" and "MN/CA9" are herein considered to be synonyms for MN. Also, the G250 antigen is considered to refer to MN protein/polypeptide. [Uemura et al., *J. Urol.* 154 (4 Suppl.): 377 (Abstract 1475; 1997).]

The MN gene is shown herein to be organized into 11 exons and 10 introns. Described herein is the cloning and sequencing of the MN cDNA and genomic sequences, and the genetic engineering of MN proteins—such as the GST-MN, MN-PA, MN-Fc and MN 20-19 proteins. The recombinant MN proteins can be conveniently purified by affinity chromatography.

MN/CA IX was first identified in HeLa cells, derived from human carcinoma of cervix uteri, as both a plasma membrane and nuclear protein with an apparent molecular weight of 58 and 54 kilodaltons (kDa) as estimated by Western blotting. It is N-glycosylated with a single 3 kDa carbohydrate chain and under non-reducing conditions forms S-S-linked oligomers [Pastorekova et al., *Virology,* 187: 620–626 (1992); Pastorek et al., *Oncocrene,* 9: 2788–2888 (1994)]. MN/CA IX is a transmembrane protein located at the cell surface, although in some cases it has been detected in the nucleus [Zavada et al., *Int. J. Cancer,* 54: 268–274 (1993); Pastorekova et al., supra].

MN is manifested in HeLa cells by a twin protein, p54/58N. Immunoblots using a monoclonal antibody reactive with p54/58N (MAb M75) revealed two bands at 54 kDa and 58 kDa. Those two bands may correspond to one type of protein that most probably differs by post-translational processing. Herein, the phrase "twin protein" indicates p54/58N.

MN expression is considered to be diagnostic/prognostic for preneoplastic/neoplastic disease. The MN twin protein, p54/58N, was found to be expressed in HeLa cells and in Stanbridge's tumorigenic (H/F-T) hybrid cells [Stanbridge et al., *Somatic Cell Genet,* 7: 699–712 (1981); and Stanbridge et al., *Science,* 215: 252–259 (1982)] but not in fibroblasts or in non-tumorigenic (H/F-N) hybrid cells [Stanbridge et al., id.]. In early studies reported in Zavada et al. WO 93/18152, supra. MN proteins were found in immunoblots prepared from human ovarian, endometrial and uterine cervical carcinomas, and in some benign neoplasias (as mammary papilloma) but not from normal ovarian, endometrial, uterine or placental tissues.

Immunohistochemical studies with the M75 MAb of cervical carcinomas and a PCR-based (RT-PCR) survey of renal cell carcinomas have identified MN expression as closely associated with those cancers and indicates that MN has utility as a tumor biomarker. [Liao et al., *Am. J. Pathol.,* 145: 598–609 (1994); Liao et al., *Cancer Epidemiol. Biomarkers Prev.,* 5: 549–557 (1996); McKiernan et al., *Cancer Res.,* 57: 2362–2365 (1997).]

Many studies have confirmed the diagnostic/prognostic utility of MN. The following articles discuss the use of the MN-specific MAb M75 in diagnosing/prognosing precancerous and cancerous cervical lesions: Leff, D. N., "Half a Century of HeLa Cells: Transatlantic Antigen Enhances Reliability of Cervical Cancer Pap Test, Clinical Trials Pending," *BioWorld® Today: The Daily Biotechnology Newspaper,* 9(55) (Mar. 24, 1998); Stanbridge, E. J., "Cervical marker can help resolve ambigous Pap smears," *Diagnostics Intelligence,* 10(5): 11 (1998); Liao and Stanbridge, "Expression of the MN Antigen in Cervical Papanicolaou Smears Is an Early Diagnostic Biomarker of Cervical Dysplasia," *Cancer Epidemiology, Biomarkers & Prevention,* 5: 549–557 (1996); Brewer et al., "A Study of Biomarkers in Cervical Carcinoma and Clinical Correlation of the Novel Biomarker MN," *Gynecologic Oncology,* 63: 337–344 (1996); and Liao et al., "Identification of the MN Antigen as a Diagnostic Biomarker of Cervical Intraepithelial Squamous and Glandular Neoplasia and Cervical Carcinomas," *American Journal of Pathology,* 145(3): 598–609 (1994).

*Premalignant and Malignant Colorectal Lesions*. MN has been detected in normal gastric, intestinal, and biliary mucosa. [Pastorekova et al., *Gastroenterology,* 112: 398–408 (1997).] Immunohistochemical analysis of the normal large intestine revealed moderate staining in the proximal colon, with the reaction becoming weaker distally. The staining was confined to the basolateral surfaces of the cryptal epithelial cells, the area of greatest proliferative capacity. As MN is much more abundant in the proliferating cryptal epithelium than in the upper part of the mucosa, it may play a role in control of the proliferation and differentiation of intestinal epithelial cells. Cell proliferation increases abnormally in premalignant and malignant lesions of the colorectal epithelium, and therefore, is considered an indicator of colorectal tumor progression. [Risio, M., *J. Cell Biochem*, 16G: 79–87 (1992); and Moss et al., *Gastroenterology*, 111: 1425–1432 (1996).]

Renal Cell Carcinoma (RCC). Nakagawa et al., *J. Urol.*, 159(5) (Suppl.): Abstract 720 (May 1998), investigated MN expression in renal cell carcinoma (RCC) by immunostaining using the MN-specific MAb G250 and RT-PCR using primers derived from the MN cDNA. "Immunohistochemistry with MAbG250 resulted in strong and homogeneous expression in 131/145 (90.3%) of RCC, whereas no expression was observed in corresponding normal tissues. RT-PCR analyses of RCC frozen specimens resulted in the clear detection of MN mRNA signals, however . . . results were not identical to immunohistochemistry. . . . PCR analysis of peripheral blood samples from the patients with progressive disease revealed the presence of circulating cancer cells in the blood."

Anticancer Drugs and Antibodies that Block Interaction of MN Protein and Receptor Molecules MN protein is considered to be a uniquely suitable target for cancer therapy for a number of reasons including the following. (1) It is localized on the cell surface, rendering it accessible. (2) It is expressed in a high percentage of human carcinomas (e.g., uterine cervical, renal, colon, breast, esophageal, lung, head and neck carcinomas, among others), but is not normally expressed to any significant extent in the normal tissues from which such carcinomas originate.

(3) It is normally expressed only in the stomach mucosa and in some epithelia of the digestive tract (epithelium of gallbladder and small intestine). An anatomic barrier thereby exists between the MN-expressing preneoplastic/neoplastic and MN-expressing normal tissues. Drugs, including antibodies, can thus be administered which can reach tumors without interfering with MN-expressing normal tissues.

(4) MAb M75 has a high affinity and specificity to MN protein. (5) MN cDNA and MN genomic clones which encompass the protein-coding and gene regulatory sequences have been isolated. (6) MN-specific antibodies have been shown to have among the highest tumor uptakes reported in clinical studies with antitumor antibodies in solid tumors, as shown for the MN-specific chimeric antibody G250 in animal studies and in phase I clinical trials with renal carcinoma patients. [Steffens et al., *J. Clin. Oncol.*, 15: 1529 (1997).] Also, MN-specific antibodies have low uptake in normal tissues.

Data, e.g. as presented herein, are consistent with the following theory concerning how MN protein acts in normal tissues and in preneoplastic/neoplastic tissues. In normal tissues (e.g., in stomach mucosa), MN protein is considered to be a differentiation factor. It binds with its normal receptor S (for stomach). Stomach carcinomas have been shown not to contain MN protein.

Ectopic expression of MN protein in other tissues causes malignant conversion of cells. Such ectopic expression is considered to be caused by the binding of MN protein with an alternative receptor H (for HeLa cells), coupled to a signal transduction pathway leading to malignancy. Drugs or antibodies which block the binding site of MN protein for receptor H would be expected to cause reversion of prenoplastic/neoplastic cells to normal or induce their death.

Design and Development of MN-Blocking Drugs or Antibodies

A process to design and develop MN-blocking drugs, e.g., peptides with high affinity to MN protein, or antibodies, has several steps. First, is to test for the binding of MN protein to receptors based on the cell adhesion assay described infra. That same procedure would also be used to assay for drugs blocking the MN protein binding site. In view of the alternative receptors S and H, stomach epithelial cells or revertants (containing preferentially S receptors), HeLa cells (containing the H receptor and lacking the S receptor) would be used in the cell adhesion assay.

To identify the receptor binding site of MN protein, deletion variants of MN protein lacking different domains can be used to identify region(s) responsible for interaction of MN protein with a receptor. Example 4 has identified MN's binding site as closely related or identical to the epitope for MAb M75, which is located in at least 2 copies within the 6-fold tandem repeat of 6 amino acids [aa 61–96 (SEQ ID NO: 97)] in the proteoglycan domain of the MN protein. Smaller deletion variants can be prepared within that relevant domain, e.g., fusion proteins with only small segments of MN protein can be prepared. Also, controlled digestion of MN protein with specific proteases followed by separation of the products can be performed.

Further, peptides comprising the expected binding site can be synthesized. All of those products can be tested in cell adhesion assays, as exemplified below. [See, e.g., Pierschbacher and Ruoslahti, *PNAS*, 81:5985 (1984); Ruoslahti and Pierschbacher, *Science*, 238: 491.]

Molecules can be constructed to block the MN receptor binding site. For example, use of a phage display peptide library kit [as Ph.D®-7 Peptide 7-Mer Library Kit from New England Biolabs; Beverly, Mass. (USA)] as exemplified in Example 5, can be used to find peptides with high affinity to the target molecules. Biologic activity of the identified peptides will be tested in vitro by inhibition of cell adhesion to MN protein, by effects on cell morphology and growth characteristics of MN-related tumor cells (HeLa) and of control cells. [Symington, *J. Biol. Chem.*, 267: 25744(1992).] In vivo screening will be carried out in nude mice that have been injected with HeLa cells.

Peptides containing the binding site of the MN protein will be prepared [e.g. MAPs (multiple antigen peptides); Tam, J. P., *PNAS* (USA) 85: 5409 (1988); Butz et al., *Peptide Res.*, 7: 20(1994)]. The MAPs will be used to immunize animals to obtain antibodies (polyclonal and/or monoclonal) that recognize and block the binding site. [See, e.g., Brooks et al., *Cell*, 79: 1157(1994).] "Vaccination" would then be used to test for protection in animals. Antibodies to the MN binding site could potentially be used to block MN protein's interaction(s) with other molecules.

Computer modeling can also be used to design molecules with specific affinity to MN protein that would mediate steric inhibition between MN protein and its receptor. A computer model of the MN binding site for the receptor will contain spatial, electrostatic, hydrophobic and other characteristics of this structure. Organic molecules complementary to the structure, that best fit into the binding site, will be designed.

The use of oncoproteins as targets for developing new cancer therapeutics is considered conventional by those of skill in the art. [See, e.g., Mendelsohn and Lippman, "Growth Factors," pp. 114–133, IN: DeVita et al. (eds.), *Cancer: Principles and Practice of Oncology* (4$^{th}$ Ed.; Lippincott; Philadelphia, 1993).] In its broadest sense, the design of blocking drugs can be based in competitive inhibition experiments. Such experiments have been used to invent drugs since the discovery of sulfonamides (competitive inhibitors of para-aminobenzoic acid, a precursor of folic acid). Also, some cytostatics are competitive inhibitors (e.g., halogenated pyrimidines, among others).

However, the application of such approaches to MN is new. In comparison to other tumor-related molecules (e.g. growth factors and their receptors), MN has the unique property of being differentially expressed in preneoplastic/neoplastic and normal tissues, which are separated by an anatomic barrier.

MN Gene-Cloning and Sequencing

FIG. 1A-C provides the nucleotide sequence for a full-length MN cDNA clone isolated as described below [SEQ ID NO: 1]. FIG. 2A-F provides a complete MN genomic sequence [SEQ ID NO: 5]. FIG. 6 shows the nucleotide sequence for a proposed MN promoter [SEQ ID NO: 27].

It is understood that because of the degeneracy of the genetic code, that is, that more than one codon will code for one amino acid [for example, the codons TTA, TTG, CTT, CTC, CTA and CTG each code for the amino acid leucine (leu)], that variations of the nucleotide sequences in, for example, SEQ ID NOS: 1 and 5 wherein one codon is substituted for another, would produce a substantially equivalent protein or polypeptide according to this invention. All such variations in the nucleotide sequences of the MN cDNA and complementary nucleic acid sequences are included within the scope of this invention.

It is further understood that the nucleotide sequences herein described and shown in FIGS. 1, 2 and 6, represent only the precise structures of the cDNA, genomic and promoter nucleotide sequences isolated and described herein. It is expected that slightly modified nucleotide sequences will be found or can be modified by techniques known in the art to code for substantially similar or homologous MN proteins and polypeptides, for example, those having similar epitopes, and such nucleotide sequences and proteins/polypeptides are considered to be equivalents for the purpose of this invention. DNA or RNA having equivalent codons is considered within the scope of the invention, as are synthetic nucleic acid sequences that encode proteins/polypeptides homologous or substantially homologous to MN proteins/polypeptides, as well as those nucleic acid sequences that would hybridize to said exemplary sequences [SEQ. ID. NOS. 1, 5 and 27] under stringent conditions, or that, but for the degeneracy of the genetic code would hybridize to said cDNA nucleotide sequences under stringent hybridization conditions. Modifications and variations of nucleic acid sequences as indicated herein are considered to result in sequences that are substantially the same as the exemplary MN sequences and fragments thereof.

Partial cDNA Clone

In Zavada et al., id., the isolation of a partial MN cDNA clone of 1397 bp in length was described. A lambda gt11 cDNA library of LMCV-infected HeLa cells was prepared and subjected to immunoscreening with Mab M75 in combination with goat anti-mouse antibodies conjugated with alkaline phosphatase. One positive clone was picked and subcloned into the NotI site of pBluescript KS [Stratagene; La Jolla, Calif. (USA)] thereby creating pBluescript-MN.

Two oppositely oriented nested deletions were made using ERASE-A-BASE® KIT [set of reagents and protocols for the construction of unidirectional nested deletion sets from plasmid or M13 clones using the procedure developed by Henikoff, S., *Gene,* 28: 351 (1984); Promega; Madison, Wis. (USA)] and sequenced by dideoxy method with a T7 sequencing kit [Pharmacia; Piscataway, N.J. (USA)]. The sequencing showed a partial cDNA clone, the insert being 1397 bp long. The sequence comprises a large 1290 bp open reading frame and 107 bp 3' untranslated region containing a polyadenylation signal (AATAAA). However, the sequence surrounding the first ATG codon in the open reading frame (ORF) did not fit the definition of a translational start site. In addition, as followed from a comparison of the size of the MN clone with that of the corresponding mRNA in a Northern blot, the cDNA was shown to be missing about 100 bp from the 5' end of its sequence.

Full-Length cDNA Clone

Attempts to isolate a full-length clone from the original cDNA library failed. Therefore, the inventors performed a rapid amplification of cDNA ends (RACE) using MN-specific primers, R1 and R2 [SEQ ID NOS: 7 and 8], derived from the 5' region of the original cDNA clone. The RACE product was inserted into pBluescript, and the entire population of recombinant plasmids was sequenced with an MN-specific primer ODN1 [SEQ ID NO: 3]. In that way, a reliable sequence at the very 5' end of the MN cDNA as shown in FIG. 1 [SEQ ID NO: 1] was obtained.

Specifically, RACE was performed using 5' RACE System [GIBCO BRL; Gaithersburg, Md. (USA)] as follows. 1 μg of mRNA (the same as above) was used as a template for the first strand cDNA synthesis which was primed by the MN-specific antisense oligonucleotide, R1 (5'-TGGGGT-TCTTGAGGATCTCCAGGAG-3') [SEQ ID NO: 7]. The first strand product was precipitated twice in the presence of ammonium acetate and a homopolymeric C tail was attached to its 3' end by TdT. Tailed cDNA was then amplified by PCR using a nested primer, R2 (5'-CTCTAACTTCAGG-GAGCCCTCTTCTT-3') [SEQ ID NO: 8] and an anchor primer that anneals to the homopolymeric tail (5'-CUAC-UACUACUAGGCCACGCGTCGACTAG-TACGGGIIGGGIIGGGIIG-3') [SEQ ID NO: 9]. The amplified product was digested with BamHI and SalI restriction enzymes and cloned into pBluescript II KS plasmid. After transformation, plasmid DNA was purified from the whole population of transformed cells and used as a template for sequencing with the MN-specific primer ODN1 [SEQ ID NO: 3; a 29-mer 5' CGCCCAGTGGGTCATCTTCCCCA-GAAGAG 3'].

Based upon results of the RACE analysis, the full-length MN cDNA sequence was seen to contain a single ORF starting at position 12, with an ATG codon that is in a good context (GCGCATGG) with the rule proposed for translation initiation [Kozak, *J. Cell. Biol.* 108: 229–241 (1989)]. The AT rich 3' untranslated region contains a polyadenylation signal (AATAAA) preceding the end of the cDNA by 10 bp. Surprisingly, the sequence from the original clone as well as from four additional clones obtained from the same cDNA library did not reveal any poly(A) tail. Moreover, just downstream of the poly(A) signal, an ATTTA motif that is thought to contribute to mRNA instability [Shaw and Kamen, *Cell,* 46: 659–667 (1986)] was found. That fact raised the possibility that the poly (A) tail is missing due to the specific degradation of the MN mRNA.

Genomic Clones

To study MN regulation, MN genomic clones were isolated. One MN genomic clone (Bd3) was isolated from a human cosmid library prepared from fetal brain using both MN cDNA as a probe and the MN-specific primers derived from the 5' end of the cDNA ODN1 [SEQ ID NO: 3, supra] and ODN2 [SEQ. ID NO.: 4; 19-mer (5' GGAATCCTCCT-GCATCCGG 3')]. Sequence analysis revealed that that genomic clone covered a region upstream from a MN transcription start site and ending with the BamHI restriction site localized inside the MN cDNA. Other MN genomic clones can be similarly isolated.

In order to identify the complete genomic region of MN, the human genomic library in Lambda FIX II vector (Stratagene) was prepared from HeLa chromosomal DNA and screened by plaque hybridization using MN cDNA as described below. Several independent MN recombinant phages were identified, isolated and characterized by restriction mapping and hybridization analyses. Four overlapping recombinants covering the whole genomic region of MN were selected, digested and subcloned into pBluescript. The subclones were then subjected to bidirectional nested deletions and sequencing. DNA sequences were compiled and analyzed by computer using the DNASIS software package.

FIG. 7 provides a schematic of the alignment of MN genomic clones according to the transcription initiation site. Plasmids containing the A4a clone and the XE1 and XE3 subclones were deposited at the American Type Culture Collection (ATCC) on Jun. 6, 1995, respectively under ATCC Deposit Nos. 97199, 97200, and 97198.

Exon-Intron Structure of Complete MN Genomic Region

The complete sequence of the overlapping clones contains 10,898 bp (SEQ ID NO: 5). FIG. 5 depicts the organization of the human MN gene, showing the location of all 11 exons as well as the 2 upstream and 6 intronic Alu repeat elements. All the exons are small, ranging from 27 to 191 bp, with the exception of the first exon which is 445 bp. The intron sizes range from 89 to 1400 bp.

Table 1 below lists the splice donor and acceptor sequences that conform to consensus splice sequences including the AG-GT motif [Mount, *Nucleic Acids Res.* 10: 459–472 (1982)].

TABLE 1

Exon-Intron Structure of the Human MN Gene

| Intron | Size | Genomic Position** | SEQ ID NO | | | SEQ ID NO |
|---|---|---|---|---|---|---|
| | | | | 5' splice donor | | |
| 1 | 445 | *3507–3951 | 28 | AGAAG | gtaagt | 67 |
| 2 | 30 | 5126–5155 | 29 | TGGAG | gtgaga | 68 |
| 3 | 171 | 5349–5519 | 30 | CAGTC | gtgagg | 69 |
| 4 | 143 | 5651–5793 | 31 | CCGAG | gtgagc | 70 |
| 5 | 93 | 5883–5975 | 32 | TGGAG | gtacca | 71 |
| 6 | 67 | 7376–7442 | 33 | GGAAG | gtcagt | 72 |
| 7 | 158 | 8777–8934 | 34 | AGCAG | gtgggc | 73 |
| 8 | 145 | 9447–9591 | 35 | GCCAG | gtacag | 74 |
| 9 | 27 | 9706–9732 | 36 | TGCTG | gtgagt | 75 |
| 10 | 82 | 10350–10431 | 37 | CACAG | gtatta | 76 |
| 11 | 191 | 10562–10752 | 38 | ATAAT end 3' splice acceptor | | |
| 1 | 1174 | 3952–5125 | 39 | atacag | GGGAT | 77 |
| 2 | 193 | 5156–5348 | 40 | ccccag | GCGAC | 78 |

TABLE 1-continued

Exon-Intron Structure of the Human MN Gene

| Intron | Size | Genomic Position** | SEQ ID NO | | | SEQ ID NO |
|---|---|---|---|---|---|---|
| 3 | 131 | 5520–5650 | 41 | acgcag | TGCAA | 79 |
| 4 | 89 | 5794–5882 | 42 | tttcag | ATCCA | 80 |
| 5 | 1400 | 5976–7375 | 43 | ccccag | GAGGG | 81 |
| 6 | 1334 | 7443–8776 | 44 | tcacag | GCTCA | 82 |
| 7 | 512 | 8935–9446 | 45 | ccctag | CTCCA | 83 |
| 8 | 114 | 9592–9705 | 46 | ctccag | TCCAG | 84 |
| 9 | 617 | 9733–10349 | 47 | tcgcag | GTGACA | 85 |
| 10 | 130 | 10432–10561 | 48 | acacag | AAGGG | 86 |

**positions are related to nt numbering in whole genomic sequence including the 5' flanking region [FIG. 2A-F]
*number corresponds to transcription initiation site determined below by Rnase protection assay The CA domain is encoded by exons 2–8, while the exons 1, 10 and 11 correspond respectively to the proteoglycan-like domain, the transmembrane anchor and cytoplasmic tail of the MN/CA IX protein. That structure suggests that MN is a chimeric gene assembled by exon shuffling. The gene diverged from an ancestral CA gene at a relatively early stage of evolution as indicated by the intron distribution in the CA domain coding region as well as by amino acid sequence homology.

The exon/intron pattern of CA coding region of MN/CA IX is closer to that of CA IV gene that encodes a membrane-associated isoenzyme than of genes corresponding to cytoplasmic and mitochondrial isoenzymes. However, based on amino acid sequence homology, MN/CA IX is more closely related to the secreted CA VI than to any other isoenzyme. Since CA IV, CA VI and CARP/CA VIII are thought to have diverged the earliest, CA VII and CA V somewhat later and CAs I, II, III more recently [Tashian, R. E., *Adv. in Genetics.* 30: 321–356 (1992)], it appears that MN/CA IX belongs to the oldest mammalian CA genes.

The structure of the genomic region coding for the CA domain of MN/CA IX is similar in possessing seven exons, to other CA genes characterized so far, except for CA I and CA IV genes that have an additional exon at their 5' end [Lowe et al., *Gene,* 93: 277–283 (1990); Okuyama et al., *Genomics,* 16: 678–684 (1993).] In the cytosolic and mitochondrial CA genes (CA I, II, III, V and VII, six introns are distributed at identical positions. The CA IV gene, encoding the membrane-bound isoenzyme, shares positions of only three 3' introns (introns 3, 4 and 6) with the cytosolic and mitochondrial CAs. The fourth position (intron 5) shows a 1 bp slippage at both the donor and acceptor sites. The remaining introns involve either separate insertion events or considerable slippage with little or no change in polypeptide length. Alignment of human CAs, whose gene structure has already been determined, shows with respect to the placement of introns 2 and 5, MN/CA IX is more similar to CA IV, than to CA I, II, III, V, and VII. However, the position of intron 1 appears closer to that of CA I, II, III, V and VII. Generally, the coding sequence of the CA domain of the MN/CA IX protein is divided in a manner analogous to sequences of other CA genes. That fact supports the view that MN/CA IX belongs to the CA gene family.

Mapping of MN Gene Transcription Initiation Site

In the earlier attempt to localize the site of transcription initiation of the MN gene by RACE (above), obtained was a major PCR fragment whose sequence placed the start site 12 bp upstream from the first codon of the ORF. That result was obtained probably due to a preferential amplification of the shortest form of mRNA. Therefore, the inventors used an RNase protection assay (RNP) for fine mapping of the 5' end of the MN gene. The probe was a uniformly labeled 470 nucleotide copy RNA (nt −205 to +265) [SEQ ID NO: 55], which was hybridized to total RNA from MN-expressing HeLa and CGL3 cells and analyzed on a sequencing gel. That analysis has shown that the MN gene transcription initiates at multiple sites, the 5' end of the longest MN transcript being 30 nt longer than that previously characterized by RACE.

Mapping of MN Gene Transcription Termination Site

An RNase protection assay was used to verify the 3' end of the MN cDNA. That was important with respect to our previous finding that the cDNA contains a poly(A) signal but lacks a poly(A) tail, which could be lost during the proposed degradation of MN mRNA due to the presence of an instability motif in its 3' untranslated region. RNP analysis of MN mRNA with the fragment of the genomic clone XE3 covering the region of interest corroborated our data from MN cDNA sequencing, since the 3' end of the protected fragment corresponded to the last base of MN cDNA (position 10,752 of the genomic sequence). That site also meets the requirement for the presence of a second signal in the genomic sequence that is needed for transcription termination and polyadenylation [McLauchlan et al., Nucleic Acids Res., 13: 1347 (1985)]. Motif TGTGTTAGT (nt 10,759–10,767) corresponds well to both the consensus sequence and the position of that signal within 22 bp downstream from the polyA signal (nt 10,737–10,742).

Characterization of the 5' Flanking Region

The Bd3 genomic clone isolated from human fetal brain cosmid library was found to cover a region of 3.5 kb upstream from the transcription start site of the MN gene. It contains no significant coding region. Two Alu repeats are situated at positions −2587 to −2296 [SEQ ID NO: 56] and −1138 to −877 [SEQ ID NO: 57] (with respect to the transcription start determined by RNP). The sequence proximal to the 5' end is strongly homologous (91.4% identity) to the U3 region of long terminal repeats of human endogenous retroviruses HERV-K [Ono, M., J. Virol, 58: 937–944 (1986)]. The LTR-like fragment is 222 bp long with an A-rich tail at its 3' end. Most probably, it represents part of a SINE (short interspersed repeated sequence) type nonviral retroposon derived from HERV-K [Ono et al., Nucleic Acids Res., 15: 8725–8373 (1987)]. There are no sequences corresponding to regulatory elements in this fragment, since the 3' part of U3, and the entire R and U5 regions of LTR are absent from the Bd3 genomic clone, and the glucocorticoid responsive element as well as the enhancer core sequences are beyond its 5' border.

However, two keratinocyte-dependent enhancers were identified in the sequence downstream from the LTR-like fragment at positions −3010 and −2814. Those elements are involved in transcriptional regulation of the E6–E7 oncogenes of human papillomaviruses and are thought to account for their tissue specificity [Cripe et al., EMBO J., 6: 3745–3753 (1987)].

Nucleotide sequence analysis of the DNA 5' to the transcription start (from nt −507) revealed no recognizable TATA box within the expected distance from the beginning of the first exon. However, the presence of potential binding sites for transcription factors suggests that this region might contain a promoter for the MN gene. There are several consensus sequences for transcription factors AP1 and AP2 as well as for other regulatory elements, including a p53 binding site [Locker and Buzard, J., DNA Sequencing and Mapping, 1: 3–11 (1990); Imagawa et al. Cell, 51: 251–260 (1987); E I Deiry et al., Nat. Genet., 1: 44–49 (1992)]. Although the putative promoter region contains 59.3% C+G, it does not have additional attributes of CpG-rich islands that are typical for TATA-less promoters of housekeeping genes [Bird, Nature, 321: 209–213 (1986)]. Another class of genes lacking TATA box utilizes the initiator (Inr) element as a promoter. Many of these genes are not constitutively active, but they are rather regulated during differentiation or development. The Inr has a consensus sequence of PyPyPyCAPyPyPyPyPy [SEQ ID NO: 23] and encompasses the transcription start site [Smale and Baltimore, Cell, 57: 103–113 (1989)]. There are two such consensus sequences in the MN putative promoter; however, they do not overlap the transcription start (FIG. 6).

An interesting region was found in the middle of the MN gene. The region is about 1.4 kb in length [nt 4,600–6,000 of the genomic sequence; SEQ ID NO: 49] and spans from the 3' part of the 1 st intron to the end of the 5th exon. The region has the character of a typical CpG-rich island, with 62.8% C+G content and 82 CpG: 131 GpC dinucleotides. Moreover, there are multiple putative binding sites for transcription factors AP2 and Sp1 [Locker and Buzard, supra; Briggs et al., Science, 234: 47–52 (1986)] concentrated in the center of this area. Particularly the 3rd intron of 131 bp in length contains three Sp1 and three AP2 consensus sequences. That data indicates the possible involvement of that region in the regulation of MN gene expression. However, functionality of that region, as well as other regulatory elements found in the proposed 5' MN promoter, remains to be determined.

MN Promoter

Study of the MN promoter has shown that it is TATA-less and contains regulatory sequences for AP-1, AP-2, as well as two p53 binding sites. The sequence of the 5' end of the 3.5 kb flanking region upstream of the MN gene has shown extensive homology to LTR of HERV-K endogenous retroviruses. Basal transcription activity of the promoter is very weak as proven by analyses using CAT and neo reporter genes. However, expression of the reporter genes is severalfold increased when driven from the 3.5 kb flanking region, indicating involvement of putative enhancers.

Utility of MN Promoter as a Tumor-Specific Promoter for Gene Therapy

Being investigated is whether the MN gene promoter can be used as a tumor-specific promoter to drive the expression of a suicide gene [thymidine kinase (tk) of HSV)] and mediate the direct and bystander killing of tumor cells. HSVtk gene transferred to tumor cells converts nucleoside analogue ganciclovir (GCV) to toxic triphophates and mediates the death of transduced and also neighboring tumor cells. The control of HSVtk by the MN gene promoter would allow its expression only in tumor cells, which are permissive for the biosynthesis of MN protein, and selectively kill such tumor cells, but not normal cells in which MN expression is repressed.

A plasmid construct in which HSVtk was cloned downstream of the MN promoter region Bd3, containing both proximal and distant regulatory elements of MN, was prepared. That plasmid pMN-HSVtk was transfected to Rat2TK-cells and C33 human cervical carcinoma cells using calcium phosphate precipitation and lipofection, respectively. Transfectants were tested for expression of HSVtk and GVC sensitivity. Analysis of the transfectants has shown the remarkable cytotoxic in vitro effect of GVC even in low concentrations (up to 95% of cells killed).

Polyclonal rabbit antiserum against HSVtk, using fusion protein with GST in pGEX-3X, has been prepared to immunodetect HSVtk synthesized in transfected cells. This model system is being studied to estimate the bystander effect, the inhibition of cloning efficiency and invasiveness of transduced and GVC-treated cells to collagen matrices. A recombinant retroviral vector with the MN promoter-driven HSVtk is to be prepared to test its in vivo efficacy using an animal model (e.g., SCID-mouse).

MN Promoter Analysis

Since the MN promoter is weak, a classical approach to study it would be limited due to the relatively low efficiency of transient transfections (up to 10%). Therefore, stable clonal cell lines expressing constructs containing the MN promoter fused to the CAT gene were prepared. In such clonal lines, 100% of the cells express the CAT gene driven from the MN promoter, and thus, the activity of the promoter is detectable easier than in transient experiments. Also, the promoter activity can be analysed repeatedly in the same cells under different conditions or treated by different factors and drugs. This approach allows for the study of the mechanisms underlying MN regulation at the level of transcription initiation.

Several types of transfections with promoter constructs linked to a reporter CAT gene (calcium precipitation, DEAE dextran combined with DMSO shock and/or chloroquine, as well as electroporation), different methods of CAT activity assay (scintillation method, thin layer chromatography) and several recipient cell lines differing in the level of MN expression and in transfection efficiency (HeLa, SiHa, CGL3, KATO III, Rat2TK$^-$ and C33 cells). Activity of the MN promoter was detected preferably by the electroporation of CGL3 cells and thin layer chromatography. Further preferably, C33 cells cotransfected with MN promoter-CAT constructs and pSV2neo were used.

1. To detect basal activity of the MN promoter and to estimate the position of the core promoter, expression of the CAT gene from constructs pMN1 to pMN7 after transfection to CGL3 cells was analyzed. Plasmids with progressive 5' deletions were transfected into CGL3 cells and activity was analyzed by CAT assay. [8 μg of DNA was used for transfection in all cases except pBLV-LTR (2 μg).]

Only very weak CAT activity was detected in cells transfected by pMN1 and pMN2 (containing respectively 933 bp and 600 bp of the promoter sequence). A little higher activity was exhibited with the constructs pMN3, pMN4 and pMN6 (containing respectively 446 bp, 243 bp and 58 bp of the promoter). A slight peak of activity was obtained with pMN5 (starting at position −172 with respect to the transcription start.) Thus, the function of the MN core promoter can be assigned to a region of approximately 500 bp immediately upstream from the MN transcription initiation site.

Interestingly, the activity of the large Bd3 region (covering 3.5 kbp upstream of the transcription start) was severalfold higher than the activity of the core promoter. However, its level was still much lower than that exhibited by a positive control, i.e., BLV-LTR transactivated by Tax, and even lower than the activity of BLV-LTR without transactivation. That the activity of Bd3 was elevated in comparison to the core promoter suggests the presence of some regulatory elements. Such elements are most probably situated in the sequence between pMN1 and Bd3 (i.e. from −1 kbp to −3.5 kbp) [SEQ ID NO: 58]. The cloning and transfection of several deletion versions of Bd3 covering the indicated region can be used to determine the location of the putative regulatory elements.

Similar results were obtained from transfecting KATO III cells with Bd3 and pMN4. The transfected cells expressed a lower level of MN than the CGL3 cells. Accordingly, the activity of the MN promoter was found to be lower than in CGL3 cells.

2. In a parallel approach to study the MN promoter, an analysis based on G418 selection of cells transfected by plasmids containing the promoter of interest cloned upstream from the neo gene was made. This approach is suitable to study weak promoters, since its sensitivity is much higher than that of a standard CAT assay. The principle underlying the method is as follows: an active promoter drives expression of the neo gene which protects transfected cells from the toxic effect of G418, whereas an inactive promoter results in no neo product being made and the cells transfected thereby die upon the action of G418. Therefore, the activity of the promoter can be estimated according to the number of cell colonies obtained after two weeks of selection with G418. Three constructs were used in the initial experiments—pMN1neo, pMN4neo and pMN7neo. As pMN7neo contains only 30 bp upstream of the transcription start site, it was considered a negative control. As a positive control, pSV2neo with a promoter derived from SV40 was used. Rat2TK$^-$ cells were chosen as the recipient cells, since they are transfectable with high efficiency by the calcium precipitation method.

After transfection, the cells were subjected to two weeks of selection. Then the medium was removed, the cells were rinsed with PBS, and the colonies were rendered visible by staining with methylene blue. The results obtained from three independent experiments corroborated the data from the CAT assays. The promoter construct pMN4neo exhibited higher transcriptional activity than pMN1neo. However, the difference between the positive control and pMN4neo was not so striking as in the CAT assay. That may have been due to both lower promoter activity of pSV2neo compared to Tax-transactivated pBLV-LTR and to different conditions for cell growth after transfection. From that point of view, stable transfection is probably more advantageous for MN expression, since the cells grow in colonies with close cell to cell contact, and the experiment lasts much longer, providing a better opportunity to detect promoter activity.

3. Stable transfectants expressing MN promoter-CAT chimeric genes were prepared by the cotransfection of relevant plasmids with pSV2neo. As recipient cells, HeLa cells were used first. However, no clones expressing the promoter-CAT constructs were obtained. That negative result was probably caused by homologic recombination of the transfected genomic region of MN (e.g. the promoter) with the corresponding endogenous sequence. On the basis of that experience, C33 cells derived from a HPV-negative cervical carcinoma were used. C33 cells do not express MN, since during the process of tumorigenesis, they lost genetic material including chromosomal region 9p which contains the MN gene. In these experiments, the absence of the MN gene may represent an advantage as the possibility of homologic recombinations is avoided.

C33 Cells Transfected with MN Promoter-CAT Constructs

C33 cells expressing the CAT gene under MN promoter regions Bd3 (−3500/+31) [SEQ ID NO: 90] and MN5 (−172/+31) [SEQ ID NO: 91] were used for initial experiments to analyze the influence of cell density on the transcriptional activity of the MN promoter. The results indicated that signals generated after cells come into close contact activate transcription of the CAT protein from the MN promoter in proportion to the density of the cell culture. Interestingly, the data indicated that the MN protein is not required for this phase of signal transduction, since the influence of density is clearly demonstrated in MN-negative C33 cells. Rather, it appears that MN protein acts as an effector molecule produced in dense cells in order to perform a certain biological function (i.e., to perturb contact inhibition). Also interestingly, the MN promoter activity is detectable even in very sparse cell cultures suggesting that MN is expressed at a very low level also is sparse subconfluent culture.

Deletion Variants. Deletion variants of the Bd3-CAT promoter construct were then prepared. The constructs were cotransfected with pSV2neo into C33 cervical cells. After selection with G418, the whole population of stably transfected cells were subjected to CAT ELISA analysis. Expression of the deletion constructs resulted in the synthesis of similar levels of CAT protein to that obtained with the Bd3-CAT construct. On the basis of that preliminary data, the inventors proposed that sequences stimulating transcription of MN are located between −3506 and −3375 bp [SEQ ID NO: 92] upstream from the transcription start. That is the sequence exhibiting homology to HERV-K LTR.

However, transient transfection studies in CGL3 cells repeatedly revealed that the LTR region is not required for the enhancement of basal MN promoter activity. Further, results obtained in CGL3 cells indicate that the activating element is localized in the region from −933 to −2179 [SEQ ID NO: 110] with respect to transcription initiation site (the position of the region having been deduced from overlapping sequences in the Bd3 deletion mutants).

Interaction of Nuclear Proteins with MN Promoter Sequences in order to identify transcription factors binding to the MN promoter and potentially regulating its activity, a series of analyses using an electrophoretic mobility shift assay (EMSA) and DNase I footprinting analysis (FTP) were performed.

EMSA

In the EMSA, purified promoter fragments MN4 (−243/+31) [SEQ ID NO: 93], MN5 (−172/+31) [SEQ ID NO: 91], MN6 (−58/+31) [SEQ ID NO: 941 and pMN7 (−30/+31) [SEQ ID NO: 95], labeled at the 3' ends by Klenow enzyme, were allowed to interact with proteins in nuclear extracts prepared from CGL1 and CGL3 cells. [40 µg of nuclear proteins were incubated with 30,000 cpm end-labeled DNA fragments in the presence of 2 µg poly(dIdC).] DNA-protein complexes were analysed by PAGE (native 6%), where the complexes created extra bands that migrated more slowly than the free DNA fragments, due to the shift in mobility which is dependent on the moiety of bound protein.

The EMSA of the MN4 and MN5 promoter fragments revealed several DNA-protein complexes; however, the binding patterns obtained respectively with CGL1 and CGL3 nuclear extracts were not identical. There is a single CGL-1 specific complex.

The EMSA of the MN6 promoter fragment resulted in the formation of three identical complexes with both CGL1 and CGL3 nuclear extracts, whereas the MN7 promoter fragment did not bind any nuclear proteins.

The EMSA results indicated that the CGL1 nuclear extract contains a specific factor, which could participate in the negative regulation of MN expression in CGL1 cells. Since the specific DNA-protein complex is formed with MN4 (−243/+31) [SEQ. ID NO.: 93] and MN5 (−172/+31) [SEQ. ID NO.: 91] promoter fragments, but not with MN6 (−58/+31) [SEQ ID NO: 94], it appears that the binding site of the protein component of that specific complex is located between −173 and −58 bp [SEQ. ID NO.: 96] with respect to transcription initiation.

The next step was a series of EMSA analyses using double stranded (ds) oligonucleotides designed according to the protected regions in FTP analysis. A ds oligonucleotide derived from the protected region PR2 [covering the sequence from −72 to −56 bp (SEQ ID NO: 111)] of the MN promoter provided confirmation of the binding of the AP-1 transcription factor in competitive EMSA using commercial ds olignucleotides representing the binding site for AP-1.

EMSA of ds oligonucleotides derived from the protected regions of PR1 [−46 to −24 bp (SEQ ID NO: 112)], PR2 [−72 to −56 bp (SEQ ID NO: 111)], PR3 [−102 to −85 (SEQ ID NO: 113)] and PR5 [−163 to −144 (SEQ ID NO: 114)] did not reveal any differences in the binding pattern of nuclear proteins extracted from CGL1 and CGL3 cells, indicating that those regions do not bind crucial transcription factors which control activation of the MN gene in CGL3, or its negative regulation in CGL1. However, EMSA of ds oligonucleotides from the protected region PR4 [−133 to −108; SEQ ID NO: 115] repeatedly showed remarkable quantitative differences between binding of CGL1 and CGL3 nuclear proteins. CGL1 nuclear proteins formed a substantially higher amount of DNA-protein complexes, indicating that the PR4 region contains a binding site for specific transcription factor(s) that may represent a negative regulator of MN gene transcription in CGL1 cells. That fact is in accord with the previous EMSA data which showed CGL-1 specific DNA-protein complex with the promoter fragments pMN4 (−243/+31; SEQ ID NO: 93) and pMN5 (−172/+31; SEQ ID NO: 91), but not with pMN6 (−58/+31; SEQ ID NO: 94).

To identify the protein involved or the formation of a specific complex with the MN promoter in the PR4 region, relevant ds oligonucleotides covalently bound to magnetic beads will be used to purify the corresponding transcription factor. Alternatively the ONE Hybrid System® [Clontech (Palo Alto, Calif. (USA); an in vivo yeast genetic assay for isolating genes encoding proteins that bind to a target, cis-actiging regulatory element or any other short DNA-binding sequence] will be used to search for and clone transcription factors involved in regulation of the analysed promoter region. A cDNA library from HeLa cells will be used for that investigation.

FTP

To determine the precise location of cis regulatory elements that participate in the transcriptional regulation of the MN gene, FTP was used. Proteins in nuclear extracts prepared respectively from CGL1 and CGL3 cells were allowed to interact with a purified ds DNA fragment of the MN promoter (MN4, −243/+31) [SEQ ID NO: 93] which was labeled at the 5' end of one strand. [MN4 fragments were labeled either at Xho1 site (−243/+31*) or at Xba1 site (*−243/+31).] The DNA-protein complex was then subjected to DNase I attack, which causes the DNA chain to break at certain bases if they are not in contact with proteins. [A control used BSA instead of DNase.] Examination of the band pattern of the denatured DNA after gel electrophoresis [8% denaturing gel] indicates which of the bases on the labeled strand were protected by protein.

FTP analysis of the MN4 promoter fragment revealed 5 regions (I–V) protected at both the coding and noncoding strand, as well as two regions (VI and VII) protected at the coding strand but not at the noncoding strand. FIG. 6 indicates the general regions on the MN promoter that were protected.

The sequences of the identified protected regions (PR) were subjected to computer analysis using the SIGNALSCAN program to see if they corresponded to known consensus sequences for transcription factors. The data obtained by that computer analyses are as follows:

| | |
|---|---|
| PR I | coding strand - AP-2, p53, GAL4 noncoding strand - JCV-repeated |
| PR II | coding strand - AP-1, CGN4 noncoding strand - TCF-1, dFRA, CGN4 |
| PR III | coding strand - no known consensus sequence, only partial overlap of AP1 noncoding strand - 2 TCF-1 sites |
| PR IV | coding strand - TCF-1, ADR-1 noncoding strand - CTCF, LF-A1, LBP-1 |
| PR V | coding strand - no known consensus motif noncoding strand - JCV repeated |
| PR VI | coding strand - no known consensus motif noncoding strand - T antigen of SV 40, GAL4 |
| PR VII | coding strand - NF-uE4, U2snRNA.2 noncoding strand - AP-2, IgHC.12, MyoD. |

In contrast to EMSA, the FTP analysis did not find any differences between CGL1 and CGL3 nuclear extracts. However, the presence of specific DNA-protein interactions detected in the CGL1 nuclear extracts by EMSA could have resulted from the binding of additional protein to form DNA protein-protein complex. If that specific protein did not contact the DNA sequence directly, its presence would not be detectable by FTP.

EMSA Supershift Analysis

The results of the FTP suggests that transcription factors AP-1, AP-2 as well as tumor suppressor protein p53 are potentially involved in the regulation of MN expression. To confirm binding of those particular proteins to the MN promoter, a supershift analysis using antibodies specific for those proteins was performed. For this analysis, DNA-protein complexes prepared as described for EMSA were allowed to interact with MAbs or polyclonal antibodies specific for proteins potentially included in the complex. The binding of antibody to the corresponding protein results in an additional shift (supershift) in mobility of the DNA-protein-antibody complex which is PAGE visualized as an additional, more slowly migrating band.

By this method, the binding of AP-2 to the MN promoter was confirmed. However, this method did not evidence binding of the AP-1 transcription factor. It is possible that MN protein binds AP-1-related protein, which is antigenically different from the AP-1 recognized by the antibodies used in this assay.

Also of high interest is the possible binding of the p53 tumor suppressor protein to the MN promoter. It is well known that wt p53 functions as a transcription factor, which activates expression of growth-restricting genes and downmodulates, directly or indirectly, the expression of genes that are required for ongoing cell proliferation. Transient co-transfection experiments using the pMN4-CAT promoter construct in combination with wt p53 cDNA and mut p53 cDNA, respectively, suggested that wt p53, but not mut p53, negatively regulates expression of MN. In addition, one of two p53-binding sites in the MN promoter is protected in FTP analysis (FIG. 6), indicating that it binds to the corresponding protein. Therefore, supershift analysis to prove that p53 binds to the MN promoter with two p53-specific antibodies, e.g. Mabs 421 and DO-1 [the latter kindly provided by Dr. Vojtesek from Masaryk Memorial Cancer Institute in Brno, Czech Republic] are to be performed with appropriate nuclear extracts, e.g. from MCF-7 breast carcinoma cells which express wt p53 at a sufficient level.

Regulation of MN Expression and MN Promoter

MN appears to be a novel regulatory protein that is directly involved in the control of cell proliferation and in cellular transformation. In HeLa cells, the expression of MN is positively regulated by cell density. Its level is increased by persistent infection with LCMV. In hybrid cells between HeLa and normal fibroblasts, MN expression correlates with tumorigenicity. The fact that MN is not present in nontumorigenic hybrid cells (CGL1), but is expressed in a tumorigenic segregant lacking chromosome 11, indicates that MN is negatively regulated by a putative suppressor in chromosome 11.

Evidence supporting the regulatory role of MN protein was found in the generation of stable transfectants of NIH 3T3 cells that constitutively express MN protein. As a consequence of MN expression, the NIH 3T3 cells acquired features associated with a transformed phenotype: altered morphology, increased saturation density, proliferative advantage in serum-reduced media, enhanced DNA synthesis and capacity for anchorage-independent growth. Further, flow cytometric analyses of asynchronous cell populations indicated that the expression of MN protein leads to accelerated progression of cells through G1 phase, reduction of cell size and the loss of capacity for growth arrest under inappropriate conditions. Also, MN expressing cells display a decreased sensitivity to the DNA damaging drug mitomycin C.

Nontumorigenic human cells, CGL1 cells, were also transfected with the full-length MN cDNA. The same pSG5C-MN construct in combination with pSV2neo plasmid as used to transfect the NIH 3T3 cells was used. Out of 15 MN-positive clones (tested by SP-RIA and Western blotting), 3 were chosen for further analysis. Two MN-negative clones isolated from CGL1 cells transfected with empty plasmid were added as controls. Initial analysis indicates that the morphology and growth habits of MN-transfected CGL1 cells are not changed dramatically, but their proliferation rate and plating efficiency is increased.

MN Promoter—Sense/Antisense Constructs

When the promoter region from the MN genomic clone, isolated as described above, was linked to MN cDNA and transfected into CGL1 hybrid cells, expression of MN protein was detectable immediately after selection. However, then it gradually ceased, indicating thus an action of a feedback regulator. The putative regulatory element appeared to be acting via the MN promoter, because when the full-length cDNA (not containing the promoter) was used for transfection, no similar effect was observed.

An "antisense" MN cDNA/MN promoter construct was used to transfect CGL3 cells. The effect was the opposite of that of the CGL1 cells transfected with the "sense" construct. Whereas the transfected CGL1 cells formed colonies several times larger than the control CGL1, the transfected CGL3 cells formed colonies much smaller than the control CGL3 cells. The same result was obtained by antisense MN cDNA transfection in SiHa and HeLa cells.

For those experiments, the part of the promoter region that was linked to the MN cDNA through a BamHI site was derived from a NcoI-BamHI fragment of the MN genomic clone [Bd3] and represents a region a few hundred bp upstream from the transcription initiation site. After the ligation, the joint DNA was inserted into a pBK-CMV expression vector [Stratagene]. The required orientation of the inserted sequence was ensured by directional cloning and subsequently verified by restriction analysis. The tranfection procedure was the same as used in transfecting the NIH 3T3 cells, but cotransfection with the pSV2neo plasmid was not necessary since the neo selection marker was already included in the pBK-CMV vector.

After two weeks of selection in a medium containing G418, remarkable differences between the numbers and sizes of the colonies grown were evident as noted above. Immediately following the selection and cloning, the MN-transfected CGL1 and CGL3 cells were tested by SP-RIA for expression and repression of MN, respectively. The isolated transfected CGL1 clones were MN positive (although the level was lower than obtained with the full-length cDNA), whereas MN protein was almost absent from the transfected CGL3 clones. However, in subsequent passages, the expression of MN in transfected CGL1 cells started to cease, and was then blocked perhaps evidencing a control feedback mechanism.

As a result of the very much lowered proliferation of the transfected CGL3 cells, it was difficult to expand the majority of cloned cells (according to SP-RIA, those with the lowest levels of MN), and they were lost during passaging. However, some clones overcame that problem and again expressed MN. It is possible that once those cells reached a higher quantity, that the level of endogenously produced MN mRNA increased over the amount of ectopically expressed antisense mRNA.

Identification of Specific Transcription Factors Involved in Control of MN Expression Control of MN expression at the transcription level involves regulatory elements of the MN promoter. Those elements bind transcription factors that are responsible for MN activation in tumor cells and/or repression in normal cells. The identification and isolation of those specific transcription factors and an understanding of how they regulate MN expression could result in their therapeutic utility in modulating MN expression.

EMSA experiments indicate the existence of an MN gene repressor. Using the One Hybrid System® [Clontech (Palo Alto, Calif.); an in vivo yeast genetic assay for isolating genes encoding proteins that bind to a target, cis-acting regulatory element or any other short DNA-binding sequence; Fields and Song, Nature, 340: 245 (1989); Wu et al., EMBO J., 13:4823 (1994)] and subtractive suppressive PCR (SSH). SSH allows the cloning of genes that are differentially expressed under conditions which are known to up or down regulate MN expression such as density versus sparsity of HeLa cells, and suspension versus adherent HeLa cells.

In experiments with HPV immobilized cervical cells (HCE 16/3), it was found that the regulation of MN expression differs from that in fully transformed carcinoma cells. For example, glucocorticoid hormones, which activate HPV transcription, negatively regulate MN expression in HCE, but stimulate MN in HeLa and SiHa. Further keratinocyte growth factors, which down regulates transcription of HPV oncogenes, stimulates MN expression in suspension HCE but not in adherent cells.

EGF and insulin are involved in the activation of MN expression in both immortalized and carcinoma cells. All the noted facts can be used in the search for MN-specific transcription factors and in the modulation of MN expression for therapeutic purposes.

No Direct Relationship in HeLa Cells Between MN Expression and Expression of HPV E6 or p53

Oncogenic potential of human papillomaviruses (HPV) is related to capacity of HPV-encoded oncoproteins to bind and inactivate tumor suppressor proteins. The interaction of p53 with HPV E6 results in aberrant regulation of various cellular genes. As the MN gene, is closely associated with cervical carcinomas, its possible involvement in regulating pathways driven by p53 and E6 was investigated. Discovered was that one of the two p53 consensus sequences present in the MN promoter participate in DNA-protein interaction, but does not bind p53. It was also found that tetracycline-inducible antisense expression of HPV18 E6 in human cervical carcinoma cells (HeLa) resulted in an increased level of p53 that did not affect the expression of MN proteins. Therefore, it was assumed that at least in HeLa cells, there is no direct relationship between expression of MN and that of E6 or p53.

Deduced Amino Acid Sequence

The ORF of the MN cDNA shown in FIG. 1 has the coding capacity for a 459 amino acid protein with a calculated molecular weight of 49.7 kd. The overall amino acid composition of the MN/CA IX protein is rather acidic, and predicted to have a pi of 4.3. Analysis of native MN/CA IX protein from CGL3 cells by two-dimensional electrophoresis followed by immunoblotting has shown that in agreement with computer prediction, the MN/CA IX is an acidic protein existing in several isoelectric forms with pls ranging from 4.7 to 6.3.

As assessed by amino acid sequence analysis, the deduced primary structure of the MN protein can be divided into four distinct regions. The initial hydrophobic region of 37 amino acids (aa) corresponds to a signal peptide. The mature protein has an N-terminal or extracellular part of 377 amino acids [aa 38–414 (SEQ ID NO: 87], a hydrophobic transmembrane segment of 20 amino acids [aa 415–434 (SEQ ID NO: 52)] and a C-terminal region of 25 amino acids [aa 435–459 (SEQ ID NO: 53)].

The extracellular part is composed of two distinct domains: (1) a proteoglycan-like domain [aa 53–111 (SEQ ID NO: 50)]; and (2) a CA domain, located close to the plasma membrane [aa 135–391 (SEQ ID NO: 51)]. [The amino acid numbers are keyed to those of FIG. 1.]

More detailed insight into MN protein primary structure disclosed the presence of several consensus sequences. One potential N-glycosylation site was found at position 346 of FIG. 1. That feature, together with a predicted membrane-spanning region are consistent with the results, in which MN was shown to be an N-glycosylated protein localized in the plasma membrane. MN protein sequence deduced from cDNA was also found to contain seven S/TPXX sequence elements [SEQ ID NOS: 25 AND 26] (one of them is in the signal peptide) defined by Suzuki, *J. Mol. Biol.*, 207: 61–84 (1989) as motifs frequently found in gene regulatory proteins. However, only two of them are composed of the suggested consensus amino acids.

Experiments have shown that the MN protein is able to bind zinc cations, as shown by affinity chromatography using Zn-charged chelating sepharose. MN protein immunoprecipitated from HeLa cells by Mab M75 was found to have weak catalytic activity of CA. The CA-like domain of MN has a structural predisposition to serve as a binding site for small soluble domains. Thus, MN protein could mediate some kind of signal transduction.

MN protein from LCMV-infected HeLA cells was shown by using DNA cellulose affinity chromatography to bind to immobilized double-stranded salmon sperm DNA. The binding activity required both the presence of zinc cations and the absence of a reducing agent in the binding buffer.

CA Domain Required for Anchorage Independence but for Increased Proliferation of Transfected NIH 3T3 Fibroblasts In transfected NIH 3T3 fibroblasts, MN protein induces morphologic transformation, increased proliferation and anchorage independence. The consequences of constitutive expression of two MN-truncated variants in NIH 3T3 cells were studied. It was found that the proteoglycan-like region is sufficient for the morphological alteration of transfected cells and displays the growth-promoting activity presumably related to perturbation of contact inhibition.

The CA domain is essential for induction of anchorage independence, whereas the TM anchor and IC tail are dispensable for that biological effect. The MN protein is also capable of causing plasma membrane ruffling in the transfected cells and appears to participate in their attachment to the solid support. The data evince the involvement of MN in the regulation of cell proliferation, adhesion and intercellular communication.

Sequence Similarities

Computer analysis of the MN cDNA sequence was carried out using DNASIS and PROSIS (Pharmacia Software packages). GenBank, EMBL, Protein Identification Resource and SWISS-PROT databases were searched for all possible sequence similarities. In addition, a search for proteins sharing sequence similarities with MN was performed in the MIPS databank with the FastA program [Pearson and Lipman, *PNAS* (USA), 85: 2444 (1988)].

The proteoglycan-like domain [aa 53–111 (SEQ ID NO: 50)], which is between the signal peptide and the CA domain, shows significant homology (38% identity and 44% positivity) with a keratan sulphate attachment domain of a human large aggregating proteoglycan aggrecan [Doege et al., *J. Biol. Chem.*, 266: 894–902 (1991)].

The CA domain [aa 135–391 (SEQ ID NO: 51)] is spread over 265 aa and shows 38.9% amino acid identity with the human CA VI isoenzyme [Aldred et al., *Biochemistry*, 30: 569–575 (1991)]. The homology between MN/CA IX and other isoenzymes is as follows: 35.2% with CA II in a 261 aa overlap [Montgomery et al., *Nucl. Acids. Res.*, 15: 4687 (1987)], 31.8% with CA I in a 261 aa overlap [Barlow et al., *Nucl. Acids Res.*, 15: 2386 (1987)], 31.6% with CA IV in a 266 aa overlap [Okuyama et al., PNAS (USA) 89: 1315–1319 (1992)], and 30.5% with CA III in a 259 aa overlap (Lloyd et al., *Genes, Dev.*, 1: 594–602 (1987)].

In addition to the CA domain, MN/CA IX has acquired both N-terminal and C-terminal extensions that are unrelated to the other CA isoenzymes. The amino acid sequence of the C-terminal part, consisting of the transmembrane anchor and the intracytoplasmic tail, shows no significant homology to any known protein sequence.

The MN gene was clearly found to be a novel sequence derived from the human genome. The overall sequence homology between the cDNA MN sequence and cDNA sequences encoding different CA isoenzymes is in a homology range of 48–50% which is considered by ones in the art to be low. Therefore, the MN cDNA sequence is not closely related to any CA cDNA sequences.

Only very closely related nt sequences having a homology of at least 80–90% would hybridize to each other under stringent conditions. A sequence comparison of the MN cDNA sequence shown in FIG. 1 and a corresponding cDNA of the human carbonic anhydrase II (CA II) showed that there are no stretches of identity between the two sequences that would be long enough to allow for a segment of the CA II cDNA sequence having 25 or more nucleotides to hybridize under stringent hybridization conditions to the MN cDNA or vice versa.

A search for nt sequences related to MN gene in the EMBL Data Library did not reveal any specific homology except for 6 complete and 2 partial Alu-type repeats with homology to Alu sequences ranging from 69.8% to 91% [Jurka and Milosavljevic, *J. Mol. Evol.* 32: 105–121 (1991)]. Below under the *Characterization of the 5' Flanking Region*, also a 222 bp sequence proximal to the 5' end of the genomic region is shown to be closely homologous to a region of the HERV-K LTR.

MN Proteins and/or Polypeptides

The phrase "MN proteins and/or polypeptides" (MN proteins/polypeptides) is herein defined to mean proteins and/or polypeptides encoded by an MN gene or fragments thereof. An exemplary and preferred MN protein according to this invention has the deduced amino acid sequence shown in FIG. 1. Preferred MN proteins/polypeptides are those proteins and/or polypeptides that have substantial homology with the MN protein shown in FIG. 1. For example, such substantially homologous MN proteins/polypeptides are those that are reactive with the MN-specific antibodies of this invention, preferably the Mabs M75, MN12, MN9 and MN7 or their equivalents.

A "polypeptide" or "peptide" is a chain of amino acids covalently bound by peptide linkages and is herein considered to be composed of 50 or less amino acids. A "protein" is herein defined to be a polypeptide composed of more than 50 amino acids.

MN proteins exhibit several interesting features: cell membrane localization, cell density dependent expression in HeLa cells, correlation with the tumorigenic phenotype of HeLa x fibroblast somatic cell hybrids, and expression in several human carcinomas among other tissues. As demonstrated herein, for example, in Example 1, MN protein can be found directly in tumor tissue sections but not in general in counterpart normal tissues (exceptions noted infra as in normal gastric mucosa and gallbladder tissues). MN is also expressed sometimes in morphologically normal appearing areas of tissue specimens exhibiting dysplasia and/or malignancy. Taken together, these features suggest a possible involvement of MN in the regulation of cell proliferation, differentiation and/or transformation.

It can be appreciated that a protein or polypeptide produced by a neoplastic cell in vivo could be altered in sequence from that produced by a tumor cell in cell culture or by a transformed cell. Thus, MN proteins and/or polypeptides which have varying amino acid sequences including without limitation, amino acid substitutions, extensions, deletions, truncations and combinations thereof, fall within the scope of this invention. It can also be appreciated that a protein extant within body fluids is subject to degradative processes, such as, proteolytic processes; thus, MN proteins that are significantly truncated and MN polypeptides may be found in body fluids, such as, sera. The phrase "MN antigen" is used herein to encompass MN proteins and/or polypeptides.

It will further be appreciated that the amino acid sequence of MN proteins and polypeptides can be modified by genetic techniques. One or more amino acids can be deleted or substituted. Such amino acid changes may not cause any measurable change in the biological activity of the protein or polypeptide and result in proteins or polypeptides which are within the scope of this invention, as well as, MN muteins.

The MN proteins and polypeptides of this invention can be prepared in a variety of ways according to this invention, for example, recombinantly, synthetically or otherwise biologically, that is, by cleaving longer proteins and polypeptides enzymatically and/or chemically. A preferred method to prepare MN proteins is by a recombinant means. Particularly preferred methods of recombinantly producing MN proteins are described below for the GST-MN, MN 20-19, MN-Fc and MN-PA proteins.

Recombinant Production of MN Proteins and Polypeptides

A representative method to prepare the MN proteins shown in FIG. 1 or fragments thereof would be to insert the full-length or an appropriate fragment of MN cDNA into an appropriate expression vector as exemplified below. In Zavada et al., WO 93/18152, supra, production of a fusion protein GEX-3X-MN (now termed GST-MN) using the partial cDNA clone (described above) in the vector pGEX-3X (Pharmacia) is described. Nonglycosylated GST-MN (the MN fusion protein MN glutathione S-transferase) from XL1-Blue cells. Herein described is the recombinant production of both a glycosylated MN protein expressed from insect cells and a nonglycosylated MN protein expressed from *E. coli* using the expression plasmid pEt-22b [Novagen Inc.; Madison, Wis. (USA)].

Baculovirus Expression Systems.

Recombinant baculovirus express vectors have been developed for infection into several types of insect cells. For example, recombinant baculoviruses have been developed for among others: *Aedes aegypti, Autographa californica, Bombyx mor, Drosphila melanogaster, Heliothis zea, Spodoptera frugiperda,* and *Trichoplusia ni* [PCT Pub. No. WO 89/046699; Wright, *Nature,* 321: 718 (1986); Fraser et al., *In Vitro Cell Dev. Biol.,* 25: 225 (1989). Methods of introducing exogenous DNA into insect hosts are well-known in the art. DNA transfection and viral infection procedures usually vary with the insect genus to be transformed. See, for example, *Autographa* [Carstens et al., *Virology,* 101: 311 (1980)]; *Spodoptera* [Kang, "Baculovirus Vectors for Expression of Foreign Genes," in: *Advances in Virus Research,* 35 (1988)]; and *Heliothis* (*virescens*) [PCT Pub. No. WO 88/02030].

A wide variety of other host-cloning vector combinations may be usefully employed in cloning the MN DNA isolated as described herein. For example, useful cloning vehicles may include chromosomal, nonchromosomal and synthetic DNA sequences such as various known bacterial plasmids such as pBR322, other *E. coli* plasmids and their derivatives and wider host range plasmids such as RP4, phage DNA, such as, the numerous derivatives of phage lambda, e.g., NB989 and vectors derived from combinations of plasmids and phage DNAs such as plasmids which have been modified to employ phage DNA expression control sequences.

Useful hosts may be eukaryotic or prokaryotic and include bacterial hosts such as *E. coli* and other bacterial strains, yeasts and other fungi, animal or plant hosts such as animal or plant cells in culture, insect cells and other hosts. Of course, not all hosts may be equally efficient. The particular selection of host-cloning vehicle combination may be made by those of skill in the art after due consideration of the principles set forth herein without departing from the scope of this invention.

The following are representative examples of genetically engineering MN proteins of this invention. The descriptions are exemplary and not meant to limit the invention in any way.

Expression of MN 20-19 Protein

A representative, recombinantly produced MN protein of this invention is the MN 20-19 protein which, when produced in baculovirus-infected Sf9 cells [*Spodoptera frugiperda* cells; Clontech; Palo Alto, Calif. (USA)], is glycosylated. The MN 20-19 protein misses the putative signal peptide (aas 1–37) of SEQ ID NO: 6 (FIG. 1), has a methionine (Met) at the N-terminus for expression, and a Leu-Glu-His-His-His-His-His-His [SEQ. ID NO.: 22] added to the C-terminus for purification.

In order to insert the portion of the MN coding sequence for the GST-MN fusion protein into alternate expression systems, a set of primers for PCR was designed. The primers were constructed to provide restriction sites at each end of the coding sequence, as well as in-frame start and stop codons. The sequences of the primers, indicating restriction enzyme cleavage sites and expression landmarks, are shown below.

```
Primer #20:N-terminus
                     ⌐Translation start
5'GTCGCTAGCTCCATGGGTCATATGCAGAGGTTGCCCCGGATGCAG 3'
     NheI  NcoI    NdeI └MN cDNA #1    [SEQ. ID. NO. 17]

Primer #19:C-terminus
                ⌐Translation stop
5'GAAGATCTCTTACTCGAGCATTCTCCAAGATCCAGCCTCTAGG 3'
    BglII    XhoI  └MN cDNA              [SEQ. ID. NO. 18]
```

The SEQ ID NOS: 17 and 18 primers were used to amplify the MN coding sequence present in the GEX-3X-MN vector using standard PCR techniques. The resulting PCR product (termed MN 20-19) was electrophoresed on a 0.5% agarose/1×TBE gel; the 1.3 kb band was excised; and the DNA recovered using the Gene Clean II kit according to the manufacturer's instructions [Bio101; LaJolla, Calif. (USA)].

MN 20-19 and plasmid pET-22b were cleaved with the restriction enzymes NdeI and XhoI, phenol-chloroform extracted, and the appropriate bands recovered by agarose gel electrophoresis as above. The isolated fragments were ethanol co-precipitated at a vector:insert ratio of 1:4. After resuspension, the fragments were ligated using T4 DNA ligase. The resulting product was used to transform competent Novablue E. coli cells [Novagen, Inc.]. Plasmid minipreps [Magic Minipreps; Promega] from the resultant ampicillin resistant colonies were screened for the presence of the correct insert by restriction mapping. Insertion of the gene fragment into the pET-22b plasmid using the NdeI and XhoI sites added a 6-histidine tail to the protein that could be used for affinity isolation.

To prepare MN 20-19 for insertion into the baculovirus expression system, the MN 20-19 gene fragment was excised from pET-22b using the restriction endonucleases XbaI and PvuI. The baculovirus shuttle vector pBacPAK8 [Clontech] was cleaved with XbaI and PacI. The desired fragments (1.3 kb for MN 20-19 and 5.5 kb for pBacPAK8) were isolated by agarose gel electrophoresis, recovered using Gene Clean II, and co-precipitated at an insert:vector ratio of 2.4:1.

After ligation with T4 DNA ligase, the DNA was used to transform competent NM522 E. coli cells (Stratagene). Plasmid mini-preps from resultant ampicillin resistant colonies were screened for the presence of the correct insert by restriction mapping. Plasmid DNA from an appropriate colony and linearized BacPAK6 baculovirus DNA [Clontech] were used to transform Sf9 cells by standard techniques. Recombination produced BacPAK viruses carrying the MN 20-19 sequence. Those viruses were plated onto Sf9 cells and overlaid with agar.

Plaques were picked and plated onto Sf9 cells. The conditioned media and cells were collected. A small aliquot of the conditioned media was set aside for testing. The cells were extracted with PBS with 1% Triton X100.

The conditioned media and the cell extracts were dot blotted onto nitrocellulose paper. The blot was blocked with 5% non-fat dried milk in PBS. Mab M75 were used to detect the MN 20-19 protein in the dot blots. A rabbit anti-mouse Ig-HRP was used to detect bound Mab M75. The blots were developed with TMB/$H_2O_2$ with a membrane enhancer [KPL; Gaithersburg, Md. (USA)]. Two clones producing the strongest reaction on the dot blots were selected for expansion. One was used to produce MN 20-19 protein in High Five™ cells [Invitrogen Corp., San Diego, Calif. (USA); BTI-TN-5BI-4; derived from Trichoplusia ni egg cell homogenate]. MN 20-19 protein was purified from the conditioned media from the virus infected High Five™ cells.

The MN 20-19 protein was purified from the conditioned media by immunoaffinity chromatography. 6.5 mg of Mab M75 was coupled to 1 g of Tresyl activated TOYOPEARL® [solid support in bead form; Tosoh, Japan (#14471)]. Approximately 150 ml of the conditioned media was run through the M75-TOYOPEARL® column. The column was washed with PBS, and the MN 20-19 protein was eluted with 1.5 M MgCl. The eluted protein was then dialyzed against PBS.

Synthetic and Biologic Production of MN Proteins and Polypeptides

MN proteins and polypeptides of this invention may be prepared not only by recombinant means but also by synthetic and by other biologic means. Synthetic formation of the polypeptide or protein requires chemically synthesizing the desired chain of amino acids by methods well known in the art. Exemplary of other biologic means to prepare the desired polypeptide or protein is to subject to selective proteolysis a longer MN polypeptide or protein containing the desired amino acid sequence; for example, the longer polypeptide or protein can be split with chemical reagents or with enzymes.

Chemical synthesis of a peptide is conventional in the art and can be accomplished, for example, by the Merrifield solid phase synthesis technique [Merrifield, J., Am. Chem. Soc., 85: 2149–2154 (1963); Kent et al., Synthetic Peptides in Biology and Medicine, 29 f.f. eds. Alitalo et al., (Elsevier Science Publishers 1985); and Haug, J. D., American Biotechnology Laboratory, 5(1): 40–47 (January/February 1987)].

Techniques of chemical peptide synthesis include using automatic peptide synthesizers employing commercially available protected amino acids, for example, Biosearch [San Rafael, Calif. (USA)] Models 9500 and 9600; Applied Biosystems, Inc. [Foster City, Calif. (USA)] Model 430; Milligen [a division of Millipore Corp.; Bedford, Mass. (USA)] Model 9050; and Du Pont's RAMP™ (Rapid Automated Multiple Peptide Synthesis) [Du Pont Compass, Wilmington, Del. (USA)].

Identification of MN Protein Partner(s)

A search for protein(s) interacting with MN was initiated using expression cloning of the corresponding cDNA(s) and a MN-Fc fusion protein as a probe. The chimerical MN-Fc cDNA was constructed in pSG5C vector by substitution of MN cDNA sequences encoding both the transmembrane anchor and the intracellular tail of MN protein with the cDNA encoding Fc fragment of the mouse IgG. The Fc fragment cDNA was prepared by RT-PCR from the mouse hybridoma producing IgG2a antibody.

The chimerical MN-Fc cDNA was expressed by transient transfection in COS cells. COS cells were transfected using leptofection. Recombinant MN-Fc protein was released to TC medium of the transfected cells (due to the lack of the transmembrane region), purified by affinity chromatography on a Protein A Sepharose and used for further experiments.

Protein extracts from mock-transfected cells and the cells transfected with pSG5C-MN-Fc were analysed by immunoblotting using the M75 MAb, SwαM-Px and ECL detection® [ECL®—enhanced chemoluminescent system to detect phosphorylated tyrosine residues; Amersham; Arlington, Hts., Ill. (USA)]. The size of MN-Fc protein expressed from the pSG5C vector corresponds to its computer predicted molecular weight.

$^{35}S$-labeled MN-Fc protein was employed in cell surface binding assay. It was found to bind to several mammalian cells, e.g., HeLa, Raji, COS, QT35, BL3. Similar results were obtained in cell adhesion assay using MN-Fc protein dropped on bacterial Petri dishes. These assays revealed that KATO III human stomach adenocarcinoma cell line is lacking an ability to interact with MN-Fc protein. This finding allowed us to use KATO III cells for expression cloning and screening of the cDNA coding for MN-binding protein.

The cDNA expression library in pBK-CMV vector was prepared from dense HeLa cells and used for transfection of KATO III cells. For the first round of screening, KATO III cells were transfected by electroporation. After two days of incubation, the ligand-expressing cells were allowed to bind to MN-Fc protein, then to Protein A conjugated with biotin and finally selected by pulling down with streptavidin-coated magnetic beads. Plasmid DNA was extracted from the selected cells and transformed to E. coli. Individual E. coli colonies were picked and pools of 8–10 clones were prepared. Plasmid DNA from the pools was isolated and used in the second round of screening.

In the second round of screening, KATO III cells were transfected by DEAE dextran method. To identify the pool containing the cDNA for MN-binding protein, an ELISA method based on the binding of MN-Fc to the transfected cells, and detection using peroxidase labelled Protein A were used. Pools are selected by ability to bind MN-Fc.

In the third round of screening, plasmid DNAs isolated from individual bacterial colonies of selected pools are transfected to KATO III cells. The transfected cells are subjected to binding with MN-Fc and detection with Protein A as before. Such exemplary screening is expected to identify a clone containing the cDNA which codes for the putative MN protein partner. That clone would then be sequenced and the expression product confirmed as binding to MN protein by cell adhesion assay. (Far-Western blotting, co-precipitation etc.) Hybridomas producing Mabs to the expression product would then be prepared which would allow the analysis of the biological characteristics of the protein partner of MN.

Nucleic Acid Probes and Test Kits

Nucleic acid probes of this invention are those comprising sequences that are complementary or substantially complementary to the MN cDNA sequence shown in FIG. 1 or to other MN gene sequences, such as, the complete genomic sequence of FIG. 2A-F [SEQ ID NO: 5] and the putative promoter sequence [SEQ ID NO: 27 of FIG. 6]. The phrase "substantially complementary" is defined herein to have the meaning as it is well understood in the art and, thus, used in the context of standard hybridization conditions. The stringency of hybridization conditions can be adjusted to control the precision of complementarity. Two nucleic acids are, for example, substantially complementary to each other, if they hybridize to each other under stringent hybridization conditions.

Stringent hybridization conditions are considered herein to conform to standard hybridization conditions understood in the art to be stringent. For example, it is generally understood that stringent conditions encompass relatively low salt and/or high temperature conditions, such as provided by 0.02 M to 0.15 M NaCl at temperatures of 50° C. to 70° C. Less stringent conditions, such as, 0.15 M to 0.9 M salt at temperatures ranging from 20° C. to 55° C. can be made more stringent by adding increasing amounts of formamide, which serves to destabilize hybrid duplexes as does increased temperature.

Exemplary stringent hybridization conditions are described in Sambrook et al., *Molecular Cloning: A Laboratory Manual*, pages 1.91 and 9.47–9.51 (Second Edition, Cold Spring Harbor Laboratory Press; Cold Spring Harbor, N.Y.; 1989); Maniatis et al., *Molecular Cloning: A Laboratory Manual*, pages 387–389 (Cold Spring Harbor Laboratory; Cold Spring Harbor, N.Y.; 1982); Tsuchiya et al., *Oral Surgery, Oral Medicine, Oral Pathology*, 71(6): 721–725 (June 1991).

Preferred nucleic acid probes of this invention are fragments of the isolated nucleic acid sequences that encode MN proteins or polypeptides according to this invention. Preferably those probes are composed of at least 25 nts, more preferably at least 27 nts, still more preferably at least 29 nts, further preferably at least 50 nts.

Nucleic acid probes of this invention need not hybridize to a coding region of MN. For example, nucleic acid probes of this invention may hybridize partially or wholly to a non-coding region of the genomic sequence shown in FIG. 2A-F [SEQ ID NO: 5]. Conventional technology can be used to determine whether fragments of SEQ ID NO: 5 or related nucleic acids are useful to identify MN nucleic acid sequences. [See for example, Benton and Davis, supra and Fuscoe et al., supra.]

Areas of homology of the MN nt sequence to other non-MN nt sequences are indicated above. In general, nucleotide sequences that are not in the Alu or LTR-like regions, of preferably 25 bases or more, or still more preferably of 50 bases or more, can be routinely tested and screened and found to hybridize under stringent conditions to only MN nucleotide sequences. Further, not all homologies within the Alu-like MN genomic sequences are so close to Alu repeats as to give a hybridization signal under stringent hybridization conditions. The percent of homology between MN Alu-like regions and a standard Alu-J sequence are indicated as follows:

| Region of Homology within MN Genomic Sequence [SEQ ID NO: 5; FIG. 2A–F] | SEQ. ID. NOS. | % Homology to Entire Alu-J Sequence |
|---|---|---|
| 921–1212 | 59 | 89.1% |
| 2370–2631 | 60 | 78.6% |
| 4587–4880 | 61 | 90.1% |
| 6463–6738 | 62 | 85.4% |
| 7651–7939 | 63 | 91.0% |
| 9020–9317 | 64 | 69.8% |
|  |  | % Homology to One Half of Alu-J Sequence |
| 8301–8405 | 65 | 88.8% |
| 10040–10122 | 66 | 73.2%. |

Nucleic acid probes of this invention can be used to detect MN DNA and/or RNA, and thus can be used to test for the presence or absence of MN genes, and amplification(s), mutation(s) or genetic rearrangements of MN genes in the cells of a patient. For example, overexpression of an MN gene may be detected by Northern blotting and RNase protection analysis using probes of this invention. Gene alterations, as amplifications, translocations, inversions, and deletions among others, can be detected by using probes of this invention for in situ hybridization to chromosomes from a patient's cells, whether in metaphase spreads or interphase nuclei. Southern blotting could also be used with the probes of this invention to detect amplifications or deletions of MN genes. Restriction Fragment Length Polymorphism (RFLP) analysis using said probes is a preferred method of detecting gene alterations, mutations and deletions. Said probes can also be used to identify MN proteins and/or polypeptides as well as homologs or near homologs thereto by their hybridization to various mRNAs transcribed from MN genes in different tissues.

Probes of this invention thus can be useful diagnostically/prognostically. Said probes can be embodied in test kits, preferably with appropriate means to enable said probes when hybridized to an appropriate MN gene or MN mRNA target to be visualized. Such samples include tissue specimens including smears, body fluids and tissue and cell extracts.

PCR Assays

RT-PCR is a preferred PCR assay to detect abnormal MN gene expression. For example, mRNA can be detected using PCR primers from the MN cDNA. [Eg., McKiernan et al., *Cancer Res.*, 57: 2362 (1997).]

To detect relatively large genetic rearrangements, hybridization tests can be used. To detect relatively small genetic rearrangements, as, for example, small deletions or amplifications, or point mutations, PCR would preferably be used. [U.S. Pat. Nos. 4,800,159; 4,683,195; 4,683,202; and Chapter 14 of Sambrook et al., *Molecular Cloning: A Laboratory Manual*, supra].

An exemplary assay would use cellular DNA from normal and cancerous cells, which DNA would be isolated and amplified employing appropriate PCR primers. The PCR products would be compared, preferably initially, on a sizing gel to detect size changes indicative of certain genetic rearrangements. If no differences in sizes are noted, further comparisons can be made, preferably using, for example, PCR-single-strand conformation polymorphism (PCR-SSCP) assay or a denaturing gradient gel electrophoretic assay. [See for example, Hayashi, K. in *PCR Methods and Applications*, 1: 34–38 (1991); and Meyers et al., *Methods in Enzymology*, 155: 501 (1987).]

Assays

Assays according to this invention are provided to detect and/or quantitate MN antigen or MN-specific antibodies in vertebrate samples, preferably mammalian samples, more preferably human samples. Such samples include tissue specimens, body fluids, tissue extracts, cells, cell lysates and cell extracts, among other samples. MN antigen may be detected by immunoassay, immunohistochemical staining, immunoelectron and scanning microscopy using immunogold among other techniques.

Preferred tissue specimens to assay by immunohistochemical staining include cell smears, histological sections from biopsied tissues or organs, and imprint preparations among other tissue samples. Such tissue specimens can be variously maintained, for example, they can be fresh, frozen, or formalin-, alcohol- or acetone- or otherwise fixed and/or paraffin-embedded and deparaffinized. Biopsied tissue samples can be, for example, those samples removed by aspiration, bite, brush, cone, chorionic villus, endoscopic, excisional, incisional, needle, percutaneous punch, and surface biopsies, among other biopsy techniques.

Preferred cervical tissue specimens include cervical smears, conization specimens, histologic sections from hysterectomy specimens or other biopsied cervical tissue samples. Preferred means of obtaining cervical smears include routine swab, scraping or cytobrush techniques, among other means. More preferred are cytobrush or swab techniques. Preferably, cell smears are made on microscope slides, fixed, for example, with 55% EtOH or an alcohol based spray fixative and air-dried.

Papanicolaou-stained cervical smears (Pap smears) can be screened by the methods of this invention, for example, for retrospective studies. Preferably, Pap smears would be decolorized and re-stained with labeled antibodies against MN antigen. Also archival specimens, for example, matched smears and biopsy and/or tumor specimens, can be used for retrospective studies. Prospective studies can also be done with matched specimens from patients that have a higher than normal risk of exhibiting abnormal cervical cytopathology.

Preferred samples in which to assay MN antigen by, for example, Western blotting or radioimmunoassay, are tissue and/or cell extracts. However, MN antigen, particularly in a soluble form, as the extracellular domain, can be detected in body fluids, which can include among other fluids: blood, serum, plasma, semen, breast exudate, gastric secretions, fecal suspensions, bile, saliva, tears, sputum, mucous, urine, lymph, cytosols, ascites, pleural effusions, amniotic fluid, bladder washes, bronchioalveolar lavages and cerebrospinal fluid. It is preferred that the MN antigen be concentrated from a larger volume of body fluid before testing. Preferred body fluids to assay would depend on the type of cancer for which one was testing, but in general preferred body fluids would be urine, serum, mucous, gastric secretions, bile, breast exudate, pleural effusions and ascites.

Diagnostic nucleic acid can be labelled, directly or indirectly, by methods known in the art, and can be used in conventional Southern or Northern hybridization assays. Such assays can be employed in identifying transformants or for in vitro diagnosis, such as to detect MN mRNA in tissues as a measure of oncogenic activity. The presence of MN mRNA or precursors thereto for most tissues being indicative of oncogenic activity, whereas the absence or a reduced level of MN mRNA in stomach and gallbladder tissues in comparison to the levels of mRNA found in the counterpart normal tissues is considered indicative of oncogenic activity. DNA which encodes MN proteins can be obtained by chemical synthesis, by screening reverse transcripts of mRNA from placental or other cells, or by screening genomic libraries from eukaryotic cells, among other methods.

MN-specific antibodies can be bound by serologically active MN proteins/polypeptides in samples of such body fluids as blood, plasma, serum, lymph, mucous, tears, urine, spinal fluid and saliva; however, such antibodies are found most usually in blood, plasma and serum, preferably in serum. Correlation of the results from the assays to detect and/or quantitate MN antigen and MN-specific antibodies reactive therewith, provides a preferred profile of the disease condition of a patient.

The assays of this invention are both diagnostic and/or prognostic, i.e., diagnostic/prognostic. The term "diagnostic/prognostic" is herein defined to encompass the following processes either individually or cumulatively depending upon the clinical context: determining the presence of disease, determining the nature of a disease, distinguishing one disease from another, forecasting as to the probable outcome of a disease state, determining the prospect as to recovery from a disease as indicated by the nature and symptoms of a case, monitoring the disease status of a patient, monitoring a patient for recurrence of disease, and/or determining the preferred therapeutic regimen for a patient. The diagnostic/prognostic methods of this invention are useful, for example, for screening populations for the presence of neoplastic or pre-neoplastic disease, determining the risk of developing neoplastic disease, diagnosing the presence of neoplastic and/or pre-neoplastic disease, monitoring the disease status of patients with neoplastic disease, and/or determining the prognosis for the course of neoplastic disease. For example, it appears that the intensity of the immunostaining with MN-specific antibodies may correlate with the severity of dysplasia present in samples tested.

The present invention is useful for screening for the presence of a wide variety of neoplastic diseases as indicated above. The invention provides methods and compositions for evaluating the probability of the presence of malignant or pre-malignant cells, for example, in a group of cells freshly removed from a host. Such an assay can be used to detect tumors, quantitate their growth, and help in the diagnosis and prognosis of disease. The assays can also be used to detect the presence of cancer metastasis, as well as confirm the absence or removal of all tumor tissue following surgery, cancer chemotherapy and/or radiation therapy. It can further be used to monitor cancer chemotherapy and tumor reappearance.

The presence of MN antigen or antibodies can be detected and/or quantitated using a number of well-defined diagnostic assays. Those in the art can adapt any of the conventional immunoassay formats to detect and/or quantitate MN antigen and/or antibodies.

Many formats for detection of MN antigen and MN-specific antibodies are, of course available. Those can be Western blots, ELISAs, RIAs, competitive EIA or dual antibody sandwich assays, immunohistochemical staining, among other assays all commonly used in the diagnostic industry. In such immunoassays, the interpretation of the results is based on the assumption that the antibody or antibody combination will not cross-react with other proteins and protein fragments present in the sample that are unrelated to MN.

Representative of one type of ELISA test for MN antigen is a format wherein a microtiter plate is coated with antibodies made to MN proteins/polypeptides or antibodies made to whole cells expressing MN proteins, and to this is added a patient sample, for example, a tissue or cell extract. After a period of incubation permitting any antigen to bind to the antibodies, the plate is washed and another set of anti-MN antibodies which are linked to an enzyme is added, incubated to allow reaction to take place, and the plate is then rewashed. Thereafter, enzyme substrate is added to the microtiter plate and incubated for a period of time to allow the enzyme to work on the substrate, and the adsorbance of the final preparation is measured. A large change in absorbance indicates a positive result.

It is also apparent to one skilled in the art of immunoassays that MN proteins and/or polypeptides can be used to detect and/or quantitate the presence of MN antigen in the body fluids, tissues and/or cells of patients. In one such embodiment, a competition immunoassay is used, wherein the MN protein/polypeptide is labeled and a body fluid is added to compete the binding of the labeled MN protein/polypeptide to antibodies specific to MN protein/polypeptide.

In another embodiment, an immunometric assay may be used wherein a labeled antibody made to a MN protein or polypeptide is used. In such an assay, the amount of labeled antibody which complexes with the antigen-bound antibody is directly proportional to the amount of MN antigen in the sample.

A representative assay to detect MN-specific antibodies is a competition assay in which labeled MN protein/polypeptide is precipitated by antibodies in a sample, for example, in combination with monoclonal antibodies recognizing MN proteins/polypeptides. One skilled in the art could adapt any of the conventional immunoassay formats to detect and/or quantitate MN-specific antibodies. Detection of the binding of said antibodies to said MN protein/polypeptide could be by many ways known to those in the art, e.g., in humans with the use of anti-human labeled IgG.

An exemplary immunoassay method of this invention to detect and/or quantitate MN antigen in a vertebrate sample comprises the steps of:

a) incubating said vertebrate sample with one or more sets of antibodies (an antibody or antibodies) that bind to MN antigen wherein one set is labeled or otherwise detectable;

b) examining the incubated sample for the presence of immune complexes comprising MN antigen and said antibodies.

Another exemplary immunoassay method according to this invention is that wherein a competition immunoassay is used to detect and/or quantitate MN antigen in a vertebrate sample and wherein said method comprises the steps of:

a) incubating a vertebrate sample with one or more sets of MN-specific antibodies and a certain amount of a labeled or otherwise detectable MN protein/polypeptide wherein said MN protein/polypeptide competes for binding to said antibodies with MN antigen present in the sample;

b) examining the incubated sample to determine the amount of labeled/detectable MN protein/polypeptide bound to said antibodies; and c) determining from the results of the examination in step b) whether MN antigen is present in said sample and/or the amount of MN antigen present in said sample.

Once antibodies (including biologically active antibody fragments) having suitable specificity have been prepared, a wide variety of immunological assay methods are available for determining the formation of specific antibody-antigen complexes. Numerous competitive and non-competitive protein binding assays have been described in the scientific and patent literature, and a large number of such assays are commercially available. Exemplary immunoassays which are suitable for detecting a serum antigen include those described in U.S. Pat. Nos. 3,984,533; 3,996,345; 4,034,074; and 4,098,876.

Antibodies employed in assays may be labeled or unlabeled. Unlabeled antibodies may be employed in agglutination; labeled antibodies may be employed in a wide variety of assays, employing a wide variety of labels.

Suitable detection means include the use of labels such as radionuclides, enzymes, coenzymes, fluorescers, chemiluminescers, chromogens, enzyme substrates or co-factors, enzyme inhibitors, free radicals, particles, dyes and the like. Such labeled reagents may be used in a variety of well known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

Immunoassay Test Kits

The above outlined assays can be embodied in test kits to detect and/or quantitate MN antigen and/or MN-specific antibodies (including biologically active antibody fragments). Kits to detect and/or quantitate MN antigen can comprise MN protein(s)/polypeptides(s) and/or MN-specific antibodies, polyclonal and/or monoclonal. Such diagnostic/prognostic test kits can comprise one or more sets of antibodies, polyclonal and/or monoclonal, for a sandwich format wherein antibodies recognize epitopes on the MN antigen, and one set is appropriately labeled or is otherwise detectable.

Test kits for an assay format wherein there is competition between a labeled (or otherwise detectable) MN protein/polypeptide and MN antigen in the sample, for binding to an antibody, can comprise the combination of the labeled protein/polypeptide and the antibody in amounts which provide for optimum sensitivity and accuracy.

Test kits for MN-specific antibodies preferably comprise labeled/detectable MN proteins(s) and/or polypeptides(s), and may comprise other components as necessary, such as, controls, buffers, diluents and detergents. Such test kits can have other appropriate formats for conventional assays.

A kit for use in an enzyme-immunoassay typically includes an enzyme-labelled reagent and a substrate for the enzyme. The enzyme can, for example, bind either an MN-specific antibody of this invention or to an antibody to such an MN-specific antibody.

Preparation of MN-Specific Antibodies

The term "antibodies" is defined herein to include not only whole antibodies but also biologically active fragments of antibodies, preferably fragments containing the antigen binding regions. Further included in the definition of antibodies are bispecific antibodies that are specific for MN protein and to another tissue-specific antigen.

Antibodies of the invention may be prepared by conventional methodology and/or by genetic engineering. Chimeric antibodies that are humanized to reduce antigenicity are preferred for in vivo use. Antibody fragments may be genetically engineered, preferably from the variable regions of the light and/or heavy chains ($V_H$ and $V_L$), including the hypervariable regions, and still more preferably from both the $V_H$ and $V_L$ regions. For example, the term "antibodies" as used herein comprehends polyclonal and monoclonal antibodies and biologically active fragments thereof including among other possibilities "univalent" antibodies [Glennie et al., Nature, 295: 712 (1982)]; Fab proteins including Fab' and F(ab')$_2$ fragments whether covalently or non-covalently aggregated; light or heavy chains alone, preferably variable heavy and light chain regions ($V_H$ and $V_L$ regions), and more preferably including the hypervariable regions [otherwise known as the complementarity determining regions (CDRs) of said $V_H$ and $V_L$ regions]; $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also by oligonucleotide-directed mutagenesis techniques [Dalbadie-McFarland et al., PNAS (USA), 79: 6409 (1982)].

Bispecific Antibodies. Bispecific antibodies can be produced by chemically coupling two antibodies of the desired specificity. Bispecific MAbs can preferably be developed by somatic hybridization of 2 hybridomas. Bispecific MAbs for targeting MN protein and another antigen can be produced by fusing a hybridoma that produces MN-specific MAbs with a hybridoma producing MAbs specific to another antigen. For example, a cell (a quadroma), formed by fusion of a hybridoma producing a MN-specific MAb and a hybridoma producing an anti-cytotoxic cell antibody, will produce hybrid antibody having specificity of the parent antibodies. [See, e.g., Immunol. Rev. (1979); Cold Spring Harbor Symposium Quant. Biol., 41: 793 (1977); van Dijk et al., Int. J. Cancer, 43: 344–349 (1989).] Thus, a hybridoma producing a MN-specific MAb can be fused with a hybridoma producing, for example, an anti-T3 antibody to yield a cell line which produces a MN/T3 bispecific antibody which can target cytotoxic T cells to MN-expressing tumor cells.

It may be preferred for therapeutic and/or imaging uses that the antibodies be biologically active antibody fragments, preferably genetically engineered fragments, more preferably genetically engineered fragments from the $V_H$ and/or $V_L$ regions, and still more preferably comprising the hypervariable regions thereof. However, for some therapeutic uses bispecific antibodies targeting MN protein and cytotoxic cells would be preferred.

There are conventional techniques for making polyclonal and monoclonal antibodies well-known in the immunoassay art. Immunogens to prepare MN-specific antibodies include MN proteins and/or polypeptides, preferably purified, and MX-infected tumor line cells, for example, MX-infected HeLa cells, among other immunogens.

Anti-peptide antibodies are also made by conventional methods in the art as described in European Patent Publication No. 44,710 (published Jan. 27, 1982). Briefly, such anti-peptide antibodies are prepared by selecting a peptide from an MN amino acid sequence as from FIG. 1, chemically synthesizing it, conjugating it to an appropriate immunogenic protein and injecting it into an appropriate animal, usually a rabbit or a mouse; then, either polyclonal or monoclonal antibodies are made, the latter by a Kohler-Milstein procedure, for example.

Besides conventional hybridoma technology, newer technologies can be used to produce antibodies according to this invention. For example, the use of the PCR to clone and express antibody V-genes and phage display technology to select antibody genes encoding fragments with binding activities has resulted in the isolation of antibody fragments from repertoires of PCR amplified V-genes using immunized mice or humans. [Marks et al., BioTechnology, 10: 779 (July 1992) for references; Chiang et al., BioTechniques, 7(4): 360 (1989); Ward et al., Nature, 341: 544 (Oct. 12, 1989); Marks et al., J. Mol. Biol., 222: 581 (1991); Clackson et al., Nature, 352: (15 Aug. 1991); and Mullinax et al., PNAS (USA), 87: 8095 (October 1990).]

Descriptions of preparing antibodies, which term is herein defined to include biologically active antibody fragments, by recombinant techniques can be found in U.S. Pat. No. 4,816,567 (issued Mar. 28, 1989); European Patent Application Publication Number (EP) 338,745 (published Oct. 25, 1989); EP 368,684 (published Jun. 16, 1990); EP 239,400 (published Sep. 30, 1987); WO 90/14424 (published Nov. 29, 1990); WO 90/14430 (published May 16, 1990); Huse et al., Science, 246: 1275 (Dec. 8, 1989); Marks et al., BioTechnology, 10: 779 (July 1992); La Sastry et al., PNAS (USA), 86: 5728 (August 1989); Chiang et al., BioTechniques, 7(40): 360 (1989); Orlandi et al., PNAS (USA), 86: 3833 (May 1989); Ward et al. Nature, 341: 544 (Oct. 12, 1989); Marks et al., J. Mol. Biol., 222: 581 (1991); and Hoogenboom et al., Nucleic Acids Res., 19(15): 4133 (1991).

Representative Mabs

Monoclonal antibodies for use in the assays of this invention may be obtained by methods well known in the art for example, Galfre and Milstein, "Preparation of Monoclonal Antibodies: Strategies and Procedures," in Methods in Enzymology: Immunochemical Techniques, 73: 1–46

[Langone and Vanatis (eds); Academic Press (1981)]; and in the classic reference, Milstein and Kohler, *Nature*, 256: 495–497 (1975).]

Although representative hybridomas of this invention are formed by the fusion of murine cell lines, human/human hybridomas [Olsson et al., *PNAS (USA)*, 77: 5429 (1980)] and human/murine hybridomas [Schlom et al., PNAS (USA), 77: 6841 (1980); Shearman et al. *J. Immunol.*, 146: 928–935 (1991); and Gorman et al., PNAS (USA), 88: 4181–4185 (1991)] can also be prepared among other possibilities. Such humanized monoclonal antibodies would be preferred monoclonal antibodies for therapeutic and imaging uses.

Monoclonal antibodies specific for this invention can be prepared by immunizing appropriate mammals, preferably rodents, more preferably rabbits or mice, with an appropriate immunogen, for example, MaTu-infected HeLa cells, MN fusion proteins, or MN proteins/polypeptides attached to a carrier protein if necessary. Exemplary methods of producing antibodies of this invention are described below.

The monoclonal antibodies useful according to this invention to identify MN proteins/polypeptides can be labeled in any conventional manner, for example, with enzymes such as horseradish peroxidase (HRP), fluorescent compounds, or with radioactive isotopes such as, $^{125}$I, among other labels. A preferred label, according to this invention is $^{125}$I, and a preferred method of labeling the antibodies is by using chloramine-T [Hunter, W. M., "Radioimmunoassay," *In: Handbook of Experimental Immunology*, pp. 14.1–14.40 (D. W. Weir ed.; Blackwell, Oxford/London/Edinburgh/Melbourne; 1978)].

Representative mabs of this invention include Mabs M75, MN9, MN12 and MN7 described below. Monoclonal antibodies of this invention serve to identify MN proteins/polypeptides in various laboratory diagnostic tests, for example, in tumor cell cultures or in clinical samples.

Mabs Prepared Against HeLa Cells

MAb M75. Monoclonal antibody M75 (MAb M75) is produced by mouse lymphocytic hybridoma VU-M75, which was initially deposited in the Collection of Hybridomas at the Institute of Virology, Slovak Academy of Sciences (Bratislava, Slovakia) and was deposited under ATCC Designation HB 11128 on Sep. 17, 1992 at the American Type Culture Collection (ATCC). The production of hybridoma VU-M75 is described in Zavada et al., WO 93/18152.

Mab M75 recognizes both the nonglycosylated GST-MN fusion protein and native MN protein as expressed in CGL3 cells equally well. The M75 MAb recognizes both native and denatured forms of MN protein [Pastorekova et al. (1992), supra].

Epitopes

The affinity of a MAb to peptides containing an epitope depends on the context, e.g. on whether the peptide is a short sequence (4–6 aa), or whether such a short peptide is flanked by longer aa sequences on one or both sides, or whether in testing for an epitope, the peptides are in solution or immobilized on a surface. Therefore, it would be expected by ones of skill in the art that the representative epitopes described herein for the MN-specific MAbs would vary in the context of the use of those MAbs.

Epitope for M75 MAb

The M75 epitope is considered to be present in at least two copies within the 6× tandem repeat of 6 amino acids [aa 61–96 (SEQ ID NO: 97)] in the proteglycan domain of the MN protein. Exemplary peptides representing that epitope depending on the context may include the following peptides from that tandem repeat: EEDLPS (SEQ ID NO: 10; aa 62–67); GEEDLP (SEQ ID NO: 98; aa 61–66; aa 79–84; aa 85–90; aa 91–96); EEDL (SEQ ID NO: 99; aa 62–65; aa 80–83; aa 86–89; aa 92–95); EEDLP (SEQ ID NO. 100; aa 62–66; aa 80–84; aa 86–90; aa 92–96); EDLPSE (SEQ ID NO: 101; aa 63–68); EEDLPSE (SEQ ID NO: 102; aa 62–68); and DLPGEE (SEQ ID NO: 103; aa 82–87, aa 88–93).

Three synthetic peptides from the deduced aa sequence for the EC domain of the MN protein shown in FIG. 1 were prepared. Those synthetic peptides are represented by aa 51–72 (SEQ ID NO: 104), aa 61–85 (SEQ ID NO: 105) and aa 75–98 (SEQ ID NO.: 106). Each of those synthetic peptides contains the motif EEDLP (SEQ ID NO: 100) and were shown to be reactive with the M75 MAb.

Mabs Prepared Against Fusion Protein GST-MN

Monoclonal antibodies of this invention were also prepared against the MN glutathione S-transferase fusion protein (GST-MN). BALB/C mice were immunized intraperitoneally according to standard procedures with the GST-MN fusion protein in Freund's adjuvant. Spleen cells of the mice were fused with SP/20 myeloma cells [Milstein and Kohler, supra].

Tissue culture media from the hybridomas were screened against CGL3 and CGL1 membrane extracts in an ELISA employing HRP labelled-rabbit anti-mouse. The membrane extracts were coated onto microtiter plates. Selected were antibodies that reacted with the CGL3 membrane extract. Selected hybridomas were cloned twice by limiting dilution.

The mabs prepared by the just described method were characterized by Western blots of the GST-MN fusion protein, and with membrane extracts from the CGL1 and CGL3 cells. Representative of the mabs prepared are Mabs MN9, MN12 and MN7.

Mab MN9. Monoclonal antibody MN9 (Mab MN9) reacts to the same epitope as Mab M75, as described above. As Mab M75, Mab MN9 recognizes both the GST-MN fusion protein and native MN protein equally well.

Mabs corresponding to Mab MN9 can be prepared reproducibly by screening a series of mabs prepared against an MN protein/polypeptide, such as, the GST-MN fusion protein, against the peptides representing the epitope for Mabs M75 and MN9. Alternatively, the Novatope system [Novagen] or competition with the deposited Mab M75 could be used to select mabs comparable to Mabs M75 and MN9.

Mab MN12. Monoclonal antibody MN12 (Mab MN12) is produced by the mouse lymphocytic hybridoma MN 12.2.2 which was deposited under ATCC Designation HB 11647 on Jun. 9, 1994 at the American Type Culture Collection (ATCC). Antibodies corresponding to Mab MN12 can also be made, analogously to the method outlined above for Mab MN9, by screening a series of antibodies prepared against an MN protein/polypeptide, against the peptide representing the epitope for Mab MN12. That peptide is aa 55–aa 60 of FIG. 1 [SEQ ID NO: 11]. The Novatope system could also be used to find antibodies specific for said epitope.

Mab MN7. Monoclonal antibody MN7 (Mab MN7) was selected from mabs prepared against nongiycosylated GST-MN as described above. It recognizes the epitope represented by the amino acid sequence from aa 127 to aa 147 [SEQ ID NO: 12] of the FIG. 1 MN protein. Analogously to methods described above for Mabs MN9 and MN12, mabs corresponding to Mab MN7 can be prepared by selecting mabs prepared against an MN protein/polypeptide that are reactive with the peptide having SEQ ID NO: 12, or by the stated alternative means.

Epitope Mapping

Epitope mapping was performed by the Novatope® system, a kit for which is commercially available from Novagen, Inc. [See, for analogous example, Li et al., *Nature*, 363: 85–88 (6 May 1993).] In brief, the MN cDNA was cut into overlapping short fragments of approximately 60 base pairs. The fragments were expressed in *E. coli*, and the *E. coli* colonies were transferred onto nitrocellulose paper, lysed and probed with the mab of interest. The MN cDNA of clones reactive with the mab of interest was sequenced, and the epitopes of the mabs were deduced from the overlapping polypeptides found to be reactive with each mab.

Therapeutic Use of MN-Specific Antibodies

The MN-specific antibodies of this invention, monoclonal and/or polyclonal, preferably monoclonal, and as outlined above, may be used therapeutically in the treatment of neoplastic and/or pre-neoplastic disease, either alone or in combination with chemotherapeutic drugs or toxic agents, such as ricin A. Further preferred for therapeutic use would be biologically active antibody fragments as described herein. Also preferred MN-specific antibodies for such therapeutic uses would be humanized monoclonal antibodies and/or bispecific antibodies.

MN-specific antibodies can be administered in a therapeutically effective amount, preferably dispersed in a physiologically acceptable, nontoxic liquid vehicle, to patients afflicted with preneoplastic/neoplastic disease. The MN-specific antibody can be given alone or as a carrier of an anti-tumor drug. Among the various antiproliferative, antineoplastic or cytotoxic agents that may be linked to the MN-specific antibodies are antimetabolites, such as the antifolate, methotrexate, or the purine or pyrimidine analogs mercaptopurine and fluorouracil. Others include antibiotics, lectins such as ricin and abrin, toxins such as the subunit of diphtheria toxin, radionuclides such as $^{211}$Astatine and $^{131}$Iodine, radiosensitizers such as misanidazole or neutron sensitizers such as boron containing organics. Such agents may be attached to the antibody by conventional techniques such as glutaraldehyde cross-linking.

MN-specific antibodies can be used to target cytoxic cells (e.g. human T cells, monocytes or NK cells). Cytotoxic cells can be attached to MN-expressing tumor cells through Fc receptors on the cytotoxic cells, which bind the Fc portion of a MN-specific antibody, or via a bridging antibody of dual specificity, that is, a bispecific antibody specific for MN protein and for the cytotoxic cell.

The cytotoxic cell can be targeted by allowing the bispecific antibody to bind the cell. After targeting, the cells can be administered to the patient. Therapy with targeted cells can be used as an adjunct to surgical therapy, radiation therapy, or chemotherapy.

Anti-Idiotype MN-Specific Antibodies as Tumor Vaccines and Anti-Anti-Idiotype Antibody Sera as Immunotherapeutic MN-specific anti-idiotype antibodies have therapeutic utility as a vaccine for neoplastic disease associated with abnormal MN expression. MN-specific anti-anti-idiotype sera also have therapeutic anti-tumor efficacy. Those therapeutic utilities are demonstrated by research done with the MN-specific G250 MAb, and anti-idiotype antibodies thereto (Ab2), and further anti-anti-idiotype sera (Ab3) as demonstrated by the studies described below.

Uemura et al., *Biotherapy* (Japan) 10(3): 241–244 (1996) (English summary) define an anti-idiotype antibody (Ab2) as "an antibody directed against an antigenic determinant located within a variable region of the immunoglobulin molecule. Ab2 mimicking the normal antigen (so-called internal image Ab2) may be used as a surrogate antigen for vaccination to trigger the host's immune system specifically against the nominal antigen."

Uemura et al., id., having previously isolated six internal image murine Ab2s directed against the G250 MAb— NUH31, 51, 71, 82 (IgG1) and NUH44 (IgG2a), explores the application of monoclonal Ab2 as tumor vaccines. Uemura et al. investigated in view of "previous results that RCC tumor-associated-antigen-related idiotype vaccination induced antigen-specific humoral as well as cellular responses, the antitumor efficacy of anti-anti-idiotype antibody (Ab3) sera obtained from mice immunized with different internal image Ab2 that . . . mimic the RCC-associated antigen . . . G250 [MN] . . . . Nu/nu BALB/c mice carrying small established NU12 human RCC xenografts (G250+, 20 mm$^3$) rr receiving an s.c. injection of 2×10$^5$ SK-RC-52 (G250+) RCC cells were treated by i.p. injection of 0.2 ml Ab3 sera. This treatment resulted in complete tumor rejection and significant tumor growth inhibition as compared to control groups (p<0.01)." Uemura et al. concluded that "immunization with Ab2s elicits powerful anti-tumor effects in immunocompetent animals."

Uemura et al., *J. Urol.*, 159(5)(Suppl.): Abstract 724 (May 1998), describe MN as an immunotherapeutic target for renal cell carcinoma (RCC). The therapeutic potential of the MN-specific MAb G250 was evaluated in combination with IFN/IL-2/MCSF (interferon, interleukin-2, macrophage colony stimulating factor) and Ab2 (NUH82)-induced mouse serum (Ab3-82). Ab2s are monoclonal anti-idiotype antibodies raised against MAbG250 which have been shown to be useful as tumor vaccines for RCC.

Uemura et al., id. reported that mice with NUR-2 RCC xenografts were treated by peri-tumor injection of MAbG250 and/or cytokines or 0.2 ml of Ab3 sera with/ without MCSF. The tumor volume in MAbG250 treated animals was significantly lower than in the controls. IFN or IL-2 treatments was similarly effective, but MCSF resulted in no significant tumor inhibition. The IFN/IL-2/MAbG250 therapy increased significantly the anti-tumor effects as compared to MAbG250 or cytokine monotherapy. Further, Ab3-based (Ab2-induced) immunotherapy resulted in tremendous tumor monotherapy growth inhibition as compared to MAbG250 or the other cytokine combination therapies.

MN-Specific Intrabodies—Targeted Tumor Killing Via Intracellular Expression of MN-Specific Antibodies to Block Transport of MN Protein to Cell Surface The gene encoding antibodies can be manipulated so that the antigen-binding domain can be expressed intracellularly. Such "intrabodies" that are targeted to the lumen of the endoplasmic reticulum provide a simple and effective mechanism for inhibiting the transport of plasma membrane proteins to the cell surface. [Marasco, W. A., "Review— Intrabodies: turning the humoral immune system outside in or intracellular immunization," *Gene Therapy*, 4: 11–15 (1997); Chen et al., "Intracellular antibodies as a new class of therapeutic molecules for gene therapy," *Hum. Gene Ther.*, 5(5): 595–601 (1994); Mhashilkar et al., *EMBO J.*, 14: 1542–1551 (1995); Mhashilkar et al., *J. Virol.*, 71: 6486–6494 (1997); Marasco (Ed.), *Intrabodies: Basic*

Research and Clinical Gene Therapy Applications, (Springer Life Sciences 1998; ISBN 3-540-64151-3) (summarizes preclinical studies from laboratories worldwide that have used intrabodies); Zanetti and Capra (Eds.), "Intrabodies: From Antibody Genes to Intracellular Communication," *The Antibodies: Volume* 4 [Harwood Academic Publishers; ISBN 90-5702-559-0 (December 1997)]; Jones and Marasco, *Advanced Drug Delivery Reviews,* 31 (1–2): 153–170 (1998); Pumphrey and Marasco, *Biodrugs,* 9(3): 179–185 (1998); Dachs et al., *Oncology Res.,* 9(6–7): 313–325 (1997); Rondon and Marasco, *Ann. Rev. Microbiol.,* 51: 257–283 (1997)]; Marasco, W. A., *Immunotechnology,* 1(1): 1–19 (1995); and Richardson and Marasco, *Trends in Biotechnology,* 13(8): 306–310 (1995).]

MN-specific intrabodies may prevent the maturation and transport of MN protein to the cell surface and thereby prevent the MN protein from functioning in an oncogenic process. Antibodies directed to MN's EC, TM or IC domains may be useful in this regard. MN protein is considered to mediate signal transduction by transferring signals from the EC domain to the IC tail and then by associating with other intracellular proteins within the cell's interior. MN-specific intrabodies could disrupt that association and perturb that MN function.

Inactivating the function of the MN protein could result in reversion of tumor cells to a non-transformed phenotype. [Marasco et al. (1997), supra.] Antisense expression of MN cDNA in cervical carcinoma cells, as demonstrated herein, has shown that loss of MN protein has led to growth suppression of the transfected cells. It is similarly expected that inhibition of MN protein transport to the cell surface would have similar effects. Cloning and intracellular expression of the M75 MAb's variable region is to be studied to confirm that expectation.

Preferably, the intracellularly produced MN-specific antibodies are single-chain antibodies, specifically single-chain variable region fragments or scFv, in which the heavy- and light-chain variable domains are synthesized as a single polypeptide and are separated by a flexible linker peptide, preferably $(Gly_4-Ser)_3$ [SEQ ID NO: 116].

MN-specific intracellularly produced antibodies can be used therapeutically to treat preneoplastic/neoplastic disease by transfecting preneoplastic/neoplastic cells that are abnormally expressing MN protein with a vector comprising a nucleic acid encoding MN-specific antibody variable region fragments, operatively linked to an expression control sequence. Preferably said expression control sequence would comprise the MN gene promoter.

Antibody-Mediated Gene Transfer Using MN-Specific Antibodies or Peptides for Targeting MN-Expressing Tumor Cells An MN-specific antibody or peptide covalently linked to polylysine, a polycation able to compact DNA and neutralize its negative charges, would be expected to deliver efficiently biologically active DNA into an MN-expressing tumor cell. If the packed DNA contains the HSVtk gene under control of the MN promoter, the system would have double specificity for recognition and expression only in MN-expressing tumor cells. The packed DNA could also code for cytokines to induce CTL activity, or for other biologically active molecules.

The M75 MAb (or, for example, as a single chain antibody, or as its variable region) is exemplary of such a MN-specific antibody. Example 5 discloses heptapeptides (SEQ ID NOS: 107–109) that bind to the enzymatic center of the CA domain of the MN protein and, selected peptides or proteins comprising such heptapeptides would also be expected to bind to a binding site on the extracellular domain of the MN protein.

Imaging Use of Antibodies

Further, the MN-specific antibodies of this invention when linked to an imaging agent, such as a radionuclide, can be used for imaging. Biologically active antibody fragments or humanized monoclonal antibodies, may be preferred for imaging use.

A patient's neoplastic tissue can be identified as, for example, sites of transformed stem cells, of tumors and locations of any metastases. Antibodies, appropriately labeled or linked to an imaging agent, can be injected in a physiologically acceptable carrier into a patient, and the binding of the antibodies can be detected by a method appropriate to the label or imaging agent, for example, by scintigraphy. Exemplary are studies with the G250 Mab.

Steffens et al., *J. Urol.,* 159(5)(Suppl.): Abstract 562 (May 1998), describe a Phase I/II study with $^{131}$I-cG250 MAb in patients with metastasized RCC. MAb cG250 is a chimeric MAb in which constant regions of the mouse immunoglobulin have been exchanged for human immunoglobulin regions. [Oosterwijk and Debruyne, *World J. Urol.,* 13: 186 (1995).] Uptake of the cG250 MAb in primary RCC was shown to be as high as 0.52 percent of the injected dose per gram of tumor tissue (% ID/g). The study concluded that "$^{131}$I-cG250 is a promising candidate for radioimmunotherapy and a phase I/II activity dose escalation study was initiated to determine the safety, maximum tolerable dose (MTD) and therapeutic potential of $^{131}$I-cG250."

Bander et al., *Proceedings Am. Urol. Assoc.,* 155(Suppl.): 583A (Abstract 1088) (May 1996), describes renal cancer imaging with the MN-specific MAb G250, which detects MN present in 85–90% of renal cancers but does not detect MN on normal kidney cells. Bander et al. reports that 48 patients were entered in clinical trials with $^{131}$I-G250 MAb.

Antisense MN Nucleic Acid Sequences

MN genes are herein considered putative oncogenes and the encoded proteins thereby are considered to be putative oncoproteins. Antisense nucleic acid sequences complementary to mRNA transcribed from MN genes, as represented by the antisense oligodeoxynucleotides ODN1 and ODN2 [SEQ ID NOS: 3 and 4] can be used to reduce or prevent expression of the MN gene. [Zamecnick, P. C., pp. 1–6, *Prospects for Antisense Nucleic Acid Therapy of Cancer and AIDS,* (Wiley-Liss, Inc., New York, N.Y., USA; 1991); Wickstrom, E., pp. 7–24, id.; Leserman et al., pp. 25–34, id.; Yokoyama, K., pp. 35–52, id.; van den Berg et al., pp. 63–70, id.; Mercola, D., pp. 83–114, id.; Inouye, *Gene,* 72: 25–34 (1988); Miller and Ts'o, *Ann. Reports Med. Chem.,* 23: 295–304 (1988); Stein and Cohen, *Cancer Res.,* 48: 2659–2668 (1988); Stevenson and Inversen, *J. Gen. Virol.,* 70: 2673–2682 (1989); Goodchild, pp. 53–77, *Oligodeoxynucleotides: Antisense Inhibitors of Gene Expression* (Cohen, J. S., ed; CRC Press, Boca Raton, Fla., USA; 1989); Dervan et al., pp. 197–210, id.; Neckers, L. M., pp. 211–232, id.; Leitner et al., *PNAS* (USA), 87: 3430–3434 (1990); Bevilacqua et al., *PNAS* (USA), 85: 831–835 (1988); Loke et al. *Curr. Top. Microbiol. Immunol.,* 141: 282–288 (1988); Sarin et al., PNAS (USA), 85: 7448–7451 (1988); Agrawal et al., "Antisense Oligonucleotides: A Possible Approach for Chemotherapy and AIDS," International Union of Biochemistry Conference on Nucleic Acid Therapeutics (Jan. 13–17, 1991; Clearwater Beach, Fla., USA); Armstrong, L., *Ber. Week*, pp. 88–89 (Mar. 5, 1990); and Weintraub et al., *Trends*, 1: 22–25 (1985).]

Antisense nucleic acid sequences, preferably oligonucleotides, by hybridizing preferably under stringent hybridization conditions, to MN mRNA, particularly at the 5' end of the mRNA, corresponding preferably to the transcription initiation site (i.e., the first 5' nt of mRNA with linked terminal 7-methylquanylate), inhibits translation of the mRNA. A major transcription initiation site was determined by RNase protection assay at position 42 upstream from the translation initiation site (nt 3465 of genomic sequence). Several minor transcription initiation sites have also been located.

Particularly preferred are MN antisense nucleic acids, particularly ODNs, that are complementary to the 5' leader sequence of mRNA (i.e., nts positioned between cap and translation initiation site). Transcription initiation sites can be detected by standard methods by searching for the 5' end of mRNA by RNase protection assay, primer extension, and 51 nuclease mapping (or RACE). The 5' end of mRNA can be deduced from the full-length cDNA.

The use of MN antisense nucleic acid sequences may be considered to be a form of cancer therapy. Example 11 of Zavada et al., WO 93/18152 (published 16 Sep. 1993) describes an in vitro screening procedure to predict if an MN antisense nucleic acid would have therapeutic utility in vivo. An MN antisense nucleic acid is added to the media of an MN-expressing cell line. After a period of incubation, extracts from the cells are analysed by immunoblotting with labeled MAb M75. Inhibition of MN protein synthesis relative to control cells is considered predictive of in vivo therapeutic efficacy.

The experiments with sense/antisense MN cDNA promoter constructs reported above also reasonably predict in vivo therapeutic efficacy of MN antisense nucleic acids. Transfection with an antisense MN cDNA construct has been shown to lower the proliferation rate of an MN-expressing, tumorigenic cell line CGL3 and reduce colony size. Analogous experiments with similar results were obtained by transfection of SiHa and HeLa cells.

The 29-mer ODN1 and 19-mer ODN2 [SEQ ID NOS: 3 and 4] are representative of the many antisense nucleic acid sequences that can function to inhibit MN gene expression. Ones of ordinary skill in the art could determine appropriate antisense nucleic acid sequences, preferably antisense oligonucleotides, from the nucleic acid sequences of FIGS. 1 and 2.

Vaccines

It will be readily appreciated that MN proteins and polypeptides of this invention can be incorporated into vaccines capable of inducing protective immunity against neoplastic disease and a dampening effect upon tumorigenic activity. Efficacy of a representative MN fusion protein GST-MN as a vaccine in a rat model is shown in Example 2.

MN proteins and/or polypeptides may be synthesized or prepared recombinantly or otherwise biologically, to comprise one or more amino acid sequences corresponding to one or more epitopes of the MN proteins either in monomeric or multimeric form. Those proteins and/or polypeptides may then be incorporated into vaccines capable of inducing protective immunity. Techniques for enhancing the antigenicity of such polypeptides include incorporation into a multimeric structure, binding to a highly immunogenic protein carrier, for example, keyhole limpet hemocyanin (KLH), or diphtheria toxoid, and administration in combination with adjuvants or any other enhancers of immune response.

Preferred MN proteins/polypeptides to be used in a vaccine according to this invention would be genetically engineered MN proteins. Preferred recombinant MN protein are the GST-MN, MN 20-19, MN-Fc and MN-PA proteins.

Other exemplary vaccines include vaccinia-MN (live vaccinia virus with full-length MN cDNA), and baculovirus-MN (full length MN cDNA inserted into baculovirus vector, e.g. in suspension of infected insect cells). Different vaccines may be combined and vaccination periods can be prolonged.

A preferred exemplary use of such a vaccine of this invention would be its administration to patients whose MN-carrying primary cancer had been surgically removed. The vaccine may induce active immunity in the patients and prevent recidivism or metastasis.

It will further be appreciated that anti-idiotype antibodies to antibodies to MN proteins/polypeptides are also useful as vaccines and can be similarly formulated. As noted above, anti-idiotype antibodies to MN-specific antibodies mimic MN protein/polypeptide. Compositions comprising such anti-idiotype antibodies may be preferred vaccines of this invention when formulated in a physiologically acceptable formulation.

An amino acid sequence corresponding to an epitope of an MN protein/polypeptide either in monomeric or multimeric form may also be obtained by chemical synthetic means or by purification from biological sources including genetically modified microorganisms or their culture media. [See Lerner, *Sci. Am.* 248(2): 66–74 (1983).] The protein/polypeptide may be combined in an amino acid sequence with other proteins/polypeptides including fragments of other proteins, as for example, when synthesized as a fusion protein, or linked to other antigenic or non-antigenic polypeptides of synthetic or biological origin. In some instances, it may be desirable to fuse a MN protein or polypeptide to an immunogenic and/or antigenic protein or polypeptide, for example, to stimulate efficacy of a MN-based vaccine.

The term "corresponding to an epitope of an MN protein/polypeptide" will be understood to include the practical possibility that, in some instances, amino acid sequence variations of a naturally occurring protein or polypeptide may be antigenic and confer protective immunity against neoplastic disease and/or anti-tumorigenic effects. Possible sequence variations include, without limitation, amino acid substitutions, extensions, deletions, truncations, interpolations and combinations thereof. Such variations fall within the contemplated scope of the invention provided the protein or polypeptide containing them is immunogenic and antibodies elicited by such a polypeptide or protein cross-react with naturally occurring MN proteins and polypeptides to a sufficient extent to provide protective immunity and/or anti-tumorigenic activity when administered as a vaccine.

Such vaccine compositions will be combined with a physiologically acceptable medium, including immunologically acceptable diluents and carriers as well as commonly employed adjuvants such as Freund's Complete Adjuvant, saponin, alum, and the like. Administration would be in immunologically effective amounts of the MN proteins or polypeptides, preferably in quantities providing unit doses of from 0.01 to 10.0 micrograms of immunologically active MN protein and/or polypeptide per kilogram of the recipient's body weight. Total protective doses may range from 0.1 to about 100 micrograms of antigen. Routes of administration, antigen dose, number and frequency of injections are all matters of optimization within the scope of the ordinary skill in the art.

The following examples are for purposes of illustration only and not meant to limit the invention in any way.

EXAMPLE 1

Immunohistochemical Staining of Tissue Specimens

To study and evaluate the tissue distribution range and expression of MN proteins, the monoclonal antibody M75 was used to stain immunohistochemically a variety of human tissue specimens. The primary antibody used in these immunohistochemical staining experiments was the M75 monoclonal antibody. A biotinylated second antibody and streptavidin-peroxidase were used to detect the M75 reactivity in sections of formalin-fixed, paraffin-embedded tissue samples. A commercially available amplification kit, specifically the DAKO LSAB™ kit [DAKO Corp., Carpinteria, Calif. (USA)] which provides matched, ready made blocking reagent, secondary antibody and steptavidin-horseradish peroxidase was used in these experiments.

M75 immunoreactivity was tested according to the methods of this invention in multiple-tissue sections of breast, colon, cervical, lung and normal tissues. Such multiple-tissue sections were cut from paraffin blocks of tissues called "sausages" that were purchased from the City of Hope [Duarte, Calif. (USA)]. Combined in such a multiple-tissue section were normal, benign and malignant specimens of a given tissue; for example, about a score of tissue samples of breast cancers from different patients, a similar number of benign breast tissue samples, and normal breast tissue samples would be combined in one such multiple-breast-tissue section. The normal multiple-tissue sections contained only normal tissues from various organs, for example, liver, spleen, lung, kidney, adrenal gland, brain, prostate, pancreas, thyroid, ovary, and testis.

Also screened for MN gene expression were multiple individual specimens from cervical cancers, bladder cancers, renal cell cancers, and head and neck cancers. Such specimens were obtained from U.C. Davis Medical Center in Sacramento, Calif. and from Dr. Shu Y. Liao [Department of Pathology; St. Joseph Hospital; Orange, Calif. (USA)].

Controls used in these experiments were the cell lines CGL3 (H/F-T hybrid cells) and CGL1 (H/F-N hybrid cells) which are known to stain respectively, positively and negatively with the M75 monoclonal antibody. The M75 monoclonal antibody was diluted to a 1:5000 dilution wherein the diluent was either PBS [0.05 M phosphate buffered saline (0.15 M NaCl), pH 7.2–7.4] or PBS containing 1% protease-free BSA as a protein stabilizer.

Immunohistochemical Staining Protocol

The immunohistochemical staining protocol was followed according to the manufacturer's instructions for the DAKO LSAB™ kit. In brief, the sections were dewaxed, rehydrated and blocked to remove non-specific reactivity as well as endogenous peroxidase activity. Each section was then incubated with dilutions of the M75 monoclonal antibody. After the unbound M75 was removed by rinsing the section, the section was sequentially reacted with a biotinylated antimouse IgG antibody and streptavidin conjugated to horseradish peroxidase; a rinsing step was included between those two reactions and after the second reaction. Following the last rinse, the antibody-enzyme complexes were detected by reaction with an insoluble chromogen (diaminobenzidine) and hydrogen peroxide. A positive result was indicated by the formation of an insoluble reddish-brown precipitate at the site of the primary antibody reaction. The sections were then rinsed, counterstained with hematoxylin, dehydrated and cover slipped. Then the sections were examined using standard light microscopy.

Interpretation. A deposit of a reddish brown precipitate over the plasma membrane was taken as evidence that the M75 antibody had bound to a MN antigen in the tissue. The known positive control (CGL3) had to be stained to validate the assay. Section thickness was taken into consideration to compare staining intensities, as thicker sections produce greater staining intensity independently of other assay parameters.

Results

Preliminary examination of cervical specimens showed that 62 of 68 squamous cell carcinoma specimens (91.2%) stained positively with M75. Additionally, 2 of 6 adenocarcinomas and 2 of 2 adenosquamous cancers of the cervix also stained positively. In early studies, 55.6% (10 of 18) of cervical dysplasias stained positively. A total of 9 specimens including both cervical dysplasias and tumors, exhibited some MN expression in normal appearing areas of the endocervical glandular epithelium, usually at the basal layer. In some specimens, whereas morphologically normal-looking areas showed expression of MN antigen, areas exhibiting dysplasia and/or malignancy did not show MN expression.

M75 positive immunoreactivity was most often localized to the plasma membrane of cells, with the most apparent stain being present at the junctions between adjacent cells. Cytoplasmic staining was also evident in some cells; however, plasma membrane staining was most often used as the main criterion of positivity.

M75 positive cells tended to be near areas showing keratin differentiation in cervical specimens. In some specimens, positive staining cells were located in the center of nests of non-staining cells. Often, there was very little, if any, obvious morphological difference between staining cells and non-staining cells. In some specimens, the positive staining cells were associated with adjacent areas of necrosis.

In most of the squamous cell carcinomas of the cervix, the M75 immunoreactivity was focal in distribution, i.e., only certain areas of the specimen stained. Although the distribution of positive reactivity within a given specimen was rather sporadic, the intensity of the reactivity was usually very strong. In most of the adenocarcinomas of the cervix, the staining pattern was more homogeneous, with the majority of the specimen staining positively.

Among the normal tissue samples, intense, positive and specific M75 immunoreactivity was observed only in normal stomach tissues, with diminishing reactivity in the small intestine, appendix and colon. No other normal tissue stained extensively positively for M75. Occasionally, however, foci of intensely staining cells were observed in normal intestine samples (usually at the base of the crypts) or were sometimes seen in morphologically normal appearing areas of the epithelium of cervical specimens exhibiting dysplasia and/or malignancy. In such, normal appearing areas of cervical specimens, positive staining was seen in focal areas of the basal layer of the ectocervical epithelium or in the basal layer of endocervical glandular epithelium. In one normal specimen of human skin, cytoplasmic MN staining was observed in the basal layer. The basal layers of these epithelia are usually areas of proliferation, suggesting the MN expression may be involved in cellular growth. In a few cervical biopsied specimens, MN positivity was observed in the morphologically normal appearing stratified squamous epithelium, sometimes associated with cells undergoing koilocytic changes.

Some colon adenomas (4 of 11) and adenocarcinomas (9 of 15) were positively stained. One normal colon specimen was positive at the base of the crypts. Of 15 colon cancer specimens, 4 adenocarcinomas and 5 metastatic lesions were MN positive. Fewer malignant breast cancers (3 of 25) and ovarian cancer specimens (3 of 15) were positively stained. Of 4 head and neck cancers, 3 stained very intensely with M75.

Although normal stomach tissue was routinely positive, 4 adenocarcinomas of the stomach were MN negative. Of 3 bladder cancer specimens (1 adenocarcinoma, 1 non-papillary transitional cell carcinoma, and 1 squamous cell carcinoma), only the squamous cell carcinoma was MN positive. Approximately 40% (12 of 30) of lung cancer specimens were positive; 2 of 4 undifferentiated carcinomas; 3 of 8 adenocarcinomas; 2 of 8 oat cell carcinomas; and, 5 of 10 squamous cell carcinomas. One hundred percent (4 of 4) of the renal cell carcinomas were MN positive.

In summary, MN antigen, as detected by M75 and immunohistochemistry in the experiments described above, was shown to be prevalent in tumor cells, most notably in tissues of cervical cancers. MN antigen was also found in some cells of normal tissues, and sometimes in morphologically normal appearing areas of specimens exhibiting dysplasia and/or malignancy. However, MN is not usually extensively expressed in most normal tissues, except for stomach tissues where it is extensively expressed and in the tissues of the lower gastrointestinal tract where it is less extensively expressed. MN expression is most often localized to the cellular plasma membrane of tumor cells and may play a role in intercellular communication or cell adhesion. Representative results of experiments performed as described above are tabulated in Table 2.

TABLE 2

Immunoreactivity of M75 in Various Tissues

| TISSUE | TYPE | POS/NEG (# pos/# tested) |
| --- | --- | --- |
| liver, spleen, lung, kidney, adrenal gland, brain, prostate, pancreas, thyroid, ovary, testis | normal | NEG (all) |
| skin | normal | POS (in basal layer) (1/1) |
| stomach | normal | POS |
| small intestine | normal | POS |
| colon | normal | POS |
| breast | normal | NEG (0/10) |
| cervix | normal | NEG (0/2) |
| breast | benign | NEG (0/17) |
| colon | benign | POS (4/11) |
| cervix | benign | POS (10/18) |
| breast | malignant | POS (3/25) |
| colon | malignant | POS (9/15) |
| ovarian | malignant | POS (3/15) |
| lung | malignant | POS (12/30) |
| bladder | malignant | POS (1/3) |
| head & neck | malignant | POS (3/4) |
| kidney | malignant | POS (4/4) |
| stomach | malignant | NEG (0/4) |
| cervix | malignant | POS (62/68) |

The results recorded in this example indicate that the presence of MN proteins in a tissue sample from a patient may, in general, depending upon the tissue involved, be a marker signaling that a pre-neoplastic or neoplastic process is occurring. Thus, one may conclude from these results that diagnostic/prognostic methods that detect MN antigen may be particularly useful for screening patient samples for a number of cancers which can thereby be detected at a pre-neoplastic stage or at an early stage prior to obvious morphologic changes associated with dysplasia and/or malignancy being evident or being evident on a widespread basis.

EXAMPLE 2

Vaccine—Rat Model

As shown in Example 7 of WO 93/18152 (International Publication Date: 16 Sep. 1993), in some rat tumors, for example, the XC tumor cell line (cells from a rat rhabdomyosarcoma), a rat MN protein, related to human MN, is expressed. Thus a model was afforded to study antitumor immunity induced by experimental MN-based vaccines. The following representative experiments were performed.

Nine- to eleven-day-old Wistar rats from several families were randomized, injected intraperitoneally with 0.1 ml of either control rat sera (the C group) or with rat serum against the MN fusion protein GST-MN (the IM group). Simultaneously both groups were injected subcutaneously with $10^6$ XC tumor cells.

Four weeks later, the rats were sacrificed, and their tumors weighed. The results indicated that the difference between the two groups—C and IM—was significant by Mann-Whitney rank test (U=84, $\alpha<0.025$). The IM group of baby rats developed tumors about one-half the size of the controls, and 5 of the 18 passively immunized rats developed no tumor at all, compared to 1 of 18 controls.

EXAMPLE 3

Transient Transformation of Mammalian Cells by MN Protein

This example (1) examines the biological consequences of transfecting human or mouse cells with MN-cDNA inserted into expression vectors, mainly from the viewpoint of the involvement of MN protein in oncogenesis; (2) determines if MN protein exerts carbonic anhydrase activity, and whether such activity is relevant for morphologic transformation of cells; and (3) tests whether MN protein is a cell adhesion molecule (CAM).

Synopsis

Methods: MN-cDNA was inserted into 3 expression vectors and was used for transfecting human or mouse cells. MN protein was detected by Western blotting, radioimmunoassay or immunoperoxidase staining; in all tests the MN-specific monoclonal antibody M75 (MAb M75) was used. Carbonic anhydrase activity was determined by the acidification velocity of carbonate buffer in $CO_2$ atmosphere.

Results: (1) Cells (human CGL-1 and mouse NIH3T3 cells) transfected with MN-cDNA showed morphologic transformation, but reverted to normal phenotype after 4–5 weeks. (2) This reversion was not due to the loss, silencing or mutation of the MN insert. (3) MN protein has the enzyme activity of a carbonic anhydrase, which can be inhibited with acetazolamide; however, the inhibition of the carbonic anhydrase enzyme activity did not affect transformation. (4) MN protein is an adhesion protein, involved in cell-to-cell contacts.

Background

This example concerns transformation of mammalian cells by MN-cDNA inserted into expression vectors derived from retroviruses. Such vectors are suitable for efficient and stable integration into cellular DNA and for continuous expression of MN protein. Cells transfected with these constructs showed morphologic transformation, but after some time, they reverted to normal phenotype.

Sulfonamides, including acetazolamide, are very potent inhibitors of known carbonic anhydrases [Maren and Ellison, Mol. Pharmacol., 3: 503–508 (1967)]. Acetazolamide was tested to determine if it inhibited also the MN-carbonic anhydrase, and if so, whether inhibition of the enzyme affected cell transformation.

There are reasons to believe that MN protein could be involved in direct cell-to-cell interactions: A) previous observations indicated a functional resemblance of MN protein to surface glycoproteins of enveloped viruses, which mediate virus adsorption to cell surface receptors, and MN participated in the formation of phenotypically mixed virions of vesicular stomatitis virus. B) Inducibility of MN protein expression by growing HeLa cells in densely packed monolayers suggests that it may be involved in direct interactions between cells. C) Finally, there is a structural similarity between the MN protein and receptor tyrosine phosphatase β, which also contains proteoglycan and carbonic anhydrase domains; those domains mediate direct contacts between cells of the developing nervous system [Peles et al., Cell, 82: 251–260 (1995)]. Therefore, MN protein was tested to see if it bound to cell surface receptors; the result was clearly positive that it does.

Materials and Methods

Cell Lines

Cells used in this example were: CCL1 and CGL3—respectively non-tumorigenic and tumorigenic HeLa×fibroblast hybrids [Stanbridge et al., Somat. Cell Genet., 7: 699–712 (1981)], mouse cell line NIH3T3, HeLa cells and monkey Vero cells. The NIH3T3 cells were seeded at very low density to obtain colonies started from single cells. The most normal appearing colony, designated subclone 2, was picked for use in the experiments reported in this example.

Expression Vectors

Full-length MN cDNA was acquired from a pBluescript subclone [Pastorek et al., Oncogene, 9: 2877–2888 (1994)]. To remove 5' and 3' noncoding sequences, that might reduce subsequent gene expression, a polymerase chain reaction (PCR) was performed. The 5' primer TAGACAGATCTACGATGGCTCCCCTGTGCCCCAG [SEQ ID NO: 88] encompasses a translation start site and BglII cloning site, and the 3' primer ATTCCTCTAGACAGTTACCGGCTCCCCCTCAGAT [SEQ ID NO: 89] encompasses a stop codon and XbaI cloning site. Full-length MN-cDNA as a template and Pfu DNA Polymerase [Stratagene; LaJolla, Calif. (USA)] were used in the reaction.

The PCR product was sequenced and found to be identical with the template; it carried no mutations. The PCR product harbouring solely the MN coding sequence was inserted into three vectors: 1. pMAMneo [Clontech; Palo Alto, Calif. (USA)] plasmid allowing dexamethasone-inducible expression driven by the MMTV-Long Terminal Repeat (LTR) promoter and containing a neo gene for selection of transformants in media supplemented with Geneticin (G418) antibiotics. 2. Retroviral expression vector pGD [Daley et al., Science, 247: 824–829 (1990); kindly provided by Prof. David Baltimore, New York-Cambridge)] containing MLV-LTR promoter and neo gene for G418 antibiotics selection. 3. Vaccinia virus expression vector pSC11 [Chakrabarti et al., Mol. Cell. Biol., 5: 3403–3409 (1985)]. Transfection was performed via a calcium-phosphate precipitate according to Sambrook et al. (eds.), Molecular cloning, A laboratory manual, 2nd ed., Cold Spring Harbor Laboratory Press (1989).

Vaccinia virus strain Praha clone 13 was used as parental virus [Kutinova et al., Vaccine, 13: 487–493 (1995)]. Vaccinia virus recombinant was prepared by a standard procedure [Perkus et al., Virology, 152: 285–297 (1986)]. Recombinant viruses were selected and plaque purified twice in rat thymidine-kinase-less RAT2 cells [Topp, W. C., Virology, 113: 408–411 (1981)] in the presence of 5'-bromodeoxyuridine (100 µg/ml). Blue plaques were identified by overlaying with agar containing 5-bromo-4-chloro-3-indolyl-β-D-galactopyranoside (X-Gal) (200 µg/ml).

CA Assay

Carbonic anhydrase activity was measured by a micromethod [Brion et al., Anal. Biochem., 175: 289–297 (1988)]. In principle, velocity of the reaction $CO_2+H_2O \rightarrow H_2CO_3$ is measured by the time required for acidification of carbonate buffer, detected with phenol red as a pH indicator. This reaction proceeds even in absence of the enzyme, with $t_0$=control time (this was set to 60 seconds). Carbonic anhydrase reduces the time of acidification to t; one unit of the enzyme activity reduces the time to one half of control time: $t/t_0=\frac{1}{2}$.

For the experiment, MN protein was immunoprecipitated with Mab M75 from RIPA buffer (1% Triton X-100, 0.1% deoxycholate, 1 mM phenylmethylsulfonylfluoride and 200 trypsin-inhibiting units/ml of Trasylol in PBS, pH 7.2) extract of Vero cells infected with vaccinia-MN construct, after the cells developed cytopathic effect, or with "empty" vaccinia as a control. The MN+antibody complex was subsequently adsorbed to protein A—Staphylococcus aureus cells [Kessler, S. W., J. Immunol., 115: 1617–1624 (1975)] and rinsed 2× with PBS and 2× with 1 mM carbonate buffer, pH 8.0. The precipitate was resuspended in the same buffer and added to the reaction mixture. Acetazolamide (Sigma) was tested for inhibition of carbonic anhydrase [Maren and Ellison, supra]. In extracts of infected cells used for immunoprecipitation, the concentration of total proteins was determined by the Lowry method [Lowry et al., J. Biol. Chem., 193: 265–275 (1951)] and that of MN protein by a competition radioimmunoassay as described in Zavada et al., Int. J. Cancer, 54: 268–274 (1993).

Western Blots

Western blotting and development of the blots using $^{125}$I-labelled M75 and autoradiography was performed as before [Pastorekova et al., Virology, 187: 620–626 (1992); and Zavada (1993), supra].

Adhesion Assay

For the adhesion assay [Hoffman S., "Assays of cell adhesion," IN: Cell-cell Interactions (Stevenson et al. eds.) pp. 1–30 (IRL Press at Oxford University Press; Oxford, N.Y., Tokyo; 1992)], 25 µl aliquots MN protein (affinity purified pGEX-3X MN) [Zavada et al. (1993), supra] or of control proteins were spotted on 5 cm-diameter bacteriological Petri dishes and allowed to bind for 2 hours at room temperature. This yielded circular protein-coated areas of 4–5 mm diameter. MN protein was diluted to 10 µg/ml in 50 mM carbonate buffer, pH 9.2. Patches of adsorbed control proteins were prepared similarly. Those included collagens type I and IV, fibronectin, laminin and gelatin (Sigma products), diluted and adsorbed according to the manufacturer's recommendations; FCS and BSA were also included. After aspiration of the drops, the dishes were rinsed 2× with PBS and saturated for 1 hour with DMEM supplied with 5% FCS. The plates were seeded with $5×10^5$ cells in 5 ml of DMEM+5% FCS and incubated overnight at 37° C. The plates were rinsed with PBS, and the attached cells were fixed with formaldehyde, post-fixed with methanol and Giemsa stained.

Results

1. Transformation and Reversion of CGL1 Cells Transfected with MN-cDNA

Since the expression of MN protein correlated with the tumorigenicity of HeLa x fibroblast hybrids [Zavada et al. (1993), supra], the non-tumorigenic hybrid CGL1 cells were first tested. Those cells, transfected with the pMAM.MN construct, after selection with Geneticin, formed colonies with varying degrees of transformation; some of them appeared normal. While normal CGL1 cells are contact inhibited, growing in a parallel orientation, the transformed cells formed very dense colonies, showing the loss of contact inhibition. Such colonies grew more slowly than the original CGL1.

After subcloning, the cells isolated from transformed colonies segregated revertants. The reversion was a gradual, step-wise process; there were colonies with different degrees of reversion. After 2 passages, all the cell population became morphologically indistinguishable from normal CGL1. This was due to the reversion of some cells and to the selective advantage of the revertants, which grew faster than the transformed cells. Despite repeated attempts, not even one single stably transformed cell clone was obtained. Mo transformed colonies were found in CGL1 cells transfected with an "empty" pMAM control plasmid.

2. Rescue of Transforming MN from the Revertants

The reversion of MN-transformed cells to normal phenotype could have at least 4 causes: A) loss of the MN insert; B) silencing of the MN insert, e.g., by methylation; C) mutation of the MN insert; D) activation of a suppressor gene, coding for a product which neutralizes transforming activity of MN protein; E) loss of a MN-binding protein. To decide among those alternatives, the following experiment was designed as graphically outlined in FIG. 9.

MN-cDNA was inserted into pGD, a vector derived from mouse leukemia virus—MLV. A defective virus was thereby engineered, which contained the MN gene and the selective marker neo instead of genes coding for viral structural proteins. With this construct, mouse NIH3T3 cells were transfected. In media supplied with Geneticin, the cells formed colonies with phenotypes ranging from strongly transformed to apparently normal. All of the transformed colonies and about 50% of the normal colonies expressed MN protein. Contrasting with normal NIH3T3 cells, the transformants were also able to form colonies in soft agar, reflective of the loss of anchorage dependence, characteristic of cell transformation. Upon passaging, the cells isolated from transformed colonies reverted to normal morphology, and at the same time, they lost the capacity to form colonies in soft agar, while still expressing the MN protein. This permanent presence of MN protein in revertants ruled out alternatives A) and B) supra, that is, loss or silencing of the MN gene as a cause of reversion.

To decide among the other 3 alternatives, the revertants were superinfected with live, replication competent MLV. This virus grows in NIH3T3 cells without any morphologic manifestations, and it works as a "helper" for the pGD.MN construct. Virus progeny from MLV-infected revertants represents an artificial virus complex [pGD.MN+MLV]. This consists of 2 types of virions: of standard type MLV particles and virions containing the pGD.MN genome, enveloped in structural proteins provided by the "helper" virus. This virus complex was infectious for fresh NIH3T3 cells; it again induced in them morphologic transformation and the capacity to form agar colonies.

Contrasting with NIH3T3 transfected with pGD.MN, all the colonies of cells infected with [pGD.MN+MLV] complex, which grew in the presence of Geneticin, were uniformly transformed and contained MN proteins. The transformants once more reverted to normal phenotype although they kept producing infectious [pGD.MN+MLV] complex, which induced transformation in fresh NIH3T3 cells. This cycle of infection-transformation-reversion was repeated 3 times with the same result. This ruled out alternative C)—mutation of MN-cDNA as a cause of reversion.

Normal NIH3T3 cells formed a contact inhibited monolayer of flat cells, which did not stain with Mab M75 and immunoperoxidase. Cells infected with [pGD.MN+MLV] complex were clearly transformed: they grew in a chaotic pattern and showed loss of contact inhibition. Some of the cells showed signs of apoptosis. Two passages later, the cell population totally reverted to original phenotype as a result of frequent emergence of revertants and of their selective advantages (faster growth and a higher efficiency of plating). In fact, the revertants appeared to grow to a somewhat lower saturation density than the original NIH3T3 cells, showing a higher degree of contact inhibition.

The control NIH3T3 cells did not contain any MN protein (Western blot); while both transformed cells and revertants contained the same amount and the same proportion of 54 and 58 kDa bands of MN protein. In a non-reducing gel, MN protein was present in the form of oligomers of 153 kDa. Consistently, by competition RIA, approximately 40 ng MN/mg total protein was found in both of the transformed cells and revertants.

3. Carbonic Anhydrase Activity and its Inhibition

Since the carbonic anhydrase domain represents a considerable part of the MN protein (see FIG. 8), tests were performed to determine whether it is indeed enzymatically active. Vero cells infected with the vaccinia.MN construct, which contained more of the MN protein than other cells used in the present experiments, served as a source of MN protein. The cells were extracted with RIPA buffer, and MN protein was concentrated and partially purified by precipitation with MAb M75 and SAC. The immunoprecipitate was tested for CA activity. 78 µl of precipitate contained 1 unit of the enzyme. From the extract, the concentration of total proteins and of MN protein was determined; 1 unit of enzyme corresponded to 145 ng of MN protein or to 0.83 mg of total protein. The immunoprecipitate from Vero cells infected with control virus had no enzyme activity.

Activity of MN carbonic anhydrase was inhibited by acetazolamide; $1.53×10^{-8}M$ concentration of the drug reduced enzyme activity to 50%.

Preliminary tests showed that confluent cultures of HeLa or of NIH3T3 cells tolerated $10^{-5}$–$10^{-3}M$ concentration of acetazolamide for 3 days without any signs of toxicity and without any effect on cell morphology. In sparse cultures, $10^{-5}M$ acetazolamide did not inhibit cell growth, but $10^{-4}M$ already caused a partial inhibition. Thus, $10^{-5}M$ acetazolamide was added to NIH3T3 cells freshly transformed with the [pGD.MN+MLV] complex. After 4 days of incubation, the colonies were fixed and stained. No difference was seen between cells growing in the presence or absence of acetazolamide; both were indistinguishable from correctly transformed NIH3T3 cells. Thus, the enzymatic activity of carbonic anhydrase is not relevant for the transforming activity of MN protein.

4. Cell Adhesion Assay

To determine whether or not MN protein is a cell adhesion molecule (CAM), adhesion assays were performed in plastic bacteriological Petri dishes (not treated for use with tissue culture). Cells do not adhere to the surfaces of such dishes, unless the dishes are coated with a binding protein. NIH3T3 cells adhered, spread and grew on patches of adsorbed MN protein. Only very few cells attached outside the areas coated with MN protein.

Other variants of the experiment demonstrated that NIH3T3 cells adhered and spread on patches of adsorbed collagen I and IV, fibronectin and laminin. NIH3T3 cells did not attach to dots of adsorbed gelatin, FCS or BSA.

CGL1, HeLa and Vero cells also adhered to MN protein, but 3 leukemia cell lines showed no adherence. CGL3 cells, strongly expressing MN protein; adhered less efficiently to MN protein dots then did CGL1. The presence of $10^{-4}$M acetazolamide in the media did not affect the cell adhesion.

To confirm the specificity of adhesion, MN protein was absorbed with SAC loaded with MAb M75 (directed to MN) or MAb M67, directed to an unrelated antigen (Pastorekova et al., supra), before it was applied to the surface of the Petri dishes. Absorption with the SAC-M75 complex totally abrogated the cell binding activity, whereas absorption with SAC-M67 was without any effect.

Additional Cell Adhesion Results

A shortened MN, missing TM and IC segments, is shed into the medium by 5ET1 cells (a HeLa X fibroblast hybrid, analogous to CGL3 cells that express MN protein abundantly) or by Vero cells infected with VV carrying MN-cDNA with deleted TM and IC sequences. The shed MN protein was purified from the media, and tested in cell adhesion assays. The cells adhered, spread and grew only on the patches covered with adsorbed complete MN protein, but not on the dots of MN lacking TM and IC regions. Analogous results have been described also for some other adhesion molecules. A variety of cells (NIH3T3, CGL1, CGL3, HeLa, XC) attached to MN protein dots suggesting that the MN receptor(s) is common on the surface of vertebrate cells.

Tests were also performed with extracellular matrix proteins or control proteins dotted on nitrocellulose. The dot-blots were treated with MN protein solution. Bound MN protein was detected with MAb M75. MN protein absorbed to the dots of collagen I and IV, but not to fibronectin, laminin, gelatine or BSA.

Discussion

The data provided herein is consistent with the view that the MN gene most likely represents a novel type of oncogene or proto-oncogene. MN protein has a very strong association with certain types of human carcinomas, and is absent from almost all normal tissues (except as shown infra). Cells are morphologically transformed by MN-cDNA, such transformation being characterized by increased cell density, a criss-cross pattern of cell growth and the acquisition of the capacity to form colonies in soft agar (Pastorek et al., supra). Those features are characteristic of cells transformed with tumor viruses or with cloned oncogenes [Todaro et al., PNAS (USA) 51: 66–73 (1964); Macpherson and Montagnier, Virology, 23: 291–294 (1964)].

Adhesion molecules mediate cell-to-cell or cell to extracellular matrix binding; they play an essential role in embryogenesis and in cell growth and differentiation. Recent data has demonstrated that besides their mechanical function, some CAMs are also involved in signal transduction cascades. Their up-regulation or ectopic expression leads to disruption of the normal program of cell differentiation. CAMs are believed to play a role in invasion and metastasis as well as in the early steps of carcinogenesis [Pigott and Power, The Adhesion Molecule (Academic Press, London (1993); Rosales et al., Biochem. Biophys. Acta, 1242: 77–98 (1995)]. Therefore, the present finding of MN being an adhesion molecule appears very plausible. The development of tumors is generally a multi-step process; in cervical carcinomas, papillomaviruses certainly play an important rule [Zur Hausen et al., Virology, 184: 9–13 (1991)]. The ectopic expression of MN protein could represent an additional step. A third factor participating in the genesis of cervical carcinomas is most likely the loss or inactivation of tumor suppressor genes.

The extracellular part of MN protein contains domains homologous to proteoglycans and to CAs. Both of those are known to be engaged in cell-to-cell contacts, or in binding of cells to the extracellular matrix. Receptor protein tyrosine phosphatase β is a cell membrane protein in embryo brains, binding by its CA domain to contactin on the surface of neurons, and by its proteoglycan domain to the glia [Peles et al., (1995) supra]. Another example is vaccinia virus, containing a CA domain in its surface glycoprotein, which is responsible for virus attachment to cellular receptors [Maa et al., J. Biol. Chem., 265: 1569–1577 (1990)]. Both of those structures related to CAs are enzymatically inactive. Due to mutations in the active center, they cannot bind $Zn^{2+}$ ions, but its pocket-like structure was preserved, with potential to accommodate other ligands than $CO_2+H_2O$.

The CA and proteoglycan domains of the MN protein could, like in the above mentioned proteins, be involved in cell-to-cell interactions. Its deregulated expression could upset correct communication among cells. Years ago, contact inhibition was shown to be mediated by direct interactions between cells [Stoker, M. G. P., J. Cell. Sci., 2: 293–304 (1967], but its molecular mechanism has not been satisfactorily elucidated up to now. MN protein may interfere in signal transmission establishing contact inhibition.

Reversion of tumor cells to normal phenotype was first described in hamster cells transformed with Rous sarcoma virus. The cells changed their chaotic growth back to the original parallel array [Macpherson, I., Science, 148: 1731–1733 (1965)]. The src oncogene was transcriptionally silenced in segregated revertants. The provirus was shown to be methylated, and the methylation is known to prevent transcription [Searle et al., Nucl. Acid. Res., 12: 5193–5210 (1984)]. Reversion was also found in other tumor cells, which was again due to the methylation of the src gene [Hejnar et al., Cell Growth Differ., 5: 277–284 (1994)]. The frequency of reversion in those cases was of the order of $10^{-2}$/cell/division.

Methylation of the MN insert was clearly not the cause of reversion in the system presented here, since the revertants contained the MN protein. In some instances, the reversion was explained by mutations of the src oncogene [Oppermann et al., Virology, 108: 47–70 (1981)], but in MN, mutation did not account for the reversion in MN-transformed cells.

All the MN-transformed cells revert within 4–5 weeks. A plausible (but not the only) explanation could be that the MN protein expressed in transfected cells, after some interval, switches on a suppressor gene(s), which code(s) for a hypothetical "normalizing" protein. This, in turn, neutralizes the transforming activity of the MN protein. This postulated suppressor gene is switched off in normal cells, not containing MN protein, and it is lost or inactivated in tumor cells.

Hybridization of HeLa cells with normal fibroblasts [Stanbridge et al., supra] indicated that HeLa cells express a critical oncogene, responsible for tumorigenicity in nude mice. This oncogene is counteracted by a tumor suppressor gene (or genes), which is absent or inactive in HeLa cells, but is functioning in fibroblasts. The original HeLa x fibroblast hybrid was non-tumorigenic, but it segregated clones with restored tumorigenicity. Tumorigenic segregants lost chromosome 11, containing the putative suppressor gene.

The MN protein is a candidate for being the product of the critical oncogene; its expression in the hybrids has been shown to correlate with their tumorigenicity [e.g., Zavada et al. (1993), supra]. The present results indicate that additional mechanisms might exist, which are able to "heal" a cancerous cell. Understanding the molecular mechanisms of action of MN protein in normal and in tumor cells and elucidating how the reversion works may provide new approaches to cancer therapy.

Prospects for Therapy. There are many new principles of cancer therapy employing oncoproteins or molecules that interact with them as targets [Mendelsohn and Lippman, "Principles of molecular cell biology of cancer: growth factors," In: DeVita et al., eds., *Cancer: principles and practice of oncology*, pp. 114–133 4th ed., Philadelphia: Lippinocott (1993); DeVita et al., eds., *Biologic therapy of cancer*, 2nd ed., Philadelphia: Lippinocott (1995)]. The MN protein and at least some of its ligands (or receptors) appear to be particularly suitable for such purposes. MN protein is located on the cell surface and is thus vulnerable. It is present in a high percentage of certain human tumors, but is normally expressed abundantly only in the gastric and gallbladder mucosa as shown infra.

EXAMPLE 4

Identification of MN's Binding Site

MN protein is a tumor-associated cell adhesion molecule (CAM). To identify its binding site, a series of overlapping oligopeptides, spanning the N-terminal domain of the MN protein were synthesized. The N-terminal domain is homologous to that of proteoglycans and contains a tandem repeat of six amino acids.

The series of oligopeptides were tested by the cell adhesion assay procedure essentially as described above in Example 3. The synthetic oligopeptides were immobilized on hydrophobic plastic surfaces to see if they would mediate the attachment, spreading and growth of cells. Also investigated were whether the oligopeptides or antibodies inhibited attachment of cells (NIH3T3, HeLa and CGL1) to purified MN protein coated onto such plastic surfaces. The MN protein was affinity purified on agarose covalently linked to sulfonamide, as the MN protein encompasses a CA domain.

Several of the oligopeptides were found to be biologically active: (i) when immobilized onto the plastic, they mediate attachment of cells (NIH3T3, HeLa and to CGL1); (ii) when added to the media, they compete for attachment to cells with the immobilized MN protein; (iii) these oligopeptides, present in the media do not inhibit attachment of cells to TC plastic, but they prevent cell-cell adhesion and formation of intercellular contacts; (iv) treatment of immobilized MN protein and of active peptides with MAb M75 abrogates their affinity for the cells; and (v) the binding site of MN was determined to be closely related or identical to the epitope for MAb M75, at least two copies of which are located in the 6-fold tandem repeat of 6 amino acids [aa 61–96 (SEQ ID NO: 97)] in the proteoglycan domain of MN protein.

It was concluded that ectopically expressed MN protein most likely participates in oncogenesis by intervention into normal cell-cell contacts. MN's binding site represents a potential target for which therapeutic agents can be designed.

EXAMPLE 5

Identification of Peptides Binding to MN Protein Using Phage Display (a) To identify peptides that are recognized by MN protein, a heptapeptide phage display library [Ph.D.®-7 Peptide 7-mer Library Kit (phage display peptide library kit); New England Biolabs; Beverly, Mass. (USA)] was screened. In screening the library, a selection process, i.e., biopanning [Parmley and Smith, *Gene*, 73: 308 (1988); Noren, C. J., *NEB Transcript*, 8(1): 1 (1996)] was carried out by incubating the phages encoding the peptides with a plate coated with MN protein, washing away the unbound phage, eluting and amplifying the specifically bound phage.

The target MN protein in this process was a glutathione-S-transferase (GST) MN fusion protein (GST-MN). GST-MN is a recombinantly produced fusion protein expressed from pGEX-3X-MN containing the cDNA for the MN protein without the signal peptide. GST-MN was produced in bacteria under modified cultivation conditions (decreased optical density, decreased temperature). Such cultivation prevented premature termination of translation and resulted in synthesis of the protein molecules which were in vast majority of the full length. The GST-MN protein was used for coating of the wells and binding the relevant phages. The bound phages were then eluted by acetazolamide, amplified and used for two additional rounds of screening.

After sequencing of several independent phage clones obtained after the third round of screening, the following heptapeptides were obtained:

(1) GETRAPL (SEQ ID NO: 107)
(2) GETREPL (SEQ ID NO: 108)
(3) GQTRSPL (SEQ ID NO: 109)
(4) GQTRSPL (")
(5) GQTRSPL (")
(6) GQTRSPL (")
(7) GQTRSPL (")

The heptapeptides show very similar or identical sequences indicating that the binding is specific. The fact that phages bearing these heptapeptides were eluted by acetazolamide, an inhibitor of carbonic anhydrase activity, indicates that the peptides bind to the CA domain of MN protein.

(b) Analogous screening of the heptapeptide phage display library is done using collagen I, shown to bind MN protein, for elution of phages. Different peptide(s) binding to different part(s) of the MN protein molecule are expected to be identified. After identifying such MN-binding peptides, the corresponding synthetic peptides shall then be analysed for their biological effects.

EXAMPLE 6

Analysis of Stomach cDNA Sequence and Expression in Tissues of Human and Rat Alimentary Tracts Pastorekova et al., *Gastroenterology*, 112: 398–408 (1997), provides an analysis of the stomach cDNA sequence and its expression in tissues of the human and rat alimentary tracts. The aim of the study was to determine if there were differences in cDNAs, to obtain an overview of distribution in the alimentary tract and to obtain data on expression in tumors.

Methods. A MN cDNA isolated from a human stomach library was sequenced along with the cDNA derived from HeLa cells. Western blotting and immunohistochemical analyses of human and animal tissues were performed using MN-specific M75 MAb and rabbit antiserum to human CA II.

Results. Sequence analysis showed no differences between the stomach- and HeLa-derived cDNAs. MN was detected at the basolateral surface of gastric, intestinal, and gallbladder epithelia. In stomach tumor samples, expression of MN was lost or reduced.

Conclusions. Differential distribution of MN in normal and tumor tissues is not associated with cDNA mutations. Evolutionary conservation in vertebrates as well as abundant expression of MN protein in normal human gastric mucosa, but not in derived tumors, indicate its physiological importance.

Details of the *Materials and Methods* used and a detailed discussion of the results of this study can be found in Pastorekova et al., id. Summarized below in Table 3 is the immunostaining data on MN's distribution in the human and rat alimentary tracts.

TABLE 3

Summary of the Distribution of MN/CA IX in the Human and Rat Alimentary Tract

| Organs | Historical site | Rat | Human |
| --- | --- | --- | --- |
| Oral mucosa | surface epithelial cells | n.d. | − |
| Parotid gland | serous cells | − | − |
| | duct cells | − | − |
| Submandibular gland | serous cells | − | − |
| | mucous cells | − | − |
| | duct cells | − | − |
| Esophagus | surface epithelial cells | n.d. | − |
| | mucous glands | n.d. | − |
| Stomach | surface epithelial cells | +++ | +++ |
| | parietal cells | +++ | +++ |
| | zymogen cells | +++ | +++ |
| Duodenum | surface epithelial cells | ++ | n.d. |
| | Brunner's glands | − | n.d. |
| Jejunum | surface nongoblet epithelial cells | − | n.d. |
| | goblet cells | − | n.d. |
| Ileum | surface nongoblet epithelial cells | − | + |
| | goblet cells | − | + |
| Colon (proximal) | surface nongoblet epithelial cells | +++ | + |
| | goblet cells | +++ | + |
| Colon (middle) | surface nongoblet epithelial cells | ++ | + |
| | goblet cells | ++ | + |
| Colon (distal) | surface nongoblet epithelial cells | + | n.d. |
| | goblet cells | + | n.d. |
| Liver | hepatocytes | − | − |
| | duct cells | + | ++ |
| Gallbladder | luminal epithelial cells | n.d | +++ |
| Pancreas | zymogen cells | − | − |
| | islets of Langerhans | − | − |
| | duct cells | − | + |

−, no staining; +, weak staining; ++, moderate staining; +++, intense staining; n.d., not done.

Data was obtained by immunohistochemical staining of several tissue samples. The intestinal metaplasia of the gastric mucosa showed a faint positive staining for MN/CA IX which is, however, considerably weaker than that of normal stomach mucosa. No positive reaction for MN/CA IX was seen in a sample from a gastric adenocarcinoma, while the neoplastic epithelial cells of the same sample showed intense signal for human CA II. Four additional samples of stomach carcinomas were found to be negative for MN/CA IX. These data indicates that the expression of MN/CA IX is lost or considerably reduced in stomach tumor cells.

EXAMPLE 7

MN/CA IX Expression in Colorectal Tumors

In the normal human colon, MN/CA IX is expressed in the proliferating zone of the crypt epithelium with gradual decrease in the distal colorectum. Saarnio et al., *Am. J. Pathol.*, 153(1): 279 (1998), reports on a study of MN expression in a series of colorectal neoplasms and a comparative analysis of MN and Ki-67 expression in colorectal tumors. Ki-67, a nuclear protein, has been reported as a reliable marker of cell proliferation in the gastrointestinal mucosa. [Lee et al., *Cancer*, 78: 1881–1897 (1996); Holt et al., *Cancer Epidemiol. Biomarkers Prev.*, 6: 131–135 (1997).] The comparative analysis confirmed that MN is expressed in areas with high proliferative capacity, and indicates that MN has utility as a marker for a cell proliferation in the colorectal mucosa. The increase and abnormal localization of MN expression observed in colorectal tumors points to MN's functional involvement in the pathogenesis of colorectal tumors.

Specimens

Studied were 69 colonic lesions from 60 patients, including 8 hyperplastic polyps, 1 juvenile polyp, 39 adenomas, and 21 adenocarcinomas. Seven metastases of colorectal adenocarcinomas were also analyzed, including six mesenteric lymph node metastases and one liver metastasis. The adenomatous lesions included 18 tubular, 11 tubulovillous, and 4 villous tumors. The grade of dysplasia was low in 13 lesions, moderate in 19, and high in 8. Some tumors showed varying dysplasia or adenomatous and invasive histology in the same lesion. There were three patients with familial adenomatous polyposis disease from whom two samples were analyzed, one from the cecum and the other from the rectum.

The group of 21 malignant colorectal tumors consisted of 6 well differentiated, 9 moderately differentiated, and 6 poorly differentiated adenocarcinomas. There were 6 adenocarcinomas with a mucinous component. There were 2 carcinomas of stage A in Dukes' classification, 10 at stage B, 7 at stage C, and 2 at stage D. The primary lesions had been isolated from the right colon (n=13), transverse colon (n=19), descending colon (n=8), sigmoid colon (n=13), and rectum (n=16).

Antibodies and Immunostaining

The MN-specific MAb M75 was used. Polyclonal anti-CA VI serum was used as a control since CA VI has the greatest homology to MN, but is not expressed in the gut. Additional controls were obtained by omitting the first antibody from immunostaining. Sections were immunostained according to the biotin-streptavidin complex method as described above. The intensity of staining for MN was scored by two of the investigators on a scale of 0 to 2 as follows: 0, absent or weak focal reaction; 1, weak reaction; 2 moderate to strong reaction. The distribution of immunoreactivity between the superficial and deep parts of the mucosa was recorded separately.

To assess proliferative activity, the serial sections were stained with a primary antibody to Ki-67 (clone MIB-1, PharMingen, San Diego, Calif.) and detected by a biotin-streptavidin-peroxidase system, and the sections were counterstained with Harris' hematoxylin. The number of MIB-1 positive cells was counted in both the superficial and the deep half of the mucosa. All positively stained nuclei, regardless of intensity, were regarded as positive. An approximation to the Ki-67 score (labeling index) was obtained for each sample as the percentage of tumor cells counted that had positively stained nuclei.

Sixteen samples containing areas of normal mucosa were used to calculate the control labeling index for Ki-67. The mean value of the score for the proliferative zone of the normal mucosa was 37% with a 95% confidence interval from 28% to 46%. To allow comparison with plasma-membrane-associated MN, the immunoreactivities of the nuclear Ki-67 were adjusted to the same scale of 0 to 2, on which 0 represents less than 28% (weak staining), 1 represents 28% to 46% (moderate staining), and 2 represents more than 46% (strong staining). Further details on the *Materials and Methods* used in this study can be found in Saarnio et al., *Am. J. Pathol.*, 153(1): 279–285 (1998).

TABLE 4

Summary of the Immunohistochemical Staining for MN in the Normal Colorectal Mucosa, Colorectal Tumors, and Metastases of Colorectal Carcinomas

|  | n | Mean MN SF (median, range) | Mean MN DE (median, range) | Mean MN SF/DE |
|---|---|---|---|---|
| Normal epithelium | 16 | 0 (0,0–0) | 0.3 (0,0–1) | 0 |
| Hyperplastic polyps | 8 | 0.1 (0,0–1) | 1.1 (1,0–2) | 0.1 |
| Adenomatous lesions | 39 | 1.1 (1,0–2) | 0.5 (0,0–2) | 2.3 |
| SD | 13 | 0.9 (1,0–2) | 0.2 (0,0–2) | 4.5 |
| MD | 19 | 1.3 (1,0–2) | 0.6 (10,0–2) | 2.2 |
| GD | 8 | 1.0 (1,0–2) | 0.7 (1,0–2) | 1.7 |
| Malignant lesions | 21 | 1.2 (2,0–2) | 1.3 (2,0–2) | 1.0 |
| Grade I | 6 | 1.7 (2,1–2) | 1.5 (2,1–2) | 1.0 |
| Grade II | 9 | 1.1 (2,0–2) | 1.2 (2,0–2) | 0.9 |
| Grade III | 6 | 0.8 (1,0–2) | 0.8 (1,0–2) | 1.0 |
| Metastases | 7 | 0.6 (0,0–2) | 0.6 (0,0–2) | 1.0 |

SF, superficial epithelial staining; DE, deep epithelial staining; SD, slight dysplasia; MD, moderate dysplasia; GD, grave dysplasia.

TABLE 5

Summary of the Immunohistochemical Staining for Ki-67 in the Normal Colorectal Mucosa, Colorectal Tumors, and Metasases of Colorectal Carcinomas

|  | n | Mean Ki-67 SF (median,range) | Mean Ki-67 DEd(median, range) | Mean Ki-67 SF/DE |
|---|---|---|---|---|
| Normal epithelium | 16 | 0 (0,0–0) | 0.9 (1,0–2) | 0 |
| Hyperplastic polyps | 8 | 0 (0,0–0) | 2.0 (2,2–2) | 0 |
| Adenomatous lesions | 39 | 1.7 (2,1–2) | 0.5 (0,0–2) | 3.4 |
| SD | 13 | 1.7 (2,1–2) | 0.2 (0,0–1) | 8.5 |
| MD | 19 | 1.6 (2,1–2) | 0.5 (0,0–2) | 3.2 |
| GD | 8 | 1.9 (2,1–2) | 1.1 (1,5,0–2) | 1.7 |
| Malignant lesions | 21 | 1.8 (2,1–2) | 1.5 (2,0–2) | 1.2 |
| Grade I | 6 | 2.0 (2,2–2) | 1.7 (2,1–2) | 1.2 |
| Grade II | 9 | 1.9 (1.5, 1–2) | 1.7 (1.5, 1–2) | 1.1 |
| Grade III | 6 | 1.4 (1,0–2) | 1.2 (1,0–2) | 1.2 |
| Metastases | 7 | 0.6 (1,0–2) | 0.6 (1,0–2) | 1.0 |

SF, superficial epithelial staining; DE, deep epithelial staining; SD, slight dysplasia; MD, moderate dysplasia; GD, grave dysplasia.

Results

An outline of the MN and Ki-67 immunoreactivities estimated in the colorectal lesions is presented in Tables 4 and 5. The intensity of MN immunostaining was compared with Ki-67 in the superficial and deep parts of the lesions. There was a significant correlation between MN and Ki-67 immunoreactivity for superficial (C=0.30, P<0.01) and for cryptal (C=0.31, P<0.01) staining (Spearman).

Normal Mucosa. Sixteen samples contained normal mucosa in which MN staining was generally quite weak or absent. The staining was localized to the basolateral plasma membrane of the cryptal epithelial cells, and it was also these cells that showed high Ki-67 immunoreactivity. Occasional epithelial cells in the superficial mucosa expressed Ki-67 (mean, 3%), whereas no reaction was detected for MN.

Nonneoplastic Polyps of the Large Intestine. The expression of MN was studied in one juvenile polyp and eight hyperplastic polyps. The immunostaining of the juvenile polyp for MN was negative. Most hyperplastic polyps showed a weak or moderate reaction only in the deep parts of the cryptal epithelium, and two of them did not show any immunoreactivity at all. There were no differences in staining intensity between the proximal and distal polyps. The cryptal cells also showed an intense immunoreaction for Ki-67.

Adenomatous Polyps

The 39 adenomatous lesions were obtained from 30 patients, including 3 with familial adenomatous polyposis disease. No staining for MN was found in eight lesions (20%), which were located mainly in the distal part of the colon and rectum. Nineteen lesions (49%) showed weak staining and twelve (31%) a moderate to strong reaction, located mainly in the basolateral plasma membrane of the superficial epithelium. The MN-positive lesions were evenly distributed along with the cranial-caudal axis of the large intestine. No differences in the immunoreactivity were observed between the adenomas obtained from patients with familial adenomatous polyposis and sporadic adenomas.

There were 13, 19, and 8 lesions showing low, moderate, or severe dysplasia, respectively. In the group with low dysplasia, eight lesions stained for MN in the superficial part of the mucosa but only two in the cryptal area as well. Furthermore, 17 adenomas with moderate dysplasia were stained superficially, whereas the cryptal epithelium was also positive in 9 lesions. Six of the eight adenomas with severe dysplasia gave a positive signal. The staining for MN was more diffuse in the more dysplastic adenomas, all of which expressed it in the superficial epithelium and five in the cryptal area. Differences in the staining intensity, however, were not statistically significant (Mann-Whitney test).

Both the Ki-67 and MN markers show an extension in staining from the crypts to the surface in adenomatous lesions relative to the normal epithelium.

Malignant Lesions

The material included 21 malignant colorectal tumours, 6 well differentiated adenocarcinomas, 9 moderately differentiated, and 6 poorly differentiated. The stage according to Dukes' classification was A in 2 carcinomas, B in 10, C in 7, and D in 2.

No staining for MN was observed in 5 carcinomas (24%), whereas 6 (29%) showed a weak positive reaction and 10 (47%) a moderate to strong reaction. The immunostaining was localized to the plasma membrane of the tumor cells. Interestingly, the most intense signals were seen in five of the six adenocarcinomas with a mucinous component. Staining intensity did not correlate with the location of the carcinoma, but it showed a trend to correlate with the histological grade, being higher in the well differentiated tumors. The mean staining intensities were 1.7, 1.2, and 0.8 in grades 1, 2, and 3, respectively (grade 1/grade 3, $P=0.05$, Mann-Whitney). Similarly, the mean staining intensity was higher (1.5) in less advanced tumors (Dukes A plus B, n=12) than in more advanced ones (1.0; Dukes C plus D, n=9; $P<0.047$, Mann-Whitney test). The MN staining was generally diffuse, being present in both the superficial and deep parts of the mucosa. A diffuse staining pattern was also characteristic of Ki-67. Interestingly, desmoplastic connective tissue in the malignant lesions occasionally showed prominent immunostaining for MN.

The data on simultaneous expression of Ki-67 and MN in both the superficial and deep parts of the mucosa show that the staining for both antigens is more intense in malignant tumors than in the normal mucosa, with only a few exceptions.

Six mesenteric lymph node metastases of colorectal carcinoma and one liver metastasis was studied. Three of six lymph node metastases were positive in the same manner as their primary tumors. The liver metastasis and its primary carcinoma also showed an intense immunoreaction for MN.

Discussion

An adenoma-carcinoma morphological model has been proposed that involves a sequence of histological changes from a normal colonic epithelium through benign adenomas that become increasingly dysplastic and finally develop into cancer. [Faeron and Vogelstein, Cell, 61: 759–767 (1990).] Colorectal cancers typically develop over decades and appear to require several genetic events for the completion of the malignant phenotype. [Lengauer et al., Nature, 386: 623–627 (1997); and Kinzler and Vogelstein, Cell, 87: 159–170 (1996).] One important consequence of these genetic aberrations is that cell proliferation is abnormally increased in premalignant and malignant lesions of the colorectal epithelium. [Risio, M., J. Cell Biochem, 16G: 79–87 (1992).]

Several important aspects of MN expression emerged from this investigation: 1) hyperplastic polyps showed immunoreaction in the cryptal area, as reported for normal mucosa, 2) MN was more widespread and abundant in the surface epithelium of adenomas, 3) the staining pattern was more diffuse in carcinomas than in benign lesions, 4) of all the carcinoma samples, the most prominent reactions were observed in the tumors with a mucinous component, and 5) the desmoplastic connective tissue of some malignant lesions revealed an intense immunoreaction. Furthermore, the results confirmed that MN is expressed on the basolateral membranes of enterocytes in hyperplastic polyps and adenomas, whereas it was the polarized expression of MN on cell surfaces that was affected in carcinomas.

To demonstrate more precisely the association of MN expression with proliferation, immunohistochemistry for Ki-67, which is one of the most reliable markers of cell proliferation was used. Ki-67 and MN were co-expressed in the same area in these lesions, indicating that MN expression is indeed related to cell proliferation.

In summary, the present results show that the majority of colorectal tumors display abnormal expression of MN, pointing to MN's involvement in their pathogenesis. Furthermore, the co-occurrence of MN and Ki-67 at the site of rapid cell proliferation indicates that MN could be used as a biomarker of increased cell proliferation in the colorectal mucosa. High expression of MN in premalignant lesions such as adenomas suggests MN's usefulness in early diagnosis of colorectal tumors.

EXAMPLE 8

Immunohistochemistry of MN in Human Gut Reveals Polarized Expression in the Epithelial Cells with the Highest Proliferative Capacity Saarnio et al., J. Histochem. Cytochem, 46(4): 497–509 (1998), presents the localization of MN (MN/CA IX) in the human gut and compares its distribution to those of carbonic anhydrases (CAs) I, II and IV, which are known to be expressed in intestinal epithelium. Immunohistochemical staining of the human gut with the M75 MAb revealed prominent polarized staining for MN in the basolateral surfaces of the enterocytes of duodenum and jejunum, the reaction being most intense in the crypts. A moderate reaction was also seen in the crypts of ileal mucosa, whereas the staining became generally weaker in the large intestine.

The results of the study indicated isozyme-specific regulation of MN expression along the cranial-caudal axis of the human gut and place MN protein at the sites of rapid cell proliferation. The unique localization of MN on the basolateral surfaces of proliferating crypt enterocytes indicates that it may serve as a ligand or a receptor for another protein that regulates intercellular communication or cell proliferation. Further, MN has a completely conserved active site domain of CAs suggesting that it could also participate in $CO_2$/bicarbonate homeostasis.

Immunohistochemistry of MN in the Gut

MN showed a unique staining pattern in human gut. First, it was highly expressed in duodenum and jejunum (as in stomach) and was distinctly less expressed in more distal segments of the gut. Second, the intestinal staining for MN was most intense in the crypts. Third, the positive signal for MN was confined to the basolateral plasma membranes in all stained enterocytes.

Table 6 shows the immunohistochemical localization of MN in different segments of the gut. Duodenum and jejunum show intense staining in the crypt enterocytes, whereas the epithelial cells in upper portions and tips of the villi showed only a weak immunoreaction. MN was also present in enterocytes of human ileum, although the positive reaction was much weaker than in duodenum and jejunum. In the large intestine, the basolateral surfaces of the crypt enterocytes showed positive staining for MN, with a gradual change in staining intensity in a distal direction. The reaction was still moderate in cecum and ascending colon, whereas the transverse and descending parts showed considerably weaker signals. Only sporadic enterocytes in sigmoid colon and rectum exhibited weak basolateral staining.

TABLE 7

Distribution of MN/CA IX, CA I, CA II, and CA IV in Human Gut*

| Segment | Histological site | MN/CA IX | CA I | CA II | CA IV |
|---|---|---|---|---|---|
| Small intestine | | | | | |
| Duodenum | SE | +/− | − | +++ | + |
| | BC | +++ | − | ++ | − |
| | BR | − | − | ++ | − |
| | ENDO | − | +++ | − | +++ |
| Jejunum | SE | +/− | − | +++ | +/− |
| | BC | +++ | + | − | − |
| | ENDO | − | +++ | − | +++ |
| Ileum | SE | +/− | − | +/− | +/− |
| | BC | ++ | + | − | − |
| | ENDO | − | +++ | − | +++ |
| Large intestine | | | | | |
| Cecum | SE | − | +++ | +++ | +++ |
| | BG | ++ | − | − | − |
| | ENDO | − | +++ | − | +++ |
| Ascending colon | SE | − | +++ | +++ | +++ |
| | BG | ++ | − | − | − |
| | ENDO | − | +++ | − | +++ |
| Transverse colon | SE | − | +++ | +++ | +++ |
| | BG | + | − | − | − |
| | ENDO | − | +++ | − | +++ |
| Descending colon | SE | − | +++ | +++ | +++ |
| | BG | + | − | − | − |
| | ENDO | − | +++ | − | +++ |
| Sigmoid colon | SE | − | +++ | +++ | +++ |
| | BG | +/− | − | − | − |
| | ENDO | − | +++ | − | +++ |
| Rectum | SE | − | +++ | +++ | +++ |
| | BG | +/− | − | − | − |
| | ENDO | − | +++ | − | +++ |

*BC, base of the crypts; BR, Brunner's glands; BG, base of the glands; ENDO, submucosal capillary endothelium; SE, surface epithelium; −, no staining; +/−, sporadic stained cells; +, weak staining; ++, moderate staining; +++, intense staining.

The major aim of the study was to investigate the regional, cellular and subcellular localization of MN in the human gut. The availability of other purified CAs expressed in the gut and antibody reagents to each of them allowed confirmation of the specificity of the anti-MN antibody (M75 MAb), and to compare MN's sites of expression to those of other CAs in parallel tissue sections. Another opportunity to verify the specificity of the M75 immunostainings was provided by the expression of MN in COS-7 cells, which produced immunoreactive protein that was localized to the plasma membrane. As reported for Western blots of human stomach, twin proteins identified by the M75 MAb on Western blots of transfected COS-7 cells were the 58-kDa form and 54-kDa form, the latter being barely apparent in this study. The M75 MAb did not cross-react with purified CA I, II, IV and VI, all of which are expressed in various parts of the alimentary tract [Parkkila and Parkkila, Scand. J. Gastorenteroli, 31: 305 (1996)], providing further evidence that the immunostaining for MN in the gut is isozyme-specific.

Saarnio et al. demonstrated that the distribution of MN in the gut has unique features. First, its subcellular localization is restricted to the basolateral surfaces of epithelial cells. Second, its cellular distribution is restricted to the crypt enterocytes, which is not seen with any other CA. Third, its regional expression is distinctive compared to other CAs, being most intense in duodenum and jejunum, and decreasing distally from moderate expression in crypts of ileum, cecum and ascending colon to only weak and sporadic expression in distal large intestine.

Restriction of MN to the epithelial cells with the greatest proliferative capacity is consistent with MN's proposed role in cell proliferation. Stem cells located in the crypts are a source for the continuous and rapid renewal of the epithelium [Gordon, J. I., J. Cell. Biol., 108: 1187–1194 (1989)]. Earlier studies in mice have shown that each small intestinal crypt produces an average of 13–16 new cells/hour [Gordon et al., FASEB J., 6: 3039–3050 (1992)]. Cell differentiation and cell migration are coupled events in the gut. The epithelial cells differentiate and mature during migration from the crypt to the apex of the villus or surface epithelial cuff [Gordon, J. I., supra (1989); Gordon et al., supra (1992) and Lipkin, M., Ann. Rev. Physiol., 47: 175–197 (1985)]. This process is completed in a few days, which makes the mammalian intestinal epithelium a unique model system for studying cell differentiation. That MN is much more abundant in the proliferating cryptal epithelium than in the upper part of the mucosa, indicates that it could be a useful marker to study the proliferation and differentiation of the intestinal epithelium. Further support for its role as a marker for cell proliferation is obtained from studies showing that the rate of cell proliferation is highest in the proximal segments of the intestine [Lipkin, M., Annu. Rev. Physiol., 47: 175 (1985); Gordon, J. I., supra (1989)], which was also the site of the highest MN expression.

As a CA-homologous transmembrane protein, MN has some structural similarity with recently described receptor-type protein tyrosine phosphatases (RPTPs) β and γ, which are members of a distinct group of phosphatases that have CA-homologous regions in their extracellular domains [Krueger and Saito, PNAS (USA) 89: 7417–7421 (1992); Levy et al., J. Biol. Chem., 268: 10573–10581 (1993); and Barnea et al., Mol. Cell. Biol., 13: 1497–1505 (1993)]. Both transmembrane and secretory forms of RPTPβ have been found to be identical with a chondroitin sulfate proteoglycan called phosphacan [Barnea et al., Cell, 76: 205 (1994); Maurel et al., PNAS (USA), 91: 2512–2516 (1994); Shitara et al., J. Biol. Chem., 269: 20189–20193 (1994); and Barnea et al., J. Biol. Chem., 269: 14349–14352 (1994)].

The CA-like domains of the RPTPβ and -γ showed about 30–50% amino acid identity with CAs [Krueger and Saito, supra (1992); Barnea et al., supra (1993); and Levy et al., supra (1993). Unlike MN, RPTPβ and -γ have only one of the three conserved histidine residues required to bind to zinc ion in catalytically active CAs. Therefore, it is unlikely that they have any CA activity.

Recent studies have indicated that the CA-like domain of RPTPβ binds to contactin, a neuronal cell recognition molecule [Peles et al., Cell, 82: 251–260 (1995)], and to tenascin, an extracellular matrix protein [Milev et al., J. Biol Chem. 270: 24650–24653 (1995)]. The CA-like domain induced cell adhesion and neurite growth of primary tectal neurons, and differentiation of neuroblastoma cells [Peles et al., supra (1995)]. MN expression, being regulated by cell density and being greatest in basolateral surfaces of proliferating cryptal enterocytes, indicates that MN may also serve as a ligand or a receptor for another protein that regulates intercellular communication and cell proliferation. However, unlike the RPTPβ and -γ, MN has a completely conserved active site domain that suggests that it could also participate in carbon dioxide/bicarbonate homeostasis.

EXAMPLE 9

Accessibility In Vivo of MN Protein Expressed in Tumor Cells and in Stomach

Lewis rats (384 g) carrying a BP6 subcutaneous tumor (about 1 cm in diameter) expressing rat MN protein were injected intraperitoneally (i.p.) with $^{125}$I-M75 Mab ($2.5 \times 10^6$ cpm). Five days later, 0.5–1 g pieces of the tumor and organs were weighed and their radioactivity was measured by a gamma counter.

Table 8 summarizes the results. The highest radioactivity was present in the tumor. Relatively high radioactivity was found in the liver and kidney, apparently reflecting the clearance of mouse IgG from the blood. The stomach continued a relatively low level of radioactivity, indicating that the M75 Mab had only limited access to MN protein exposed in the gastric mucosa.

TABLE 8

Distribution of radioactivity of $^{125}$I-M75 in rat organs and in the tumor

| Organ | cpm/g | | | | |
|---|---|---|---|---|---|
| Kidney | 2153 | 2184 | | | |
| Spleen | 653 | 555 | | | |
| Liver | 1993 | 1880 | | | |
| Lung | 1183 | 1025 | | | |
| Blood | 1449 | | | | |
| Heart | 568 | 477 | | | |
| Stomach | 1184 | 1170 | | | |
| Testis | 812 | 779 | | | |
| Tail | 647 | | | | |
| Tumor | 3646 | 4058 | 3333 | 8653 | 3839 |

EXAMPLE 10

FACS Analysis of MN Protein Expression in CGL3 Cells—Apoptosis

A FACS investigation was designed to determine the conditions that influence the synthesis of MN protein and to analyse the cell cycle distribution of MN-positive versus MN-negative cells in a CGL3 population stimulated to apoptosis. Previous Western blotting analyses have shown CGL3 cells to express a relatively high amount of MN protein under different cultivation conditions. CGL3 cells are considered a constitutive producer of MN proteins. However, Western blotting does not recognize small differences in the level of protein. In contrast FACS allows the detection of individual MN-positive cells, a calculation of their percentage in the analysed population, an estimation of the level of MN protein in the cells, and a determination of the cell cycle distribution.

To study the effect of cultivation conditions on MN expression in CGL3 cells, the CGL3 cells were plated in different relative densities and serum concentrations. Three days after plating, the cells were collected, surface labeled by M75 Mab followed by FITC-conjugated anti-mouse IgG and immediately analysed by FACS.

The analysis showed that in adherent cells, MN expression is dependent on cell density as is HeLa cells. However, low density cultures still produced detectable amounts of MN protein. In low density cultures, serum concentration does not seem to play a role. In relatively high density cultures, a decreasing serum concentration resulted in slightly diminished MN expression, probably due to a lower density that the cells were able to reach during the three days of cultivation.

The effect of the actual cell density is remarkable, and MN expression (detectable in 15–90% of the cells) represents a very sensitive monitoring factor. In all experiments, there was about a 5% higher percentage of cycling cells in the MN-positive part of the population, compared to the MN-negative part. That fact prompted the analysis of the cell cycle distribution of MN-positive CGL3 cells under unfavorable growth conditions, that is, after induction of apoptosis.

Apoptosis

CGL3 cells were stimulated to apoptotic death by several drugs, including cycloheximide, actimonycin D and dexamethasone. The FACS study showed that the onset of apoptosis is delayed in MN-positive cells suggesting a protective role of MN in this process. It was also observed that the induction of apoptosis resulted in the down-regulation of MN expression in a time-dependent manner. That same phenomenon was described for Bcl-2 anti-apoptotic protein, and there is existing opinion that the down-regulation of certain regulatory genes during apoptosis sensitizes the cells to undergo apoptotic death. To prove the role of MN in apoptosis, a similar study with cells transfected by MN cDNA is to be performed.

The preliminary results indicate the possible involvement of MN in the suppression of apoptosis. The recent view that tumors arise both as a consequence of increased proliferation and decreased cell death appears to be consistent with the association of the MN protein with tumors in vivo.

ATCC Deposits. The materials listed below were deposited with the American Type Culture Collection (ATCC) now at 10810 University Blvd., Manassus, Va. 20110-2209 (USA). The deposits were made under the provisions of the Budapest Treaty on the International Recognition of Deposited Microorganisms for the Purposes of Patent Procedure and Regulations thereunder (Budapest Treaty). Maintenance of a viable culture is assured for thirty years from the date of deposit. The hybridomas and plasmids will be made available by the ATCC under the terms of the Budapest Treaty, and subject to an agreement between the Applicants and the ATCC which assures unrestricted availability of the deposited hybridomas and plasmids to the public upon the granting of patent from the instant application. Availability of the deposited strain is not to be construed as a license to practice the invention in contravention of the rights granted under the authority of any Government in accordance with its patent laws.

| Hybridoma | Deposit Date | ATCC # |
|---|---|---|
| VU-M75 | Sep. 17, 1992 | HB 11128 |
| MN 12.2.2 | Jun. 9, 1994 | HB 11647 |
| Plasmid | Deposit Date | ATCC # |
| A4a | Jun. 6, 1995 | 97199 |
| XE1 | Jun. 6, 1995 | 97200 |
| XE3 | Jun. 6, 1995 | 97198 |

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated.

All references cited herein are hereby incorporated by reference.

SEQUENCE LISTING

<160> NUMBER OF SEQ ID NOS: 116

<210> SEQ ID NO 1
<211> LENGTH: 1522
<212> TYPE: DNA
<213> ORGANISM: HUMAN
<220> FEATURE:
<221> NAME/KEY: CDS
<222> LOCATION: (13)..(1389)
<221> NAME/KEY: mat_peptide
<222> LOCATION: (124)..(1389)

<400> SEQUENCE: 1

```
acagtcagcc gc atg gct ccc ctg tgc ccc agc ccc tgg ctc cct ctg ttg        51
          Met Ala Pro Leu Cys Pro Ser Pro Trp Leu Pro Leu Leu
              -35                 -30                 -25 atc ccg gcc cct gct cca ggc ctc act gtg caa ctg ctg ctg tca ctg          99
Ile Pro Ala Pro Ala Pro Gly Leu Thr Val Gln Leu Leu Leu Ser Leu
            -20                 -15                 -10 ctg ctt ctg atg cct gtc cat ccc cag agg ttg ccc cgg atg cag gag         147
Leu Leu Leu Met Pro Val His Pro Gln Arg Leu Pro Arg Met Gln Glu
         -5              -1   1                   5 gat tcc ccc ttg gga gga ggc tct tct ggg gaa gat gac cca ctg ggc         195
Asp Ser Pro Leu Gly Gly Gly Ser Ser Gly Glu Asp Asp Pro Leu Gly
     10                  15                  20 gag gag gat ctg ccc agt gaa gag gat tca ccc aga gag gag gat cca         243
Glu Glu Asp Leu Pro Ser Glu Glu Asp Ser Pro Arg Glu Glu Asp Pro
 25                  30                  35                  40 ccc gga gag gag gat cta cct gga gag gag gat cta cct gga gag gag         291
Pro Gly Glu Glu Asp Leu Pro Gly Glu Glu Asp Leu Pro Gly Glu Glu
                 45                  50                  55 gat cta cct gaa gtt aag cct aaa tca gaa gaa gag ggc tcc ctg aag         339
Asp Leu Pro Glu Val Lys Pro Lys Ser Glu Glu Glu Gly Ser Leu Lys
             60                  65                  70 tta gag gat cta cct act gtt gag gct cct gga gat cct caa gaa ccc         387
Leu Glu Asp Leu Pro Thr Val Glu Ala Pro Gly Asp Pro Gln Glu Pro
         75                  80                  85 cag aat aat gcc cac agg gac aaa gaa ggg gat gac cag agt cat tgg         435
Gln Asn Asn Ala His Arg Asp Lys Glu Gly Asp Asp Gln Ser His Trp
     90                  95                 100 cgc tat gga ggc gac ccg ccc tgg ccc cgg gtg tcc cca gcc tgc gcg         483
Arg Tyr Gly Gly Asp Pro Pro Trp Pro Arg Val Ser Pro Ala Cys Ala
105                 110                 115                 120 ggc cgc ttc cag tcc ccg gtg gat atc cgc ccc cag ctc gcc gcc ttc         531
Gly Arg Phe Gln Ser Pro Val Asp Ile Arg Pro Gln Leu Ala Ala Phe
                125                 130                 135 tgc ccg gcc ctg cgc ccc ctg gaa ctc ctg ggc ttc cag ctc ccg ccg         579
Cys Pro Ala Leu Arg Pro Leu Glu Leu Leu Gly Phe Gln Leu Pro Pro
            140                 145                 150 ctc cca gaa ctg cgc ctg cgc aac aat ggc cac agt gtg caa ctg acc         627
Leu Pro Glu Leu Arg Leu Arg Asn Asn Gly His Ser Val Gln Leu Thr
        155                 160                 165
```

-continued

| | | |
|---|---|---|
| ctg cct cct ggg cta gag atg gct ctg ggt ccc ggg cgg gag tac cgg<br>Leu Pro Pro Gly Leu Glu Met Ala Leu Gly Pro Gly Arg Glu Tyr Arg<br>170                           175                       180 | 675 |
| gct ctg cag ctg cat ctg cac tgg ggg gct gca ggt cgt ccg ggc tcg<br>Ala Leu Gln Leu His Leu His Trp Gly Ala Ala Gly Arg Pro Gly Ser<br>185                         190                          195                     200 | 723 |
| gag cac act gtg aa ggc cac cgt ttc cct gcc gag atc cac gtg gtt<br>Glu His Thr Val Glu Gly His Arg Phe Pro Ala Glu Ile His Val Val<br>                     205                         210                         215 | 771 |
| cac ctc agc acc gcc ttt gcc aga gtt gac gag gcc ttg ggg cgc ccg<br>His Leu Ser Thr Ala Phe Ala Arg Val Asp Glu Ala Leu Gly Arg Pro<br>                220                         225                       230 | 819 |
| gga ggc ctg gcc gtg ttg gcc gcc ttt ctg gag gag ggc ccg gaa gaa<br>Gly Gly Leu Ala Val Leu Ala Ala Phe Leu Glu Glu Gly Pro Glu Glu<br>                       235                        240                       245 | 867 |
| aac agt gcc tat gag cag ttg ctg tct cgc ttg gaa gaa atc gct gag<br>Asn Ser Ala Tyr Glu Gln Leu Leu Ser Arg Leu Glu Glu Ile Ala Glu<br>               250                         255                     260 | 915 |
| gaa ggc tca gag act cag gtc cca gga ctg gac ata tct gca ctc ctg<br>Glu Gly Ser Glu Thr Gln Val Pro Gly Leu Asp Ile Ser Ala Leu Leu<br>265                           270                       275                     280 | 963 |
| ccc tct gac ttc agc cgc tac ttc caa tat gag ggg tct ctg act aca<br>Pro Ser Asp Phe Ser Arg Tyr Phe Gln Tyr Glu Gly Ser Leu Thr Thr<br>                       285                         290                     295 | 1011 |
| ccg ccc tgt gcc cag ggt gtc atc tgg act gtg ttt aac cag aca gtg<br>Pro Pro Cys Ala Gln Gly Val Ile Trp Thr Val Phe Asn Gln Thr Val<br>                     300                         305                       310 | 1059 |
| atg ctg agt gct aag cag ctc cac acc ctc tct gac acc ctg tgg gga<br>Met Leu Ser Ala Lys Gln Leu His Thr Leu Ser Asp Thr Leu Trp Gly<br>                   315                        320                       325 | 1107 |
| cct ggt gac tct cgg cta cag ctg aac ttc cga gcg acg cag cct ttg<br>Pro Gly Asp Ser Arg Leu Gln Leu Asn Phe Arg Ala Thr Gln Pro Leu<br>               330                         335                     340 | 1155 |
| aat ggg cga gtg att gag gcc tcc ttc cct gct gga gtg gac agc agt<br>Asn Gly Arg Val Ile Glu Ala Ser Phe Pro Ala Gly Val Asp Ser Ser<br>345                           350                       355                     360 | 1203 |
| cct cgg gct gct gag cca gtc cag ctg aat tcc tgc ctg gct gct ggt<br>Pro Arg Ala Ala Glu Pro Val Gln Leu Asn Ser Cys Leu Ala Ala Gly<br>                365                         370                     375 | 1251 |
| gac atc cta gcc ctg gtt ttt ggc ctc ctt ttt gct gtc acc agc gtc<br>Asp Ile Leu Ala Leu Val Phe Gly Leu Leu Phe Ala Val Thr Ser Val<br>                     380                         385                     390 | 1299 |
| gcg ttc ctt gtg cag atg aga agg cag cac aga agg gga acc aaa ggg<br>Ala Phe Leu Val Gln Met Arg Arg Gln His Arg Arg Gly Thr Lys Gly<br>               395                         400                     405 | 1347 |
| ggt gtg agc tac cgc cca gca gag gta gcc gag act gga gcc<br>Gly Val Ser Tyr Arg Pro Ala Glu Val Ala Glu Thr Gly Ala<br>410                           415                       420 | 1389 |
| tagaggctgg atcttggaga atgtgagaag ccagccagag gcatctgagg gggagccggt | 1449 |
| aactgtcctg tcctgctcat tatgccactt ccttttaact gccaagaaat ttttaaaat | 1509 |
| aaatatttat aat | 1522 |

<210> SEQ ID NO 2
<211> LENGTH: 459
<212> TYPE: PRT
<213> ORGANISM: HUMAN

<400> SEQUENCE: 2

Met Ala Pro Leu Cys Pro Ser Pro Trp Leu Pro Leu Leu Ile Pro Ala

-continued

```
            -35                 -30                 -25
Pro Ala Pro Gly Leu Thr Val Gln Leu Leu Ser Leu Leu Leu
    -20                 -15                 -10

Met Pro Val His Pro Gln Arg Leu Pro Arg Met Gln Glu Asp Ser Pro
 -5              -1   1               5                  10

Leu Gly Gly Ser Ser Gly Glu Asp Asp Pro Leu Gly Glu Glu Asp
             15                  20                  25

Leu Pro Ser Glu Glu Asp Ser Pro Arg Glu Glu Asp Pro Gly Glu
         30                  35                  40

Glu Asp Leu Pro Gly Glu Glu Asp Leu Pro Gly Glu Glu Asp Leu Pro
     45                  50                  55

Glu Val Lys Pro Lys Ser Glu Glu Gly Ser Leu Lys Leu Glu Asp
 60              65                  70                  75

Leu Pro Thr Val Glu Ala Pro Gly Asp Pro Gln Glu Pro Gln Asn Asn
                 80                  85                  90

Ala His Arg Asp Lys Glu Gly Asp Asp Gln Ser His Trp Arg Tyr Gly
             95                 100                 105

Gly Asp Pro Pro Trp Pro Arg Val Ser Pro Ala Cys Ala Gly Arg Phe
         110                 115                 120

Gln Ser Pro Val Asp Ile Arg Pro Gln Leu Ala Ala Phe Cys Pro Ala
     125                 130                 135

Leu Arg Pro Leu Glu Leu Leu Gly Phe Gln Leu Pro Pro Leu Pro Glu
140                 145                 150                 155

Leu Arg Leu Arg Asn Asn Gly His Ser Val Gln Leu Thr Leu Pro Pro
                 160                 165                 170

Gly Leu Glu Met Ala Leu Gly Pro Gly Arg Glu Tyr Arg Ala Leu Gln
             175                 180                 185

Leu His Leu His Trp Gly Ala Ala Gly Arg Pro Gly Ser Glu His Thr
         190                 195                 200

Val Glu Gly His Arg Phe Pro Ala Glu Ile His Val Val His Leu Ser
     205                 210                 215

Thr Ala Phe Ala Arg Val Asp Glu Ala Leu Gly Arg Pro Gly Gly Leu
220                 225                 230                 235

Ala Val Leu Ala Ala Phe Leu Glu Glu Gly Pro Glu Glu Asn Ser Ala
                 240                 245                 250

Tyr Glu Gln Leu Leu Ser Arg Leu Glu Glu Ile Ala Glu Glu Gly Ser
             255                 260                 265

Glu Thr Gln Val Pro Gly Leu Asp Ile Ser Ala Leu Leu Pro Ser Asp
         270                 275                 280

Phe Ser Arg Tyr Phe Gln Tyr Glu Gly Ser Leu Thr Thr Pro Pro Cys
     285                 290                 295

Ala Gln Gly Val Ile Trp Thr Val Phe Asn Gln Thr Val Met Leu Ser
300                 305                 310                 315

Ala Lys Gln Leu His Thr Leu Ser Asp Thr Leu Trp Gly Pro Gly Asp
                 320                 325                 330

Ser Arg Leu Gln Leu Asn Phe Arg Ala Thr Gln Pro Leu Asn Gly Arg
             335                 340                 345

Val Ile Glu Ala Ser Phe Pro Ala Gly Val Asp Ser Ser Pro Arg Ala
         350                 355                 360

Ala Glu Pro Val Gln Leu Asn Ser Cys Leu Ala Ala Gly Asp Ile Leu
     365                 370                 375

Ala Leu Val Phe Gly Leu Leu Phe Ala Val Thr Ser Val Ala Phe Leu
380                 385                 390                 395
```

```
Val Gln Met Arg Arg Gln His Arg Arg Gly Thr Lys Gly Gly Val Ser
                400                 405                 410

Tyr Arg Pro Ala Glu Val Ala Glu Thr Gly Ala
            415                 420

<210> SEQ ID NO 3
<211> LENGTH: 29
<212> TYPE: DNA
<213> ORGANISM: HUMAN

<400> SEQUENCE: 3
cgcccagtgg gtcatcttcc ccagaagag                                           29

<210> SEQ ID NO 4
<211> LENGTH: 19
<212> TYPE: DNA
<213> ORGANISM: HUMAN

<400> SEQUENCE: 4
ggaatcctcc tgcatccgg                                                      19

<210> SEQ ID NO 5
<211> LENGTH: 10898
<212> TYPE: DNA
<213> ORGANISM: HUMAN
<220> FEATURE:
<221> NAME/KEY: gene
<222> LOCATION: (1)..(10898)
<223> OTHER INFORMATION: full-length MN genomic sequence
<221> NAME/KEY: unsure of base at position 1974
<222> LOCATION: (1974)
<223> OTHER INFORMATION: unsure of base at position 1974, which is in
      the 5' region flanking the transcription initiation site (3507)
      as determined by RNase protection assay.

<400> SEQUENCE: 5
ggatcctgtt gactcgtgac cttaccccca accctgtgct ctctgaaaca tgagctgtgt         60
ccactcaggg ttaaatggat taagggcggt gcaagatgtg ctttgttaaa cagatgcttg        120
aaggcagcat gctcgttaag agtcatcacc aatccctaat ctcaagtaat cagggacaca        180
aacactgcgg aaggccgcag ggtcctctgc ctaggaaaac cagagacctt tgttcacttg        240
tttatctgac cttccctcca ctattgtcca tgaccctgcc aaatccccct ctgtgagaaa        300
cacccaagaa ttatcaataa aaaataaat ttaaaaaaaa aatacaaaaa aaaaaaaaa          360 aaaaaaaaaa gacttacgaa tagttattga taaatgaata gctattggta aagccaagta        420
aatgatcata ttcaaaacca gacggccatc atcacagctc aagtctacct gatttgatct        480
ctttatcatt gtcattcttt ggattcacta gattagtcat catcctcaaa attctccccc        540
aagttctaat tacgttccaa acatttaggg gttacatgaa gcttgaacct actaccttct        600
ttgcttttga gccatgagtt gtaggaatga tgagtttaca ccttacatgc tggggattaa        660
tttaaacttt acctctaagt cagttgggta gcctttggct tattttgta gctaattttg         720 tagttaatgg atgcactgtg aatcttgcta tgatagtttt cctccacact ttgccactag        780
gggtaggtag gtactcagtt ttcagtaatt gcttacctaa gaccctaagc cctatttctc        840
ttgtactggc ctttatctgt aatatgggca tatttaatac aatataattt ttggagtttt        900
tttgtttgtt tgtttgtttg ttttttttgag acggagtctt gcatctgtca tgcccaggct        960
ggagtagcag tggtgccatc tcggctcact gcaagctcca cctcccgagt tcacgccatt       1020
ttcctgcctc agcctcccga gtagctggga ctacaggcgc ccgccaccat gcccggctaa      1080
```

-continued

```
tttttttgtat ttttggtaga gacggggttt caccgtgtta gccagaatgg tctcgatctc   1140
ctgacttcgt gatccacccg cctcggcctc ccaaagttct gggattacag gtgtgagcca   1200
ccgcacctgg ccaattttttt gagtctttta aagtaaaaat atgtcttgta agctggtaac   1260
tatggtacat ttcctttttat taatgtggtg ctgacggtca tataggttct tttgagtttg   1320
gcatgcatat gctactttttt gcagtccttt cattacattt ttctctcttc atttgaagag   1380
catgttatat cttttagctt cacttggctt aaaaggttct ctcattagcc taacacagtg   1440
tcattgttgg taccacttgg atcataagtg aaaaacagt caagaaattg cacagtaata   1500
cttgtttgta agagggatga ttcaggtgaa tctgacacta agaaactccc ctacctgagg   1560
tctgagattc ctctgacatt gctgtatata ggcttttcct ttgacagcct gtgactgcgg   1620
actatttttc ttaagcaaga tatgctaaag ttttgtgagc ctttttccag agagaggtct   1680
catatctgca tcaagtgaga acatataatg tctgcatgtt tccatatttc aggaatgttt   1740
gcttgtgttt tatgctttta tatagacagg gaaacttgtt cctcagtgac ccaaaagagg   1800
tgggaattgt tattggatat catcattggc ccacgctttc tgaccttgga aacaattaag   1860
ggttcataat ctcaattctg tcagaattgg tacaagaaat agctgctatg tttcttgaca   1920
ttccacttgg taggaaataa gaatgtgaaa ctcttcagtt ggtgtgtgtc cctngttttt   1980
ttgcaatttc cttcttactg tgttaaaaaa agtatgatc ttgctctgag aggtgaggca   2040
ttcttaatca tgatctttaa agatcaataa tataatcctt tcaaggatta tgtctttatt   2100
ataataaaga taatttgtct ttaacagaat caataatata atcccttaaa ggattatatc   2160
tttgctgggc gcagtggctc acacctgtaa tcccagcact tgggtggcc aaggtggaag   2220
gatcaaattt gcctacttct atattatctt ctaaagcaga attcatctct cttccctcaa   2280
tatgatgata ttgacagggt ttgccctcac tcactagatt gtgagctcct gctcagggca   2340
ggtagcgttt tttgttttttg tttttgtttt tcttttttga cagggtct tgctctgtca   2400
cccaggccag agtgcaatgg tacagtctca gctcactgca gcctcaaccg cctcggctca   2460
aaccatcatc ccatttcagc ctcctgagta gctgggacta caggcacatg ccattacacc   2520
tggctaattt ttttgtattt ctagtagaga cagggtttgg ccatgttgcc cgggctggtc   2580
tcgaactcct ggactcaagc aatccaccca cctcagcctc ccaaaatgag gaccgtgtc   2640
ttattcattt ccatgtccct agtccatagc ccagtgctgg acctatggta gtactaaata   2700
aatatttgtt gaatgcaata gtaaatagca tttcagggag caagaactag attaacaaag   2760
gtggtaaaag gtttggagaa aaaaataata gtttaatttg gctagagtat gagggagagt   2820
agtaggagac aagatggaaa ggtctcttgg gcaaggtttt gaaggaagtt ggaagtcaga   2880
agtacacaat gtgcatatcg tggcaggcag tggggagcca atgaaggctt ttgagcagga   2940
gagtaatgtg ttgaaaaata aatataggtt aaacctatca gagcccctct gacacataca   3000
cttgctttttc attcaagctc aagtttgtct cccacatacc cattacttaa ctcaccctcg   3060
ggctccccta gcagcctgcc ctacctcttt acctgcttcc tggtggagtc agggatgtat   3120
acatgagctg cttttccctct cagccagagg acatggggg ccccagctcc cctgcctttc   3180
cccttctgtg cctggagctg ggaagcaggc caggttagc tgaggctggc tgcaagcag    3240
ctgggtggtg ccagggagag cctgcatagt gccaggtggt gccttgggtt ccaagctagt   3300
ccatggcccc gataaccttc tgcctgtgca cacacctgcc cctcactcca cccccatcct   3360
agctttggta tgggggagag ggcacagggc cagacaaacc tgtgagactt tggctccatc   3420
```

```
tctgcaaaag ggcgctctgt gagtcagcct gctcccctcc aggcttgctc ctccccacc      3480
cagctctcgt ttccaatgca cgtacagccc gtacacaccg tgtgctggga caccccacag    3540
tcagccgcat ggctcccctg tgccccagcc cctggctccc tctgttgatc ccggcccctg    3600
ctccaggcct cactgtgcaa ctgctgctgt cactgctgct tctggtgcct gtccatcccc    3660
agaggttgcc ccggatgcag gaggattccc ccttgggagg aggctcttct ggggaagatg    3720
acccactggg cgaggaggat ctgcccagtg aagaggattc acccagagag gaggatccac    3780
ccggagagga ggatctacct ggagaggagg atctacctgg agaggaggat ctacctgaag    3840
ttaagcctaa atcagaagaa gagggctccc tgaagttaga ggatctacct actgttgagg    3900
ctcctggaga tcctcaagaa ccccagaata atgcccacag ggacaaagaa ggtaagtggt    3960
catcaatctc caaatccagg ttccaggagg ttcatgactc cctcccata ccccagccta     4020
ggctctgttc actcagggaa ggaggggaga ctgtactccc cacagaagcc cttccagagg    4080
tcccatacca atatccccat ccccactctc ggaggtagaa agggacagat gtggagagaa    4140
aataaaaagg gtgcaaaagg agagaggtga gctggatgag atgggagaga aggggaggc    4200
tggagaagag aaagggatga gaactgcaga tgagagaaaa aatgtgcaga cagaggaaaa    4260
aaataggtgg agaaggagag tcagagagtt tgaggggaag agaaaaggaa agcttgggag    4320
gtgaagtggg taccagagac aagcaagaag agctggtaga agtcatctca tcttaggcta    4380
caatgaggaa ttgagaccta ggaagaaggg acacagcagg tagagaaacg tggcttcttg    4440
actcccaagc caggaatttg gggaaagggg ttggagacca tacaaggcag agggatgagt    4500
ggggagaaga aagaagggag aaaggaaaga tggtgtactc actcatttgg gactcaggac    4560
tgaagtgccc actcactttt tttttttttt tttttgagac aaactttcac ttttgttgcc    4620
caggctggag tgcaatggcg cgatctcggc tcactgcaac ctccacctcc cgggttcaag    4680
tgattctcct gcctcagcct ctagccaagt agctgcgatt acaggcatgc gccaccacgc    4740
ccggctaatt tttgtatttt tagtagagac ggggtttcgc catgttggtc aggctggtct    4800
cgaactcctg atctcaggtg atccaaccac cctggcctcc caaagtgctg ggattatagg    4860
cgtgagccac agcgcctggc ctgaagcagc cactcacttt tacagaccct aagacaatga    4920
ttgcaagctg gtaggattgc tgtttggccc acccagctgc ggtgttgagt ttgggtgcgg    4980
tctcctgtgc tttgcacctg gcccgcttaa ggcatttgtt accccgtaatg ctcctgtaag    5040
gcatctgcgt ttgtgacatc gttttggtcg ccaggaaggg attggggctc taagcttgag    5100
cggttcatcc ttttcattta tacaggggat gaccagagtc attggcgcta tggaggtgag    5160
acacccaccc gctgcacaga cccaatctgg gaacccagct ctgtggatct cccctacagc    5220
cgtccctgaa cactggtccc gggcgtccca ccgccgccc accgtccac cccctcacct      5280
tttctacccg ggttccctaa gttcctgacc taggcgtcag acttcctcac tatactctcc    5340
caccccaggc gacccgccct ggccccgggt gtccccagcc tgcgcgggcc gcttccagtc    5400
cccggtggat atccgccccc agctcgccgc cttctgcccg gccctgcgcc cctggaact    5460
cctgggcttc cagctcccgc cgctcccaga actgcgcctg cgcaacaatg ccacagtgg    5520
tgaggggtc tccccgccga cttgggga tgggcgggg cgcagggaag ggaaccgtcg        5580
cgcagtgcct gcccgggggt tgggctggcc ctaccgggcg gggccggctc acttgcctct    5640
ccctacgcag tgcaactgac cctgcctcct gggctagaga tggctctggg tcccgggcgg    5700
gagtaccggg ctctgcagct gcatctgcac tgggggggctg caggtcgtcc gggctcggag    5760
cacactgtgg aaggccaccg tttccctgcc gaggtgagcg cggactggcc gagaagggc    5820
```

-continued

```
aaaggagcgg ggcggacggg ggccagagac gtggccctct cctaccctcg tgtccttttc     5880
agatccacgt ggttcacctc agcaccgcct ttgccagagt tgacgaggcc ttggggcgcc     5940
cgggaggcct ggccgtgttg gccgcctttc tggaggtacc agatcctgga cacccctac     6000 tccccgcttt cccatcccat gctcctcccg gactctatcg tggagccaga daccccatcc    6060
cagcaagctc actcaggccc ctggctgaca aactcattca cgcactgttt gttcatttaa    6120
cacccactgt gaaccaggca ccagccccca acaaggattc tgaagctgta ggtccttgcc    6180
tctaaggagc ccacaccag tgggggaggc tgacatgaca dacacatagg aaggacatag     6240
taaagatggt ggtcacagag gaggtgacac ttaaagcctt cactggtaga aagaaaagg     6300 aggtgttcat tgcagaggaa acagaatgtg caaagactca gaatatggcc tatttaggga    6360
atggctacat acaccatgat tagaggaggc ccagtaaagg gaagggatgg tgagatgcct    6420
gctaggttca ctcactcact tttatttatt tatttatttt tttgacagtc tctctgtcgc    6480
ccaggctgga gtgcagtggt gtgatcttgg gtcactgcaa cttccgcctc ccgggttcaa    6540
gggattctcc tgcctcagct tcctgagtag ctggggttac aggtgtgtgc caccatgccc    6600
agctaatttt tttttgtatt tttagtagac agggtttcac catgttggtc aggctggtct    6660
caaactcctg gcctcaagtg atccgcctga ctcagcctac caaagtgctg attacaagtg    6720
tgagccaccg tgcccagcca cactcactga ttctttaatg ccagccacac agcacaaagt    6780
tcagagaaat gcctccatca tagcatgtca atatgttcat actcttaggt tcatgatgtt    6840
cttaacatta ggttcataag caaaataaga aaaagaata taaataaaa gaagtggcat      6900 gtcaggacct cacctgaaaa gccaaacaca gaatcatgaa ggtgaatgca gaggtgacac    6960
caacacaaag gtgtatatat ggtttcctgt ggggagtatg tacggaggca gcagtgagtg    7020
agactgcaaa cgtcagaagg gcacgggtca ctgagagcct agtatcctag taaagtgggc    7080
tctctccctc tctctccagc ttgtcattga aaaccagtcc accaagcttg ttggttcgca    7140
cagcaagagt acatagagtt tgaaataata cataggattt taagagggag acactgtctc    7200
taaaaaaaaa aacaacagca acaacaaaaa gcaacaacca ttacaatttt atgttccctc    7260
agcattctca gagctgagga atgggagagg actatgggaa cccccttcat gttccggcct    7320
tcagccatgg ccctggatac atgcactcat ctgtcttaca atgtcattcc cccaggaggg    7380
cccggaagaa aacagtgcct atgagcagtt gctgtctcgc ttggaagaaa tcgctgagga    7440
aggtcagttt gttggtctgg ccactaatct ctgtggccta gttcataaag aatcaccctt    7500
tggagcttca ggtctgaggc tggagatggg ctccctccag tgcaggaggg attgaagcat    7560
gagccagcgc tcatcttgat aataaccatg aagctgacag acacagttac ccgcaaacgg    7620
ctgcctacag attgaaaacc aagcaaaaac cgccgggcac ggtggctcac gcctgtaatc    7680
ccagcacttt gggaggccaa ggcaggtgga tcacgaggtc aagagatcaa gaccatcctg    7740
gccaacatgg tgaaacccca tctctactaa aaatacgaaa aaatagccag gcgtggtggc    7800
gggtgcctgt aatcccagct actcgggagg ctgaggcagg agaatggcat gaacccggga    7860
ggcagaagtt gcagtgagcc gagatcgtgc cactgcactc cagcctgggc aacagagcga    7920
gactcttgtc tcaaaaaaaa aaaaaaaaaa gaaaaccaag caaaaaccaa aatgagacaa    7980
aaaaaacaag accaaaaaat ggtgtttgga aattgtcaag gtcaagtctg gagagctaaa    8040 cttttctga gaactgttta tctttaataa gcatcaaata ttttaacttt gtaaatactt     8100
ttgttggaaa tcgttctctt cttagtcact cttgggtcat tttaaatctc acttactcta    8160
```

```
ctagaccttt taggtttctg ctagactagg tagaactctg cctttgcatt tcttgtgtct    8220
gttttgtata gttatcaata ttcatattta tttacaagtt attcagatca ttttttcttt    8280 tcttttttt  ttttttttt  tttttacat  ctttagtaga gacagggttt caccatattg    8340
gccaggctgc tctcaaactc ctgaccttgt gatccaccag cctcggcctc ccaaagtgct    8400
gggattcatt ttttctttt  aatttgctct gggcttaaac ttgtggccca gcactttatg    8460
atggtacaca gagttaagag tgtagactca gacggtcttt cttctttcct tctcttcctt    8520
cctcccttcc ctcccacctt cccttctctc cttcctttct ttcttcctct cttgcttcct    8580
caggcctctt ccagttgctc caaagccctg tactttttt  tgagttaacg tcttatggga    8640
agggcctgca cttagtgaag aagtggtctc agagttgagt taccttggct tctgggaggt    8700
gaaactgtat ccctataccc tgaagcttta agggggtgca atgtagatga ccccaaca     8760 tagatcctct tcacaggctc agagactcag gtcccaggac tggacatatc tgcactcctg    8820
ccctctgact tcagccgcta cttccaatat gaggggtctc tgactacacc gccctgtgcc    8880
cagggtgtca tctggactgt gtttaaccag acagtgatgc tgagtgctaa gcaggtgggc    8940
ctggggtgtg tgtggacaca gtgggtgcgg gggaaagagg atgtaagatg agatgagaaa    9000
caggagaaga aagaaatcaa ggctgggctc tgtggcttac gcctataatc ccaccacgtt    9060
gggaggctga ggtgggagaa tggtttgagc ccaggagttc aagacaaggc ggggcaacat    9120
agtgtgaccc catctctacc aaaaaaaccc caacaaaacc aaaatagcc  gggcatggtg    9180 gtatgcggcc tagtcccagc tactcaagga ggctgaggtg ggaagatcgc ttgattccag    9240
gagtttgaga ctgcagtgag ctatgatccc accactgcct accatcttta ggatacattt    9300
atttatttat aaaagaaatc aagaggctgg atggggaata caggagctgg agggtggagc    9360
cctgaggtgc tggttgtgag ctggcctggg acccttgttt cctgtcatgc catgaaccca    9420
cccacactgt ccactgacct ccctagctcc acaccctctc tgacccctg  tggggacctg    9480 gtgactctcg gctacagctg aacttccgag cgacgcagcc tttgaatggg cgagtgattg    9540
aggcctcctt ccctgctgga gtggacagca gtcctcgggc tgctgagcca ggtacagctt    9600
tgtctggttt ccccccagcc agtagtccct tatcctccca tgtgtgtgcc agtgtctgtc    9660
attggtggtc acagcccgcc tctcacatct ccttttctc  tccagtccag ctgaattcct    9720
gcctggctgc tggtgagtct gcccctcctc ttggtcctga tgccaggaga ctcctcagca    9780
ccattcagcc ccagggctgc tcaggaccgc ctctgctccc tctccttttc tgcagaacag    9840
accccaaccc caatattaga gaggcagatc atggtgggga ttcccccatt gtccccagag    9900
gctaattgat tagaatgaag cttgagaaat ctcccagcat ccctctcgca aaagaatccc    9960 ccccccttt  tttaaagata gggtctcact ctgtttgccc caggctgggg tgttgtggca   10020
cgatcatagc tcactgcagc ctcgaactcc taggctcagg caatcctttc accttagctt   10080
ctcaaagcac tgggactgta ggcatgagcc actgtgcctg gccccaaacg gccctttttac  10140 ttggctttta ggaagcaaaa acggtgctta tcttacccct tctcgtgtat ccaccctcat   10200
cccttggctg gcctcttctg gagactgagg cactatgggg ctgcctgaga actcggggca   10260
ggggtggtgg agtgcactga ggcaggtgtt gaggaactct gcagacccct cttccttccc   10320
aaagcagccc tctctgctct ccatcgcagg tgacatccta gccctggttt ttggcctcct   10380
ttttgctgtc accagcgtcg cgttccttgt gcagatgaga aggcagcaca ggtattacac   10440 tgacccttc  ttcaggcaca agcttccccc acccttgtgg agtcacttca tgcaaagcgc   10500
atgcaaatga gctgctcctg ggccagtttt ctgattagcc tttcctgttg tgtacacaca   10560
```

-continued

```
gaaggggaac caaagggggt gtgagctacc gcccagcaga ggtagccgag actggagcct      10620
agaggctgga tcttggagaa tgtgagaagc cagccagagg catctgaggg ggagccggta      10680
actgtcctgt cctgctcatt atgccacttc cttttaactg ccaagaaatt ttttaaaata      10740
aatatttata ataaaatatg tgttagtcac ctttgttccc caaatcagaa ggaggtattt      10800
gaatttccta ttactgttat tagcaccaat ttagtggtaa tgcatttatt ctattacagt      10860
tcggcctcct tccacacatc actccaatgt gttgctcc                              10898
```

<210> SEQ ID NO 6
<211> LENGTH: 37
<212> TYPE: PRT
<213> ORGANISM: HUMAN

<400> SEQUENCE: 6

Met Ala Pro Leu Cys Pro Ser Pro Trp Leu Pro Leu Leu Ile Pro Ala
1               5                   10                  15

Pro Ala Pro Gly Leu Thr Val Gln Leu Leu Ser Leu Leu Leu Leu
            20                  25                  30

Met Pro Val His Pro
        35

<210> SEQ ID NO 7
<211> LENGTH: 25
<212> TYPE: DNA
<213> ORGANISM: HUMAN

<400> SEQUENCE: 7

```
tggggttctt gaggatctcc aggag                                              25
```

<210> SEQ ID NO 8
<211> LENGTH: 26
<212> TYPE: DNA
<213> ORGANISM: HUMAN

<400> SEQUENCE: 8

```
ctctaacttc agggagccct cttctt                                             26
```

<210> SEQ ID NO 9
<211> LENGTH: 48
<212> TYPE: DNA
<213> ORGANISM: HUMAN
<220> FEATURE:
<221> NAME/KEY: primer_bind
<222> LOCATION: (1)..(48)
<223> OTHER INFORMATION: anchor primer that anneals to the homopolymeric
      tail.
<221> NAME/KEY: inosine
<222> LOCATION: (36)..(37) (41)..(42) (46)..(47)
<223> OTHER INFORMATION: each of the modified_bases at positions (36),
      (37), (41), (42), (46) and (47) are inosine

<400> SEQUENCE: 9

```
cuacuacuac uaggccacgc gtcgactagt acgggaaggg aagggaag                    48
```

<210> SEQ ID NO 10
<211> LENGTH: 6
<212> TYPE: PRT
<213> ORGANISM: HUMAN

<400> SEQUENCE: 10

Glu Glu Asp Leu Pro Ser
1               5

<210> SEQ ID NO 11
<211> LENGTH: 6
<212> TYPE: PRT
<213> ORGANISM: HUMAN

<400> SEQUENCE: 11

Gly Glu Asp Asp Pro Leu
1               5

<210> SEQ ID NO 12
<211> LENGTH: 21
<212> TYPE: PRT
<213> ORGANISM: HUMAN

<400> SEQUENCE: 12

Asn Asn Ala His Arg Asp Lys Glu Gly Asp Asp Gln Ser His Trp Arg
1               5                   10                  15

Tyr Gly Gly Asp Pro
            20

<210> SEQ ID NO 13
<211> LENGTH: 16
<212> TYPE: PRT
<213> ORGANISM: HUMAN

<400> SEQUENCE: 13

His Pro Gln Arg Leu Pro Arg Met Gln Glu Asp Ser Pro Leu Gly Gly
1               5                   10                  15

<210> SEQ ID NO 14
<211> LENGTH: 24
<212> TYPE: PRT
<213> ORGANISM: HUMAN

<400> SEQUENCE: 14

Glu Glu Asp Ser Pro Arg Glu Glu Asp Pro Pro Gly Glu Glu Asp Leu
1               5                   10                  15

Pro Gly Glu Glu Asp Leu Pro Gly
            20

<210> SEQ ID NO 15
<211> LENGTH: 13
<212> TYPE: PRT
<213> ORGANISM: HUMAN

<400> SEQUENCE: 15

Leu Glu Glu Gly Pro Glu Glu Asn Ser Ala Tyr Glu Gln
1               5                   10

<210> SEQ ID NO 16
<211> LENGTH: 16
<212> TYPE: PRT
<213> ORGANISM: HUMAN

<400> SEQUENCE: 16

Met Arg Arg Gln His Arg Arg Gly Thr Lys Gly Gly Val Ser Tyr Arg
1               5                   10                  15

<210> SEQ ID NO 17
<211> LENGTH: 45
<212> TYPE: DNA
<213> ORGANISM: HUMAN

```
<400> SEQUENCE: 17
gtcgctagct ccatgggtca tatgcagagg ttgccccgga tgcag            45

<210> SEQ ID NO 18
<211> LENGTH: 43
<212> TYPE: DNA
<213> ORGANISM: HUMAN

<400> SEQUENCE: 18
gaagatctct tactcgagca ttctccaaga tccagcctct agg              43

<210> SEQ ID NO 19
<211> LENGTH: 10
<212> TYPE: DNA
<213> ORGANISM: HUMAN

<400> SEQUENCE: 19
ctccatctct                                                   10

<210> SEQ ID NO 20
<211> LENGTH: 10
<212> TYPE: DNA
<213> ORGANISM: HUMAN

<400> SEQUENCE: 20
ccaccccat                                                    10

<210> SEQ ID NO 21
<211> LENGTH:
<212> TYPE:
<213> ORGANISM:

<400> SEQUENCE: 21

000

<210> SEQ ID NO 22
<211> LENGTH: 8
<212> TYPE: PRT
<213> ORGANISM: HUMAN

<400> SEQUENCE: 22

Leu Glu His His His His His His
 1               5

<210> SEQ ID NO 23
<211> LENGTH: 10
<212> TYPE: DNA
<213> ORGANISM: HUMAN
<220> FEATURE:
<221> NAME/KEY: misc_feature
<222> LOCATION: (1)..(10)

<400> SEQUENCE: 23 yyycayyyyy                                                   10

<210> SEQ ID NO 24
<211> LENGTH: 10
<212> TYPE: DNA
<213> ORGANISM: HUMAN
<300> PUBLICATION INFORMATION:
<301> AUTHORS: Locker and Buzard,
<303> JOURNAL: DNA Sequencing and Mapping
<304> VOLUME: 1
<306> PAGES: 3-11
<307> DATE: 1990
```

```
<400> SEQUENCE: 24
tgtgagactt                                                              10

<210> SEQ ID NO 25
<211> LENGTH: 4
<212> TYPE: PRT
<213> ORGANISM: HUMAN
<220> FEATURE:
<221> NAME/KEY: SITE
<222> LOCATION: (1)..(4)
<223> OTHER INFORMATION: sequence element defined by Suzuki, J. Mol.
      Biol., 207: 61-84 (1989) as motif frequently found in gene
      regulatory proteins.
<221> NAME/KEY: VARIANTS
<222> LOCATION: (3)..(4)
<223> OTHER INFORMATION: variants in sequence element defined by Suzuki,
      J. Mol. Biol., 207: 61-84 (1989) as motif frequently found in
      gene regulatory proteins.

<400> SEQUENCE: 25

Ser Pro Xaa Xaa
 1

<210> SEQ ID NO 26
<211> LENGTH: 4
<212> TYPE: PRT
<213> ORGANISM: HUMAN
<220> FEATURE:
<221> NAME/KEY: SITE
<222> LOCATION: (1)..(4)
<223> OTHER INFORMATION: sequence element defined by Suzuki, J. Mol.
      Biol., 207: 61-84 (1989) as a motif frequently found in gene
      regulatory proteins.
<221> NAME/KEY: VARIANTS
<222> LOCATION: (3)..(4)
<223> OTHER INFORMATION: variants in sequence element defined by Suzuki,
      J. Mol. Biol., 207: 61-84 (1989) as a motif frequently found in
      gene regulatory proteins.
<400> SEQUENCE: 26

Thr Pro Xaa Xaa
 1

<210> SEQ ID NO 27
<211> LENGTH: 540
<212> TYPE: DNA
<213> ORGANISM: HUMAN
<220> FEATURE:
<221> NAME/KEY: promoter
<222> LOCATION: (1)..(540)

<400> SEQUENCE: 27
cttgcttttc attcaagctc aagtttgtct cccacatacc cattacttaa ctcaccctcg        60
ggctccccta gcagcctgcc ctacctcttt acctgcttcc tggtggagtc agggatgtat      120
acatgagctg ctttccctct cagccagagg acatgggggg cccagctcc cctgcctttc       180 cccttctgtg cctggagctg ggaagcaggc cagggttagc tgaggctggc tggcaagcag      240
ctgggtggtg ccaggagag cctgcatagt gccaggtggt gccttgggtt ccaagctagt      300
ccatggcccc gataaccttc tgcctgtgca cacacctgcc cctcactcca ccccatcct      360 agctttggta tgggggagag ggcacagggc cagacaaacc tgtgagactt ggctccatc      420 tctgcaaaag ggcgctctgt gagtcagcct gctcccctcc aggcttgctc ctcccccacc     480
cagctctcgt ttccaatgca cgtacagccc gtacacaccg tgtgctggga cacccacag     540
```

<210> SEQ ID NO 28
<211> LENGTH: 445
<212> TYPE: DNA
<213> ORGANISM: HUMAN
<220> FEATURE:
<221> NAME/KEY: exon
<222> LOCATION: (1)
<223> OTHER INFORMATION: 1st MN exon

<400> SEQUENCE: 28

| gcccgtacac | accgtgtgct | gggacacccc | acagtcagcc | gcatggctcc | cctgtgcccc | 60 |
| agcccctggc | tccctctgtt | gatcccggcc | cctgctccag | gcctcactgt | gcaactgctg | 120 |
| ctgtcactgc | tgcttctggt | gcctgtccat | cccagaggt | tgccccggat | gcaggaggat | 180 |
| tcccccttgg | gaggaggctc | ttctggggaa | gatgacccac | tgggcgagga | ggatctgccc | 240 |
| agtgaagagg | attcacccag | agaggaggat | ccacccggag | aggaggatct | acctggagag | 300 |
| gaggatctac | ctggagagga | ggatctacct | gaagttaagc | ctaaatcaga | agaagagggc | 360 |
| tccctgaagt | tagaggatct | acctactgtt | gaggctcctg | gagatcctca | agaaccccag | 420 |
| aataatgccc | acagggacaa | agaag | | | | 445 |

<210> SEQ ID NO 29
<211> LENGTH: 30
<212> TYPE: DNA
<213> ORGANISM: HUMAN
<220> FEATURE:
<221> NAME/KEY: exon
<222> LOCATION: (1)
<223> OTHER INFORMATION: 2nd MN exon

<400> SEQUENCE: 29
gggatgacca gagtcattgg cgctatggag                                         30

<210> SEQ ID NO 30
<211> LENGTH: 171
<212> TYPE: DNA
<213> ORGANISM: HUMAN
<220> FEATURE:
<221> NAME/KEY: exon
<222> LOCATION: (1)
<223> OTHER INFORMATION: 3rd MN exon

<400> SEQUENCE: 30

| gcgacccgcc | ctggccccgg | gtgtcccag | cctgcgcggg | ccgcttccag | tccccggtgg | 60 |
| atatccgccc | ccagctcgcc | gccttctgcc | cggccctgcg | cccccctggaa | ctcctgggct | 120 |
| tccagctccc | gccgctccca | gaactgcgcc | tgcgcaacaa | tggccacagt | g | 171 |

<210> SEQ ID NO 31
<211> LENGTH: 143
<212> TYPE: DNA
<213> ORGANISM: HUMAN
<220> FEATURE:
<221> NAME/KEY: exon
<222> LOCATION: (1)
<223> OTHER INFORMATION: 4th MN exon

<400> SEQUENCE: 31

| tgcaactgac | cctgcctcct | gggctagaga | tggctctggg | tcccgggcgg | gagtaccggg | 60 |
| ctctgcagct | gcatctgcac | tgggggggctg | caggtcgtcc | gggctcggag | cacactgtgg | 120 |
| aaggccaccg | tttccctgcc | gag | | | | 143 |

<210> SEQ ID NO 32

<211> LENGTH: 93
<212> TYPE: DNA
<213> ORGANISM: HUMAN
<220> FEATURE:
<221> NAME/KEY: exon
<222> LOCATION: (1)
<223> OTHER INFORMATION: 5th MN exon

<400> SEQUENCE: 32

```
atccacgtgg ttcacctcag caccgccttt gccagagttg acgaggcctt ggggcgcccg      60
ggaggcctgg ccgtgttggc cgcctttctg gag                                    93
```

<210> SEQ ID NO 33
<211> LENGTH: 67
<212> TYPE: DNA
<213> ORGANISM: HUMAN
<220> FEATURE:
<221> NAME/KEY: exon
<222> LOCATION: (1)
<223> OTHER INFORMATION: 6th MN exon

<400> SEQUENCE: 33

```
gagggcccgg aagaaaacag tgcctatgag cagttgctgt ctcgcttgga agaaatcgct      60
gaggaag                                                                 67
```

<210> SEQ ID NO 34
<211> LENGTH: 158
<212> TYPE: DNA
<213> ORGANISM: HUMAN
<220> FEATURE:
<221> NAME/KEY: exon
<222> LOCATION: (1)
<223> OTHER INFORMATION: 7th MN exon

<400> SEQUENCE: 34

```
gctcagagac tcaggtccca ggactggaca tatctgcact cctgccctct gacttcagcc      60
gctacttcca atatgagggg tctctgacta caccgccctg tgcccagggt gtcatctgga     120
ctgtgtttaa ccagacagtg atgctgagtg ctaagcag                             158
```

<210> SEQ ID NO 35
<211> LENGTH: 145
<212> TYPE: DNA
<213> ORGANISM: HUMAN
<220> FEATURE:
<221> NAME/KEY: exon
<222> LOCATION: (1)
<223> OTHER INFORMATION: 8th MN exon

<400> SEQUENCE: 35

```
ctccacaccc tctctgacac cctgtgggga cctggtgact ctcggctaca gctgaacttc      60
cgagcgacgc agcctttgaa tgggcgagtg attgaggcct ccttccctgc tggagtggac     120
agcagtcctc gggctgctga gccag                                           145
```

<210> SEQ ID NO 36
<211> LENGTH: 27
<212> TYPE: DNA
<213> ORGANISM: HUMAN
<220> FEATURE:
<221> NAME/KEY: exon
<222> LOCATION: (1)
<223> OTHER INFORMATION: 9th MN exon

<400> SEQUENCE: 36

```
tccagctgaa ttcctgcctg gctgctg                                          27
```

-continued

<210> SEQ ID NO 37
<211> LENGTH: 82
<212> TYPE: DNA
<213> ORGANISM: HUMAN
<220> FEATURE:
<221> NAME/KEY: exon
<222> LOCATION: (1)
<223> OTHER INFORMATION: 10th MN exon

<400> SEQUENCE: 37

| | | | | |
|---|---|---|---|---|
| gtgacatcct agccctggtt tttggcctcc tttttgctgt caccagcgtc gcgttccttg | | | | 60 |
| tgcagatgag aaggcagcac ag | | | | 82 |

<210> SEQ ID NO 38
<211> LENGTH: 191
<212> TYPE: DNA
<213> ORGANISM: HUMAN
<220> FEATURE:
<221> NAME/KEY: exon
<222> LOCATION: (1)
<223> OTHER INFORMATION: 11th MN exon

<400> SEQUENCE: 38

| | | | | |
|---|---|---|---|---|
| aaggggaacc aaaggggtg tgagctaccg cccagcagag gtagccgaga ctggagccta | | | | 60 |
| gaggctggat cttggagaat gtgagaagcc agccagaggc atctgagggg gagccggtaa | | | | 120 |
| ctgtcctgtc ctgctcatta tgccacttcc ttttaactgc caagaaattt tttaaaataa | | | | 180 |
| atatttataa t | | | | 191 |

<210> SEQ ID NO 39
<211> LENGTH: 1174
<212> TYPE: DNA
<213> ORGANISM: HUMAN
<220> FEATURE:
<221> NAME/KEY: intron
<222> LOCATION: (1)..(1174)
<223> OTHER INFORMATION: 1st MN intron

<400> SEQUENCE: 39

| | | | | |
|---|---|---|---|---|
| gtaagtggtc atcaatctcc aaatccaggt tccaggaggt tcatgactcc cctcccatac | | | | 60 |
| cccagcctag gctctgttca ctcagggaag gaggggagac tgtactcccc acagaagccc | | | | 120 |
| ttccagaggt cccataccaa tatccccatc cccactctcg gaggtagaaa gggacagatg | | | | 180 |
| tggagagaaa ataaaaaggg tgcaaaagga gagaggtgag ctggatgaga tgggagagaa | | | | 240 |
| gggggaggct ggagaagaga aagggatgag aactgcagat gagagaaaaa atgtgcagac | | | | 300 |
| agaggaaaaa aataggtgga gaaggagagt cagagagttt gaggggaaga gaaaaggaaa | | | | 360 |
| gcttgggagg tgaagtgggt accagagaca agcaagaaga gctggtagaa gtcatctcat | | | | 420 |
| cttaggctac aatgaggaat tgagacctag gaagaaggga cacagcaggt agagaaacgt | | | | 480 |
| ggcttcttga ctcccaagcc aggaatttgg ggaaagggt tggagaccat acaaggcaga | | | | 540 |
| gggatgagtg gggagaagaa agaagggaga aggaaagat ggtgtactca ctcatttggg | | | | 600 |
| actcaggact gaagtgccca ctcactttt ttttttttt ttttgagaca aactttcact | | | | 660 |
| tttgttgccc aggctggagt gcaatggcgc gatctcggct cactgcaacc tccacctccc | | | | 720 |
| gggttcaagt gattctcctg cctcagcctc tagccaagta gctgcgatta caggcatgcg | | | | 780 |
| ccaccacgcc cggctaattt ttgtattttt agtagagacg gggtttcgcc atgttggtca | | | | 840 |
| ggctggtctc gaactcctga tctcaggtga tccaaccacc ctggcctccc aaagtgctgg | | | | 900 |

```
gattataggc gtgagccaca gcgcctggcc tgaagcagcc actcactttt acagaccocta    960 agacaatgat tgcaagctgg taggattgct gtttggccca cccagctgcg gtgttgagtt   1020
tgggtgcggt ctcctgtgct ttgcacctgg cccgcttaag gcatttgtta cccgtaatgc   1080
tcctgtaagg catctgcgtt tgtgacatcg ttttggtcgc aggaaggga ttggggctct    1140 aagcttgagc ggttcatcct tttcatttat acag                              1174

<210> SEQ ID NO 40
<211> LENGTH: 193
<212> TYPE: DNA
<213> ORGANISM: HUMAN
<220> FEATURE:
<221> NAME/KEY: intron
<222> LOCATION: (1)..(193)
<223> OTHER INFORMATION: 2nd MN intron

<400> SEQUENCE: 40
gtgagacacc cacccgctgc acagacccaa tctgggaacc cagctctgtg gatctcccct     60
acagccgtcc ctgaacactg gtcccgggcg tcccaccogc cgcccaccgt cccacccoct    120 cacctttttct acccgggttc cctaagttcc tgacctaggc gtcagacttc ctcactatac   180
tctcccaccc cag                                                       193

<210> SEQ ID NO 41
<211> LENGTH: 131
<212> TYPE: DNA
<213> ORGANISM: HUMAN
<220> FEATURE:
<221> NAME/KEY: intron
<222> LOCATION: (1)..(131)
<223> OTHER INFORMATION: 3rd MN intron

<400> SEQUENCE: 41 gtgaggggt ctccccgccg agacttgggg atgggcggg gcgcagggaa gggaaccgtc       60
gcgcagtgcc tgcccggggg ttgggctggc cctaccgggc ggggccggct cacttgcctc    120
tccctacgca g                                                         131

<210> SEQ ID NO 42
<211> LENGTH: 89
<212> TYPE: DNA
<213> ORGANISM: HUMAN
<220> FEATURE:
<221> NAME/KEY: intron
<222> LOCATION: (1)..(89)
<223> OTHER INFORMATION: 4th MN intron

<400> SEQUENCE: 42
gtgagcgcgg actggccgag aagggcaaa ggagcggggc ggacgggggc cagagacgtg      60
gccctctcct accctcgtgt ccttttcag                                       89

<210> SEQ ID NO 43
<211> LENGTH: 1400
<212> TYPE: DNA
<213> ORGANISM: HUMAN
<220> FEATURE:
<221> NAME/KEY: intron
<222> LOCATION: (1)..(1400)
<223> OTHER INFORMATION: 5th MN intron

<400> SEQUENCE: 43
gtaccagatc ctggacaccc cctactcccc gctttcccat cccatgctcc tcccggactc      60
tatcgtggag ccagagaccc catcccagca agctcactca ggcccctggc tgacaaactc     120
```

-continued

```
attcacgcac tgtttgttca tttaacaccc actgtgaacc aggcaccagc ccccaacaag    180
gattctgaag ctgtaggtcc ttgcctctaa ggagcccaca gccagtgggg gaggctgaca    240
tgacagacac ataggaagga catagtaaag atggtggtca cagaggaggt gacacttaaa    300
gccttcactg gtagaaaaga aaaggaggtg ttcattgcag aggaaacaga atgtgcaaag    360
actcagaata tggcctattt agggaatggc tacatacacc atgattagag gaggcccagt    420
aaagggaagg gatggtgaga tgcctgctag gttcactcac tcacttttat ttatttattt    480
atttttttga cagtctctct gtcgcccagg ctggagtgca gtggtgtgat cttgggtcac    540
tgcaacttcc gcctcccggg ttcaagggat tctcctgcct cagcttcctg agtagctggg    600
gttacaggtg tgtgccacca tgcccagcta atttttttt gtattttttag tagacagggt     660 ttcaccatgt tggtcaggct ggtctcaaac tcctggcctc aagtgatccg cctgactcag    720
cctaccaaag tgctgattac aagtgtgagc caccgtgccc agccacactc actgattctt    780
taatgccagc cacacagcac aaagttcaga gaaatgcctc catcatagca tgtcaatatg    840
ttcatactct taggttcatg atgttcttaa cattaggttc ataagcaaaa taagaaaaaa    900
gaataataaa taaagaagt ggcatgtcag gacctcacct gaaaagccaa acacagaatc     960
atgaaggtga atgcagaggt gacaccaaca caaaggtgta tatatggttt cctgtgggga   1020
gtatgtacgg aggcagcagt gagtgagact gcaaacgtca gaagggcacg ggtcactgag   1080
agcctagtat cctagtaaag tgggctctct ccctctctct ccagcttgtc attgaaaacc   1140
agtccaccaa gcttgttggt tcgcacagca agagtacata gagtttgaaa taatacatag   1200
gattttaaga gggagacact gtctctaaaa aaaaaaacaa cagcaacaac aaaaagcaac   1260
aaccattaca attttatgtt ccctcagcat tctcagagct gaggaatggg agaggactat   1320
gggaaccccc ttcatgttcc ggccttcagc catggccctg gatacatgca ctcatctgtc   1380
ttacaatgtc attcccccag                                              1400
```

<210> SEQ ID NO 44
<211> LENGTH: 1334
<212> TYPE: DNA
<213> ORGANISM: HUMAN
<220> FEATURE:
<221> NAME/KEY: intron
<222> LOCATION: (1)..(1334)
<223> OTHER INFORMATION: 6th MN intron

<400> SEQUENCE: 44

```
gtcagtttgt tggtctggcc actaatctct gtggcctagt tcataaagaa tcaccctttg     60
gagcttcagg tctgaggctg gagatgggct ccctccagtg caggagggat tgaagcatga    120
gccagcgctc atcttgataa taaccatgaa gctgacagac acagttaccc gcaaacggct    180
gcctacagat tgaaaaccaa gcaaaaaccg ccgggcacgg tggctcacgc ctgtaatccc    240
agcactttgg gaggccaagg caggtggatc acgaggtcaa gagatcaaga ccatcctggc    300
caacatggtg aaaccccatc tctactaaaa atacgaaaaa atagccaggc gtggtggcgg    360
gtgcctgtaa tcccagctac tcgggaggct gaggcaggag aatggcatga acccgggagg    420
cagaagttgc agtgagccga gatcgtgcca ctgcactcca gcctgggcaa cagagcgaga    480
ctcttgtctc aaaaaaaaaa aaaaaaaga aaccaagca aaaccaaaa tgagacaaaa        540 aaaacaagac caaaaaatgg tgtttggaaa ttgtcaaggt caagtctgga gagctaaact    600
ttttctgaga actgtttatc tttaataagc atcaaatatt ttaactttgt aaatacttttt   660
```

-continued

```
gttggaaatc gttctcttct tagtcactct tgggtcattt taaatctcac ttactctact      720 agaccttta ggtttctgct agactaggta gaactctgcc tttgcatttc ttgtgtctgt       780
tttgtatagt tatcaatatt catatttatt tacaagttat tcagatcatt ttttcttttc     840
tttttttttt tttttttttt ttttacatct ttagtagaga cagggtttca ccatattggc     900
caggctgctc tcaaactcct gaccttgtga tccaccagcc tcggcctccc aaagtgctgg     960
gattcatttt ttcttttaa tttgctctgg gcttaaactt gtggcccagc actttatgat    1020
ggtacacaga gttaagagtg tagactcaga cggtctttct tctttccttc tcttccttcc    1080
tcccttccct cccaccttcc cttctctcct tcctttcttt cttcctctct tgcttcctca    1140
ggcctcttcc agttgctcca aagccctgta cttttttttg agttaacgtc ttatgggaag    1200
ggcctgcact tagtgaagaa gtggtctcag agttgagtta ccttggcttc tgggaggtga    1260
aactgtatcc ctataccctg aagctttaag ggggtgcaat gtagatgaga ccccaacata    1320
gatcctcttc acag                                                      1334
```

<210> SEQ ID NO 45
<211> LENGTH: 512
<212> TYPE: DNA
<213> ORGANISM: HUMAN
<220> FEATURE:
<221> NAME/KEY: intron
<222> LOCATION: (1)..(512)
<223> OTHER INFORMATION: 7th MN intron

<400> SEQUENCE: 45

```
gtgggcctgg ggtgtgtgtg gacacagtgg gtgcgggga aagaggatgt aagatgagat       60
gagaaacagg agaagaaaga aatcaaggct gggctctgtg gcttacgcct ataatcccac      120
cacgttggga ggctgaggtg ggagaatggt ttgagcccag gagttcaaga caaggcgggg     180
caacatagtg tgaccccatc tctaccaaaa aaacccaac aaaaccaaaa atagccgggc      240
atggtggtat gcggcctagt cccagctact caaggaggct gaggtgggaa gatcgcttga    300
ttccaggagt ttgagactgc agtgagctat gatcccacca ctgcctacca tctttaggat   360
acatttattt atttataaaa gaaatcaaga ggctggatgg ggaatacagg agctggaggg    420
tggagccctg aggtgctggt tgtgagctgg cctgggaccc ttgtttcctg tcatgccatg    480
aacccaccca cactgtccac tgacctccct ag                                  512
```

<210> SEQ ID NO 46
<211> LENGTH: 114
<212> TYPE: DNA
<213> ORGANISM: HUMAN
<220> FEATURE:
<221> NAME/KEY: intron
<222> LOCATION: (1)..(114)
<223> OTHER INFORMATION: 8th MN intron

<400> SEQUENCE: 46

```
gtacagcttt gtctggtttc cccccagcca gtagtccctt atcctcccat gtgtgtgcca      60
gtgtctgtca ttggtggtca cagcccgcct ctcacatctc cttttctct ccag            114
```

<210> SEQ ID NO 47
<211> LENGTH: 617
<212> TYPE: DNA
<213> ORGANISM: HUMAN
<220> FEATURE:
<221> NAME/KEY: intron
<222> LOCATION: (1)..(617)
<223> OTHER INFORMATION: 9th MN intron -continued

```
<400> SEQUENCE: 47
gtgagtctgc ccctcctctt ggtcctgatg ccaggagact cctcagcacc attcagcccc      60
agggctgctc aggaccgcct ctgctccctc tccttttctg cagaacagac cccaacccca     120
atattagaga ggcagatcat ggtggggatt cccccattgt ccccagaggc taattgatta     180
gaatgaagct tgagaaatct cccagcatcc ctctcgcaaa agaatccccc ccccttttt      240 taaagatagg gtctcactct gtttgcccca ggctgggtg ttgtggcacg atcatagctc      300
actgcagcct cgaactccta ggctcaggca atcctttcac cttagcttct caaagcactg     360
ggactgtagg catgagccac tgtgcctggc cccaaacggc ccttttactt ggcttttagg     420
aagcaaaaac ggtgcttatc ttacccctc tcgtgtatcc accctcatcc cttggctggc      480
ctcttctgga gactgaggca ctatgggct gcctgagaac tcggggcagg ggtggtggag      540
tgcactgagg caggtgttga ggaactctgc agacccctct tccttcccaa agcagccctc     600
tctgctctcc atcgcag                                                    617

<210> SEQ ID NO 48
<211> LENGTH: 130
<212> TYPE: DNA
<213> ORGANISM: HUMAN
<220> FEATURE:
<221> NAME/KEY: intron
<222> LOCATION: (1)..(130)
<223> OTHER INFORMATION: 10th MN intron

<400> SEQUENCE: 48
gtattacact gacccttct tcaggcacaa gcttccccca cccttgtgga gtcacttcat      60
gcaaagcgca tgcaaatgag ctgctcctgg gccagttttc tgattagcct ttcctgttgt     120
gtacacacag                                                            130

<210> SEQ ID NO 49
<211> LENGTH: 1401
<212> TYPE: DNA
<213> ORGANISM: HUMAN

<400> SEQUENCE: 49
caaactttca cttttgttgc ccaggctgga gtgcaatggc gcgatctcgg ctcactgcaa      60
cctccacctc ccgggttcaa gtgattctcc tgcctcagcc tctagccaag tagctgcgat     120
tacaggcatg cgccaccacg cccggctaat ttttgtattt ttagtagaga cggggtttcg     180
ccatgttggt caggctggtc tcgaactcct gatctcaggt gatccaacca ccctggcctc     240
ccaaagtgct gggattatag gcgtgagcca gcgcctgg cctgaagcag ccactcactt      300
ttacagaccc taagacaatg attgcaagct ggtaggattg ctgtttggcc cacccagctg     360
cggtgttgag tttgggtgcg gtctcctgtg ctttgcacct ggcccgctta aggcatttgt     420
tacccgtaat gctcctgtaa ggcatctgcg tttgtgacat cgttttggtc gccaggaagg     480
gattggggct ctaagcttga gcggttcatc cttttcattt atacagggga tgaccagagt     540
cattggcgct atggaggtga gacacccacc cgctgcacag acccaatctg ggaacccagc     600
tctgtggatc tcccctacag ccgtccctga acactggtcc cgggcgtccc accgccgcc      660 caccgtccca cccccctcacc ttttctaccc gggttcccta agttcctgac ctaggcgtca     720
gacttcctca ctatactctc ccacccagg cgacccgccc tggccccggg tgtccccagc      780
ctgcgcgggc cgcttccagt cccggtgga tatccgcccc cagctcgccg ccttctgccc     840
```

-continued

| | |
|---|---|
| ggccctgcgc ccctggaac tcctgggctt ccagctcccg ccgctcccag aactgcgcct | 900 |
| gcgcaacaat ggccacagtg gtgaggggt ctccccgccg agacttgggg atggggcggg | 960 |
| gcgcagggaa gggaaccgtc gcgcagtgcc tgcccggggg ttgggctggc cctaccgggc | 1020 |
| ggggccggct cacttgcctc tccctacgca gtgcaactga ccctgcctcc tgggctagag | 1080 |
| atggctctgg gtcccgggcg ggagtaccgg gctctgcagc tgcatctgca ctgggggct | 1140 |
| gcaggtcgtc cgggctcgga gcacactgtg aaggccacc gtttccctgc cgaggtgagc | 1200 |
| gcggactggc cgagaagggg caaaggagcg gggcggacgg gggccagaga cgtggccctc | 1260 |
| tcctacccctc gtgtcctttt cagatccacg tggttcacct cagcaccgcc tttgccagag | 1320 |
| ttgacgaggc cttggggcgc ccgggaggcc tggccgtgtt ggccgccttt ctggaggtac | 1380 |
| cagatcctgg acaccccta c | 1401 |

<210> SEQ ID NO 50
<211> LENGTH: 59
<212> TYPE: PRT
<213> ORGANISM: HUMAN

<400> SEQUENCE: 50

Ser Ser Gly Glu Asp Asp Pro Leu Gly Glu Glu Asp Leu Pro Ser Glu
  1               5                  10                  15

Glu Asp Ser Pro Arg Glu Glu Asp Pro Pro Gly Glu Glu Asp Leu Pro
             20                  25                  30

Gly Glu Glu Asp Leu Pro Gly Glu Glu Asp Leu Pro Glu Val Lys Pro
         35                  40                  45

Lys Ser Glu Glu Glu Gly Ser Leu Lys Leu Glu
     50                  55

<210> SEQ ID NO 51
<211> LENGTH: 257
<212> TYPE: PRT
<213> ORGANISM: HUMAN

<400> SEQUENCE: 51

Gly Asp Asp Gln Ser His Trp Arg Tyr Gly Gly Asp Pro Pro Trp Pro
  1               5                  10                  15

Arg Val Ser Pro Ala Cys Ala Gly Arg Phe Gln Ser Pro Val Asp Ile
             20                  25                  30

Arg Pro Gln Leu Ala Ala Phe Cys Pro Ala Leu Arg Pro Leu Glu Leu
         35                  40                  45

Leu Gly Phe Gln Leu Pro Pro Leu Pro Glu Leu Arg Leu Arg Asn Asn
     50                  55                  60

Gly His Ser Val Gln Leu Thr Leu Pro Pro Gly Leu Glu Met Ala Leu
 65                  70                  75                  80

Gly Pro Gly Arg Glu Tyr Arg Ala Leu Gln Leu His Leu His Trp Gly
                 85                  90                  95

Ala Ala Gly Arg Pro Gly Ser Glu His Thr Val Glu Gly His Arg Phe
            100                 105                 110

Pro Ala Glu Ile His Val Val His Leu Ser Thr Ala Phe Ala Arg Val
        115                 120                 125

Asp Glu Ala Leu Gly Arg Pro Gly Gly Leu Ala Val Leu Ala Ala Phe
    130                 135                 140

Leu Glu Glu Gly Pro Glu Glu Asn Ser Ala Tyr Glu Gln Leu Leu Ser
145                 150                 155                 160

Arg Leu Glu Glu Ile Ala Glu Glu Gly Ser Glu Thr Gln Val Pro Gly

```
                165                 170                 175
Leu Asp Ile Ser Ala Leu Leu Pro Ser Asp Phe Ser Arg Tyr Phe Gln
            180                 185                 190

Tyr Glu Gly Ser Leu Thr Thr Pro Pro Cys Ala Gln Gly Val Ile Trp
            195                 200                 205

Thr Val Phe Asn Gln Thr Val Met Leu Ser Ala Lys Gln Leu His Thr
            210                 215                 220

Leu Ser Asp Thr Leu Trp Gly Pro Gly Asp Ser Arg Leu Gln Leu Asn
225                 230                 235                 240

Phe Arg Ala Thr Gln Pro Leu Asn Gly Arg Val Ile Glu Ala Ser Phe
                245                 250                 255

Pro

<210> SEQ ID NO 52
<211> LENGTH: 20
<212> TYPE: PRT
<213> ORGANISM: HUMAN

<400> SEQUENCE: 52

Ile Leu Ala Leu Val Phe Gly Leu Leu Phe Ala Val Thr Ser Val Ala
1               5                   10                  15

Phe Leu Val Gln
            20

<210> SEQ ID NO 53
<211> LENGTH: 25
<212> TYPE: PRT
<213> ORGANISM: HUMAN

<400> SEQUENCE: 53

Met Arg Arg Gln His Arg Arg Gly Thr Lys Gly Gly Val Ser Tyr Arg
1               5                   10                  15

Pro Ala Glu Val Ala Glu Thr Gly Ala
            20                  25

<210> SEQ ID NO 54
<211> LENGTH: 59
<212> TYPE: PRT
<213> ORGANISM: HUMAN

<400> SEQUENCE: 54

Ser Ala Ser Glu Glu Pro Ser Pro Ser Glu Val Pro Phe Pro Ser Glu
1               5                   10                  15

Glu Pro Ser Pro Ser Glu Gly Pro Phe Pro Ser Val Arg Pro Phe Pro
            20                  25                  30

Ser Val Val Leu Phe Pro Ser Glu Glu Pro Phe Pro Ser Lys Glu Pro
            35                  40                  45

Ser Pro Ser Glu Glu Pro Ser Ala Ser Glu Glu
        50                  55

<210> SEQ ID NO 55
<211> LENGTH: 470
<212> TYPE: RNA
<213> ORGANISM: HUMAN

<400> SEQUENCE: 55
cauggccccg auaaccuucu gccugugcac acaccugccc cucacuccac ccccauccua      60
gcuuugguau gggggagagg gcacagggcc agacaaaccu gugagacuuu ggcuccaucu     120
```

| | |
|---|---|
| cugcaaaagg gcgcucugug agucagccug cucccucca ggcuugcucc uccccaccc | 180 |
| agcucucguu uccaaugcac guacagcccg uacacaccgu gugcugggac accccacagu | 240 |
| cagccgcaug gcuccccugu gcccagccc cuggcuccu cuguugaucc cggcccugc | 300 |
| uccaggccuc acugugcaac ugcugcuguc acugcugcuu cuggugccug uccauccca | 360 |
| gagguugccc cggaugcagg aggauuccc cuugggagga ggcucuucug gggaagauga | 420 |
| cccacugggc gaggaggauc ugcccaguga agaggauuca cccagagagg | 470 |

<210> SEQ ID NO 56
<211> LENGTH: 292
<212> TYPE: DNA
<213> ORGANISM: HUMAN

<400> SEQUENCE: 56

| | |
|---|---|
| gtttttttga dacggagtct tgcatctgtc atgcccaggc tggagtagca gtggtgccat | 60 |
| ctcggctcac tgcaagctcc acctcccgag ttcacgccat tttcctgcct cagcctcccg | 120 |
| agtagctggg actacaggcg cccgccacca tgcccggcta attttttgta tttttggtag | 180 |
| agacggggtt tcaccgtgtt agccagaatg gtctcgatct cctgacttcg tgatccaccc | 240 |
| gcctcggcct cccaaagttc tgggattaca ggtgtgagcc accgcacctg gc | 292 |

<210> SEQ ID NO 57
<211> LENGTH: 262
<212> TYPE: DNA
<213> ORGANISM: HUMAN

<400> SEQUENCE: 57

| | |
|---|---|
| tttctttttt gagacagggt cttgctctgt cacccaggcc agagtgcaat ggtacagtct | 60 |
| cagctcactg cagcctcaac cgcctcggct caaaccatca tcccatttca gcctcctgag | 120 |
| tagctgggac tacaggcaca tgccattaca cctggctaat ttttttgtat ttctagtaga | 180 |
| gacagggttt ggccatgttg cccgggctgg tctcgaactc ctggactcaa gcaatccacc | 240 |
| cacctcagcc tcccaaaatg ag | 262 |

<210> SEQ ID NO 58
<211> LENGTH: 2501
<212> TYPE: DNA
<213> ORGANISM: HUMAN
<220> FEATURE:
<221> NAME/KEY: misc_feature
<222> LOCATION: (1)..(2501)
<223> OTHER INFORMATION: region 5' to transcription initiation site as
      determined by RNase protection assay (nucleotide 3507 of Figures
      2A-2F and of SEQ ID NO: 5), corresponding to region of SEQ ID NO:
      5 and Figures 2A-2F from nucleotide (7) to nucleotide (2507), in
      which region some regulatory elements are probably situated.
<221> NAME/KEY: unsure what base is at position 1968
<222> LOCATION: (1968)
<223> OTHER INFORMATION: unsure of base at position 1968, which is the
      same unknown base as that at position 1974 of SEQ ID NO: 5, i.e.,
      the full-length MN genomic sequence, and that unknown at position
      1968 of SEQ ID NO: 90, and unknown at position 647 of SEQ ID NO:
      110. That unknown base is in the 5' region flanking the
      transcription initiation site (3507) as determined by RNase
      protection assay.

<400> SEQUENCE: 58

| | |
|---|---|
| tgttgactcg tgaccttacc cccaaccctg tgctctctga acatgagct gtgtccactc | 60 |
| agggttaaat ggattaaggg cggtgcaaga tgtgctttgt taaacagatg cttgaaggca | 120 |
| gcatgctcgt taagagtcat caccaatccc taatctcaag taatcaggga cacaaacact | 180 |

-continued

```
gcggaaggcc gcagggtcct ctgcctagga aaaccagaga cctttgttca cttgtttatc      240
tgaccttccc tccactattg tccatgaccc tgccaaatcc ccctctgtga gaaacaccca      300
agaattatca ataaaaaaat aaatttaaaa aaaaaataca aaaaaaaaaa aaaaaaaaaa      360
aaaagactta cgaatagtta ttgataaatg aatagctatt ggtaaagcca agtaaatgat      420
catattcaaa accagacggc catcatcaca gctcaagtct acctgatttg atctctttat      480
cattgtcatt ctttggattc actagattag tcatcatcct caaaattctc ccccaagttc      540
taattacgtt ccaaacattt aggggttaca tgaagcttga acctactacc ttctttgctt      600
ttgagccatg agttgtagga atgatgagtt tacaccttac atgctgggga ttaatttaaa      660
ctttacctct aagtcagttg ggtagccttt ggcttatttt tgtagctaat tttgtagtta      720
atggatgcac tgtgaatctt gctatgatag ttttcctcca cactttgcca ctaggggtag      780
gtaggtactc agttttcagt aattgcttac ctaagaccct aagccctatt tctcttgtac      840
tggcctttat ctgtaatatg ggcatattta atacaatata attttttggag tttttttgtt      900
tgtttgtttg tttgttttttt tgagacggag tcttgcatct gtcatgccca ggctggagta      960
gcagtggtgc catctcggct cactgcaagc tccacctccc gagttcacgc cattttcctg     1020
cctcagcctc ccgagtagct gggactacag gcgcccgcca ccatgcccgg ctaatttttt     1080
gtattttttgg tagagacggg gtttcaccgt gttagccaga atggtctcga tctcctgact     1140
tcgtgatcca cccgcctcgg cctcccaaag ttctgggatt acaggtgtga gccaccgcac     1200
ctggccaatt ttttgagtct tttaaagtaa aaatatgtct tgtaagctgg taactatggt     1260
acatttcctt ttattaatgt ggtgctgacg gtcatatagg ttcttttgag tttggcatgc     1320
atatgctact ttttgcagtc cttttcattac atttttctct cttcatttga agagcatgtt     1380
atatctttta gcttcacttg gcttaaaagg ttctctcatt agcctaacac agtgtcattg     1440
ttggtaccac ttggatcata agtggaaaaa cagtcaagaa attgcacagt aatacttgtt     1500
tgtaagaggg atgattcagg tgaatctgac actaagaaac tcccctacct gaggtctgag     1560
attcctctga cattgctgta tataggcttt tcctttgaca gcctgtgact gcggactatt     1620
tttcttaagc aagatatgct aaagttttgt gagcctttt ccagagagag gtctcatatc      1680
tgcatcaagt gagaacatat aatgtctgca tgtttccata tttcaggaat gtttgcttgt     1740
gttttatgct tttatataga cagggaaact tgttcctcag tgacccaaaa gaggtgggaa     1800
ttgttattgg atatcatcat tggcccacgc tttctgacct tggaaacaat taagggttca     1860
taatctcaat tctgtcagaa ttggtacaag aaatagctgc tatgtttctt gacattccac     1920
ttggtaggaa ataagaatgt gaaactcttc agttggtgtg tgtccctngt ttttttgcaa     1980
tttccttctt actgtgttaa aaaaagtat gatcttgctc tgagaggtga ggcattctta      2040
atcatgatct ttaaagatca ataatataat cctttcaagg attatgtctt tattataata     2100
aagataattt gtctttaaca gaatcaataa tataatccct taaaggatta tatctttgct     2160
gggcgcagtg gctcacacct gtaatcccag cactttgggt ggccaaggtg gaaggatcaa     2220
atttgcctac ttctatatta tcttctaaag cagaattcat ctctcttccc tcaatatgat     2280
gatattgaca gggtttgccc tcactcacta gattgtgagc tcctgctcag ggcaggtagc     2340
gttttttgtt tttgttttttg ttttttcttt ttgagacagg gtcttgctct gtcacccagg     2400
ccagagtgca atggtacagt ctcagctcac tgcagcctca accgcctcgg ctcaaaccat     2460
catcccattt cagcctcctg agtagctggg actacaggca c                          2501
```

<210> SEQ ID NO 59
<211> LENGTH: 292
<212> TYPE: DNA
<213> ORGANISM: HUMAN
<220> FEATURE:
<221> NAME/KEY: misc_feature
<222> LOCATION: (1)

<400> SEQUENCE: 59
tttttttgag acggagtctt gcatctgtca tgcccaggct ggagtagcag tggtgccatc    60
tcggctcact gcaagctcca cctcccgagt tcacgccatt ttcctgcctc agcctcccga   120
gtagctggga ctacaggcgc ccgccaccat gcccggctaa ttttttgtat ttttggtaga   180
gacggggttt caccgtgtta gccagaatgg tctcgatctc ctgacttcgt gatccacccg   240
cctcggcctc ccaaagttct gggattacag gtgtgagcca ccgcacctgg cc           292

<210> SEQ ID NO 60
<211> LENGTH: 262
<212> TYPE: DNA
<213> ORGANISM: HUMAN

<400> SEQUENCE: 60 ttctttttg agacagggtc ttgctctgtc acccaggcca gagtgcaatg gtacagtctc     60
agctcactgc agcctcaacc gcctcggctc aaaccatcat cccatttcag cctcctgagt   120
agctgggact acaggcacat gccattacac ctggctaatt tttttgtatt tctagtagag   180
acagggtttg gccatgttgc ccgggctggt ctcgaactcc tggactcaag caatccaccc   240
acctcagcct cccaaaatga gg                                            262

<210> SEQ ID NO 61
<211> LENGTH: 294
<212> TYPE: DNA
<213> ORGANISM: HUMAN

<400> SEQUENCE: 61
tttttttttg agacaaactt tcacttttgt tgcccaggct ggagtgcaat ggcgcgatct    60
cggctcactg caacctccac ctcccgggtt caagtgattc tcctgcctca gcctctagcc   120
aagtagctgc gattacaggc atgcgccacc acgcccggct aatttttgta ttttagtag    180 agacggggtt tcgccatgtt ggtcaggctg gtctcgaact cctgatctca ggtgatccaa   240
ccacccctgg ctcccaaagt gctgggatta taggcgtgag ccacagcgcc tggc          294

<210> SEQ ID NO 62
<211> LENGTH: 276
<212> TYPE: DNA
<213> ORGANISM: HUMAN

<400> SEQUENCE: 62
tgacagtctc tctgtcgccc aggctggagt gcagtggtgt gatcttgggt cactgcaact    60
tccgcctccc gggttcaagg gattctcctg cctcagcttc ctgagtagct ggggttacag   120
gtgtgtgcca ccatgcccag ctaatttttt tttgtatttt tagtagacag ggtttcacca   180
tgttggtcag gctggtctca aactcctggc tcaagtgat ccgcctgact cagcctacca    240
aagtgctgat tacaagtgtg agccaccgtg cccagc                              276

<210> SEQ ID NO 63
<211> LENGTH: 289
<212> TYPE: DNA
<213> ORGANISM: HUMAN

-continued

```
<400> SEQUENCE: 63
cgccgggcac ggtggctcac gcctgtaatc ccagcacttt gggaggccaa ggcaggtgga      60
tcacgaggtc aagagatcaa gaccatcctg gccaacatgg tgaaacccca tctctactaa    120
aaatacgaaa aaatagccag gcgtggtggc gggtgcctgt aatcccagct actcgggagg    180
ctgaggcagg agaatggcat gaacccggga ggcagaagtt gcagtgagcc gagatcgtgc    240
cactgcactc cagcctgggc aacagagcga gactcttgtc tcaaaaaaa                289

<210> SEQ ID NO 64
<211> LENGTH: 298
<212> TYPE: DNA
<213> ORGANISM: HUMAN

<400> SEQUENCE: 64
aggctgggct ctgtggctta cgcctataat cccaccacgt tgggaggctg aggtgggaga     60
atggtttgag cccaggagtt caagacaagg cggggcaaca tagtgtgacc ccatctctac    120
caaaaaaacc ccaacaaaac caaaaatagc cgggcatggt ggtatgcggc ctagtcccag    180
ctactcaagg aggctgaggt gggaagatcg cttgattcca ggagtttgag actgcagtga    240
gctatgatcc caccactgcc taccatcttt aggatacatt tatttattta taaagaa      298

<210> SEQ ID NO 65
<211> LENGTH: 105
<212> TYPE: DNA
<213> ORGANISM: HUMAN

<400> SEQUENCE: 65 tttttttacat ctttagtaga gacagggttt caccatattg gccaggctgc tctcaaactc     60
ctgaccttgt gatccaccag cctcggcctc ccaaagtgct gggat                    105

<210> SEQ ID NO 66
<211> LENGTH: 83
<212> TYPE: DNA
<213> ORGANISM: HUMAN

<400> SEQUENCE: 66
cctcgaactc ctaggctcag gcaatccttt caccttagct tctcaaagca ctgggactgt     60
aggcatgagc cactgtgcct ggc                                            83

<210> SEQ ID NO 67
<211> LENGTH: 11
<212> TYPE: DNA
<213> ORGANISM: HUMAN

<400> SEQUENCE: 67
agaaggtaag t                                                          11

<210> SEQ ID NO 68
<211> LENGTH: 11
<212> TYPE: DNA
<213> ORGANISM: HUMAN

<400> SEQUENCE: 68
tggaggtgag a                                                          11

<210> SEQ ID NO 69
<211> LENGTH: 11
<212> TYPE: DNA
```

<213> ORGANISM: HUMAN

<400> SEQUENCE: 69
cagtcgtgag g 11

<210> SEQ ID NO 70
<211> LENGTH: 11
<212> TYPE: DNA
<213> ORGANISM: HUMAN

<400> SEQUENCE: 70
ccgaggtgag c 11

<210> SEQ ID NO 71
<211> LENGTH: 11
<212> TYPE: DNA
<213> ORGANISM: HUMAN

<400> SEQUENCE: 71
tggaggtacc a 11

<210> SEQ ID NO 72
<211> LENGTH: 11
<212> TYPE: DNA
<213> ORGANISM: HUMAN

<400> SEQUENCE: 72
ggaaggtcag t 11

<210> SEQ ID NO 73
<211> LENGTH: 11
<212> TYPE: DNA
<213> ORGANISM: HUMAN

<400> SEQUENCE: 73
agcaggtggg c 11

<210> SEQ ID NO 74
<211> LENGTH: 11
<212> TYPE: DNA
<213> ORGANISM: HUMAN

<400> SEQUENCE: 74
gccaggtaca g 11

<210> SEQ ID NO 75
<211> LENGTH: 11
<212> TYPE: DNA
<213> ORGANISM: HUMAN

<400> SEQUENCE: 75
tgctggtgag t 11

<210> SEQ ID NO 76
<211> LENGTH: 11
<212> TYPE: DNA
<213> ORGANISM: HUMAN

<400> SEQUENCE: 76
atacagggga t 11

<210> SEQ ID NO 77
<211> LENGTH: 11

```
<212> TYPE: DNA
<213> ORGANISM: HUMAN

<400> SEQUENCE: 77
atacagggga t                                                              11

<210> SEQ ID NO 78
<211> LENGTH: 11
<212> TYPE: DNA
<213> ORGANISM: HUMAN

<400> SEQUENCE: 78
ccccaggcga c                                                              11

<210> SEQ ID NO 79
<211> LENGTH: 11
<212> TYPE: DNA
<213> ORGANISM: HUMAN

<400> SEQUENCE: 79
acgcagtgca a                                                              11

<210> SEQ ID NO 80
<211> LENGTH: 11
<212> TYPE: DNA
<213> ORGANISM: HUMAN

<400> SEQUENCE: 80
tttcagatcc a                                                              11

<210> SEQ ID NO 81
<211> LENGTH: 11
<212> TYPE: DNA
<213> ORGANISM: HUMAN

<400> SEQUENCE: 81
ccccaggagg g                                                              11

<210> SEQ ID NO 82
<211> LENGTH: 11
<212> TYPE: DNA
<213> ORGANISM: HUMAN

<400> SEQUENCE: 82
tcacaggctc a                                                              11

<210> SEQ ID NO 83
<211> LENGTH: 11
<212> TYPE: DNA
<213> ORGANISM: HUMAN

<400> SEQUENCE: 83
ccctagctcc a                                                              11

<210> SEQ ID NO 84
<211> LENGTH: 11
<212> TYPE: DNA
<213> ORGANISM: HUMAN

<400> SEQUENCE: 84
ctccagtcca g                                                              11

<210> SEQ ID NO 85
```

-continued

<210> SEQ ID NO 85
<211> LENGTH: 12
<212> TYPE: DNA
<213> ORGANISM: HUMAN

<400> SEQUENCE: 85
tcgcaggtga ca                                                         12

<210> SEQ ID NO 86
<211> LENGTH: 11
<212> TYPE: DNA
<213> ORGANISM: HUMAN

<400> SEQUENCE: 86
acacagaagg g                                                          11

<210> SEQ ID NO 87
<211> LENGTH: 377
<212> TYPE: PRT
<213> ORGANISM: HUMAN

<400> SEQUENCE: 87

Gln Arg Leu Pro Arg Met Gln Glu Asp Ser Pro Leu Gly Gly Gly Ser
 1               5                  10                  15

Ser Gly Glu Asp Asp Pro Leu Gly Glu Glu Asp Leu Pro Ser Glu Glu
            20                  25                  30

Asp Ser Pro Arg Glu Glu Asp Pro Pro Gly Glu Glu Asp Leu Pro Gly
        35                  40                  45

Glu Glu Asp Leu Pro Gly Glu Glu Asp Leu Pro Glu Val Lys Pro Lys
    50                  55                  60

Ser Glu Glu Glu Gly Ser Leu Lys Leu Glu Asp Leu Pro Thr Val Glu
65                  70                  75                  80

Ala Pro Gly Asp Pro Gln Glu Pro Gln Asn Asn Ala His Arg Asp Lys
                85                  90                  95

Glu Gly Asp Asp Gln Ser His Trp Arg Tyr Gly Gly Asp Pro Pro Trp
            100                 105                 110

Pro Arg Val Ser Pro Ala Cys Ala Gly Arg Phe Gln Ser Pro Val Asp
        115                 120                 125

Ile Arg Pro Gln Leu Ala Ala Phe Cys Pro Ala Leu Arg Pro Leu Glu
    130                 135                 140

Leu Leu Gly Phe Gln Leu Pro Pro Leu Pro Glu Leu Arg Leu Arg Asn
145                 150                 155                 160

Asn Gly His Ser Val Gln Leu Thr Leu Pro Pro Gly Leu Glu Met Ala
                165                 170                 175

Leu Gly Pro Gly Arg Glu Tyr Arg Ala Leu Gln Leu His Leu His Trp
            180                 185                 190

Gly Ala Ala Gly Arg Pro Gly Ser Glu His Thr Val Glu Gly His Arg
        195                 200                 205

Phe Pro Ala Glu Ile His Val Val His Leu Ser Thr Ala Phe Ala Arg
    210                 215                 220

Val Asp Glu Ala Leu Gly Arg Pro Gly Gly Leu Ala Val Leu Ala Ala
225                 230                 235                 240

Phe Leu Glu Glu Gly Pro Glu Glu Asn Ser Ala Tyr Glu Gln Leu Leu
                245                 250                 255

Ser Arg Leu Glu Glu Ile Ala Glu Glu Gly Ser Glu Thr Gln Val Pro
            260                 265                 270

Gly Leu Asp Ile Ser Ala Leu Leu Pro Ser Asp Phe Ser Arg Tyr Phe
        275                 280                 285

```
Gln Tyr Glu Gly Ser Leu Thr Thr Pro Pro Cys Ala Gln Gly Val Ile
    290                 295                 300

Trp Thr Val Phe Asn Gln Thr Val Met Leu Ser Ala Lys Gln Leu His
305                 310                 315                 320

Thr Leu Ser Asp Thr Leu Trp Gly Pro Gly Asp Ser Arg Leu Gln Leu
                325                 330                 335

Asn Phe Arg Ala Thr Gln Pro Leu Asn Gly Arg Val Ile Glu Ala Ser
            340                 345                 350

Phe Pro Ala Gly Val Asp Ser Ser Pro Arg Ala Ala Glu Pro Val Gln
        355                 360                 365

Leu Asn Ser Cys Leu Ala Ala Gly Asp
    370                 375

<210> SEQ ID NO 88
<211> LENGTH: 34
<212> TYPE: DNA
<213> ORGANISM: HUMAN

<400> SEQUENCE: 88
tagacagatc tacgatggct cccctgtgcc ccag                               34

<210> SEQ ID NO 89
<211> LENGTH: 34
<212> TYPE: DNA
<213> ORGANISM: HUMAN

<400> SEQUENCE: 89
attcctctag acagttaccg gctcccctc agat                                34

<210> SEQ ID NO 90
<211> LENGTH: 3532
<212> TYPE: DNA
<213> ORGANISM: HUMAN
<220> FEATURE:
<221> NAME/KEY: misc_feature which includes the MN gene promoter
<222> LOCATION: (1)..(3532)
<223> OTHER INFORMATION: region including the transcription initiation
      site (nucleotide 3507 of SEQ ID NO: 5 and of Figures 2A-2F) as
      determined by RNase protection assay, which region is inclusive of
      the MN gene promoter, and corresponds to nucleotide 7 to
      nucleotide 3538 of SEQ ID NO: 5 and of Figures 2A-2F.
<221> NAME/KEY: unsure what base is at position 1968
<222> LOCATION: (1968)
<223> OTHER INFORMATION: unsure of the base at position 1968, which is
      the same unknown base at position 1974 of SEQ ID NO: 5 (the full-
      length MN genomic sequence), position 1968 of SEQ ID NO: 58 and
      position 647 of SEQ ID NO: 110.  That unknown base is in the
      region that includes the transcription initiation site (nucleotide
      3507 of SEQ ID NO: 5 and of Figures 2A-2F) as determined by RNase
      protection assay, which region is inclusive of the MN gene
      promoter.

<400> SEQUENCE: 90
tgttgactcg tgaccttacc cccaaccctg tgctctctga acatgagct gtgtccactc      60 agggttaaat ggattaaggg cggtgcaaga tgtgctttgt taaacagatg cttgaaggca   120
gcatgctcgt taagagtcat caccaatccc taatctcaag taatcaggga cacaaacact   180
gcggaaggcc gcagggtcct ctgcctagga aaaccagaga cctttgttca cttgtttatc   240
tgaccttccc tccactattg tccatgaccc tgccaaatcc ccctctgtga gaaacaccca   300
agaattatca ataaaaaaat aaatttaaaa aaaaaataca aaaaaaaaaa aaaaaaaaa    360 aaaagactta cgaatagtta ttgataaatg aatagctatt ggtaaagcca agtaaatgat   420
```

-continued

| | |
|---|---|
| catattcaaa accagacggc catcatcaca gctcaagtct acctgatttg atctctttat | 480 |
| cattgtcatt ctttggattc actagattag tcatcatcct caaaattctc ccccaagttc | 540 |
| taattacgtt ccaaacattt aggggttaca tgaagcttga acctactacc ttctttgctt | 600 |
| ttgagccatg agttgtagga atgatgagtt tacaccttac atgctgggga ttaatttaaa | 660 |
| ctttacctct aagtcagttg ggtagccttt ggcttatttt tgtagctaat tttgtagtta | 720 |
| atggatgcac tgtgaatctt gctatgatag ttttcctcca cactttgcca ctaggggtag | 780 |
| gtaggtactc agttttcagt aattgcttac ctaagaccct aagccctatt tctcttgtac | 840 |
| tggcctttat ctgtaatatg ggcatattta atacaatata atttttggag ttttttttgtt | 900 |
| tgtttgtttg tttgttttttt tgagacggag tcttgcatct gtcatgccca ggctggagta | 960 |
| gcagtggtgc catctcggct cactgcaagc tccacctccc gagttcacgc catttttcctg | 1020 |
| cctcagcctc ccgagtagct gggactacag gcgcccgcca ccatgcccgg ctaatttttt | 1080 |
| gtattttttgg tagagacggg gtttcaccgt gttagccaga atggtctcga tctcctgact | 1140 |
| tcgtgatcca cccgcctcgg cctcccaaag ttctgggatt acaggtgtga gccaccgcac | 1200 |
| ctggccaatt ttttgagtct tttaaagtaa aaatatgtct tgtaagctgg taactatggt | 1260 |
| acatttcctt ttattaatgt ggtgctgacg gtcatatagg ttcttttgag tttggcatgc | 1320 |
| atatgctact ttttgcagtc cttttcattac attttttctct cttcatttga agagcatgtt | 1380 |
| atatcttta gcttcacttg gcttaaaagg ttctctcatt agcctaacac agtgtcattg | 1440 |
| ttggtaccac ttggatcata agtggaaaaa cagtcaagaa attgcacagt aatacttgtt | 1500 |
| tgtaagaggg atgattcagg tgaatctgac actaagaaac tcccctacct gaggtctgag | 1560 |
| attcctctga cattgctgta tataggctttt tcctttgaca gcctgtgact gcggactatt | 1620 |
| tttcttaagc aagatatgct aaagttttgt gagcctttt ccagagagag gtctcatatc | 1680 |
| tgcatcaagt gagaacatat aatgtctgca tgtttccata tttcaggaat gtttgcttgt | 1740 |
| gttttatgct tttatataga cagggaaact tgttcctcag tgacccaaaa gaggtgggaa | 1800 |
| ttgttattgg atatcatcat tggcccacgc tttctgacct tggaaacaat taagggttca | 1860 |
| taatctcaat tctgtcagaa ttggtacaag aaatagctgc tatgtttctt gacattccac | 1920 |
| ttggtaggaa ataagaatgt gaaactcttc agttggtgtg tgtccctngt ttttttgcaa | 1980 |
| tttccttctt actgtgttaa aaaaaagtat gatcttgctc tgagaggtga ggcattctta | 2040 |
| atcatgatct ttaaagatca ataatataat cctttcaagg attatgtctt tattataata | 2100 |
| aagataattt gtctttaaca gaatcaataa tataatccct taaaggatta tatctttgct | 2160 |
| gggcgcagtg gctcacacct gtaatcccag cactttgggt ggccaaggtg aaggatcaa | 2220 |
| atttgcctac ttctatatta tcttctaaag cagaattcat ctctcttccc tcaatatgat | 2280 |
| gatattgaca gggtttgccc tcactcacta gattgtgagc tcctgctcag ggcaggtagc | 2340 |
| gtttttttgtt tttgttttg ttttttctttt ttgagacagg gtcttgctct gtcacccagg | 2400 |
| ccagagtgca atggtacagt ctcagctcac tgcagcctca accgcctcgg ctcaaaccat | 2460 |
| catcccattt cagcctcctg agtagctggg actacaggca catgccatta cacctggcta | 2520 |
| atttttttgt atttctagta gagacagggt ttggccatgt tgcccgggct ggtctcgaac | 2580 |
| tcctggactc aagcaatcca cccacctcag cctcccaaaa tgagggaccg tgtcttattc | 2640 |
| atttccatgt ccctagtcca tagcccagtg ctggacctat ggtagtacta ataaatatt | 2700 |
| tgttgaatgc aatagtaaat agcatttcag ggagcaagaa ctagattaac aaaggtggta | 2760 |
| aaaggtttgg agaaaaaaat aatagtttaa tttggctaga gtatgaggga gagtagtagg | 2820 |

```
agacaagatg gaaaggtctc ttgggcaagg ttttgaagga agttggaagt cagaagtaca    2880
caatgtgcat atcgtggcag gcagtgggga gccaatgaag gcttttgagc aggagagtaa    2940
tgtgttgaaa ataaatata ggttaaacct atcagagccc ctctgacaca tacacttgct    3000
tttcattcaa gctcaagttt gtctcccaca tacccattac ttaactcacc ctcgggctcc    3060
cctagcagcc tgccctacct cttttacctgc ttcctggtgg agtcagggat gtatacatga    3120
gctgctttcc ctctcagcca gaggacatgg ggggcccag ctccctgcc tttccccttc      3180 tgtgcctgga gctgggaagc aggccagggt tagctgaggc tggctggcaa gcagctgggt    3240
ggtgccaggg agagcctgca tagtgccagg tggtgccttg ggttccaagc tagtccatgg    3300
ccccgataac cttctgcctg tgcacacacc tgccctcac tccaccccca tcctagcttt     3360
ggtatggggg agagggcaca gggccagaca aacctgtgag actttggctc catctctgca    3420
aaagggcgct ctgtgagtca gcctgctccc ctccaggctt gctcctcccc cacccagctc    3480
tcgtttccaa tgcacgtaca gcccgtacac accgtgtgct gggacacccc ac            3532

<210> SEQ ID NO 91
<211> LENGTH: 204
<212> TYPE: DNA
<213> ORGANISM: HUMAN

<400> SEQUENCE: 91
cctgcccctc actccacccc catcctagct ttggtatggg ggagagggca cagggccaga     60
caaacctgtg agactttggc tccatctctg caaaagggcg ctctgtgagt cagcctgctc    120
ccctccaggc ttgctcctcc cccacccagc tctcgtttcc aatgcacgta cagcccgtac    180
acaccgtgtg ctgggacacc ccac                                           204

<210> SEQ ID NO 92
<211> LENGTH: 132
<212> TYPE: DNA
<213> ORGANISM: HUMAN

<400> SEQUENCE: 92
ggatcctgtt gactcgtgac cttacccca accctgtgct ctctgaaaca tgagctgtgt      60
ccactcaggg ttaaatggat taagggcggt gcaagatgtg cttttgttaaa cagatgcttg    120 aaggcagcat gc                                                        132

<210> SEQ ID NO 93
<211> LENGTH: 275
<212> TYPE: DNA
<213> ORGANISM: HUMAN

<400> SEQUENCE: 93
gcatagtgcc aggtggtgcc ttgggttcca agctagtcca tggccccgat aaccttctgc      60
ctgtgcacac acctgcccct cactccaccc ccatcctagc tttggtatgg gggagagggc    120
acagggccag acaaacctgt gagactttgg ctccatctct gcaaaagggc gctctgtgag    180
tcagcctgct cccctccagg cttgctcctc ccccacccag ctctcgtttc caatgcacgt    240
acagcccgta cacaccgtgt gctgggacac cccac                               275

<210> SEQ ID NO 94
<211> LENGTH: 89
<212> TYPE: DNA
<213> ORGANISM: HUMAN
```

-continued

```
<400> SEQUENCE: 94
ctgctcccct ccaggcttgc tcctccccca cccagctctc gtttccaatg cacgtacagc      60
ccgtacacac cgtgtgctgg gacaccccca                                       89

<210> SEQ ID NO 95
<211> LENGTH: 61
<212> TYPE: DNA
<213> ORGANISM: HUMAN

<400> SEQUENCE: 95
cacccagctc tcgtttccaa tgcacgtaca gcccgtacac accgtgtgct gggacacccc      60
a                                                                      61

<210> SEQ ID NO 96
<211> LENGTH: 116
<212> TYPE: DNA
<213> ORGANISM: HUMAN

<400> SEQUENCE: 96
acctgcccct cactccaccc ccatcctagc tttggtatgg gggagagggc acagggccag      60
acaaacctgt gagactttgg ctccatctct gcaaaagggc gctctgtgag tcagcc         116

<210> SEQ ID NO 97
<211> LENGTH: 36
<212> TYPE: PRT
<213> ORGANISM: HUMAN

<400> SEQUENCE: 97

Gly Glu Glu Asp Leu Pro Ser Glu Glu Asp Ser Pro Arg Glu Glu Asp
 1               5                  10                  15

Pro Pro Gly Glu Glu Asp Leu Pro Gly Glu Glu Asp Leu Pro Gly Glu
             20                  25                  30

Glu Asp Leu Pro
         35

<210> SEQ ID NO 98
<211> LENGTH: 6
<212> TYPE: PRT
<213> ORGANISM: HUMAN

<400> SEQUENCE: 98

Gly Glu Glu Asp Leu Pro
 1               5

<210> SEQ ID NO 99
<211> LENGTH: 4
<212> TYPE: PRT
<213> ORGANISM: HUMAN

<400> SEQUENCE: 99

Glu Glu Asp Leu
 1

<210> SEQ ID NO 100
<211> LENGTH: 5
<212> TYPE: PRT
<213> ORGANISM: HUMAN

<400> SEQUENCE: 100

Glu Glu Asp Leu Pro
 1               5
```

```
<210> SEQ ID NO 101
<211> LENGTH: 6
<212> TYPE: PRT
<213> ORGANISM: HUMAN

<400> SEQUENCE: 101

Glu Asp Leu Pro Ser Glu
 1               5

<210> SEQ ID NO 102
<211> LENGTH: 7
<212> TYPE: PRT
<213> ORGANISM: HUMAN

<400> SEQUENCE: 102

Glu Glu Asp Leu Pro Ser Glu
 1               5

<210> SEQ ID NO 103
<211> LENGTH: 6
<212> TYPE: PRT
<213> ORGANISM: HUMAN

<400> SEQUENCE: 103

Asp Leu Pro Gly Glu Glu
 1               5

<210> SEQ ID NO 104
<211> LENGTH: 22
<212> TYPE: PRT
<213> ORGANISM: HUMAN

<400> SEQUENCE: 104

Gly Gly Ser Ser Gly Glu Asp Asp Pro Leu Gly Glu Glu Asp Leu Pro
 1               5                  10                  15

Ser Glu Glu Asp Ser Pro
             20

<210> SEQ ID NO 105
<211> LENGTH: 25
<212> TYPE: PRT
<213> ORGANISM: HUMAN

<400> SEQUENCE: 105

Gly Glu Glu Asp Leu Pro Ser Glu Asp Ser Pro Arg Glu Glu Asp
 1               5                  10                  15

Pro Pro Gly Glu Glu Asp Leu Pro Gly
             20                  25

<210> SEQ ID NO 106
<211> LENGTH: 24
<212> TYPE: PRT
<213> ORGANISM: HUMAN

<400> SEQUENCE: 106

Glu Asp Pro Pro Gly Glu Glu Asp Leu Pro Gly Glu Glu Asp Leu Pro
 1               5                  10                  15

Gly Glu Glu Asp Leu Pro Glu Val
             20

<210> SEQ ID NO 107
<211> LENGTH: 7
```

-continued

```
<212> TYPE: PRT
<213> ORGANISM: HUMAN

<400> SEQUENCE: 107

Gly Glu Thr Arg Ala Pro Leu
 1               5

<210> SEQ ID NO 108
<211> LENGTH: 7
<212> TYPE: PRT
<213> ORGANISM: HUMAN

<400> SEQUENCE: 108

Gly Glu Thr Arg Glu Pro Leu
 1               5

<210> SEQ ID NO 109
<211> LENGTH: 7
<212> TYPE: PRT
<213> ORGANISM: HUMAN

<400> SEQUENCE: 109

Gly Gln Thr Arg Ser Pro Leu
 1               5

<210> SEQ ID NO 110
<211> LENGTH: 1247
<212> TYPE: DNA
<213> ORGANISM: HUMAN
<220> FEATURE:
<221> NAME/KEY: misc_feature
<222> LOCATION: (1)..(1247)
<223> OTHER INFORMATION: region 5' to the transcription initiation site
      as determined by RNase protection assay (nucleotide 3507 of SEQ ID
      NO: 5 and of Figures 2A-2F) in which an activating element is
      localized, which region corresponds to nucleotide
      1328 to nucleotide 2574 of SEQ ID NO: 5 and of Figures 2A-2F.
<221> NAME/KEY: unsure what base is at position 647
<222> LOCATION: (647)
<223> OTHER INFORMATION: unsure of the base at position 647, which is
      the same unknown base as that     at position 1974 of SEQ ID NO:
      5, and 58 and 90.  That unknown base at position 647 is in a
      region in which an activating element is localized and is 5' to
      the transcription initiation site.

<400> SEQUENCE: 110
tatgctactt tttgcagtcc tttcattaca tttttctctc ttcatttgaa gagcatgtta      60
tatcttttag cttcacttgg cttaaaaggt tctctcatta gcctaacaca gtgtcattgt     120
tggtaccact tggatcataa gtggaaaaac agtcaagaaa ttgcacagta atacttgttt     180
gtaagaggga tgattcaggt gaatctgaca ctaagaaact cccctacctg aggtctgaga     240
ttcctctgac attgctgtat ataggctttt cctttgacag cctgtgactg cggactattt     300
ttcttaagca agatatgcta aagttttgtg agcctttttc cagagagagg tctcatatct     360
gcatcaagtg agaacatata atgtctgcat gttccatat ttcaggaatg tttgcttgtg      420
ttttatgctt ttatatagac agggaaactt gttcctcagt gacccaaaag aggtgggaat     480
tgttattgga tatcatcatt ggcccacgct ttctgacctt ggaaacaatt aagggttcat     540
aatctcaatt ctgtcagaat tggtacaaga aatagctgct atgtttcttg acattccact     600
tggtaggaaa taagaatgtg aaactcttca gttggtgtgt gtccctngtt tttttgcaat     660
ttccttctta ctgtgttaaa aaaagtatg atcttgctct gagaggtgag gcattcttaa      720
tcatgatctt taaagatcaa taatataatc ctttcaagga ttatgtcttt attataataa     780
```

-continued

```
agataatttg tctttaacag aatcaataat ataatcccctt aaaggattat atctttgctg      840
ggcgcagtgg ctcacacctg taatcccagc actttgggtg gccaaggtgg aaggatcaaa      900
tttgcctact tctatattat cttctaaagc agaattcatc tctcttccct caatatgatg      960
atattgacag ggtttgccct cactcactag attgtgagct cctgctcagg gcaggtagcg     1020 tttttttgttt ttgttttttgt ttttcttttt tgagacaggg tcttgctctg tcacccaggc   1080
cagagtgcaa tggtacagtc tcagctcact gcagcctcaa ccgcctcggc tcaaaccatc    1140
atcccatttc agcctcctga gtagctggga ctacaggcac atgccattac acctggctaa    1200
tttttttgta tttctagtag agacagggtt tggccatgtt gcccggg                  1247
```

<210> SEQ ID NO 111
<211> LENGTH: 17
<212> TYPE: DNA
<213> ORGANISM: HUMAN

<400> SEQUENCE: 111

```
ctctgtgagt cagcctg                                                    17
```

<210> SEQ ID NO 112
<211> LENGTH: 23
<212> TYPE: DNA
<213> ORGANISM: HUMAN

<400> SEQUENCE: 112

```
aggcttgctc ctcccccacc cag                                             23
```

<210> SEQ ID NO 113
<211> LENGTH: 18
<212> TYPE: DNA
<213> ORGANISM: HUMAN

<400> SEQUENCE: 113

```
agactttggc tccatctc                                                   18
```

<210> SEQ ID NO 114
<211> LENGTH: 20
<212> TYPE: DNA
<213> ORGANISM: HUMAN

<400> SEQUENCE: 114

```
cactccaccc ccatcctagc                                                 20
```

<210> SEQ ID NO 115
<211> LENGTH: 26
<212> TYPE: DNA
<213> ORGANISM: HUMAN

<400> SEQUENCE: 115

```
gggagagggc acagggccag acaaac                                          26
```

<210> SEQ ID NO 116
<211> LENGTH: 20
<212> TYPE: PRT
<213> ORGANISM: HUMAN

```
<400> SEQUENCE: 116

Gly Gly Gly Gly Ser Gly Gly Gly Gly Ser Gly Gly Gly Gly Ser Gly
  1               5                  10                  15

Gly Gly Gly Ser
            20
```

The invention claimed is:

1. An anti-idiotype antibody to an idiotype of a second antibody, wherein said idiotype of said second antibody specifically binds to an epitope of MN protein, wherein said anti-idiotype antibody comprises an internal image corresponding to said epitope of said MN protein, and wherein said MN protein has an amino acid sepuence of SEQ ID NO: 2 that is encoded by a nucleic acid selected from the group consisting of:
   (a) SEQ ID NO: 1; and
   (b) polynucleotides that differ from SEQ ID NO: 1 due to the degeneracy of the genetic code.

2. An anti-idiotype antibody according to claim 1, wherein said second antibody that is specific for said epitope of the MN protein, is either the M75 monoclonal antibody secreted from the hybridoma VU-M75, which was deposited at the American Type Culture Collection under ATCC No. HB 11128, or the MN12 monoclonal antibody that is secreted from the hybridoma MN 12.2.2, which was deposited at the American Type Culture Collection under ATCC No. HB 11647.

3. The anti-idiotype antibody according to claim 1 where said second antibody is an antigen-binding antibody fragment.

* * * * *

UNITED STATES PATENT AND TRADEMARK OFFICE
CERTIFICATE OF CORRECTION

PATENT NO. : 7,115,715 B2
APPLICATION NO. : 09/967237
DATED : October 3, 2006
INVENTOR(S) : Jan Zavada et al.

It is certified that error appears in the above-identified patent and that said Letters Patent is hereby corrected as shown below:

Column 23, Table 1,
Line 52, "Intron" should read -- Exon --.

Column 24,
Line 19, "Rnase" should read -- RNase --.

Columns 129 and 130,
consisting of a portion of the SEQUENCE LISTING containing SEQ ID NOS: 69-77 should be deleted and the attached new sheet containing SEQ ID NOS: 69-77 should be inserted therefor.

Columns 149 and 150,
consisting of a portion of the SEQUENCE LISTING containing SEQ ID NO: 116 should be deleted and the attached new sheet containng SEQ ID NO: 116 should be inserted therefor.

Signed and Sealed this

Sixth Day of February, 2007

JON W. DUDAS
*Director of the United States Patent and Trademark Office*

<213> ORGANISM: HUMAN

<400> SEQUENCE: 69
cagtcgtgag g             11

<210> SEQ ID NO 70
<211> LENGTH: 11
<212> TYPE: DNA
<213> ORGANISM: HUMAN

<400> SEQUENCE: 70
ccgaggtgag c             11

<210> SEQ ID NO 71
<211> LENGTH: 11
<212> TYPE: DNA
<213> ORGANISM: HUMAN

<400> SEQUENCE: 71
tggaggtacc a             11

<210> SEQ ID NO 72
<211> LENGTH: 11
<212> TYPE: DNA
<213> ORGANISM: HUMAN

<400> SEQUENCE: 72
ggaaggtcag t             11

<210> SEQ ID NO 73
<211> LENGTH: 11
<212> TYPE: DNA
<213> ORGANISM: HUMAN

<400> SEQUENCE: 73
agcaggtggg c             11

<210> SEQ ID NO 74
<211> LENGTH: 11
<212> TYPE: DNA
<213> ORGANISM: HUMAN

<400> SEQUENCE: 74
gccaggtaca g             11

<210> SEQ ID NO 75
<211> LENGTH: 11
<212> TYPE: DNA
<213> ORGANISM: HUMAN

<400> SEQUENCE: 75
tgctggtgag t             11

<210> SEQ ID NO 76
<211> LENGTH: 11
<212> TYPE: DNA
<213> ORGANISM: HUMAN

<400> SEQUENCE: 76
cacaggtatt a             11

<210> SEQ ID NO 77
<211> LENGTH: 11

<400> 116
Gly Gly Gly Gly Ser Gly Gly Gly Gly Ser Gly Gly Gly Gly Ser
1               5                  10                  15

UNITED STATES PATENT AND TRADEMARK OFFICE
CERTIFICATE OF CORRECTION

| | |
|---|---|
| PATENT NO. | : 7,115,715 B2 |
| APPLICATION NO. | : 09/967237 |
| DATED | : October 3, 2006 |
| INVENTOR(S) | : Jan Zavada et al. |

It is certified that error appears in the above-identified patent and that said Letters Patent is hereby corrected as shown below:

Column 1,
line 21, after "patent", please insert -- and also under 35 USC § 119 from the now abandoned Czechoslovakian patent application PV-709-92 (filed March 11, 1992) --.

Signed and Sealed this

Eighth Day of September, 2009

David J. Kappos
*Director of the United States Patent and Trademark Office*